US006524841B1

(12) United States Patent
McDaniel et al.

(10) Patent No.: US 6,524,841 B1
(45) Date of Patent: Feb. 25, 2003

(54) RECOMBINANT MEGALOMICIN BIOSYNTHETIC GENES AND USES THEREOF

(75) Inventors: Robert McDaniel, Palo Alto, CA (US); Yanina Volchegursky, Emeryville, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/679,279

(22) Filed: Oct. 4, 2000

Related U.S. Application Data

(60) Provisional application No. 60/190,024, filed on Mar. 17, 2000, and provisional application No. 60/158,305, filed on Oct. 8, 1999.

(51) Int. Cl.[7] ............................................... C12N 1/20
(52) U.S. Cl. ........................... 435/252.3; 435/252.35; 435/254.11; 435/325; 435/419; 435/320.1; 536/23.1; 536/23.2; 536/23.7
(58) Field of Search ................. 536/23.1, 23.2, 536/23.7; 435/320.1, 252.3, 254.11, 419, 325, 252.35

(56) References Cited

U.S. PATENT DOCUMENTS

| | | | |
|---|---|---|---|
| 3,819,611 A | 6/1974 | Weinstein et al. | 260/210 |
| 5,672,491 A | 9/1997 | Khosla et al. | 435/148 |
| 5,824,513 A | 10/1998 | Katz et al. | 435/76 |
| 5,962,290 A | 10/1999 | Khosla et al. | 435/183 |
| 6,066,721 A | 5/2000 | Khosla et al. | 536/23.1 |
| 6,080,555 A | 6/2000 | Khosla et al. | 435/41 |
| 6,117,659 A | 9/2000 | Ashley et al. | 435/155 |
| 6,251,636 B1 | 6/2001 | Betlach et al. | 435/76 |

FOREIGN PATENT DOCUMENTS

| | | |
|---|---|---|
| WO | WO 97/23630 | 7/1997 |
| WO | WO 98/49315 | 11/1998 |
| WO | WO 99/05283 | 2/1999 |
| WO | WO 99/61599 | 12/1999 |
| WO | WO 00/00500 | 1/2000 |
| WO | WO 00/24907 | 5/2000 |
| WO | WO 00/63361 | 10/2000 |

OTHER PUBLICATIONS

Kao et al. Engineered Biosynthesis of a Complete Macrolactone in a Heterologous Host. Science (1994) 265:509–512.*
Carreras et al, Current Opinion in Biotechnology (1998) 9(4):403–411.
Hutchinson, Current Opinion in Microbiology (1998) 1(3):319–329.
Katz, Chemical Reviews (1997) 97(7):2557–2575.
Liu et al., Annual Review of Microbiology (1994) 48:223–256.

(List continued on next page.)

Primary Examiner—Ponnathapu Achutamurthy
Assistant Examiner—Kathy Kerr
(74) Attorney, Agent, or Firm—Morrision & Foerster LLP

(57) ABSTRACT

Recombinant nucleic acids that encode all or a portion of the megAI gene of the megalomicin polyketide synthase (PKS) of *Micromonospora megalomicea* are used to produce recombinant PKS enzymes in host cells to make megalomicin, megalomicin derivatives, and other polyketides that are useful as antibiotics, motilides, and antiparasitics.

7 Claims, 70 Drawing Sheets

OTHER PUBLICATIONS

Malpartida et al., Nature (1987) 325:818–821.
McDaniel et al., Proceedings of the National Academy of Sciences of USA (1999) 96:1846–1851.
Nakagawa et al., Macrolide Antibiotics, Omura (ed.) Publisher: Academic, Orlando, Florida (1984) pp. 37–84.
Olano et al., Molecular and General Genetics (1998) 259(3):299–308.
Otten et al., Journal of Bacteriology (1995) 177(22):6688–6692.
Otten et al., Journal of Bacteriology (1997) 179(13):4446–4450.
Summers et al., Microbiology (1997) 143:3251–3262.
Swan et al., Molecular and General Genetics (1994) 242(3):358–362.
Torkkell et al., Molecular and General Genetics (1997) 256(2):203–209.
Volchegursky et al., Molecular Microbiology (2000) 37(4):752–762.
Xue et al., Proc. Natl. Acad. Sci. USA (1998) 95:12111–12116.

* cited by examiner

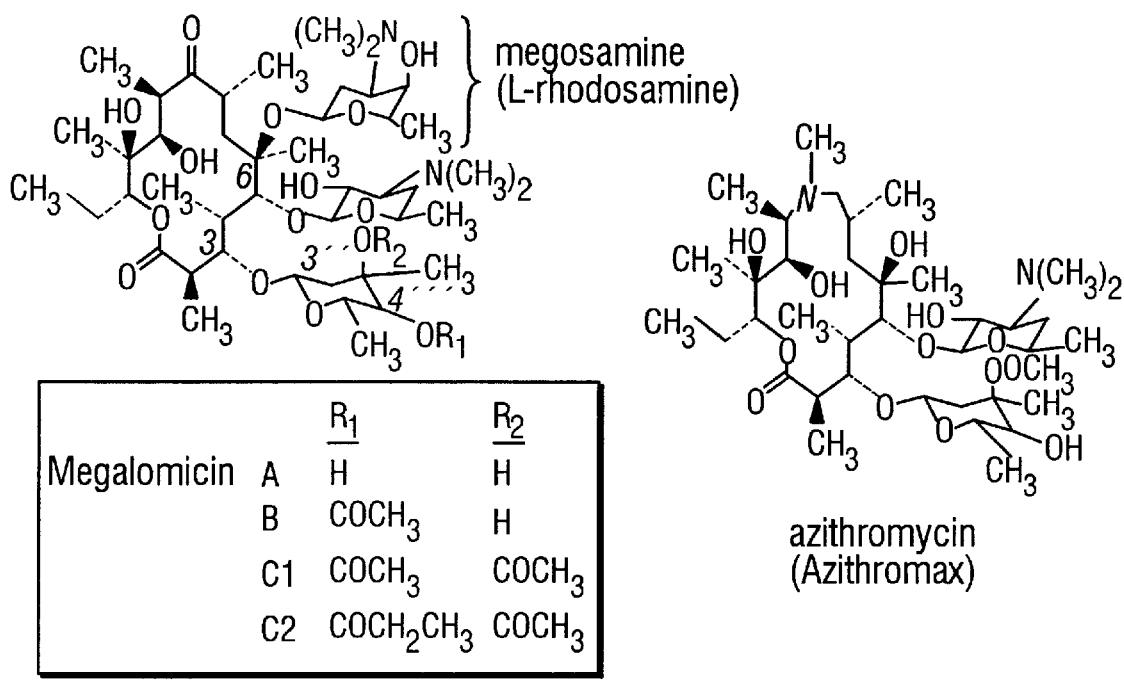
| | $R_1$ | $R_2$ |
|---|---|---|
| Megalomicin A | H | H |
| B | COCH$_3$ | H |
| C1 | COCH$_3$ | COCH$_3$ |
| C2 | COCH$_2$CH$_3$ | COCH$_3$ |
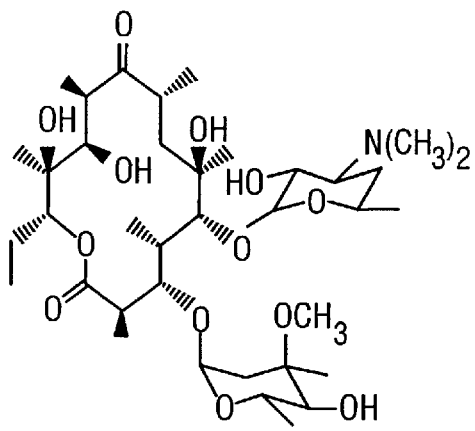
Erythromycin A
*FIG. 3*

```
LOCUS                    1          47981 bp    DNA             01-MAY-2000
DEFINITION  Megalomicin biosynthetic gene cluster, polyketide synthase,
            desosamine, megosamine, and mycarose biosynthesis genes.
ACCESSION   1
VERSION
KEYWORDS    .
SOURCE      Micromonospora megalomicea.
  ORGANISM  Micromonospora megalomicea
            Unclassified.
REFERENCE   1  (bases 1 to 47981)
  AUTHORS   Volchegursky,Y., Hu,Z., Katz,L. and McDaniel,R.
  TITLE     Biosynthesis of the Anti-Parasitic Agent Megalomicin:
            Transformation of Erythromycin to Megalomicin in Sacharopolyspora
            erythraea
  JOURNAL   Unpublished
REFERENCE   2  (bases 1 to 47981)
  AUTHORS   McDaniel,r. and Volchegursky,Y.
  TITLE     Direct Submission
  JOURNAL   Submitted (01-MAY-2000) Kosan Biosciences, Inc., 3828 Bay Center
            Place, Hayward, CA 94545, USA
FEATURES             Location/Qualifiers
     source          1..47981
                     /organism="Micromonospora megalomicea"
```

*FIG. 7-1*

```
gene        /strain="NRRL3275"
            /sub_species="nigra"
            complement (<1..144)
            /gene="megT"
CDS         complement (<1..144)
            /gene="megT"
            /codon_start=1
            /transl_table=11
            /product="TDP-4-keto-6-deoxyglucose-2,3-dehydratase"
            /translation="MGDRVNGHATPESTQSAIRFLTRHGGPPTATDDVHDWLAHRAAE
            HRLE" (SEQ ID NO: 2)
gene        928..2061
            /gene="megDVI"
CDS         928..2061
            /gene="megDVI"
            /codon_start=1
            /transl_table=11
            /product="TDP-4-keto-6-deoxyhexose 3,4-isomerase"
            /translation="MAVGDRRRLGRELQMARGLYWGFGANGDLYSMLLSGRDDDPWTW
            YERLRAAGRGPYASRAGTWVVGDHRTAAEVLADPGFTHGPPDAARWMQVAHCPAASWA
            GPFREFYARTEDAASVTVDADWLQQRCARLVTELGSRFDLVNDFAREVPVLALGTAPA
            LKGVDPDRLRSWTSATRVCLDAQVSPQQLAVTEQALTALDEIDAVTGGRDAAVLVGVV
            AELAANTVGNAVLAVTELPELAARLADDPETATRVVTEVSRTSPGVHLERRTAASDRR
```

FIG. 7-2

```
gene            2072..3382
                /gene="megDI"
CDS             2072..3382
                /gene="megDI"
                /codon_start=1
                /transl_table=11
                /product="TDP-megosamine glycosyltransferase"
                /translation="MRVVFSSMAVNSHLFGLVPLASAFQAAGHEVRVVASPALTDDVT
                GAGLTAVPVGDDVELVEWHAHAGQDIVEYMRTLDWVDQSHTTMSWDDLLGMQTTETPT
                FFALMSPDSLIDGMVEFCRSWRPDWIVWEPLTFAAPIAARVTGTPHARMLWGPDVATR
                ARQSFLRLLAHQEVEHREDPLAEWFDWTLRRFGDDPHLSFDEELVLGQWTVDPIPEPL
                RIDTGVRTVGMRYVPYNGPSVVPAWLLREPERRVCLTLGGSSREHGIGQVSIGEMLD
                AIADIDAEFVATFDDQQLVGVGSVPANVRTAGFVPMNVLLPTCAATVHHGGTGSWLTA
                AIHGVPQIILSDADTEVHAKQLQDLGAGLSLPVAGMTAEHLRGAIERVLDEPAYRLGA
                ERMRDGMRTDPSPAQVVGICQDLAADRAARGRQPRRTAEPHLPR"(SEQ ID NO: 4)
```

Text at top (SEQ ID NO: 3 translation continuation):
```
VGGVDVPTGGEVTVVVAAANRDPEVFTDPDREDVDRGGDAEILSSRPGSPRTDLDALV
ATLATAALRAAAPVLPRLSRSGPVIRRRRSPVARGLSRCPVEL" (SEQ ID NO: 3)
```

*FIG. 7-3*

```
       /product="mycarose O-acyltransferase"
       /translation="MVTSTNLDTTARPALNSLTGMRFVAAFLVFFTHVLSRLIPNSYV
       YADGLDAFWQTTGRVGVSFFFILSGFVLTWSARASDSVWSFWRRRVCKLFPNHLVTAF
       AAVVLFLVTGQAVSGEALIPNLLLIHAWFPALEISFGINPVSWSLACEAFFYLCFPLF
       LFWISGIRPERLWAMAAVVFAAIWAVPVVADLLLPSSPPLIPGLEYSAIQDWFLYTFP
       ATRSLEFILGIILARILITGRWINVGLLPAVLLFPVFFVASLFLPGVYAISSSMMILP
       LVLIIASGATADLQQKRTFMRNRVMVWLGDVSFALYMVHFLVIVYGADLLGFSQTEDA
       PLGLALFMIIPFLAVSLVLSWLLYRFVELPVMRNWARPASARRKPATEPEQTPSRR"
                                                               (SEQ ID NO: 5)
gene   4651..5775
       /gene="megDII"
CDS    4651..5775
       /gene="megDII"
       /codon_start=1
       /transl_table=11
       /product="TDP-3-keto-6-deoxyhexose 3-aminotransaminase"
       /translation="MTTYVWSYLLEYERERADILDAVQKVFASGSLILGQSVENFETE
       YARYHGIAHCVGVDNGTNAVKLALESVGVGRDDEVVTVSNTAAPTVLAIDEIGARPVF
       VDVRDEDYLMDTDLVEAAVTPRTKAIVPVHLYGQCVDMTALRELADRRGLKLVEDCAQ
       AHGARRDGRLAGTMSDAAAFSYPTKVLGAYGDGGAVVTNDDETARALRRLRYGMEE
       VYYVTRTPGHNSRLDEVQAEILRRKLTRLDAYVAGRRAVAQRYVDGLADLQDSHGLEL
       PVVTDGNEHVFYVVVRHPRRDEIIKRLRDGYDISLNISYPWPVHTMTGFAHLGVASG
       SLPVTERLAGEIFSLPMYPSLPHDLQDRVIEAVREVITGL" (SEQ ID NO: 6)
gene   5822..6595
```

*FIG. 7-4*

```
CDS      /gene="megDIII"
         5822..6595
         /gene="megDIII"
         /codon_start=1
         /transl_table=11
         /product="daunosaminyl-N,N-dimethyltransferase"
         /translation="MPNSHSTTSSTDVAPYERADIYHDFYHGRGKGYRAEADALVEVA
         RKHTPQAATLLDVACGTGSHLVELADSFREVVGVDLSAAMLATAARNDPGRELHQGDM
         RDFSLDRRFDVVTCMFSSTGYLVDEAELDRAVANLAGHLAPGGTLVVEPWWFPETFRP
         GWVGADLVTSGDRRISRMSHTVPAGLPDRTASRMTIHYTVGSPEAGIEHFTEVHVMTL
         FARAAYEQAFQRAGLSCSYVGHDLFSPGLFVGVAAEPGR" (SEQ ID NO: 7)
gene     6592..7197
         /gene="megDIV"
CDS      6592..7197
         /gene="megDIV"
         /codon_start=1
         /transl_table=11
         /product="TDP-4-keto-6-deoxyhexose 3,5-epimerase"
         /translation="MRVEELGIEGVFTFTPQTFADERGVFGTAYQEDVFVAALGRPLF
         PVAQVSTTRSRRGVVRGVHFTTMPGSMAKYVYCARGRAMDFAVDIRPGSPTFGRAEPV
         ELSAESMVGLYLPVGMGHLFVSLEDDTTLVYLMSAGYVPDKERAVHPLDPELALPIPA
         DLDLVMSERDRVAPTLREARDQGILPDYAACRAAAHRVVRT" (SEQ ID NO: 8)
gene     7220..8206
```

FIG. 7-5

```
    CDS             7220..8206
                    /gene="megDV"
                    /gene="megDV"
                    /codon_start=1
                    /transl_table=11
                    /product="TDP-4-keto-6-deoxyhexose 4-ketoreductase"
                    /translation="MVVLGASGFLGSAVTHALADLPVRVRLVARREVVVPSGAVADYE
                    THRVDLTEPGALAEVVADARAVFPFAAQIRGTSGWRISEDDVVAERTNVGLVRDLIAV
                    LSRSPHAPVVVFPGSNTQVGRVTAGRVIDGSEQDHPEGVYDRQKHTGEQLLKEATAAG
                    AIRATSLRLPPVFGVPAAGTADDRGVVSTMIRRALTGQPLTMWHDGTVRRELLYVTDA
                    ARAFVTALDHADALAGRHFLLGTGRSWPLGEVFQAVSRSVARHTGEDPVPVVSVPPPA
                    HMDPSDLRSVEVDPARFTAVTGWRATVTMAEAVDRTVAALAPRRAAAPSEPS"
                                                        (SEQ ID NO: 9)
    gene            complement (8228..9220)
                    /gene="megDVII"
    CDS             complement (8228..9220)
                    /gene="megDVII"
                    /codon_start=1
                    /transl_table=11
                    /product="TDP-4-keto-6-deoxyhexose 2,3-reductase"
                    /translation="MGTTGAGSARVRVGRSALHTSRLWLGTVNFSGRVTDDDALRLMD
                    HALERGVNCIDTADIYGWRLYKGHTEELVGRWFAQGGRREETVLATKVGSEMSERVN
                    DGGLSARHIVAACENSLRRLGVDHIDIYQTHHIDRAAPWDEVWQAAEHLVGSGKVGYV
                    GSSNLAGWHIAAAQESAARRNLLGMISHQCLYNLAVRHPELDVLPAAQAYGVGVFAWS
```

*FIG. 7-6*

```
                PLHGGLLSGVLEKLAAGTAVKSAQGRAQVLLPAVRPLVEAYEDYCRRLGADPAEVGLA
                WVLSRPGILGAVIGPRTPEQLDSALRAAELTLGEEELRELEAIFPAPAVDGPVP"
                                                              (SEQ ID NO: 10)
     gene        complement (9226..10479)
                 /gene="megBV"
     CDS         complement (9226..10479)
                 /gene="megBV"
                 /codon_start=1
                 /transl_table=11
                 /product="TDP-mycarose glycosyltransferase"
                 /translation="MRVLLTSFAHRTHFQGLVPLAWALHTAGHDVRVASQPELTDVVV
                GAGLTSVPLGSDHRLFDISPEAAAQVHRYTTDLDFARRGPELRSWEFLHGIEEATSRF
                VFPVVNNDSFVDELVEFAMDWRPDLVLWEPFTFAGAVAAKACGAAHARLLWGSDLTGY
                FRSRSQDLRGQRPADDRPDPLGGWLTEVAGRFGLDYSEDLAVGQWSVDQLPESFRLET
                GLESVHTRTLPYNGSSVVPQWLRTSDGVRRVCFTGGYSALGITSNPQEFLRTLATLAR
                FDGEIVVTRSGLDPASVPDNVRLVDFVPMNILLPGCAAVIHHGGAGSWATALHHGVPQ
                ISVAHEWDCVLRGQRTAELGAGVFLRPDEVDADTLWQALATVVEDRSHAENAEKLRQE
                ALAAPTPAEVVPVLEALAHQHRADR" (SEQ ID NO: 11)
     gene        complement (10483..11424)
                 /gene="megBIV"
     CDS         complement (10483..11424)
                 /gene="megBIV"
                 /codon_start=1
                 /transl_table=11
```

*FIG. 7-7*

```
        /product="TDP-4-keto-6-deoxyhexose 4-ketoreductase"
        /translation="MTRHVTLLGVSGFVGSALLREFTTHPLRLRAVARTGSRDQPPGS
        AGIEHLRVDLLEPGRVAQVVADTDVVVHLVAYAAGGSTWRSAATVPEAERVNAGIMRD
        LVAALRARPGPAPVLLFASTTQAANPAAPSRYAQHKIEAERILRQATEDGVVDGVILR
        LPAIYGHSGPSGQTGRGVVTAMIRRALAGEPITMWHEGSVRRNLLHVEDVATAFTAAL
        HNHEALVGDVWTPSADEARPLGEIFETVAASVARQTGNPAVPVVSVPPPENAEANDFR
        SDDFDSTEFRTLTGWHPRVPLAEGIDRTVAALISTKE"          (SEQ ID NO: 12)
gene    12181..22821
        /gene="megAI"
CDS     12181..22821
        /gene="megAI"
        /note="polyketide synthase"
        /codon_start=1
        /transl_table=11
        /product="megalomicin 6-deoxyerythronolide B synthase 1"
        /translation="MVDVPDLLGTRTPHPGPLPFPWPLCGHNEPELRARARQLHAYLE
        GISEDDVVAVGAALARETRAQDGPHRAVVVASSVTELTAALAALAQGRPHPSVVRGVA
        RPTAPVVFVLPGQAQWPGMATRLLAESPVFAAAMRACERAFDEVTDWSLTEVLDSPE
        HLRRVEVVQPALFAVQTSLAALWRSFGVRPDAVLGHSIGELAAAEVCGAVDVEAAARA
        AALWSREMVPLVGRGDMAAVALSPAELAARVERWDDDVVPAGVNGPRSVLLTGAPEPI
        ARRVAELAAQGVRAQVVNVSMAAHSAQVDAVAEGMRSALTWFAPGDSDVPYYAGLTGG
        RLDTRELGADHWPRSFRLPVRFDEATRAVLELQPGTFIESSPHPVLAASLQQTLDEVG
        SPAAIVPTLQRDQGGLRRFLLAVAQAYTGGVTVDWTAAYPGVTPGHLPSAVAVETDEG
```

FIG. 7-8

```
PSTEFDWAAPDHVLRARLLEIVGAETAALAGREVDARATFRELGLDSVLAVQLRTRLA
TATGRDLHIAMLYDHPTPHALTEALLRGPQEEPGRGEETAHPTEAEPDEPVAVVAMAC
RLPGGVTSPEEFWELLAEGRDAVGGLPTDRGWDLDSLFHPDPTRSGTAHQRAGGFLTG
ATSFDAAFFGLSPREALAVEPQQRITLELSWEVLERAGIPPTSLRTSRTGVFVGLIPQ
EYGPRLAEGGEGVEGYLMTGTTTSVASGRVAYTLGLEGPAISVDTACSSSLVAVHLAC
QSLRRGESTMALAGGVTVMPTPGMLVDFSRMNSLAPDGRSKAFSAAADGFGMAEGAGM
LLERLSDARRHGHPVLAVIRGTAVNSDGASNGLSAPNGRAQVRVIRQALAESGLTPH
TVDVVETHGTGTRLGDPIEARALSDAYGGDREHPLRIGSVKSNIGHTQAAAGVAGLIK
LVLAMQAGVLPRTLHADEPSPEIDWSSGAISLLQEPAAWPAGERPRRAGVSSFGISGT
NAHAIIEEAPPTGDDTRPDRMGPVVPWVLSASTGEALRARAARLAGHLREHPDQDLDD
VAYSLATGRAALAYRSGFVPADASTALRILDELAAGGSGDAVTGTARAPQRVVFVFPG
QGWQWAGMAVDLLDGDPVFASVLRECADALEPYLDFEIVPFLRAEAQRRTPDHTLSTD
RVDVVQPVLFAVMVSLAARWRAYGVEPAAVIGHSQGEIAAACVAGALSLDDAARAVAL
RSRVIATMPGNGAMASIAASVDEVAARIDGRVEIAAVNGPRAVVVSGDRDDLDRLVAS
CTVEGVRAKRLPVDYASHSSHVEAVRDALHAELGEFRPLPGFVPFYSTVTGRWVEPAE
LDAGYWFRNLRHRVRFADAVRSLADQGYTTFLEVSAHPVLTTAIEEIGEDRGGDLVAV
HSLRRGAGGPVDFGSALARAFVAGVAVDWESAYQGAGARRVPLPTYPFQRERFWLEPN
PARRVADSDDVSSLRYRIEWHPTDPGEPGRLDGTWLLATYPGRADDRVEAARQALESA
GARVEDLVVEPRTGRVDLVRRLDAVGPVAGVLCLFAVAEPAAEHSPLAVTSLSDTLDL
TQAVAGSGRECPIWVVTENAVAVGPFERLRDPAHGALWALGRVVALENPAVWGGLVDV
PSGSVAELSRHLGTTLSGAGEDQVALRPDGTYARRWCRAGAGGTGRWQPRGTVLVTGG
TGGVGRHVARWLARQGTPCLVLASRRGPDADGVEELLTELADLGTRATVTACDVTDRE
QLRALLATVDDEHPLSAVFHVAATLDDGTVETLTGDRIERANRAKVLGARNLHELTRD
```

FIG. 7-9

ADLDAFVLFSSSTAAFGAPGLGGYVPGNAYLDGLAQQRRSEGLPATSVAWGTWAGSGM
AEGPVADRFRRHGVMEMHPDQAVEGLRVALVQGEVAPIVVDIRWDRFLLAYTAQRPTR
LFDTLDEARRAAPGPDAGPGVAALAGLPVGEREKAVLDLVRTHAAAVLGHASAEQVPV
DRAFAELGVDSLSALELRNRLTTATGVRLATTVFDHPDVRTLAGHLAAELGGGSGRE
RPGGEAPTVAPTDEPIAIVGMACRLPGGVDSPEQLWELIVSGRDTASAAPGDRSWDPA
ELMVSDTTGTRTAFGNFMPGAGEFDAAFFGISPREALAMDPQQRHALETTWEALENAG
IRPESLRGTDTGVFVGMSHQGYATGRPKPEDEVDGYLLTGNTASVASGRIAYVLGLEG
PAITVDTACSSSLVALHVAAGSLRSGDCGLAVAGGVSVMAGPEVFREFSRQGALAPDG
RCKPFSDEADGFGLGEGSAFVVLQRLSVAVREGRRVLGVVVGSAVNQDGASNGLAAPS
GVAQQRVIRRAWGRAGVSGGDVGVVEAHGTGTRLGDPVELGALLGTYGVGRGGVGPVV
VGSVKANVGHVQAAAGVVGVIKVVLGLGRGLVGPMVCRGGLSGLVDWSSGGLVVADGV
RGWPVGVDGVRRGGVSAFGVSGTNAHVVAEAPGSVVGAERPVEGSSRGLVGVVGGVV
PVVLSAKTETALHAQARRLADHLETHPDVPMTDVVWTLTQARQRFDRRAVLLAADRTQ
AVERLRGLAGGEPGTGVVSGVASGGGVVFVFPGQGGQWVGMARGLLSVPVFVESVVEC
DAVVSSVVGFSVLGVLEGRSGAPSLDRVDVVQPVLFVVMVSLARLWRWCGVVPAAVVG
HSQEIAAAVVAGVLSVGDGARVVALRARALRALAGHGGMASVRRGRDDVQKLLDSGP
WTGKLEIAAVNGPDAVVVSGDPRAVTELVEHCDGIGVRARTIPVDYASHSAQVESLRE
ELLSVLAGIEGRPATVPFYSTLTGGFVDGTELDADYWRNLRHPVRFHAAVEALAARD
LTTFVEVSPHPVLSMAVGETLADVESAVTVGTLERDTDDVERFLTSLAEAHVHGVPVD
WAAVLGSGTLVDLPTYPFQGRRFWLHPDRGPRDDVADWFHRVDWTATATDGSARLDGR
WLVVVPEGYTDDGWVVEVRAALAAGGAEPVVTTVEEVTDRVGDSDAVVSMLGLADDGA
AETLALLRRLDAQASTTPLWVTVGAVAPAGPVQRPEQATVWGLALVASLERGHRWTG
LLDLPQTPDPQLRPRLVEALAGAEDQVAVRADAVHARRIVPTPVTGAGPYTAPGGTIL

*FIG. 7-10*

```
VTGGTAGLGAVTARWLAERGAEHLALVSRRGPGTAGVDEVVRDLTGLGVRVSVHSCDV
GDRESVGALVQELTAAGDVVRGVVHAAGLPQQVPLTDMDPADLADVVAVKVDGAVHLA
DLCPEAELFLFSSGAGVWGSARQGAYAAGNAFLDAFARHRRDRGLPATSVAWGLWAA
GGMTGDQEAVSFLRERGVRPMSVPRALSALERVLTAGETAVVVADVDWAAFAESYTSA
RPRPLLHRLVTPAAAVGERDEPREQTLRDRLAALPRAERSAELVRLVRRDAAAVLGSD
AKAVPATTPFKDLGFDSLAAVRFRNRLAAHTGLRLPATLVFEHPNAAAVADLLHDRLG
EAGEPTPVRSVGAGLAALEQALPDASDTERVELVERLERMLAGLRPEAGAGADAPTAG
DDLGEAGVDELLDALERELDAR" (SEQ ID NO: 13)

misc_feature    12505..13470
                /gene="megAI"
                /function="AT-L"
misc_feature    13576..13791
                /gene="megAI"
                /function="ACP-L"
misc_feature    13849..15126
                /gene="megAI"
                /function="KS1"
misc_feature    15427..16476
                /gene="megAI"
                /function="AT1"
misc_feature    17155..17694
                /gene="megAI"
                /function="KR1"
```

*FIG. 7-11*

```
misc_feature    17947..18207
                /gene="megAI"
                /function="ACP1"
misc_feature    18268..19548
                /gene="megAI"
                /function="KS2"
misc_feature    19876..20910
                /gene="megAI"
                /function="AT2"
misc_feature    21517..22053
                /gene="megAI"
                /function="KR2"
misc_feature    22318..22575
                /gene="megAI"
                /function="ACP2"
gene            22867..33555
                /gene="megAII"
CDS             22867..33555
                /gene="megAII"
                /note="polyketide synthase"
                /codon_start=1
                /transl_table=11
                /product="megalomicin 6-deoxyerythronolide B synthase 2"
```

FIG. 7-12

/translation="MTDNDKVAEYLRRATLDLRAARKRLRELQSDPIAVVGMACRLPG
GVHLPQHLWDLLRQGHETVSTFPTGRGWDLAGLFHPDPHPGTSYVDRGGFLDDVAGF
DAEFFGISPREATAMDPQQRLLLETSWELVESAGIDPHSLRGTPTGVFLGVARLGYGE
NGTEAGDAEGYSVTGVAPAVASGRISYALGLEGPSISVDTACSSSLVALHLAVESLRL
GESSLAVVGGAAVMATPGVFVDFSRQRALAADGRSKAFGAAADGFGFSEGVSLVLLER
LSEAESNGHEVLAVIRGSALNQDGASNGLAAPNGTAQRKVIRQALRNCGLTPADVDAV
EAHGTGTTLGDPIEANALLDTYGRDRDPDHPLWLGSVKSNIGHTQAAAGVTGLLKMVL
ALRHEELPATLHVDEPTPHVDWSSGAVRLATRGRPWRRGDRPRRAGVSAFGISGTNAH
VIVEEAPERTTERTVGGDVGPVPLVVSARSAAALRAQAAQVAELVEGSDVGLAEVGRS
LAVTRARHEHRAAVVASTRAEAVRGLREVAAVEPRGEDTVTGVAETSGRTVVFLFPGQ
GSQWVGMGAELLDSAPAFADTIRACDEAMAPLQDWSVSDVLRQEPGAPGLDRVDVVQP
VLFAVMVSLARLWQSYGVTPAAVGHSQGEIAAAHVAGALSLADAARLVVGRSRLLRS
LSGGGGMSAVALGEAEVRRRLRSWEDRISVAAVNGPRSVVVAGEPEALREWGREREAE
GVRVREIDVDYASHSPQIDRVRDELLTVTGEIEPRSAEITFYSTVDVRAVDGTDLDAG
YWYRNLRETVRFADAMTRLADSGYDAFVEVSPHPVVVSAVAEAVEEAGVEDAVVVGTL
SRGDGGPGAFLRSAATAHCAGVDVDWTPALPGAATIPLPTYPFQRKPYWLRSSAPAPA
SHDLAYRVSWTPITPPGDGVLDGDWLVVHPGGSTGWVDGLAAAITAGGGRVVAHPVDS
VTSRTGLAEAALARRDGTFRGVLSWVATDERHVEAGAVALLTLAQALGDAGIDAPLWCL
TQEAVRTPVDGDLARPAQAALHGFAQVARLELARRFGGVLDLPATVDAAGTRLVAAVL
AGGGEDVVAVRGDRLYGRRLVRATLPPPGGGFTPHGTVLVTGAAGPVGGRLARWLAER
GATRLVLPGAHPGEELLTAIRAAGATAVCEPEAEALRTAIGGELPTALVHAETLTNF
AGVADADPEDFAATVAAKTALPTVLAEVLGDHRLEREVYCSSVAGVWGGVGMAAYAAG
SAYLDALVEHRRARGHASASVAWTPWALPGAVDDGRLRERGLRSLDVADALGTWERLL

FIG. 7-13

RAGAVSVAVADVDWSVFTEGFAAIRPTPLFDELLDRRGDPDGAPVDRPGEPAGEWGRR
IAALSPQEQRETLLTLVGETVAEVLGHETGTEINTRRAFSELGLDSLGSMALRQRLAA
RTGLRMPASLVFDHPTVTALARYLRRLVVGDSDPTPVRVFGPTDEAEPVAVVGIGCRF
PGGIATPEDLWRVVSEGTSITTGFPTDRGWDLRRLYHPDPDHPGTSYVDRGGFLDGAP
DFDPGFFGITPREALAMDPQQRLTLEIAWEAVERAGIDPETLLGSDTGVFVGMNGQSY
LQLLTGEGDRLNGYQGLGNSASVLSGRVAYTFGWEGPALTVDTACSSSLVAIHLAMQS
LRRGECSLALAGGVTVMADPYTFVDFSAQRGLAADGRCKAFSAQASGFALAEGVAALV
LEPLSKARRNGHQVLAVLRGSAVNQDGASNGLAAPNGPSQERVIRQALTASGLRPADV
DMVEAHGTGTELGDPIEAGALIAAYGRDRDRPLWLGSVKTNIGHTQAAAGAAGVIKAV
LAMRHGVLPRSLHADELSPHIDWADGKVEVLREARQWPPGERPRRAGVSSFGVSGTNA
HVIVEEAPAEPDPEPVPAAPGGPLPFVLHGRSVQTVRSQARTLAEHLRTTGHRDLADT
ARTLATGRARFDVRAAVLGTDREGVCAALDALAQDRPSPDVVAPAVFAARTPVLVFPG
QGSQWVGMARDLLDSSEVFAESMGRCAEALSPYTDWDLLDVVRGVGDPDPYDRVDVLQ
PVLFAVMVSLARLWQSYGVTPGAVVGHSQGEIAAAHVAGALSLADAARVALRSRVLR
ELDDQGGMVSVGTSRAELDSVLRRWDGRVAVAAVNGPGTLVVAGPTAELDEFLAVAEA
REMRPRRIAVRYASHSPEVARVEQRLAAELGTVTAVGGTVPLYSTATGDLLDTTAMDA
GYWYRNLRQPVLFEHAVRSLLERGFETFIEVSPHPVLLMAVEETAEDAERPVTGVPTL
RRDHDGPSEFLRNLLGAHVHGVDVDLRPAVAHGRLVDLPTYPFDRQRLWPKPHRRADT
SSLGVRDSTHPLLHAAVDVPGHGGAVFTGRLSPDEQQWLTQHVVGGRNLVPGSVLVDL
ALTAGADVGVPVLEELVLQQPLVLTAAGALLRLSVGAADEDGRRPVEIHAAEDVSDPA
EARWSAYATGTLAVGVAGGGRDGTQWPPPGATALTLTDHYDTLAELGYEYGPAFQALR

*FIG. 7-14*

```
AAWQHGDVVYAEVSLDAVEEGYAFDPVLLDAVAQTFGLTSRAPGKLPFAWRGVTLHAT
GATAVRVVATPAGPDAVALRVTDPTGQLVATVDALVVRDAGADRDQPRGRDGDLHRLE
WVRLATPDPTPAAVVHVAADGLDDLLRAGGPAPQAVVVRYRPDGDDPTAEARHGVLWA
ATLVRRWLDDDRWPATTLVVATSAGVEVSPGDDVPRPGAAAVWGVLRCAQAESPDRFV
LVDGDPETPPAVPDNPQLAVRDGAVFVPRLTPLAGPVPAVADRAYRLVPGNGGSIEAV
AFAPVPDADRPLAPEEVRVAVRATGVNFRDVLLALGMYPEPAEMGTEASGVVTEVGSG
VRRFTPGQAVTGLFQGAFGPVAVADHRLLTPVPDGWRAVDAAAVPIAFTTAHYALHDL
AGLQAGQSVLVHAAAGGVGMAAVALARRAGAEVFATASPAKHPTLRALGLDDDHIASS
RESGFGERPAARTGGRGVDVVLNSLTGDLLDESARLLADGGVFVEMGKTDLRPAEQFR
GRYVPFDLAEAGPDRLGEILEEVVGLLAAGALDRLPVSWELSAAPAALTHMSRGRHV
GKLVLTQPAPVHPDGTVLVTGGTGTLGRLVARHLVTGHGVPHLLVASRRGPAAPGAAE
LRADVEGLGATIEIVACDTADREALAALLDSIPADRPLTGVVHTAGVLADGLVTSIDG
TATDQVLRAKVDAAWHLHDLTRDADLSFFVLFSSAASVLAGPGQGVYAAANGVLNALA
GQRRALGLPAKALGWLMAQASEMTSGLGDRIARTGVAALPTERALALFDAALRSGGE
VLFPLSVDRSALRRAEYVPEVLRGAVRSTPRAANRAETPGRGLLDRLVGAPETDQVAA
LAELVRSHAAAVAGYDSADQLPERKAFKDLGFDSLAAVELRNRLGVTTGVRLPSTLVF
DHPTPLAVAEHLRSELFADSAPDVGVGARLDDLERALDALPDAQGHADVGARLEALLR
RWQSRRPPETEPVTISDDASDDELFSMLDRRLGGGGDV" (SEQ ID NO: 14)

misc_feature    22957..24237
                /gene="megAII"
                /function="KS3"
misc_feature    24544..25581
                /gene="megAII"
                /function="AT3"
```

FIG. 7-15

```
misc_feature    26230..26733
                /gene="megAII"
                /function="KR3" (inactive)
misc_feature    26998..27258
                /gene="megAII"
                /function="ACP3"
misc_feature    27393..28590
                /gene="megAII"
                /function="KS4"
misc_feature    28897..29931
                /gene="megAII"
                /function="AT4"
misc_feature    29953..30477
                /gene="megAII"
                /function="DH4"
misc_feature    31396..32244
                /gene="megAII"
                /function="ER4"
misc_feature    32257..32799
                /gene="megAII"
                /function="KR4"
misc_feature    33052..33312
                /gene="megAII"
                /function="ACP4"
```

*FIG. 7-16*

```
gene    33666..43271
        /gene="megAIII"
CDS     33666..43271
        /gene="megAIII"
        /note="polyketide synthase"
        /codon_start=1
        /transl_table=11
        /product="megalomicin 6-deoxyerythronolide B synthase 3"
        /translation="MSESSGMTEDRLRRYLKRTVAELDSVTGRLDEVEYRAREPIAVV
        GMACRFPGGVDSPEAFWEFIRDGGDAIAEAPTDRGWPPAPRPRLGGLLAEPGAFDAAF
        FGISPREALATDPQQRLMLEISWEALERAGFDPSSLRGSAGGVFTGVGAVDYGPRPDE
        APEEVLGYVGIGTASSVASGRVAYTLGLEGPAVTVDTACSSGLTAVHLAMESLRRDEC
        TLVLAGGVTVMSSPGAFTEFRSQGGLAEDGRCKPFSRAADGFGLAEGAGVLVLQRLSV
        ARAEGRPVLAVLRGSAINQDGASNGLTAPSGPAQRRVIRQALERARLRPVDVDYVEAH
        GTGTRLGDPIEAHALLDTYGADREPGRPLWVGSVKSNIGHTQAAAGVAGVMKTVLALR
        HREIPATLHFDEPSPHVDWDRGAVSVVSETRPWPVGERPRRAGVSSFGISGTNAHVIV
        EEAPSPQAADLDPTPGPATGATPGTDAAPTAEPGAEAVALVFSARDERALRAQAARLA
        DRLTDDPAPSLRDTAFTLVTRRATWEHRAVVVGGGEEVLAGLRAVAGGRPVDGAVSGR
        ARAGRRVVLVFPGQGAQWQGMARDLLRQSPTFAESIDACERALAPHVDWSLREVLDGE
        QSLDPVDVVQPVLFAVMVSLARLWQSYGVTPGAVVGHSQGEIAAAHVAGALSLADAAR
        VVALRSRVLRRLGGHGGMASFGLHPDQAAERIARFAGALTVASVNGPRSVVLAGENGP
        LDELIAECEAEGVTARRIPVDYASHSPQVESLREELLAALAGVRPVSAGIPLYSTLTG
        QVIETATMDADYWFANLREPVRFQDATRQLAEAGFDAFVEVSPHPVLTVGVEATLEAV
        LPPDADPCVTGTLRRERGGLAQFHTALAEAYTRGVEVDWRTAVGEGRPVDLPVYPFQR
```

FIG. 7-17

QNFWLPVPLGRVPDTGDEWRYQLAWHPVDLGRSSLAGRVLVVTGAAVPPAWTDVVRDG
LEQRGATVVLCTAQSRARIGAALDAVDGTALSTVVSLLALAEGGAVDDPSLDTLALVQ
ALGAAGIDVPLWLVTRDAAAVTVGDDVDPAQAMVGGLGRVVGVESPARWGGLVDLREA
DADSARSLAAILADPRGEEQFAIRPDGVTVARLVPAPARAAGTRWTPRGTVLVTGGTG
GIGAHLARWLAGAGAEHLVLLNRRGAEAAGAADLRDELVALGTGVTITACDVADRDRL
AAVLDAARAQGRVVTAVFHAAGISRSTAVQELTESEFTEITDAKVRGTANLAELCPEL
DALVLFSSNAAVWGSPGLASYAAGNAFLDAFARRGRRSGLPVTSIAWGLWAGQNMAGT
EGGDYLRSQGLRAMDPQRAIEELRTTLDAGDPWVSVVDLDRERFVELFTAARRRPLFD
ELGGVRAGAEETGQESDLARRLASMPEAERHEHVARLVRAEVAAVLGHGTPTVIERDV
AFRDLGFDSMTAVDLRNRLAAVTGVRVATTIVFDHPTVDRLTAHYLERLVGEPEATTP
AAAVVPQAPGEADEPIAIVGMACRLAGGVRTPDQLWDFIVADGDAVTEMPSDRSWDLD
ALFDPDPERHGTSYSRHGAFLDGAADFDAAFFGISPREALAMDPQQRQVLETTWELFE
NAGIDPHSLRGTDTGVFLGAAYQGYGQNAQVPKESEGYLLTGGSSAVASGRIAYVLGL
EGPAITVDTACSSSLVALHVAAGSLRSGDCGLAVAGGVSVMAGPEVFTEFSRQGALAP
DGRCKPFSDQADGFGFAEGVAVLLQRLSVAVREGRRVLGVVVGSAVNQDGASNGLAA
PSGVAQQRVIRRAWGRAGVSGGDVGVVEAHGTGTRLGDPVELGALLGTYGVGRGGVGP
VVVGSVKANVGHVQAAAGVVGVIKVVLGLGRGLVGPMVCRGGLSGLVDWSSGGLVVAD
GVRGWPVGVDGVRRGGVSAFGVSGTNAHVVAEAPGSVVGAERPVEGSSRGLVGVAGG
VVPVVLSAKTETALTELARRLHDAVDDTVALPAVAATLATGRAHLPYRAALLARDHDE
LRDRLRAFTTGSAAPGVVSGVASGGGVVFVFPGQGGQWVGMARGLLSVPVFVESVVEC
DAVVSSVVGFSVLGVLEGRSGAPSLDRVDVVQPVLFVVMVSLARLWRWCGVVPAAVVG
HSQGEIAAAVVAGVLSVGDGARVVALRARALRALAGHGGMVSLAVSAERARELIAPWS
DRISVAAVNSPTSVVVSGDPQALAALVAHCAETGERAKTLPVDYASHSAHVEQIRDTI
LTDLADVTARRPDVALYSTLHGARGAGTDMDARYWYDNLRSPVRFDEAVEAAVADGYR

*FIG. 7-18*

```
VFVEMSPHPVLTAAVQEIDDETVAIGSLHRDTGERHLVAELARAHVGVPVDWRAILP
ATHPVPLPNYPFEATRYWLAPTAADQVADHRYRVDWRPLATTPAELSGSYLVFGDAPE
TLGHSVEKAGGLLVPVAAPDRESLAVALDEAAGRLAGVLSFAADTATHLARHRLLGEA
DVEAPLWLVTSGGVALDDHDPIDCDQAMVWGIGRVMGLETPHRWGGLVDVTVEPTAED
GVVFAALLAADDHEDQVALRDGIRHGRRLVRAPLTTRNARWTPAGTALVTGGTGALGG
HVARYLARSGVTDLVLLSRSGPDAPGAAELAAELADLGAEPRVEACDVTDGPRLRALV
QELREQDRPVRIVVHTAGVPDSRPLDRIDELESVSAAKVTGARLLDELCPDADTFVLF
SSGAGVWGSANLGAYAAANAYLDALAHRRQAGRAATSVAWGAWAGDGMATGDLDGLT
RRGLRAMAPDRALRACTRRWTTHDTCVSVADVDWDRFAVGFTAARPRPLIDELVTSAP
VAAPTAAAAPVPAMTADQLLQFTRSHVAAILGHQDPDAVGLDQPFTELGFDSLTAVGL
RNQLQQATGRTLPAALVFQHPTVRRLADHLAQQLDVGTAPVEATGSVLRDGYRRAGQT
GDVRSYLDLLANLSEFRERFTDAASLGGQLELVDLADGSGPVTVICCAGTAALSGPHE
FARLASALRGTVPVRALAQPGYEAGEPVPASMEAVLGVQADAVLAAQGDTPFVLVGHS
AGALMAYALATELADRGHPPRGVVLLDVYPPGHQEAVHAWLGELTAALFDHETVRMDD
TRLTALGAYDRLTGRWRPRDTGLPTLVVAASEPMGEWPDDGWQSTWPFGHDRVTVPGD
HFSMVQEHADAIARHIDAWLSGERA" (SEQ ID NO: 15)

misc_feature  33780..35027
              /gene="megAIII"
              /function="KS5"
misc_feature  35385..36419
              /gene="megAIII"
              /function="AT5"
```

*FIG. 7-19*

```
misc_feature    37068..37604
                /gene="megAIII"
                /function="KR5"
misc_feature    37860..38120
                /gene="megAIII"
                /function="ACP5"
misc_feature    38187..39470
                /gene="megAIII"
                /function="KS6"
misc_feature    39795..40811
                /gene="megAIII"
                /function="AT6"
misc_feature    41406..41936
                /gene="megAIII"
                /function="KR6"
misc_feature    42168..42425
                /gene="megAIII"
                /function="ACP6"
misc_feature    42585..43271
                /gene="megAIII"
                /function="TE"
gene            43268..44344
                /gene="megCII"
```

*FIG. 7-20*

```
CDS             43268..44344
                /gene="megCII"
                /codon_start=1
                /transl_table=11
                /product="TDP-4-keto-6-deoxyglucose 3,4-isomerase"
                /translation="MNTTDRAVLGRRLQMIRGLYWGYGSNGDPYPMLLCGHDDDPHRW
                YRGLGGSGVRRSRTETWVVTDHATAVRVLDDPTFTRATGRTPEWMRAAGAPASTWAQP
                FRDVHAASWDAELPDPQEVEDRLTGLLPAPGTRLDLVRDLAWPMASRGVGADDPDVLR
                AAWDARVGLDAQLTPQPLAVTEAAIAAVPGDPHRRALFTAVEMTATAFVDAVLAVTAT
                AGAAQRLADDPDVAARLVAEVLRLHPTAHLERRTAGTETVVGEHTVAAGDEVVVVVAA
                ANRDAGVFADPDRLDPDRADADRALSAQRGHPGRLEELVVLTTAALRSVAKALPGLT
                AGGPVVRRRRSPVLRATAHCPVEL" (SEQ ID NO: 16)

gene            44355..45623
                /gene="megCIII"
CDS             44355..45623
                /gene="megCIII"
                /codon_start=1
                /transl_table=11
                /product="TDP-desosamine glycosyltransferase"
                /translation="MRVVFSSMASKSHLFGIVPLAWAFRAAGHEVRVVASPALTDDIT
                AAGLTAVPVGTDVDLVDFMTHAGYDIIDYVRSLDFSERDPATSTWDHLLGMQTVLTPT
                FYALMSPDSLVEGMISFCRSWRPDWSSGPQTFAASIAATVTGVAHARLLWGPDITVRA
                RQKFLGLLPGQPAAHREDPLAEWLTWSVERFGGRVPQDVEELVVGQWTIDPAPVGMRL
```

*FIG. 7-21*

```
                DTGLRTVGMRYVDYNGPSVVPDWLHDEPTRRRVCLTLGISSRENSIGQVSVDDLLGAL
                GDVDAEIIATVDEQQLEGVAHVPANIRTVGFVPMHALLPTCAATVHHGGPGSWHTAAI
                HGVPQVILPDGWDTGVRAQRTEDQGAGIALPVPELTSDQLREAVRRVLDDPAFTAGAA
                RMRADMLAEPSPAEVVDCAGLVGERTAVG" (SEQ ID NO: 17)
     gene       45620..46591
                /gene="megBII"
     CDS        45620..46591
                /gene="megBII"
                /codon_start=1
                /transl_table=11
                /product="TDP-4-keto-6-deoxyglucose 2,3 dehydratase"
                /translation="MSTDATHVRLGRCALLTSRLWLGTAALAGQDDADAVRLLDHARS
                RGVNCLDTADDDSASTSAQVAEESVGRWLAGDTGRREETVLSVTVGVPPGGQVGGGGL
                SARQIIASCEGSLRRLGVDHVDVLHLPRVDRVEPWDEVWQAVDALVAAGKVCYVGSSG
                FPGWHIVAAQEHAVRRHRLGLVSHQCRYDLTSRHPELEVLPAAQAYGLGVFARPTRLG
                GLLGGDGPGAAAARASGQPTALRSAVEAYEVFCRDLGEHPAEVALAWVLSRPGVAGAV
                VGARTPGRLDSALRACGVALGATELTALDGIFPGVAAAGAAPEAWLR"
                (SEQ ID NO: 18)
     gene       complement(46660..47403)
                /gene="megH"
     CDS        complement(46660..47403)
                /gene="megH"
                /note="putative thioesterase"
```

FIG. 7-22

```
                /codon_start=1
                /transl_table=11
                /product="TEII"
                /translation="MNTWLRRFGSADGHRARLYCFPHAGAAADSYLDLARALAPEVDV
                WAVQYPGRQDRRDERALGTAGEIADEVAAVLRDLVGEVPFALFGHSMGALVAYETARR
                LEARPGVRPLRLFVSGQTAPRVHERRTDLPDEDGLVEQMRRLGVSEAALADQGLLDMS
                LPVLRADHRVLRSYAWQAGPPLRAGITTLCGDTDPLTTVEDAQRWLPYSVVPGRTRTF
                PGGHFYLADHVGEVAESVAPDLLRLTPTG" (SEQ ID NO: 19)
    gene        complement (47411..>47981)
                /gene="megF"
    CDS         complement (47411..>47980)
                /gene="megF"
                /codon_start=1
                /transl_table=11
                /product="C-6 hydroxylase"
                /translation="IRVQDDDADRLSRDELTSIAIVLLLAGFEASVSLIGIGTYLLLT
                HPDQLALVRKDPALLPGAVEEILRYQAPPETTRFATAEVEIGGVTIPAYSTVLIANG
                AANRDPGQFPDPDRFDVTRDSRGHLTFGHGIHYCMGRPLAKLEGEVALGALFDRFPKL
                SLGFPSDEVVWRRSLLLRGIDHLPVRPNG" (SEQ ID NO: 20)
BASE COUNT   5962 a  16875 c  18045 g   7099 t
ORIGIN
    1 ctcgagccga tgctcggcgg cgcggtgggc caaccagtcg tggacgtcgt cggtggcggt
   61 gggagtccg ccgtgccgag tcaggaaacg tattgccgat tgtgtggatt ccggagtcgc
```

FIG. 7-23

```
 121  atgaccgttg  acccgatccc  ccatacgcct  ctcccgtgat  gtcgtgggcg  gtccgtgcgg
 181  taccgcccgg  actgacattc  gtcgatcaag  accccgccca  gtgtagggct  ccgcccgcga
 241  cgggagaagg  tccgtcgaac  aacttccggg  tgaccggtcg  ccggcgtcgg  tgaaacgggc
 301  gtcggagcac  ccgatcattg  ctgtcggtga  acttcctaac  tgtcggcgcg  cacatctttc
 361  tgaccggtgt  gttccgtggt  atgacgcgtt  cccggcccgt  ctggaactgt  gcgtgggact
 421  gaccggttgc  gcgtgtttt   cgcccgtttc  cgaactgcgg  attcgtcgat  cgcgcaggtg
 481  ggagcgggtg  gctgaccggg  atgatctgca  tcaatgacga  tctcttgtag
 541  catggtccgc  gccgagggtc  cgacaggccc  gaaacgcccg  gcatccagcc  tgttcgacga
 601  cgtcgacatc  accgtgcaag  ccgcgatgac  accgacacca  cgccatgctg  gtgccgcact
 661  ggaagggtgg  cgcgatcagg  gaaatggccg  tgtcactaga  cagacgccaa  acagctgtcc
 721  gggcctgcgg  aaacagcatc  gatctgcgtc  agccgttcat  tgccccggcg  gcaccgcctt
 781  ggaaatccgt  gccaccggtc  gtccgcagtg  acgatcgcgg  acccgggttt  cgagacagca
 841  ggtagtaggc  gatgcaggcg  tttcgtctcg  cgccggacgc  gtcgcactag  gtggaatccg
 901  tcacagtctt  caatccggga  gcgttctatg  gcagttggcg  atcgaaggcg  gctggccgg
 961  gagttgcaga  tgcccgggga  tctctactgg  gggttcggtg  ccaacggcga  tctgtactcg
1021  atgctcctgt  ccggacggga  cgacgaccc   tggacctggt  acgaacggtt  gcgggccgcc
1081  ggacggggac  cgtacgccag  tcgggccgga  acgtgggtgg  tcgttgacca  ccggaccgcc
1141  gccgaggtgc  tcgccgatcc  gggcttcacc  cacggcctgc  ccgacgctgc  ccggtggatg
1201  caggtggccc  actgcccggc  ggcctcctgg  gccgccccct  tcgggagtt   ctacgcccgc
1261  accgaggacg  cggcgtcggt  gacagtggac  gccgactggc  tccagcagcg  gtgcgccagg
1321  ctggtgaccg  agctggggtc  gcgcttcgat  gcgcttcgat  ctcgtgaacg  acttcgcccg  ggaggtcccg
1381  gtgctggcgc  tcggtaccgc  gcccgcactc  aagggcgtgg  accccgaccg  tctccggtcc
```

FIG. 7-24

```
1441  tggacctcgg  cgacccggt  atgcctggac  gcccaggtca  gcccgcaaca  gctcgcggtg
1501  accgaacagg  cgctgaccgc  cctcgacgag  atcgacgcgg  tcaccggcgg  tcgggacgcc
1561  gcggtgctgg  tggggtggt  ggcggagctg  gcgccaaca  cggtgggcaa  cgccgtcctg
1621  gccgtcaccg  agcttcccga  actggcggca  cgacttgccg  acgacccgga  gaccgcgacc
1681  cgtgtggtga  cggagtgtc  gcggacgagt  cccggcgtcc  acctggaacg  ccgcaccgcc
1741  gcgtcggacc  cggggtggg  gcggtcgac  cggggcgtcg  gtggcgaggt  gacagtggtc
1801  gtcgcgcgg  cgaaccgtga  tcccgaggtc  ttcaccgatc  ccgaccggtt  cgacgtggac
1861  cgtggcggcg  acgccctggc  cctgtcgtcc  cggcccggct  ccgaccgcac  cgacctcgac
1921  gccctggtgg  ccaccggcg  cacggcggcg  ctgcgggcg  ccgtcggtca  cccgcgccg  gttgccccgg
1981  ctgtcccgtt  ccgggccggt  gatcagacga  cgtcggtcac  ccgtcgcccg  gtgttttcat  cgatgctgt
2041  cgttgcccgg  tcgagctgta  gaggaagaaac  gatgcgcgtc  ttccaggcgg  ccgacacga
2101  caacagccat  ctgttcgggc  tggtcccgct  cgcaagcgcc  ccggacgcgc  gtctgaccgc
2161  ggtacgggtc  gtcgcctcgc  cggccctgac  cgacgacgtc  accggtgccg  gtctgaccgc
2221  cgtgcccgtc  ggtgacgacg  tggaacttgt  ggagtggcac  gcccacgcgg  gccagagcat
2281  cgtcgagtac  atgcggaccc  tcaccttcac  cgaccagagc  caccaccacca  tgtcctggga
2341  cgacctcctg  ggcatgcaga  ccacctttcac  cccgaccttc  ttcgcctgga  tgagccccga
2401  ctcgctcatc  gacggatgg  tcgagttctg  ccgctcctgg  ggcccggact  ggatcgtctg
2461  ggagccgctg  gacttcgccg  cccgatcgc  ggcccgggtc  accggaaccc  cgcacgcccg
2521  gatgctgtgg  ggtccggacg  tcgcaccg  tcgccaccg  agcttcctgc  gactgctggc
2581  ccaccaggag  gtggagcacc  gggaggatcc  gctggccag  tggttcgact  ggacgctgcg
2641  gcgcttcggc  gacgaccccc  acctgagctt  ggccgaggaa  cacaccggc  ggacgtggac
2701  cgtgaccc  atccccgagc  cgctgcgat  cgacaccggc  gtccggacgg  ggcagtgcg
2761  gtacgtcccc  tacaacggcc  cctcggtggt  gccgcctgg  ctgttgcggg  aacccgaacg
```

FIG. 7-25

| | | | | |
|---|---|---|---|---|
| 2821 | tcgcgggtc | tgcctgaccc | tcggcggttc | cagccgggaa | cacggcatcg | ggcaggtctc |
| 2881 | catcggcgag | atgttggacg | ccatcgccga | catcgacgcc | gagttcgtgg | ccacctcga |
| 2941 | cgaccagcag | ttggtcggcg | tggcagcgt | tccggcaaac | gtccgtaccg | ccggttcgt |
| 3001 | gccgatgaac | gtcctgctgc | ccacctgcgc | ggccacggtg | caccacggga | gcaccggcag |
| 3061 | ttggctgacc | gccgccatcc | acggcgtacc | gcagatcatc | ctctcgacg | ccgacaccga |
| 3121 | ggtgcacgcc | aagcagctcc | aggacctcgg | cgcggggctg | tcgctcccgg | tcgcggggat |
| 3181 | gaccgcgag | cacctgcgtg | gggcgatcga | cgcgggttctc | gacgagccgg | cgtaccgcct |
| 3241 | cggtgcggag | cggatgcggg | acgggatgcg | gaccgacccg | gcgcacgcgg | tcgccgggccc | aggtggtcgg |
| 3301 | catctgtcag | gacctggccg | ccgaccggc | ggcacgcggc | aggcagccgc | gtcgaaccgc |
| 3361 | cgagccgcac | ctgtcgcgat | gactttccc | tctgacacg | accaccggga | ccggctgatg | ccggtcccgg |
| 3421 | aatccacacg | ccgactttcc | ttctgacacg | agggccc | ggtggttacc | tccaccaact |
| 3481 | tggacacgac | agcaggccg | gcactgaact | cgttgacgg | gatgcggttc | gtgccgcct |
| 3541 | tcctggtctt | cttcacgcac | gtcctgtcga | ggctcatccc | gaacagctac | gtgtacgccg |
| 3601 | acggcctgga | cgccttcttc | cagaccaccg | tggtcggcgc | ggtgtcgttc | ttctttattc |
| 3661 | tcagcggttt | cgtgctgacc | tgtgcaagctc | tgttcccaacc | ctcggtgtgg | tcgttctggc |
| 3721 | gcagacgggt | ctgcaagctc | ttccccaacc | acctggtcac | cgcctttcgcc | gccgtggtgt |
| 3781 | tgttcctggt | caccgggcag | gcggtgagcg | gtgaggcgct | gatcccgaac | ctccgtgta |
| 3841 | tccacgcctg | gttcccgcc | ctggagatct | cctttcggcat | caaccccgtg | agctggtcgt |
| 3901 | tggcctgcga | ggcgttcttc | tacctgtgct | cctgttcgtt | cctgttctgg | atctccggta |
| 3961 | tccgcccgga | ggcgtgtgg | gcctgggccg | ccgtggtgtt | cgccgcgatc | tgggcggtac |
| 4021 | cggtgtcgc | cgacctcctg | ctgccgagtt | ccccgccgct | gatcccgggg | cttgagtact |
| 4081 | ccgccatcca | ggactggttc | ctctacacct | tccctgcgac | gcggagcctg | gagttcatcc |
| 4141 | tcggatcat | cctgccccgc | atcctgatca | ccggtcggtg | gatcaacgtc | gggctgctcc |

FIG. 7-26

```
4201  ccgcggtgct  gttgttcccg  gtcttcttcg  tcgcctcgct  cttcctgccg  ggtgtctacg
4261  ccatctcctc  gtcgatgatg  atccttcccc  tggttctgat  catcgccagc  ggcgcgacgg
4321  ccgacctcca  gcagaagcgc  acttcatgc   gtaaccgggt  gatggtgtgg  ctcggcgacg
4381  tctccttcgc  gctctacatg  gtccacttcc  tggtgatcgt  ctacggggcg  gacctgctgg
4441  ggttcagcca  gaccgaggac  gccccgctgg  gtctcgcact  cttcatgatc  attccgttcc
4501  tcgcggtctc  cctggtgctg  tcgtgcgctg  tgtacaggtt  cgtcgagcta  cccgtcatgc
4561  gtaactgggc  cctggtgcgc  tcgcccggcc  gcaaacccgc  cacggaaccc  gaacagaccc
4621  cttcccgccg  gtaagaagga  cggtgcatcg  gtgaccacct  acgtctggtc  ctatctgttg
4681  gagtacgagc  gggaacgagc  cgacatcctc  gatgcggtgc  agaaggtctt  cgccagtggc
4741  agcctgatcc  tcggtcagag  tgtggagaac  ttcgagaccg  agtacgcccg  ctaccacggg
4801  atcgcgcact  gcgtgggcgt  cgacaacggc  accaacgctg  tgaaactcgc  gctggagtcg
4861  gtaggtgtcg  gacgcgacga  cgagcgtcgt  c         acggtctcca  acaccgccgc  cccacagtc
4921  ctggccatcg  acagatcgg   cgcccggccg  acggtctgtg  g acgtccgcga  cgaggactac
4981  ctcatggaca  ccgacctggt  ggaggcggcg  gtcaccccg   gtaccaaggc  catcgtcccg
5041  gtgcacctgt  acgggcagtg  cgtggacatg  acagccctgc  gggaactggc  cgaccgccgg
5101  ggcctcaagc  tcgtggagga  ctgcgcccag  gcccacggtg  cccggcggga  cggtcggctg
5161  gccggacga   tgagcgacgc  ggcggcgcgt  ggcggccttc  tcgttctacc  cctcggcgcc
5221  tacggcgacg  gcggcgcggt  cgtcaccaac  gacgacgaga  cagcccgcgc  cctgcgcgcc
5281  ctgcgtact   acggatgga   ggaggtctac  tacgtcaccc  ggacccggg   tcacaacagc
5341  cgcctcgacg  agtgcaggc   cgagatcctg  cggcgcaaac  tgacccgct   cgacgcgtac
5401  gtcgcggtc   ggcggggcgt  cgcccggt    tacgtcgacg  ggctcgcga   cctccaagac
5461  tcgcacggcc  tcgaactccc  agtggtcacc  gacggcaaac  acacgtctt   ctacgtgtac
5521  gtcgtccgcc  acccgcgccg  cgacgagatc  atcaagcgtc  tccggacgg   gtacgacatc
```

*FIG. 7-27*

```
5581  tccctgaaca  tcagctaccc  ctggccggtg  cacaccatga  ccggcttcgc  ccacctcggt
5641  gtcgcgtcgg  ggtcgcgtgcc  ggtcaccgaa  cggctggccg  gcgagatctt  ctcccttccc
5701  atgtaccccct  ccctccctca  cgacctgcc   gacaggtga   tcgaggcggt  gcggaggtc
5761  atcaccgggc  tgtgacgagc  ccgcgtgtcg  tcagcgaaga  cccactctgg  aaggccggt
5821  catgccgaac  agccactcga  ccacgtcgag  ccacgacgtc  gccccgtacg  agcgggcgga
5881  catctaccac  gacttctacc  acggccgtgg  caagggatac  gccgcgaag   ccgacgcgct
5941  cgtggaggtc  gcccgcaagc  acaccccaca  ggcgggcgacc ctgctggacg  tggcctgcgg
6001  gaccggatcc  cacctggtcg  agctggcgga  cagcttccgg  gaggtggtgg  gggtcgacct
6061  gtcggccgcc  atgctcgcca  ccgcgcccg   caacgaccc   gggcgggaac  tgcaccaggg
6121  cgacatgcgc  gacttctccc  tcgaccgcag  gttcgacgtc  gtcacctgca  tgttcagctc
6181  caccgttac   ctcgtcgacg  aggccgaact  ggaccgtgcc  gtgcgaacc   tggccggtca
6241  cctcgcgcct  ggcgcaccc   tcgtcgtgga  gccctggtgg  gccctggtgg  cgttccggcc
6301  cggctgggtc  ggggccgacc  cggtgaccgg  cggtacccgg  aggatctccc  ggatgtcgca
6361  caccgtcccg  gcgggtctgc  cgcctcccgc  cgcccgcac   atgaccatcc  actacacggt
6421  gggtcaccg   gaggccggga  tcgagcactt  caccgaggtg  cacgtgatga  ccctgttcgc
6481  ccgcgccgcc  tacgagcagg  cctccagcg   ggcgggcctg  agctgctcgt  acgtcggcca
6541  cgacctgttc  tcgccgggcc  tttcgtcgg   ggtcgcggcg  gagccgttcgc gtgagggtc
6601  gaggagctgg  gcatcgaggg  ggtcttcacc  ttcacccccgc agacgttcgc  cgacgagcgg
6661  gggtgttcg   gcacggcgta  ccaggaggac  gtgttcgtgg  cggcgctcgg  ccgcccgctg
6721  ttccggtgg   cccaggtcag  tcccgcggg   tccccgggg   gtgttggtccg ggggtgcac
6781  ttcacgacga  tgccggctc   catgcgggctc cgacctttcg  gcgccaggg   tagggcgatg
6841  gacttcgcg   tcgacatccg  gcccggttcc  ccgaccttcg  gccgcaggcga gccgtcgag
6901  ctctccgccg  agtcgatggt  cgggctgtac  cttcccgtgg  gcatgggcca  cctgttcgtc
```

FIG. 7-28

```
6961  tccctggagg  acgacaccac  cctcgtctac  ctgatgtccg  ccggttacgt  cccgacaag
7021  gaacgggcgg  tgcaccccct  ggatccggag  ctggcgttgc  cgatcccggc  cgacctcgac
7081  ctcgtcatgt  ccgagcggga  ccggtcgca   cccaccctcc  gggaggcccg  ggaccaggg
7141  atcctgcccg  actacgccgc  ctgccgggcc  gccgcgcacc  gggtggtgcg  gacgtgaccc
7201  cggccgggcg  tgcggggcgg  tggtggtgct  cgccgcgtcg  ggtttcctgg  gttcggcggt
7261  cacccacgcc  ctggccgacc  tcccggtgcg  ggtgcggctc  gtcgcccggc  gggaggtcgt
7321  cgtgccctcc  ggtgccgtcg  ccgactacga  gacgcaccgg  gtgcggctcc  ccgaacccgg
7381  agcgctcgcg  gaggtggtcg  cggacgcccg  ggcgtcttc   cgttcgccg   cccagatcag
7441  gggtacgtca  gggtggcgga  tcagcgagga  ggcgtggtc   gccgaacgga  cgaacgtcgg
7501  cctgtccgg   gacctgatcg  ccgtcctgtc  ccgctcgccg  cacgcccgg   tggtgtctt
7561  cccgggcagc  aacacgcagg  tcggcagggt  caccgccggc  cgggtcatcg  acggcagcga
7621  gcaggaccac  cccgagggcg  tctacgacag  gcagaaacac  accggggaac  agctgctcaa
7681  ggaggccact  gcggccgggg  cgatccgggc  gaccagtctg  cggctgcccc  cggtgttcgg
7741  ggtgccgcc   gccgccaccg  ccgacgaccg  ggggtggtc   tccaccatga  tccgtcgggc
7801  cctgaccggc  caaccgctga  cgatgtggca  cgacggcacc  gtccggcgtg  aactgctgta
7861  cgtgaccgac  gccgcccggg  gccgccgtca  ccttcgtcac  cagcgcggac  cgctcgccgg
7921  acgccacttc  ctgttgggga  cggcccgttc  cgggcgttc   ggcgaggtct  tccaggcgg
7981  ctcgcgcagc  gtcgcccggc  acaccggtga  ggacccggtg  cggttggtct  cggtgccgcc
8041  tccgcgcac   atggacccgt  cggacctgcg  gtcgaccgcg  gtcgacccg   cccggttcac
8101  ggctgtcacc  gggtggcggg  ccacgtcac   gatgcggag   gcggtcgacc  ggacggtggc
8161  ggcgttggcc  cccccgcggg  cccgcgcccc  cggcgagccc  gtccgagcc   tcctgaccgg  ggtcaccgg
8221  gttcgtccta  cggcacccgg  ccgtcgacgg  ccggtgccgg  gaagatcgct  tcgagttccc
8281  ggagttcctc  ctcgcccagc  gtcagctcgg  cggcccgtaa  cgccgagtcg  agctgctcgg
```

FIG. 7-29

```
8341  gtgtgcggg  gccgatgaca  gcgcccagga  tcccggggcg  ggacaggacc  caggccagac
8401  cgacctcggc  cgggtccgcg  ccgaggcgtc  ggcagtagtc  ctcgtacgcc  tcgacgaggg
8461  ggcgtacggc  ggggaggagc  acctgggcgc  gtccctgcgc  cgacttgacg  gcggttccgg
8521  ctgccaactt  ctccagtacg  ccgctgagca  gcccgcgtg   caggggac    caggcgaaca
8581  cgcccacccc  gtacgcctgg  gcggcgggca  ggacgtccag  ctcggggtgg  cggacggcca
8641  ggttgtacag  gcactggtgg  gagatcatgc  ggacgcaggtt gcgcgtgcc   gcgctctcct
8701  gggcggcggc  gatgtgccag  cccgccaggt  tggaggagcc  gacgtacccg  accttcccac
8761  tgccgaccag  atgttcggcg  gcctgccaca  cctcgtccca  cggtgcggcg  cggtcgatgt
8821  ggtgcgtctg  gtagatgtcg  atgtggtcga  cccgaggcg   gcggagggag  ttctcgcagg
8881  cggcgacgat  gtgtcgggcg  gagagcccgc  cgtcgttgac  ccgttcgtc   atctcgctgc
8941  ccacctttggt cgccaggacg  gtctcctcgc  gtcgacctcc  gccctgggcg  aaccaccgtc
9001  cgacgagttc  ctcgtggtgg  cccttgtaga  gccgccagcc  gtagatgtcg  gcggtgtcga
9061  tgcagttgac  gccccgctcg  agggcgtggt  ccatcagccg  cagcgcgtcg  tcgtcggtca
9121  cccgtccact  gaagttcacg  gtgccgagcc  agagtcggct  ggtgtgcaac  gccgatcgtc
9181  cgacgcgtac  ccgggcggac  ccggcccgg   tggttcccac  gtcggtcacc  tgtcggcgcg
9241  gtgctggtgg  gcgagcgcct  ccagcacggg  tacgacctcg  gcggggtcg   gcgcggccag
9301  cgcctcctgc  cgcagcttct  cggcgttctc  ggcgtgggaa  cggtcctcga  ccactgtggc
9361  gagagcctgc  cagagggtgt  cggcgtcgac  ctcgtccgga  cggagaaga   cacccgctcc
9421  cagctcggcg  gtgcgctgac  cggcgcagga  acagtcccac  cggagcgga   cggagatctg
9481  cggtacgccg  tggtgcagcg  cggtggccca  gcttccggca  tcgtgggcga  ggatgacggc
9541  ggcacagccc  ggatcgagcc  cggtggcagga tgttcatggg  aacgaagtcc  accaggcgga  cgttgtccgg
9601  caccgacgcc  ggatcgagcc  cggagcgggt  caccacgatc  tcgccgtcga  accgcgcgag
9661  ggtggccagt  gtccggagga  actcctgcgg  gttcgaggtg  atgcccagcg  ccgagtatcc
```

FIG. 7-30

```
9721   cccggtgaag  cagacccggc  ggactccgtc  cgaggtcctg  agccactgcg  gcacgacgga
9781   ggacccgttg  tagggcaaag  tccgggtgtg  caccgactcc  agtccggtct  ccaggcggaa
9841   gctctcgggc  agctggtcga  cgctccactg  tccgacacag  aggtcctcgc  tgtagtcgag
9901   gccgaaccgg  ccggcgacct  cggtgagcca  gccgccgagc  gggtccggcc  ggtcgtcggc
9961   gggacgctgc  ccgcgcaggt  cctgggagcg  gctgcggaag  tagccggtga  ggtcgctgcc
10021  ccacagcagc  cgggcgtggg  cggccccgca  ggccttgcc   gcgaccgcc   cggcgaaggt
10081  gaagggctcc  cagagcacca  ggtcgggacg  ccagtccatg  gcgaactcga  cgagttcgtc
10141  gacgaaggag  tcgtttgtga  ccaccgggaa  gacgaaccgg  gaggtggcct  cctcgatgcc
10201  gtgcaggaac  tcccacgagc  gcagttccgg  tccgcgtcgg  gcgaagtcca  ggtcggtggt
10261  gtagcggttg  acctgcgcgg  gcagtgtcg   ggagatgtcg  gcgaagtcg   ggtccgagcc
10321  gagtcggtgc  gaggtcagtc  ccgcgccgac  gacgacgtcg  gtgagctcgg  gctgactggc
10381  caccccgacg  tcgtggccgg  cgcccaggcc  cgccaggcc   agggggacga  ggccctggaa
10441  gtgggtacgg  tgcgcgaacg  cggcgcact   gaccccggc   ggtcactcct  tggtcgagat
10501  gagggcagca  acggtccggt  cgatgccctc  ggccagcggc  acccgggggt  gccagccggt
10561  cagcgtccgg  aactcggtgg  agtcgaagtc  gtcgctgcgg  aagtcgttgg  cctccggtt
10621  ctccggtgga  gggacgctga  cgacgggcac  cgcaggggttg  ccggtccgcc  gtgccacgct
10681  ggcggcgacg  gtctcgaaga  tctcgcgag   gggtcggcg   tcgtccgcgc  tcggcgtcca
10741  gacgtccgcg  accagcgcct  cgtggttgtg  cagtgcggcg  gtgaacgcgg  tggccacgtc
10801  ctcgacgtgc  aggaggtgc   ggcgcacgct  gccctcgtgc  cacatcgtga  tcggctcacc
10861  ggcgagggct  cgccggatca  tggcggtgac  gacgcccgg   ccggtctgcc  ccgacgggcc
10921  gctgtggccg  tagatccgcg  gcaggcgcag  gatcaccccg  tcgacgaccc  cgtcctcggt
10981  ggcctgacgc  aggatccgct  cggcctcgat  cttgtgctgg  gcgtaccggc  tggggggc
11041  ggggttcgcg  gcctgggtgg  tgctggcgaa  caggagcacc  ggcgcgggtc  cgggtcttgc
```

FIG. 7-31

```
11101  ccgcagcgcg  gcgacgaggt  cgcgcatgat  gcccgcgttg  acgcgttcgg  cctcgggcac
11161  cgtggcggcg  ctgcgccagg  tcgacccgcc  ggcggcgtag  gcgaccagat  gcacgacgac
11221  gtcggtgtcg  gcgacgacct  gcgacccgcc  gccgggttcg  agcaggtcga  ctcgaaggtg
11281  ctcgatcccg  gcgctgcctg  gtggctggtc  gcgagacccg  gtgcgcgcga  cggcccgcag
11341  tcggagaggg  tgtgtggtaa  attcgcgaag  aagggcgctt  ccgacgaatc  cagaaacgcc
11401  gagaagtgtg  acatgtcttg  tcatctacta  atgcattccg  atagccaccg  gcgcatggaa
11461  tccatttgtt  cccccaggg   tggtgtcggg  tgacaaatcc  ggcctcaggt  cggcctcaag
11521  cctctttcga  gcgggtgctg  aggcttcccg  cgtaccctcg  gtggcctgcg  ttcgggcggg
11581  tgtcgggaa   agggcggatc  gaggagttcg  gtagggcgtc  gcggcgcgta  ctccggact
11641  gatccggggt  gacgcccga   ttcctcccga  cgtgtcgatc  cgtgccgcc   gtaccgccgg
11701  ttttcggcga  tggtcgcaga  cgtcgtggac  gtcggagacc  tcattggttc  tcccgggtgt
11761  ggccgcaccg  tcggtggcct  cgtcggcct   gtcggagacc  gggtcgatcg  ccgtccccgg
11821  ccgtgccgac  cagggtccgg  ccgtcggcgt  ggtgggtcac  cgtcggggtgg  accggtccg
11881  ccggcggcca  ccgcccgatc  gtgcccacct  tcgcctccgc  gggtaaatgc  ttcgtcgatc
11941  tgatcgacac  ttccggcgac  gctatcaccg  gagcattccc  cggcaccacc  ggtcgatgcc
12001  tcgcgcttc   caaacaggga  aaacagcagc  tcacagcgc   tccaggcgcc  gggcaatcct
12061  agcgaagagt  ctcgatgggg  tcaaggtgaa  ttctgtcaca  gatgttttg   ttaaatgtac
12121  tttcttcagc  caccctcgac  gttcatacaa  ttggccggca  tctctaccaa  ggggagtga
12181  gtggttgacg  tgcccgatct  actcggcacc  ttggccgcc   accaggcc    gctccattc
12241  ccgtggcccc  tgtgcggtca  caacgaaccg  cggactccgc  cccgcgcgg   tcaattgcac
12301  gcatatctcg  aaggcattc   cgaggatgac  gagctgcgg   gtggtggccg  cctcgcgcgc
12361  gagacacgcg  cgcaggacgg  gccgcaccg   gccgtcgtcg  tgcctcctc   ggtcaccgag
12421  ctgaccgccg  cgtcgcccgc  cctcgcccag  ggccgcccac  acccctcggt  ggtacgcggt
```

*FIG. 7-32*

```
12481  gtcgcccgac  ccacggcacc  ggtggtgttc  gtcctgcccg  gtcagggcgc  ccagtggccc
12541  ggcatggcga  cccgactgct  cgccgagtcg  cccgtcttcg  ccgcggcgat  gcgggcctgc
12601  gagcgggcct  tcgacgaggt  caccgactgg  tcgttgaccg  aggtcctgga  ctcacccgag
12661  caccctgcgc  gcgtcgaggt  ggtccagccc  gcgctcttcg  cggtgcagac  ctcactggcc
12721  gccctgtgcc  ggtcgttcgg  ggtgccgacc  gacgccgtac  tcggacacag  catcggtgag
12781  ctgccgccg   ccgaggtctg  cggccgcgtc  cggccgcgag  cgccgcgcg   ggccgcccgcc
12841  ctgtggagcc  gcgagatggt  cccactggtg  gacgtcgagc  acatggcggc  ggtggcgctc
12901  tccccggccg  gcgagatggt  cccactggtg  ggccggggtg  ggccggcggg  gccggccggg
12961  gtcaacggtc  cccgtcggt   gctgctcacc  cggctcacc   acgacgtcgt  acggcgggtc
13021  gccgagctgg  cggcacaggg  cgtacgcgcc  caggtcgtca  acgtgtcgat  ggcggcgcac
13081  tcggcgcagg  tcgacgccgt  cgccgagggc  atgccgggcg  cgctgacctg  gttcgcccccc
13141  ggcgactcgc  agctggccca  ctacgccggc  ctcaccggcg  ggcggctgga  caccggggaa
13201  ctcggcgccg  acgtgcccgt  gcgcagtttc  cggctcccgg  tgcgcttcga  cgaggcgacc
13261  cgtgcggtcc  tggaactgca  gccggcacg   ttcatcgagt  cgagcccgca  cccggtgctg
13321  gcggcctccc  tgcagcagac  cctcggcacg  gtcgggtccc  cggtgccgat  cgtgccgacc
13381  ctgcaacgcg  accagggcgg  tctgcggcgg  ttcctgctcg  ccgtggcgca  ggcgtacacc
13441  ggtggcgtga  cagtcgactg  gaccgaggc   taccccgggg  tgaccccgg   ccacctgccg
13501  tcggccgtcg  ccgtcgagac  cgacgaggga  ccctcgacgg  agttcgactg  ggccgtcctcg
13561  gaccacgtac  tgcgcgcgcg  gctgctgag   atcgtcggag  ccgagacggc  cgcgctcgac
13621  gggcgggagg  tcgacgcccg  ggccaccttc  cgggaactgg  gccacctc    ggtcctcgcg
13681  gtcagctgc   ggaccccgcct cgccacgcg   accggcacgcg accggcacgcg cgccatgctc
13741  tacgaccacc  cgaccccgca  cgccctgccc  gaggcggcgg  atctgcacat  cgcaggaggag
13801  ccggggcggg  gtgaggagac  ggcacacccg  ggcacacccg  aacccgacga  acccgtcgcc
```

FIG. 7-33

```
13861  gtggtcgcca  tgcgtgccg  gctgcccggc  ggcgtcacct  caccggagga  gttctgggag
13921  ctgctggccg  aggggcggga  cgccgtcggc  gggctgccca  ccgaccgggg  atggacctg
13981  gactcgctgt  tccacccgga  cccgaccccgg  tcgggcacgg  cgcaccagcg  cgctggtggc
14041  ttcctcaccg  gcgccacctc  cttcgacgct  gccttcttcg  ggctgtcgcc  acggaggca
14101  ctgcgtcgtcg  agccgcagca  gcggatcacg  ttggagctgt  cgtgggaggt  gctggaacgc
14161  gccgggatcc  cccgacgtc  gttgcggacc  tcccggaccg  gggtgttcgt  cggtctgatc
14221  cccaggagt  cccgccccg  gctggccgag  gggtgagg  gcgtcgaggg  ctacctgatg
14281  accgggacca  acggccacgg  gctgcgcct  cgggtcgcct  acaccctcgg  cctgagggg
14341  ccggcgatca  gcgtcgacac  cgcctcgctc  cgcctctcg  tcgtcgtcgcg  cctgcgtgc
14401  cagtcgctgc  ggcgcggcga  gtcgacgatg  gcgctcgcg  gtgcgtgac  ggtgatgccg
14461  acaccgggca  tgctcgtgga  cttcagtcgg  atgaactccc  aaggcgcagg  cggacggtcc
14521  aaggcgtttct  cggccgccgc  ggcatggttc  ggccatggccg  tgctcgccgt  gatgctcctg
14581  ctggaacgcc  tctcgacgc  cgaccgccac  ggccgccac  cccgaacgg  gatcagggc
14641  accgctgtca  actccgacgg  cgcgagcaac  ggactctccg  ccccacacac  ccggcccag
14701  gtccgggtga  tccgagaggc  cctcgcgctc  tccggctga  cgccccacgg  cgtcgacgtc
14761  gtggagaccc  acggcaccgg  cgtgatccga  tcgaggcacg  gcgctctcc
14821  gacgcgtacg  acggcaccg  gctcgttcaa  gtccaacatc  gtccaacatc
14881  gggcaccacc  aggccgcccg  tgagcaccccg  gctcggtcaa  aactggtgtt  ggcgatgcag
14941  gccggtcgtcc  tgccccgcac  ccggcgcgcg  gacgagccgt  caccggaccgt  cgactggtcc
15001  tcggcgcga  tcagcctgct  cctcgcacgc  gtgcctggc  ccggagcgc  gcggcccgc
15061  cggcccgcga  tgtcctcgtt  cggcatcagc  ggcaccaacg  cacacgcgat  catcgaggag
15121  gcgccgacga  cggtgacga  cggcatggg  gccggatgg  gccggtggtg  gccctgggtg
15181  ctctcggcga  gcaccggcga  ggcgttgcgc  gcccgggcgg  gccgttggc  cggcaccta
```

FIG. 7-34

```
15241  cgcgagcacc  ccgaccagga  cctggacgac  gtcgcctact  cgctggccac  cggtcgggcc
15301  gcgctggcgt  accgtagtgg  gttcgtgccc  gccgacgcgt  ccacggcgct  gcggatcctc
15361  gacgaactcg  ccgccggtgg  atccgggggac  gcggtgaccg  gcaccgcccg  cgccccgcag
15421  cgcgtcgtct  tcgtcttccc  cggccaggga  gcggcagtgg  cggggatggc  agtcgacctg
15481  ctcgacggcg  acccgtctt   cgcctcggtg  ctgcgggagt  gcgccgacgc  gttggaaccg
15541  tacctggact  tcgagatcgt  cccgttcctg  cgggccgagg  gcagcgcccg  gaccccgac
15601  cacacgctct  ccacgaccg   cgtcgacgtg  gtccagccgg  tgctgttcgc  ggtgatggtg
15661  tccctggcgg  cccgtggcg   ggcgtacggg  gtggaaccgg  cggccgtcat  cggacactcc
15721  caggggaga   ttgccgcggc  gtgtgtggcc  ggggcgctct  cggctggacga cgcggcccgg
15781  gcggtgccc   tgcgcagccg  ggtcatcgcc  accatgcccg  gcaacggcgc  gatgccctcg
15841  atcgccgcct  ccgtcgacga  ggtggcgggt  cggatcgggc  ggcgggtcga  gatccgcgcc
15901  gtcgcggtc   cgcgcgcggt  ggtggtctcc  ggcgaccgtg  acgacctgga  ccgctggtc
15961  gcctcctgca  ccgtcgaggg  ggtgcggggc  aagcgggccg  cggtggacta  cgcgtcgcac
16021  tcctcgcacg  tcgaggccgt  ccgtgacgcg  ctccacgccg  aactcggcga  gttccggccg
16081  ctgccgggct  tcgtgccgtt  ctactcgaca  gtcaccgacc  gctggtcga   gccgcccgaa
16141  ctcgacgccg  ggtactggtt  tgcaacctg   cgccacaggg  gtcaccggac  cccggtc
16201  cgctccctcg  ccgagcaggg  gtacacgacg  ttcctggagg  tccagcgcca  ccggtgctc
16261  accacgcga   tcgaggagat  cggtgaggac  cgtggcggtg  acctcgtcgc  tgtccactcg
16321  ctgcgacgtg  gggccgcgg   tcccgagggc  ttcggctccg  cgcttcgtg
16381  gccggcgtcg  cagtggactg  ggagtcggcg  taccagggtg  cggggcgcg   tcgggtgccg
16441  ctgcccacgt  accgcttcca  gcgtgagcgc  ttctggttgg  aaccgaatcc  ggccgcagg
16501  gtcgccgact  ccgacgacgt  ctcgtccctg  cggtaccgca  tcgaatgcga  cccgaccgat
16561  ccgggtgagc  cgggacggct  tggctgctgg  tggcggcacc  cgacgtaccc  cggtcgggcc
```

FIG. 7-35

```
16621 gacgaccggg tcgaggcggc gcggcaggcg ctggagtccg ccggggcgcg ggtcgaggac
16681 ctggtggtgg agcccggac gggccgggtc gacctggtgc gacctggtgc gcggcctcga cgccgtgggt
16741 ccggtggcgg gcgtgctctg cctgttcgct gtcgcggagc cggcggccga acactcccg
16801 ctggcggtga cgtcgttgtc ggacacgctc gacctgaccc aggcggtggc cgggtcggc
16861 cgggagtgtc cgatctgggt ggtcaccgag aacgccgtcg ccgtcggcc cttcgaacgg
16921 ctccgcgacc cggcccacgg cgcgctctgg gccctcggtc gggtcgtcgc cctggagaac
16981 cccgccgtct ggggcggcct ggtcgacgtg ccgtcggtt ccgtcgggt gctgtcgcgt
17041 cacctcggga cgacctgtc cggcgccggc gaggaccagg tcgccctccg acccgacggg
17101 acgtacgccc gccggtggtg cagggccggc gcgggccggc cgggccggtg gcagccccgg
17161 ggcacgctgc tcgtcaccgg cgcagccccgt ggacgtcgc ggcacgtcgc ccggtggctg
17221 gcccgccagg gcacccccgtg cctggtgctg gccagccgcc ggggaccgga cgccgacggg
17281 gtcgaggagc tactcaccga cggcccgac ctggcgcgca ggccaccgt caccgcctgc
17341 gacgtcaccg acgggagca gctccgcgcc ctcctcgcga cgggcggcg cgagcaccg
17401 ctgtcggcgg tgttccacgt cgcgcgacg ctcgacgacg ccgtcgacga gaccctcacc
17461 ggtgaccgca tcgaacgggc caaccggacg aaggtgctcg gtgcccgcaa cctgcacgag
17521 ctgacccgca acgccgacct cgacgcgttc gtgctcttct cctcctccac cgcgcgttc
17581 ggcgcgccgc ggctcgaggg ctacgtcccc gccgccacc gcaacgcct acctcgcggg tctcgcccag
17641 cagcgacgca gcgaggact cccgccacc tcgcggtgc tcggtggcgt ggggtaccg ggcgcagc
17701 gggatggccg agggtccggt cgcgcgacct acgggtcat ggagatgcac
17761 cccgaccagg tctcgagg tctcgggtg gcactggtgc agggtgaggt agcccgatc
17821 gtcgtcgaca tcaggtggga ccggttcctc ctcgcgtaca ccgcgcagcg ccccaccgg
17881 ctcttcgaca cccctcgacga ggcccgtcgg ggcccgacgc gtcccgacgc cgggccgggg
17941 gtggcggcgc tggccgggct gcccgtcggg gaacgcgaga aggcggtcct cgacctggta
```

FIG. 7-36

```
18001 cggacgcacg cggctgccgt cctcggccac gcctcggccg agcaggtgcc cgtcgacagg
18061 gccttcgccg aactcggcgt cgactcgctg tcggccctgg aactgcgcaa ccggctgacc
18121 actgcgaccg gggtccggct ggccacgacg acggtctttcg accacccgga cgtacggacc
18181 ctggccggac acctggccgc cgaactgggc ggcggatcgg ggcgggagcg gccggggggc
18241 gaggcccga cggtggcccc gaccgacgag ccgatcgcca tcgtcgggat ggcctgccgg
18301 ctgccgggg gagtggactc acggagcag ctgtgggagt tgatcgtctc cgggcgggac
18361 accgcctcgg cggcaccgg ggaccggagc cggagttgat ggtctccgac
18421 acgacgggca cccgtaccgc cttcggcaac ttcatgcccg gttcgacgcg
18481 gcgttcttcg ggatctcgcc gcgtgaggcg ttggcgatgg gccgcagca gcgcacgcc
18541 ctggagacca cctggagggc gctgaggc gcccgagtc gttgcgcggt
18601 acggacaccg gtgtcttcgt gggcatgtcc catcaggggt acgccaccgg ccgcccgaag
18661 cccgaggacg cctggagggg gttggaggg ccggcgatca ctgtggacac cgcctccggt
18721 cggatcgcgt acgtgtttgg cgtgcggcg ggttcgttgc gtctgggga ggcgtgttcg
18781 tcgtcgcttg tgggtttgca cgtcgggggc ggtgatggcc ggtccggagg tgttcaggga gttctcccgg
18841 gcggtggcgg gtggtgtc ggcaggtgc cggcggaggc tgttcaggga gttctcccgg
18901 cagggcgcgt tggctccgga cggcaggtgc cttcgtcgtg ttgcagcggt ggtcggcgg
18961 ggtctgggg aggggtcggc tggttgggtgt ttgcagcggt tcgcggtga gtaat
19021 gggcgtcggg tgttgggtgt cgccgtcggg gtggcgcag atcaggatgg ggcgagtaat
19081 gggttggcgg cgcgtcggg ccggtgggc cggtgtga ttcggcgggc gtggggtcgt
19141 gcgggtgtgt cgggtgggga tgtggtgtg gtgggcgcag atgggcgc gacggggttg
19201 gggatccgg tggagtttgg gcgtttgttg ggacgtatg gggtgggtcg gggtggggtg
19261 ggtccggtgg tggtgggttc ggtgaaggcg aatgtgggtc atgtgcaggc ggcgcgggt
19321 gtggtgggtg ggtgttggg ttggtcggg ttgggtggg ggttggtgtg tccgatggtg
```

*FIG. 7-37*

| | | | | | |
|---|---|---|---|---|---|
| 19381 | tgtcggggtg | ggttgtcggg | gttggtggat | tggtcgtcgg | gtgggttggt | ggtggcggat |
| 19441 | ggggtgcggg | ggtggccggt | gggtgtggat | ggggtgcgtc | gggtggggt | gtcggcgttt |
| 19501 | ggggtgtcgg | ggacgaatgc | tcatgtggtg | cgccggggtc | cgcggtgggg | ggtggcgttg |
| 19561 | gcggaacggc | cggtggaggg | gtcgtcgcgg | gggttggtgg | gggttggtgg | tggtgtggtg |
| 19621 | ccggtggtgc | tgtcggcaaa | gaccgaaacc | gccctgcacg | cccaggcacg | tcgactcgcc |
| 19681 | gaccacctgg | agacgcaccc | cgacgtcccg | atgaccgacg | tggtgtggac | gctgacgcag |
| 19741 | gcccgccaac | gcttcgacag | gcgcgcggtc | ctcctcgccg | ccgaccggac | ccaggccgtg |
| 19801 | gaacggctgc | gcggcctcgc | cggggcgaa | ccggggaccg | gtgtggtgtc | ggggtggcg |
| 19861 | tcgggtggtg | gtgtggtgtt | tgttttcct | ggtcagggtg | gtcagtgggt | ggggatggcg |
| 19921 | cggggttgt | tgtcggttcc | ggtgtttgtg | gagtcggtgg | tgcggcggt | tgcggtggtg |
| 19981 | tcgtcggtgg | tgggttttc | ggtgttgggg | gtgttggagg | gtcggtcggg | tgcgccgtcg |
| 20041 | ttgatcggg | tggatgtggt | gcagccggtg | gtgttcgtgg | ttgttcgtgg | gttggcgcgg |
| 20101 | tttgtggcgg | ggtgtggggt | tgtgcctgcg | tgtcaggtg | gcggtggtg | gtcattcgca | ggggagatc |
| 20161 | gcggcgcggg | tggtgggcgg | ggtgcgggt | gtgttgtcg | gtgtggccgg | gtgcgcgggt | ggtggcgttg |
| 20221 | cggggcggg | cgttgccggc | gttgccgag | cacgcggca | tggcctcggt | acgccgagc |
| 20281 | cgcgacgacg | tacagaagct | cctcgacagc | ggccctgga | cggggaagct | ggagatcgcc |
| 20341 | gcggtcaacg | gccccgacgc | ggtgtggtc | tccccgtcga | gaccgagctg |
| 20401 | gtcgagcact | gtgacgggat | cgggtccggg | gcccggacga | tcacgcctcc |
| 20461 | cactccgcac | aggtcgagtc | gctccggag | agctgctct | ccgtcctggc | cggatcgag |
| 20521 | ggccgcccgg | cgacggtgcc | gttctactcc | acccctcaccg | gtggttcgt | gtggcacc |
| 20581 | gaactgacg | cgactactg | gtaccgcaac | ctgcgccacc | cggtgcggtt | ccacgccgcc |
| 20641 | gtcgaggcgc | tggcagcgcg | tgacctcacc | acgttcgtcg | aggtcagccg | gcaccccgtg |
| 20701 | ctgtcgatgg | cggtcgggga | gacgcttgcc | gacgtggagt | gacgtggagt | ccgccgtcac | tgtgggcacc |

FIG. 7-38

```
20761  ctggaacgcg  acaccgacga  cgtcgagcgc  ttcctcacct  ccctcgcga   ggcgcacgtc
20821  cacggcgtac  ccgtggactg  ggcggcggtc  ctcgctccg   gaaccctggt  cgacctgccc
20881  acctatccct  tccaggacg   gcggttctgg  ctgcaccccg  accgtggtcc  gcgtgacgat
20941  gtcgccgact  ggttccaccg  ggtcgactgg  acggcgacgg  ccaccgacgg  gtcggcccga
21001  ctcgacggtc  gctggctggt  ggtcgtaccc  gaggggtaca  cggacgacgg  ctgggtcgtg
21061  gaggtgcggg  ccgccctcgc  cgccggtggt  gccgagccgg  tggtgacgac  ggtcgaggag
21121  gtcaccgacc  gggtcggtga  cagcgacgcg  gtggtgtcga  tgctcggct   ggccgacgac
21181  ggtgcggccg  agaccctggc  gctgctgcga  cgactcgacg  cacaggcgtc  caccaccca
21241  ctgtgggtgg  tcaccgtggg  ggcccgtcgc  cccgccggtc  cggtgcagcg  cccgaacag
21301  gcgacggtgt  ggggtttggc  ccttgtcgcc  tccctggaac  gcggacaccg  gtgaccggc
21361  ctgctggatc  tgccgcagac  accggacccg  cagctacgac  cccggctggt  cgaggcgctc
21421  gccgtggcgg  aggaccaggt  agcgggagc   gccgacgccg  gcgggacgat  tcggatcgtc
21481  cccacccgg   tcaccggagc  cgggccgtac  accgcccccgg  gcgggacgcg  cctcgtcacc
21541  ggggcaccg   ccggtctggg  tgccgtcacc  gccgatggc   tgcgcgagcg  cggtgccgaa
21601  cacctcgccc  tggtcagccc  gcgcggcccg  gcaccgccg   gcgtcgacga  cggtggtccgg
21661  gacctgaccg  ggctcggcgt  acgggtgtcg  gtgcactcct  gcgacgtcgg  cgaccgcgag
21721  tcggtcggcg  cccgtgtgca  ggagttgaca  gcagccgtg   acgtggtccg  ggggtggtc
21781  cacgctgccg  gtctgcccca  gcaggtgcca  ctgaccgaca  tggaccggcc  cgacctgcc
21841  gacgtggtgg  ccgtgaaggt  cgtaccgcg   gtgcacctgg  ccgacctgtg  ccggaggcc
21901  gaactgttcc  tgctgttctc  ctccgggcc   ggggtgtggg  gcagtgcccg  tcaggtgctg
21961  tacgccgccg  gaaacgcctt  ctccgacgcc  ttcgcccgac  accggcggga  ccggcgcggg
22021  cccgccacct  cggtgcgtg   cctgcgtctgg  gggctctgg   gcgccccgac  ggaccaggag
22081  gcggtgtcgt  tcctgcgtga  gcggggcgta  gcgggcgag   cggccgatgt  ggcactggaa
```

FIG. 7-39

```
22141 gcgctgaac gggtcctcac cgccggggag accgcggtgg tcgtcgccga cgtcgactgg
22201 gcggccttcg ccgagtcgta caccctccgc cggccccggc cgctgctcca ccggctcgtc
22261 acacctgcgg ccgcggtcgg cgagcgcgac gagccgcgtg agcagacccc ccggaccgg
22321 ctggcggccc tgccccgggc tgccgagctg gcggagctgg tacgctggt ccggcgggac
22381 gccgcagccg tgctcggcag cgacgcgcag gccgtacccg ttccgtaacc gttcaaggac
22441 ctcgggttcg actcgctggc cgcggtccgg ttcttcgag cacggaacg ccacaccggt
22501 ctgcgtctgc cggccaccct ggtcttcgag caccgaaacg ccgcagccgt cgccgacctc
22561 ctccacgacc gactcggacg ggccgcgag cacccccccg tccggtcggt gggcgccgga
22621 ctggccgcgc tggagcaggc cctgcccgac gcctccgaca cggagcggt cgagctggtc
22681 gagcgcctgg aacggatgct cgcccgggtc ggggaggcc gccgtcgaca cggagccgg ggccgacgcc
22741 ccgaccgccg gtgacgacct aaccaggtg aactccctga ggccgacc cgcgctcgaa
22801 cgggaactcg acgccaggtg ctgacaacga gacgcagcc gagtacctcc gctcgacctg
22861 ggacctgtga ctgacaacga cggcgagct gcagccgaag gtcgtgcgac gctcgacctg
22921 cggccgccc gcaagcgcct gcgcgagcct gagtacctcc gatcgcggt cgtcggcatg
22981 gcctgccgcc taccggcgg ggtgcacctc caatccgacc tgtggacct cctgccgcag
23041 gggcacgaga cggtgtccac cttcccccacc ccgcagcacc gggacctggc cgggctcttc
23101 cacccggacc ccgaccagc cggcaccagc ggcgcgggct cctcgacgac
23161 gtggcgggct tcgacgccga gttcttcggg atctctccgc gcgaggccac ggccatggac
23221 ccgcaacagc ggctgctgtt ggagaccagt tgggagctgg tggagagcgc ggccatcgat
23281 ccgcactccc tgcgtggcac cccgaccggc gtcttcctcg gcgtggcgcg gctcggctac
23341 ggcgagaacg gcaccgaagc cggtgacgcc gagggctatt cggtgaccgg ggtggcaccc
23401 gctgtcgcct ccgggcggat ctcctacgcc ctcgggctgg agggtccgtc gatcagcgtg
23461 gacaccgcgt gctcgtcgtc gttggtggcg ctgcacctgg cggtcgagtc gctgcggctg
```

FIG. 7-40

```
23521  ggcgagtcga  gtctcgctgt  cgtcggcggg  gcggcggtca  tggcgacacc  aggggtgttc
23581  gtcgacttca  gccgccagcg  ggcgttggcc  gctgacggca  ggtcgaaggc  cttcggggcc
23641  gccgccgacg  ggttcggctt  ctccgagggg  gtctcccctcg  tcctgctcga  acggctctcc
23701  gaggccgaaa  gcaacggcca  cgaggtgttg  gctgtcatcc  gtggctccgc  cctcaaccag
23761  gacggggcca  gcaaacggtct  cgccgcgcca  aacggaccg  cccagcgcaa  ggtgatccgg
23821  caggcgctac  gaaactgcgg  cctgaccccg  gccgacgtgg  acgccgtgga  ggcgcacggc
23881  accggcacca  cgctcggcgg  cccgatcgag  gccaacgccc  tgctggacac  ctacggccgt
23941  gaccgggatc  cggaccaccc  gctgtggctg  gggtcggtga  agtcgaacat  cggccacacg
24001  caggcggcgg  cgggcgtcac  cgggctgctc  aagatggtgc  tggcactgcg  ccacgaggaa
24061  ctgcccgcca  ccctgcacgt  cgacgagccc  acccccgcacg  tggactggtc  ctcgggagcg
24121  gtacgcctgg  cgacccgggg  ccgccgtgg  cggccgtgag  accggccgag  gcgggccggg
24181  gtgtcggcgt  tcggcatcag  cgggaccaac  gcccacgtga  tcgtcgagga  gcaccggga
24241  cggaccaccg  agcgcaccgt  cggcgcggac  gtcggcccgg  tcccgctcgt  ggtgtccgcc
24301  cggtcggcgg  agcgcgctacg  cgggcggagc  ggccaggtcg  ccgagctggt  ggagggctcc
24361  gacgtcgggg  tggcggaggt  cgggcggagc  ctgccgtga  cccgggcgcg  acacgagcac
24421  cgggcggcgg  tggtggcgtc  gacccgggcc  gaggcggtgc  ggggcgtgcg  cgaggtcgcg
24481  gcgtcgaac  cgcgcggcga  ggacacgtcc  acggggtcg  ccgagacgtc  cgggcgcacc
24541  gtcgtcttcc  tcttcccggg  acaggggtcc  cagtgggtcg  ggatgggcgc  ggagctgctg
24601  gactccggcac  cggcgttcgc  cgacacgatc  cgcgcctgcg  acgaggcgat  ggcaccgttg
24661  caggactggt  cggtctccga  cgtgctccgg  caggagccgg  gggcaccgg  actggaccgg
24721  gtcgacgtgg  tgcagccggt  gctgttcgcg  gtgatggtgt  cgttggcgcg  gttgtggcag
24781  tcgtacgggg  tcaccccgc  gctcggggtg  gggcactcgc  aggggagat  cgccgccgcc
24841  cacgtggcgg  gtgcgctctc  cctcgccgac  gcggcgaggc  tggtggtggg  ccgcagccgg
```

FIG. 7-41

```
24901  ttgctgcggt  cgctgtccgg  gggcggcggc  atgagcgccg  tcgcgctcgg  tgaggccgag
24961  gtacgccgcc  gactgcggtc  gtgggaggac  cggatctccg  tggccgccgt  caacggaccc
25021  cggtcggtgg  tggtggccgg  ggaaccggag  gcgctgcggg  agtgggacg   ggagcggag
25081  gccgagggcg  tacgggtccg  cgagatcgac  gtcgactacg  cctcgcactc  gccgcagatc
25141  gacaggtcc   gtgacgaact  cctgacggtc  acggggaga   tcgagcccg   gtcggcggag
25201  atcacctcct  actcgacggt  cgacgtccgt  gctgtcgacg  gcaccgacct  ggacgcgggg
25261  tactggtacc  gcaacctgcg  ggagacggtc  cggttcgccg  acgcgatgac  ccggttggcc
25321  gactcggat   acgacgcgtt  cgtcgaggtc  agcccgcatc  cggtggtggt  gtcggcggtc
25381  gccgaggcgg  tcgaggaggc  aggtgtcgag  gacgccgtcg  tcgtcggcac  cctgtcccgg
25441  ggcgacggcg  gaccggggc   gttcctgcgg  cccccactg   ccgccgtgtg  cgcggtgtg
25501  gacgtcgact  ggacgccgc   cctcccggga  gctgcgacga  tccgttgcc   gacgtaccg
25561  ttccaacgga  agccgtactg  cctgcgcctc  tctgctcccg  ccccgcctc   ccacgatctc
25621  gcctacggg   tgtcctggac  gccgatcacc  ccgcccgggg  acggcgtact  cgacggcgac
25681  tggctggtgg  tgcaccggg   gggcagcacc  ggatgggtcg  acggttggc   ggcggcgatc
25741  accgccgcg   gtgcccgggt  cgtcgcccac  ccggtggact  ccgtgacctc  ccggaccggc
25801  ctggccgagg  cgctcgccg   gcgggacggc  acgttccggg  gggtgctgtc  gtgggtggcg
25861  accgacgaac  ggcacgtcga  gccggcggc   acggcggcg   tgcgccggc   gcaggcgttg
25921  ggtgacgccg  gaatcgacgc  accactgtgg  tgcctgaccc  tgaccctggc  ccgtaccccg
25981  gtcgacggtg  acctggccg   accggcgcag  gccgcccgc   acggtttcgc  ccaggtcgcc
26041  cggctggagc  tggcccgccg  cttcggtggg  gtgctcgacc  tgcccgccac  cgtcgacgcc
26101  gcgggacgc   gtctggtcgc  ggcggcggcc  acgttcctc   gcgaggacgt  cgtcgccgtc
26161  cgtgcgacc   gtctctacgg  ccggcccctg  gtcaggcgca  ccctgccgcc  gccgcggg
26221  gggttcaccc  cgcacggcac  accggccgg   accggcggtc  ccggtccggt  gggcggtcgg
```

*FIG. 7-42*

```
26281  ctggcccggt  ggctcgccga  acgggtgcc  acccgactcg  tcctgcccgg  cgcacacccg
26341  ggcgaggagt  tgctgaccgc  gatccggcc  gccggtgcca  ccgccgtggt  gtgcgaaccg
26401  gaggcggagg  cactgcgtac  ggcgatcggc  ggggagttgc  cgaccgcgct  cgtacacgcc
26461  gagacgttga  cgaacttcgc  cggcgtcgcc  gacgccgacc  ccgaggactt  cgccgccacc
26521  gtcgcggcga  agaccgcgct  gccgacggtc  ctgcggagg   tgctcggcga  ccaccgcctc
26581  gaacgggagg  tctactgctc  gtcggtggcc  ggggtctggg  gtggggtcgg  catgccgcg
26641  tacgcgcccg  gcagcgccta  cctcgacgcc  ctggtcgagc  accgtcgcgc  ccggggcac
26701  gccagcgcct  cggtggcctg  gcccgtgg   gccctgcccg  gcgcggtcga  cgacggtcgg
26761  ctgcgcgagc  gcggcctgcg  gacctcgac  gtgccgacg   cctcgggac   gtgggaacgt
26821  ctgctccgcg  ccggtgcggt  gtcggtggcc  gtcgccgacg  tcgactggtc  ggtcttcaca
26881  gagggttcg   cggccatccg  gccgaccccg  ctcttcgacg  aactcctcga  ccggcgcggg
26941  gacccggacg  gcgcgcccgc  cgaccggcc  ggggagccgg  cgggcgagtg  gggtcgacga
27001  atcgcggcgc  tgtcccgca   ggaacagcgg  gagacgttgc  tgaccctcgt  cggcgagacg
27061  gtcgcggagg  tgctggaca   cgagaccggc  accgagatca  acaccccgtcg  ggccttcagc
27121  gaactcggcc  tcgactcgct  gggctcgatg  gccctgcgtc  agcgcctggc  ggcccgtacc
27181  ggcctgcgga  tgccggcctc  gctggtctta  gaccaccga   cggtcaccgc  ggccccgcgg
27241  tacctgcgtc  gactggtcgt  cgggactcc   gacccgaccc  cggtacgggt  gttcggcccc
27301  accgacgagg  ccgaacccgt  cgccgtggtc  gaccatcggct  gccggttccc  cggcggcatc
27361  gccacccccg  aggacctctg  gcgggtggtg  tccgagggca  cctccatcac  caccgattc
27421  cccaccgacc  aggactggga  cctccggcgg  ctctaccacc  ccgacccgga  ccccgggttc
27481  accagctacg  tcgacagggg  gggattcctc  gacggggccc  cggacttcga  cccccggtc
27541  ttcgggatca  ccccccgcga  ggcgctggcg  atggaccccgc  agcagcggct  caccctggag
27601  atcgcgtggg  aggcggtgga  acgggcggg   atcgacccgg  agaccctcct  cggcagcgac
```

FIG. 7-43

| | | | | |
|---|---|---|---|---|
| 27661 | acggcgtct | tcgtcgcat | gaacggccag | tcctacctgc | cggggaggt |
| 27721 | gaccggctca | acggctacca | ggggttgggc | aactcggcga | cggccgtgtc |
| 27781 | gcctacacct | tcgggtggga | gggccggtgg | acaccgcctg | ctcgtcctcg |
| 27841 | ctggtcgcca | tccacctcgc | ctgcagtcg | ctgcgtcggg | gctgcgttg |
| 27901 | gccggcgggg | tgacggtcat | ggccgaccg | tacaccttcg | tggacttcag |
| 27961 | gggctcgccg | ccgacgggcg | gtgcaaggcg | ttctccgcgc | gttcgccctc |
| 28021 | gccgaggcg | tcgcggcgct | cgtcctccaa | ccgttgtcca | aaacggccac |
| 28081 | caggtgctgg | cggtgctgcg | cgcagcagc | gtcaaccagg | caacggcctc |
| 28141 | gccgcccga | acgggccgtc | gcaggaacg | gtgatcaggc | cgcctccggg |
| 28201 | ctgcgtcccg | ccgacgtcga | catgtggag | gcgcacggga | actcggcgac |
| 28261 | ccgatcgagg | ccgggcgct | catcgcgcg | tacgccggg | gcggctctgg |
| 28321 | ctgggctcgg | tgaagacgaa | catcggccac | acccagccg | ccgccgggtg |
| 28381 | atcaaggcgg | tcctggcgat | gcggcacggc | gtactcccga | ggtcgctgca |
| 28441 | ttgtcccgc | acatcgactg | ggcggacggg | aaggtcgagg | tgctccgcga |
| 28501 | tggccccg | gtgagcgcc | ccgccgcc | ggggtgtcct | ccttcggcgt |
| 28561 | aacgcccacg | tcatcgtcga | ggagcaccc | gccgaaccg | acccgggacc |
| 28621 | gccccggcg | ggcccctgcc | cttcgtcctg | cacggacgca | ggttcccgcc |
| 28681 | caggcgcgga | ccctcgccga | acaccctgcc | accaccggt | gcgtccagac |
| 28741 | gccccgtacc | tggccaccgg | tcgcgcccgt | ttcgacgtcc | accggaccc |
| 28801 | gaccgggagg | gtgtctgcgc | cgccctcgac | gggccgcagt | gctcggcacc |
| 28861 | gtcgtcgccc | cggcggtctt | cgcgcctgc | gccccgtcc | aggatcgcc |
| 28921 | tcgcagtggc | tcggcatggc | cgtgacctg | accccgccc | tggtcttccc |
| 28981 | atgggccggt | gcgccgaggc | gctgtcgccg | tacaccgact | gggaccgac |

FIG. 7-44

```
29041  cgtggggtcg  gcgacccga   cccgtacgac  cggtggacg   tgctccagcc  ggtgctgttc
29101  gcggtgatgg  tgtcgctggc  gcggttgtgg  cagtcgtacg  gggtgactcc  gggtgcggtg
29161  gtgggtcact  cgcaggggga  gatcgccgcc  gcgcacgtgg  ctgtgcgtt   gtcgttggcc
29221  gacgccgcca  gggtggtggc  gttgcgcagc  cggtgctgc   gggagctcga  cgaccaggcc
29281  ggcatggtgt  cggtcggcac  ctcccgcgcc  cggtgctgac  t cggtcctgc  ccggtgggac
29341  gggcggtcg   cggtggcggc  ggtgaacgga  cccggcacgc  cggtggtggc  cggacccacc
29401  gccgaactgg  acgagttcct  cgcggtggcc  gaggcccgcg  agatgaggcc  cggtcggatc
29461  gcggtgcgct  acgcgtcgca  ctccccggag  gtggcccggg  tcgaacagcg  gctcgccgcc
29521  gaactcggca  ccgtcaccgc  acggtcccgc  ctactccac   tctactccac  cgccaccggg
29581  gacctcctcg  acaccacagc  catggacgcc  gggtactggt  accgcaacct  gcgccaacct
29641  gtgctgttcg  agcacgccgt  ccgcagccgt  ctggagcggg  gattcgagac  gttcatcgag
29701  gtcagccgc   acctgtcg    gctgatggcg  gtcgaggaga  ccgccgagga  cgccgagcgc
29761  ccggtcaccg  gcgtgccgac  gctgcgccgc  gaccacgacg  ggccgtcgga  ggccgtcgga
29821  aacctcctgg  gcacgccacgt gcacggggtc  gacgtcgacc  tgctgccgcc  gttcctccgc
29881  ggccgcctgg  tcgacctgcc  cacctacccc  ttcgacaggc  agcggctctg  gccaagccg
29941  caccgcaggg  ccgacacctc  gtcgctgggg  gtccgtgact  cgacccaccc  gctgctgcac
30001  gccgcagtcg  acgtacccca  gcacgtggtg  gcggtgttca  ccggcgcact  ctccccgac
30061  gagcagcagt  ggctgaccc   gcacgtggtg  ggtgggcgga  acctggtgcc  cggcagtgtc
30121  ctggtcgacc  tcgcgctcac  cgccggggcc  gacgtcggcg  acctggtgct  ggaggaactc
30181  gtcctgcagc  agccgctggt  gttgaccggt  tgctgcgcct  tgctgcgcct  gtcggtcggc
30241  gccgcgacg   aggacgggcg  gcgccggtc   gagatccacg  cggccgagga  cgtctccgac
30301  ccggccgagg  cccggtggtc  ggcgtacgcg  accgggaccc  accgcgtcgg  cgtgccggc
30361  ggcggccggg  acggcacaca  gtggccccg   ccggccgcca  ccgccctgac  gttgaccgac
```

FIG. 7-45

```
30421 cactacgaca ccctcgccga actgggctac gagtacgggc cggcgttcca ggcgctgcgc
30481 gccgcgtggc agcacgcgga cgtgtctac  gcggaggtgt  cgggaggag   cgtcgaggag
30541 gggtacgcgt tcgacccggt gctgctcgac gccgtcgccc agacctggg   cctgaccagt
30601 cgcgccccg  ggaagctccc cttcgcctgg gccgtcgacgc ccctgcacgc caccgggcc
30661 actgcggtac gggtggtggc gacccggaccg cggtggccct gcggtcacc
30721 gaccggaccg gtcagctcgt cgccacggtg gaccgggacg tcgtcaggga cgccggggcg
30781 gatcgggacc agccgcgcgg cgccacggtg gacctgcacc gcctggagtg ggtacggctg
30841 gccaccccgg accccgaccc ggcggcggtg gtgcacgtgg cggccgacgg gctcgacgac
30901 ctgctcggcg accacccgtc cggtggtcc  gccgtcgtcg tccgtctggg tcccgacggc
30961 gacgaccgga cggccgaggc ccgtcacggg gccacacag  cggccacgct cgtgcgccgt
31021 tggctcgacg acgaccgtg  gccgccacc acccggttgg tggccacgtc cgcagggtc
31081 gaggtctccc ccggggacga cgtgccgcgc gccgccgcg  ccgccgtgtg ggggtgctg
31141 cgctgcgcc  aggcggagtc cccggaccgc ttcgtgctcg tcgacggcga cccggagacg
31201 cccccgcgg  tgccgaaacaa tccggcagtc gcggtgcgtg acggtgcggt gttcgtgcca
31261 cggctgacgc cgctcgcccg tcccgtgccg tccgtgccg  gcggggcgta ccggctggtg
31321 cccggcaaca gccgcgtcgc cgaggcagtg gcctcgcc   accggcgt   cgccgacgg
31381 ccctgcgcgc cggaggaggt acgcgtcgcc gtccgcgcca gcctcggtgaa cttccgtgac
31441 gtcctgctcg cgctcggcat gtacccggaa ccggccgaga tgggcaccga ggcgtccggt
31501 gtggtcaccg agtccggtc gggtcggg   cggccaggc   ccggccaggc   ggtgacgggc
31561 ctgttccagg ggccttcg   gccgtggcg  gtcgccgacg accggctcct caccccggtc
31621 cccgacgggt ggcgggcggt ggacgcccgca gccgtaccca ccgggcag   caccgccac
31681 tacgcgctgc acgaccggg  acggttgcag gcggttgcag ccgtgctggt ccacgccgcc
31741 gccggcgggg tgggatggc  tgccgtcgcg ttggccggtc ggcccgtc   ggaggtgttc
```

FIG. 7-46

```
31801  gccacggcca  gcccggccaa  acaccgacg   ctgcgggcgc  tcggcctcga  cgacgaccac
31861  atcgcctcgt  cccggagag   cggttcgt    gagcggttcg  ccgcgcgtac  cggggggcgg
31921  ggcgtcgacg  tggtcctgaa  ctcgctcacc  ggcgacctgc  tcgacgagtc  cgcgcggctg
31981  ctcgccgacg  gcggggtctt  cgtcgagatg  ggcaagaccg  acctgcgggcc ggcggagcag
32041  ttccggggcc  ggtacgtccc  gttcgacctg  ggccgaggcg  gtcccgatcg  gctcggcgag
32101  atcctggagg  aggtcgtcgg  tctgctggcc  gccggtgccc  tcgaccggtt  gccggtgtcg
32161  gtgtgggagt  tgtcggcgg   cccgccgcg   ctcacccaca  tgagccgggg  ccgacacgtg
32221  ggcaagctcg  tcctcaccca  gtgcaccccg  gtgcaccccg  acgaacggt   gctggtcacc
32281  ggcgggaccg  gcacccctggg ccggctggtc  gcccgccacc  tggtgaccgg  gcacggcgta
32341  cccaccctcc  tggtgccag   ccggcgcggt  ccggcgccc   cgggcgcgcgg cgagctgcgc
32401  gccgacgtcg  aaggcctcgg  cgcgaccatc  gagatcgtcg  cctgcgacac  cgccgaccgg
32461  gaggcgctcg  cggcgctgct  cgactcgatc  cccgcgatc   gtcacctcca  cggggtggtg
32521  cacaccgccg  gggtcctggc  cgacgggctg  cgacgcggcg  tggcacctgc  cgccaccgat
32581  caggtcctgc  gggccaaggt  cgagtacgtc  cgagcggcg   acgacctgac  ccggacgcg
32641  gacctgagct  tcttcgtgct  gttctcgtgt  gcgcgtcg    tgctggccgg  tcccggcag
32701  ggcggtacg   cggcggccaa  cgggtggggc  gcggccctgg  ccgggcaacg  gcgggccctc
32761  ggactgcccg  cgaaggcgct  cgggtggggc  ctgtggggcg  aggccagcga  gatgaccagc
32821  ggcctgcgtg  acccggatcgc ccgtaccggg  gtcgccgcgc  ccgacgatca  gcgggcgctg
32881  gcccctgttcg  acgcgctct  gcgcagcggc  ggggaggtgc  tgttcccgct  gtctgtcgac
32941  aggtcggcgc  tgcgccgggc  cgagtacgtc  cccgagggtgc tgcgcggcgc  ggtccggtcc
33001  acgccacggg  ccgccaacag  ggccgagacc  cccgagggcg  tgcgctgcga  ccgtctcgtc
33061  ggtgcaccccg agaccgatca  ggtggccgcg  ctggccgagc  gctggcgctc  gcacggcg
33121  gcggtcgccg  gctacgactc  ggccgaccag  ctgcccgaac  gcaaggcgtt  caaggacctc
```

*FIG. 7-47*

```
33181  gggttcgact  cgctggcggc  ggtggagctg  cgcaaccggc  tcggcgtcac  caccggcgta
33241  cggctgccca  gcacgctggt  gttcgaccac  ccgacaccgc  tggcggtggc  cgaacacctg
33301  cggtcggagt  tgttcgccga  ctccgcgccg  gacgtcgggg  tcggtgcgcg  cctcgacgac
33361  ctggaacggg  cgctcgacgc  cctgcccgac  gcgcaggac   acgccgacgt  cggggcccgc
33421  ctggaggcgc  tgctgcgccg  gtgcagagc   cgacgacccc  cggagaccga  gccagtgacg
33481  atcagtgacg  acgccagtga  cgacgagctg  ttctcgatgc  tcgacaggcg  tctcggcggg
33541  ggaggggacg  tctagtgac   aggtcgattc  cgcccgcgg   cagtggaccg  taccgccctg
33601  acaggtccac  cgggttcgcg  tcgcctccca  caccccgacg  ccggggtatc  cacggaaggg
33661  atccgatgag  cgagagcagc  ggcatgaccg  aggaccgcct  ccggcgctat  ctcaagcgca
33721  ccgtcgccga  actcgactcg  gtgacaggtc  ggctcgacga  ggtcgagtac  cggcccgcg
33781  aaccgatcgc  cgtcgtcggc  atggcctgcc  ggttccccgg  gggtgtggac  tcgccggagg
33841  cgttctggga  gttcatccgc  gacaggtgtg  acgcgatcgc  cgaggcgccc  acggaccgtg
33901  gctggccgcc  ggcaccgcg   cccccgcga   gtggtctcct  cgcggagccg  ggcgcgttcg
33961  acgccgcctt  cttcggcatc  tcacccccgg  agggcgctgc  gacgacccc   cagcagcgcc
34021  tgatgctgga  gatctcctgg  gaggcgttgg  agcgtgcggg  tttcgaccg   tcgagcctgc
34081  gcggcagcgc  cgaggaggtc  ttcaccggtg  tcggtgcggt  ggactacgga  cccaggccgg
34141  acgaggcacc  cgaggagttgg ctcggctacg  tcggcatcgg  caccgcctcc  agcgtcgcct
34201  ccggacgggt  ggcgtacacc  ctgggttgg   agggtccagc  cgtcaccgtc  gacaccgcct
34261  gctcctccgg  gctcaccgcg  gtgcaccctg  gtcaccgtga  cgatggagtc  gctgcgcgc  gacgagtgca
34321  ccctgtcct   cgccgtggg   gtcaccgtga  gtcaccgtga  gggtgcgttc  accgagttcc
34381  gcagccaggg  cgggtttggcc gaggacggcc  gctgcaaacc  gttctcccgc  gcgcgcgacg
34441  gcttcgggct  cgccgagggg  gccggaggcc  gctgtctcca  acggctgtcc  gtcgcccggg
34501  ccgagggccg  gccggtgctg  gccgtactgc  gtggctcggc  gtgctctgc   gatcaaccag  gacggtgcca
```

FIG. 7-48

```
34561  gcaacggct  caccgcgccg  agcggcccg  cccagcggcg  ggtgatcagg  caggcgttgg
34621  agcgggcgcg  gctgcgtccc  gtcgacgtgg  actacgtgga  ggcccacggc  accgcaccc
34681  ggctgggcga  tccgatcgag  cgcacgcgcc  tgctcgacac  gtacggtgcc  gaccggaac
34741  ccggccgccc  gctctgggtc  ggatcggtga  agtccaacat  cggtcacacc  caggcggcgg
34801  cggggtggc  cgggtgatg  aagaccgtgc  tggcgctgcg  gcatcggag  atccggcga
34861  cgttgcactt  cgacgagccc  cgaccgcacg  tcgccgcacg  ccggggtgcg  gtgtcggtgg
34921  tgtccgagac  ccggccctgg  cgactggga  tcgactggga  ccggcgggg  gtgtcctcgt
34981  tcggcatcag  cggcaccaac  gcgcccgcc  agcgcccgcc  ggcgccgagc  ccgcaggcgg
35041  ccgacctcga  cgcgaccccc  gcgcacgtca  tcgtcgagga  ggcccggaacg  gatgccgccc
35101  ccaccgcgca  gcgggtgcg  gaggcggtcg  cactggtgtt  ctccgcgcgc  gacgagcggg
35161  cctgcgcgc  ccaggcggcc  cgctcgcgcc  accgtctcac  accgacccg  gcccctcgt
35221  tgcgcgacac  cgccttcacc  ctggtcaccac  gccgtccac  ctgggagcat  cggcggtcg
35281  tcgtcggcgg  gggcgaggag  gtcctcgcg  gccctcgcg  gcctcgcggg  ggacgtccg
35341  tcgacggagc  cgtcagcgg  cgggcgccg  cgggcgccg  gtgtgctg  gtcttccccg
35401  ggcaggcgc  acagtggcag  ggcatggcc  gggaccgct  gcggcagtcg  ccgaccttcg
35461  cggagtccat  cgacgcctgc  gagcgggcgc  tcgccccgca  cgtggactgg  tcgctgcgcg
35521  aggtgctcga  cggcgagcag  tcgttggacc  ccgtcgacgt  ggtgcagccg  gtgctgttcg
35581  cggtgatggt  gtcgttggcg  cggttgtggc  ccgttgtggc  gtgactccg  gtgcggtgg
35641  tgggtcactc  gcaggggag  atccgccagc  agtcgtacgg  cgcacgtggc  tcgttggcg
35701  acgccgccag  gttggtggcg  ttgcgcagcc  gggtgctgcg  gggtgctgcg  ggtcacgccg
35761  ggatggcgtc  gttcgggctc  caccccgacc  aggccgcgca  gcggatcgcg  gcttcgcgg
35821  gtgcgctgac  tgtcgcctcg  gtcaacggtc  cccgttcggt  ggtgctggcc  ggggagaacg
35881  gcccgttgga  cgagctgatc  cgagctgatc  aggccgaggg  cgtgaccgcc  cgtcggatcc
```

*FIG. 7-49*

```
35941 ccgtcgacta cgcctcacac tccccgcagg tggagtcgct gcgtgaggag ctgctcgccg
36001 cactggcgg  ggtccgtccg gtgtcggccg ggatccccct gtactcgacc ctgaccggtc
36061 aggtcatcga aacggcgacg atggacgccg actactggtt cgccaacctc cgggagccgg
36121 tgcgcttcca ggacgccacc agcagctcg  ccgaggccgg gttcgacgcc ttcgtcgagg
36181 tcagcccgca cccggtgttg acagtcggtg tcgaggccac cctcgaggca gtgctgcccc
36241 ccgacgcgga tccgtgtgtc acaggcaccc tgcgccgcga acgggcggt  ctcgcgcagt
36301 tccacacggc gctcgccgag gcgtacaccc gggggtgga  ggtcgactgg cgtaccgcag
36361 tgggtgaggg acgcccggtc gacctgccgg tctacccgtt ccaacgacag aacttctggc
36421 tcccgtcccc cctggccgg  gtccccgaca cggccgacga gtgcgttac  cagctcgcct
36481 gcaccccgt  cgaccttcgg cggtcctccc tggccgacg  ggtcctggtg gtgaccggag
36541 cggcagtacc cccgcctgg  acggacgtgg tccgcgacg  cctggaacag cgcgggcga
36601 ccgtcgtgtt gtgcaccact cagtcgccgc cccgatcgg  cgccgagggc gacgccgtcg
36661 acggcaccgc cctgtccact gtggtctctc tgctcgcgct cgccgaggc  ggtgctgtcg
36721 acgaccccag cctggacacc ctggtcggtg tccaggcgct cgtcggagac gggatcgacg
36781 tccccctgtg gctggtgacc agggacgccg ccgcgtgac  cgtggagtcc cccgcgatc
36841 cggcccaggc catggtcggt gggctcggcc gggtggtggg cgtgggcgg  ctggccgccg
36901 ggggtgcct  ggtggacctg cgcgaggccg gaggagcagt acgccgactc gccccggtcg
36961 tactggccga cccgcgcggc gaggagcagt gccgacgcgg gccccgacgg gtcaccgtcg
37021 cccgtctcgt cccggcacc  cccgcgcgg  cggtacccgg gccacgcgcg cgcggaccg
37081 tcctggtcac cggcggcatc gcgcgcacct ggacgcctgg ggccgcctgg ctcgccggtg
37141 cgggcgcga  gcacctggtg ctgctcaaca ggcgggagc  ggaggcggcc gttgccgccg
37201 acctgcgtga cgaactggtc gcgctcggca cgggagtcac catcacggcc tgcgacgtcg
37261 ccgaccgcga ccggttggcg ccgtcctcg  gcgtcctcg  acgccgcacg ggcgcagga  cggtggtca
```

FIG. 7-50

```
37321  cggcggtgtt  ccacgccgcc  gggatctccc  ggtccacagc  ggtacaggag  ctgaccgaga
37381  gcgagttcac  cgagatcacc  gacgcgaagg  tgcggggtac  ggcgaacctg  gccgaactct
37441  gtcccgagct  ggacgccctc  gtgctgttct  cctcgaacgc  ggcggtgtgg  ggcagccgg
37501  ggctggcctc  ctacgcggcg  ggcaacgcct  tcctcgacgc  ggcgggcccgt  cgtggtcggc
37561  gcagtggct   gccggtcacc  tcgatcgcct  gggtctgtg   ggccgggcag  aacatggccg
37621  gtaccgaggg  cggcgactac  ctgcgcagcc  agggcctgcg  cgccatggac  ccgcagcggg
37681  cgatcgagga  gctgcggacc  acccgtgcg   gtgggtgtcg  gtggtggacc
37741  tggaccggga  gcggttcgtc  gaactgttca  ccgggaccg   cgccggcc    ctcttcgacg
37801  aactcggtgg  ggtccgcgcc  ggggccgagg  agaccggtca  ggaatcggat  ctcgcccggc
37861  ggctggcgtc  gatgccggac  gccgaacgtc  acgagcatgt  cgcccggctg  gtccgagccg
37921  aggtggcagc  ggtgctgggc  cacggcacgc  cgacggtgat  cgagcgtgac  gtcgccttcc
37981  gtgacctggg  attcgactcc  atgaccgccg  tcgacctgcg  gaaccggtc   gcggcggtga
38041  ccgggtccgg  ggtggccacg  accatcgtct  tcgaccaccc  gacagtggac  cgcctcaccg
38101  cgcactacct  ggaacgactc  gtcggtgagc  cggaggcgac  gaccccggct  gcggcggtcg
38161  tcccgcaggc  accgggggag  gccgacgagc  cgatcgcgat  cgtcgggatg  gcctgccgcc
38221  tcgccggtgg  agtgcgtacc  cccgaccagt  tgtgggactt  catcgtcgcc  gacggcgacg
38281  cggtcaccga  gatgcgtcg   gaccgtccg   ggacctcga   cgcgctgttc  gacccgacc
38341  ccgagcggca  cggcaccagc  gacccgtcct  tactcccggc  acggcgcgtt  cctggacggg  gcggccgact
38401  tcgacgcggc  gttcttcggg  atctcgcccg  gtgacgctgt  acggcgcgtt  ggcgatggat  ggcagcagc
38461  ggcaggtcct  ggagacgacg  tgggagctgt  tcgagaacgc  ggcatcgac   ccgcactccc
38521  tgcgcggtac  ggacaccggt  gtcttcctcg  gcgctgcgta  ccaggggtac  ggccagaacg
38581  cgcaggtgcc  gaaggagagt  tgctcaccgg  tgctcaccgg  tggttcctcg  gcggtcgcct
38641  ccggtcggat  cgcgtacgtg  ttggggttgg  agggccggc   gatcactgtg  gacacggcgt
```

FIG. 7-51

```
38701  gttcgtcgtc  gcttgtggcg  ttgcacgtgg  cggccgggtc  gctgcgatcg  ggtgactgtg
38761  ggctcgcggt  ggcggtggg   gtgtcggtga  tgccggtcc   ggaggtgttc  accgagttct
38821  ccaggcaggg  cgcgctggcc  cccgacggtc  ggtgcaagcc  cttctccgac  caggccgacg
38881  ggttcggatt  cgcgaggc   gtcgctgtgg  tgctcctgca  gcggttgtcg  gtggcggtgg
38941  gggaggggcg  tcgggtgttg  ggtgtggtgg  tgggttcgc   ggtgaatcag  gatgggcg
39001  gtaatgggtt  ggcgcgcccg  tcggggtgg   cgcagcagcg  ggtgattcgg  cgggcgtggg
39061  gtcgtgcggg  tgtgtcggt   gtgtggtgga  gtgtggtgg   ggcgcatggg  acggggacgc
39121  ggttgggga   tccggtggag  ttgggggcgt  tgttggggac  gtatggggtg  ggtcggggtg
39181  gggtggtcc   ggtggtgtg   ggttcggtg   aggcgaatgt  gggtcatgtg  caggcggcgg
39241  cgggtgtggt  gggtgtgatc  aaggtggtgt  tgggtttggg  gtggggttg   gtgggtccga
39301  tgggtgggt   gggtgggttg  tcgggtggtc  tcgggtggg   tcggggtggg  ttggttggtc
39361  cggatgggg   gcgggggtg   ccggtggggg  tggatgggt   gcgtcggggt  gcgggggcgt
39421  cgtttggggt  gtcggggacg  aatgctcatg  tggtggtgc   ggaggcgccg  gggtcggtgg
39481  tgggggcgga  acgccgggtg  gaggggtt   cgcgggggtt  ggtggggtg   gctggtgtg
39541  tggtgccggt  ggtgctgtcg  gcaaagaccg  gacccgccct  gaccgagctc  gcccgacgac
39601  tgcacgcgc   cgtcgacgac  accgtcgcc   tcccggcggt  ggccgccacc  ctcgccaccg
39661  gacgcgccca  cctgccctac  cggcccgcgc  tgcctggccg  cgaccacgac  gaactgcgcg
39721  acaggctgcg  ggcgttcacc  actggttcgg  cggccgtcgg  tgtgtggtcg  ggggcggt
39781  cgggtggtgg  tgtggtgtt   gtttttcctg  gtcagggtg   tcagtgggtg  gggatggcgc
39841  gggggttgtt  gtcggttgtg  agtcggttgg  ggagtggtgat  ggagtgtgat  gcggttgtgt
39901  cgtcggtggt  gggggttcg   gtgttgggg   tgttggaggg  tcggtggt   gcgccgtcgt
39961  tggatcgggt  cagccggtg   tgttcgtggt  gttcgtggt   gatggtgtcg  ttggcgggt
40021  tgtggcggtg  gtgtgggtt   gtgcctgcgc  cggtggtggg  tcattcgcag  gggagatcg
```

FIG. 7-52

```
40081  cggcggcggt  ggtggcgggg  gtgttgtcgg  tgggtgatgg  tgcgcgggtg  gtggcgttgc
40141  gggcgcgggc  gttgcggcg   ttggccggcc  acggcggcat  ggtctccctc  gcggtctccg
40201  ccgaacgcgc  ccggagctg   atcgcaccct  ggtccgaccg  gatctcggtg  gcggcggtca
40261  actccccgac  ctcggtggtg  gtctcgggtg  acccacaggc  cctcgccgcc  ctcgtcgccc
40321  actgcgccga  gaccggtgag  cgggccaaga  cgctgcctgt  ggactacgcc  tcccactccg
40381  cccacgtcga  acagatccgc  gacacgatcc  tcaccgacct  ggccgacgtc  acggcgcgcc
40441  gacccgacgt  cgccctctac  tccacgctgc  acggcgcccg  gggcgccggc  acggacatgg
40501  acgcccggta  ctggtacgac  aacctgcgct  cacccggtcg  cttcgacgag  gccgtcgagg
40561  ccgccgtcgc  cgacggctac  cgggtcttcg  tcgagatgag  cccacacccg  gtcctcaccg
40621  ccgcggtgca  ggagatcgac  gacgagacgg  tggccatcgg  ctcgctgcac  cggacaccg
40681  gcgagcggca  cctgtcgcgcc  gaactcgcgc  gggccacgt   gcacggcgta  ccagtggact
40741  ggcgggcgat  cctcccccgcc  acccaccgg  ttcccctgcc  gaactaccg  ttcgaggcga
40801  cccggtactg  gctcgcccccg  acgcggccg  accaggtcgc  cgaccaccgc  taccgcgtcg
40861  actggcggcc  cctgccacc   acccggccgg  agctgtccgg  cagctacctc  gtcttcggcg
40921  acgccccga   gacccggtcc  cacagcgtcg  agaaggccgg  cgggctcctc  gtcccggtgg
40981  ccgctcccga  ccggagtcc   ctcgcggtcg  ccctggacga  ggcggccgga  cgactcgccg
41041  gtgtgctctc  cttcgccgcc  gacacgcgcca  ccccaccttggc  ccggcaccga  ctccctcggcg
41101  aggccgacgt  cgaggcccca  ctctgcctgg  tcaccagcgg  cggcgtcgca  ctcgacgacc
41161  acgaccgat   cgactgcgac  caggcaatgg  tgtggggggat  cggacgggtg  atgggtctgg
41221  agacccccgca  ccggtggggc  ggcctggtgg  acgtgaccgt  cgaacccacc  gccgaggacg
41281  gggtggtctt  cgccgccctc  ctggccgccg  acgaccacga  ggaccaggtg  gcgctgcgcg
41341  acggcatccg  ccacgccga   cggcctcgtcc  gcccccgct   gaccaccgg   aacgccaggt
41401  ggacaccggc  gggcacgcg   ctcgtcacgg  gcggtacggg  tgccctcggc  ggccacgtcg
```

FIG. 7-53

```
41461  cgcggtacct  ggcccggtcc  ggggtgaccg  atctcgtcct  gctcagcagg  agcggcccg
41521  acgcaccgg   tgccgccgaa  ctggccgccg  aactggccga  cctcgggcc   gagccgagag
41581  tcgaggcgtg  cgacgtcacc  gacggccac   gcctgcgcgc  cctggtgcag  gagctacggg
41641  aacaggaccg  gccggtccgg  atcgtcgtcc  acaccgcagg  ggtgcccgac  tcccgtcccc
41701  tcgaccggat  cgacgaactg  gagtcggtca  gcgccgcgaa  ggtgaccggg  gcgcggctgc
41761  tcgacgagct  ctgcccggac  gccgacacct  tcgtcctgtt  ctcctcgggg  gcgggagtgt
41821  ggggtagcgc  gaacctgggc  gcgtacgcgg  cagccaacgc  ctacctggac  gccctggccc
41881  accgccgccg  ccaggcgggc  cgggccgcga  cctcgtcgc   ctggggggcg  tgggccggcg
41941  acggcatggc  caccgggcg   ctcgacgggc  cctcgacggc  cggtctgcgg  gcgatggcac
42001  cggaccggc   gctgcgcgc   tgcaccagc   gttggaccac  ccacgacacc  tgtgtgtcgg
42061  tagccgacgt  cgactgggac  cgcttcgccg  tgggtttcac  cgccgcccgg  cccagaccc
42121  tgatcgacga  actcgtcacc  tccgcgccg   tggccgcccg  caccgctgcg  gcggcccgg
42181  tccggcgat   gaccgccgac  cagctactcc  agttcacgcg  caccgcgcg   gccgcgatcc
42241  tcggtcacca  ggaccgccgg  gcggtcgggt  tggaccgag   cttcaccgag  ctggcttcg
42301  actcgctcac  cgccgtcggc  ctgcgcaacc  agctccagca  ggccaccggg  cggacgctgc
42361  ccggcctccc  ggtgttccag  caccccacgg  tacgcagact  cgccgaccac  ctcgcgcagc
42421  agctcgacgt  cggcaccgcc  cgtgttccag  cgacgggcag  cgtcctgcgg  gacggctacc
42481  ggcggccgg   gcagaccggc  gcacgccgt   gacgtccggt  cctgctggcg  aacctgtcgg
42541  agttccggga  gcggttcacc  gacgggcga   cgtacctgga  acagctggaa  ctcgtcgacc
42601  tggccgacgg  atccggcccg  gtcactgtga  tctgtgttgc  gggcactgcg  gcgctctccg
42661  ggccgcacga  gttcgcccga  ctcgccgg    cgctgccgg   caccgtgccg  gtgcgcgccc
42721  tcgcgcaacc  cgggtacgag  gcgggtgaac  gtcgatggag  gtcgatgag   gcagtgctcg
42781  gggtgcaggc  ggacgcggtc  ctcgcggcac  agggcgacac  gccgttcgtg  ctggtcggac
```

*FIG. 7-54*

```
42841  actcggcggg  ggccctgatg  gcgtacgccc  tggcgaccga  gctggccgac  cggggccacc
42901  cgccacgtgg  cgtcgtgctc  ctcgacgtgt  acccaccgag  tcaccaggag  gcgtgcacg
42961  cctggctcgg  cgagctgacc  gccgccctgt  tcgaccacga  gaccgtacgg  atggacgaca
43021  cccggctcac  ggccctgggg  gcgtacgaca  ggctgaccgg  caggtgcgt  ccgagggaca
43081  ccggtctgcc  cacgctggtg  gcgtgccgca  gcgagccgat  ggggagtgg  ccgacgacg
43141  gttggcagtc  cacgtggccg  ttcgggcacg  acaggtcac  ggtgccggt  gaccacttct
43201  cgatggtgca  ggagcacgcc  gacgcgatcg  cgacgcacat  cgacgcctgg  ttgagcgggg
43261  agagggcatg  aacacgaccg  atcgcgccgt  gctgggccga  cgactccaga  tgatccgggg
43321  actgtactgg  ggttacggca  gcaacggaga  cccgtacccg  atgctgttgt  gcgggcacga
43381  cgacgaccg  caccgctggt  accggggct  gggcggatcc  ggggtccggc  gcagccgtac
43441  cgagacgtgg  gtggtgaccg  accacgccac  cgccgtgcgg  gtgctcgacg  acccgacctt
43501  caccgccgcc  acggccggga  cgccggagtg  gatgcgggcc  gcgggccc  cggcctcgac
43561  ctgggcgcag  ccgttccgtg  acgtgcacgc  cgcgcacgc  gatcgcacgc  tgccgaac
43621  gcaggaggtg  gaggaccggc  ccgccgtct  tgacgggtct  cctgcctgcc  gcctggacct
43681  ggtccgcgac  ctcgcctggc  cgatgcgtc  cgggggtc  cggggaccc  acccgacct
43741  gctgcgcgcc  gcgtgggacg  ctcggccgg  ccttcgacgcc  ggcgggacg  cgagccct
43801  ggcggtgacc  gagcggcga  tcgaccgcgt  cccggtcgg  gccggggac  gggcgctgtt
43861  caccgccgtc  gagatgacag  ccaccgcgtt  cgtcgcgcgg  gtgctggcgg  tgaccgccac
43921  ggcggggcg  gcccagcgt  tcgccgcgtc  cccggccgtc  gccgccgtc  tcgtcgcgga
43981  ggtgctgcgc  gccatcgcga  gccatccga  ggaacgcaca  accgccggca  ccgagacggt
44041  ggtgggcgag  cacacggtcg  cggcgcacg  cgcgcgtcg  gtggtgtcg  ccgccgccaa
44101  ccgtgacgcg  gggtcttcg  ccgaccgcg  ccgacccgga  ccgcctcgac  ccgacgcga
44161  ccggccctg  tcgcccagc  gcggtcaccc  gcggtcaccc  gaggagctgg  tggtggtcct
```

```
44221  gaccaccgcc  gcactgcgca  gcgtcgccaa  ggcgctgccc  ggtctcaccg  ccggtggccc
44281  ggtcgtcagg  cgacgtcgtt  caccggtcct  gcgagccacc  gcccactgcc  cggtcgaact
44341  ctgaggtgcc  tgcgatgcgc  gtcgtcttct  cctccatggc  cagcaagagc  cacctgttcg
44401  gtctcgttcc  cctcgcctga  gccttccgcg  cggcgggcca  cgaggtacgg  gtcgtcgcct
44461  caccgcttct  caccgacgac  atcacgcgcg  cccggactga  ggccgtaccg  gtcggcaccg
44521  acgtcgacct  tgtcgacttc  atgaccacg   ccgggtacga  catcatcgac  tacgtcgca
44581  gcctggactt  cagcgagcgg  gacccggcca  ccggtacga   ggaccacctg  ctcggcatgc
44641  agaccgtcct  caccccgacc  ttctacgccc  cctccacctg  ggactcgctg  gtcgaggca
44701  tgatctcctt  ctgtcggtcg  tggcgaccg   actggtcgtc  tggaccgcag  accttcgccg
44761  cgtcgatcgc  ggcgacggtg  accggcgtgg  cccacgcccg  actcctgtgg  ggacccgaca
44821  tcacggtacg  ggcccggcag  aagttcctcg  gctgctgcc   cggacagccc  gccgcccacc
44881  gggaggaccc  cctcgccgag  tggctcacct  ggtctgtgga  gaggttcggc  ggccggggtgc
44941  cgcaggacgt  cgaggagctg  gtggtcgggc  agtgacgat   cgacccgcc   ccggtcggga
45001  tgcgcctcga  caccgggctg  aggacggtgg  gcatgcgcta  cgtcgcgcg   aacggcccgt
45061  cggtggtgcc  ggactggctg  cacgacgagc  cgaccccgcg  acgggtctgc  ctcaccctgg
45121  gcatctccag  ccgggagaac  agcatcgggc  aggtctccgt  cgacgacctg  ttgggtgcgc
45181  tcggtgacgt  cgacgccgag  atcatcgga  cagtgacgtcg  gcagcagctc  gaaggcgtcg
45241  cccacgtccc  ggccaacatc  cgtacggtcg  ggttcgtccc  cggagcagca  ctgctgccga
45301  cctgcgcggc  gacggtgcac  cacggcgcct  cccgacgctg  gcacaccgcc  gccatccacg
45361  gcgtgccgca  ggtgatcctg  cccgacggct  gggacaccgg  gtccgcgcc   cagcggaccg
45421  aggaccaggg  ggcgggcatc  gccctgccgg  tgcccgagct  gacctccgac  cagctccgcg
45481  aggcggtgcg  gcgggtcctg  gacgatcccg  cctttcaccgc  cggtgcggcg  cggatgcggg
45541  ccgacatgct  cgccgagccg  tcccccgccg  aggtcgtcga  cgtctgtgcg  gggctggtcg
```

FIG. 7-56

```
45601  gggaacggac  cgccgtcgga  tgagcaccga  cgccacccac  gtccggctcg  gccggtgcgc
45661  cctgctgacc  agccggctct  ggctgggtac  ggcagccctc  gccggccagg  acgacgccga
45721  cgcagtacgc  ctgctcgacc  acgcccgttc  ccggggcgtc  aactgcctcg  acaccgccga
45781  cgacgactct  gcgtcgacca  gtgcccaggt  ccggcgagga  tcggtcggcc  ggtggttggc
45841  cgggacacc   ggtcgcggg   aggagaccgt  cctgtcgtg   acggtgggtg  tcccaccggg
45901  cggcaggtc   ggcggggcg   gcctctccgc  ccggcagatc  atcgcctcct  gtgagggctc
45961  cctgcgcgt   ctcggtgtcg  accacgtcga  cgtccttcac  ctgccccggg  tggaccgggt
46021  ggagccgtgg  gacgaggtct  ggcaggcggt  ggacgccctc  gtggccgccg  gaaaggtctg
46081  ttacgtcggg  tcgtcgggct  tccccggatg  gcacatcgtc  gccgcccagg  agcacgccgt
46141  ccgccgtcac  cgccctcggc  tggtgtccca  ccagtgtcgg  tacgacctga  cgtcgcgcca
46201  tcccgaactg  gaggtcctgc  ccgcgcgca   ctcgggtcggg ctcgggtct   tcgccaggcc
46261  gacccgcctc  ggcggtctgc  tcggcggcga  cggtccgggc  gccgcagccg  cacggcgtc
46321  gggacagccg  acggcactgc  gctcggcggt  ggaggcgtac  gaggtgttct  gcagagacct
46381  cggcgagcac  cccgccgagg  tcgcactggc  gtgggtgctg  tcccggcccg  gtgtgcggg
46441  ggcggtcgtc  ggtgcgcgga  cgcccggacg  gctcgactcc  gcgctccgcg  cctgcggcgt
46501  cgccctcggc  gcgacggaac  tcaccgccct  ggacgggatc  ttccccgggg  tcgccgcagc
46561  aggggcggc   ccggaggcgt  ggctacggtg  agagcccgcc  cctgacctgc  gggaacccgt
46621  gtcggtgcgg  cggacgggcc  gcccggtcc   cgcccccgt   cagccggtgg  gggtgagccg
46681  cagcaggtcc  ggccaccacg  actcggccac  ctccccgacg  tggtcggcga  ggtagaagtg
46741  cccgcccggg  aaggtccggg  tacgccgggg  gactaccgag  taggcagcc   agcgttgggc
46801  gtcctccacc  gtcgtcaacg  ggtcggtgtc  accgcagagg  gtggtgatgc  cggcccgcag
46861  cggcggcccg  gcctgccagg  cgtaggagcg  cagcacccgg  tggtcggccc  gcagcaccgg
46921  cagcgacatg  tccaacagcc  cctggtcggc  caatgcgggc  tcgctgaccc  cgagcctgcg
```

*FIG. 7-57*

```
46981 catctgctcg acgagtccgt cctcgtcggg caggtcggtg cgccgctcgt ggacccgggg
47041 ggcggtctgc ccggagacga acaaccgcag cggtcgcacc cccgacgag cctccaggcg
47101 acgggcggtc tcgtaggcga ccagggcgcc catgctgtga ccgaacaggg cgaacggaac
47161 ctcgccgacg agtcgcgca gcacggccgc gacctcgtcg gcgatctccc cggcggtgcc
47221 gagagcccgc tcgtcacgtc ggtcctgccg gcccggtac tgcaccgccc acacgtcgac
47281 ctccggggcc agtgcccggg cgaggtcgag gtacgagtcg gcggcggctc ccgcgtgcgg
47341 gaagcagtac agccgggccc ggtgtccgtc ggcggacccg aaccgccgca accaggtgtt
47401 catcggtgtc tcatccgttc ggtcgcaccg gcaggtggtc gatgccgcgc agcaggagcg
47461 accgcccgcca gacaacctcg tcggagggga gcccagcga cagcttcggg aagcggtcga
47521 acaggccccc cagggcgacc tctccctcca gcttggccag cgggcggccc atgcagtagt
47581 ggatgccgtg cccgaaggtg aggtgtccct ggctgtccct ggtgacgtcg aaccggtcgg
47641 ggtcgggga ctgtcccggg tcgcggttgg ccgcccccgtt ggcgatcagg acggtgctgt
47701 acgccgggat cgtcacccg ccgatctcca cctcggcggt ggcgaaccgg gtggtggtct
47761 ccggtgggc ctggtagcgc aggatctcct ccaccgctcc gggcagcagt gccgggtcct
47821 tccggaccag cgcgagctgg tcggggtggg tcagcagcag gtaggtgccg atcccgatga
47881 ggctcaccga cgcctcgaat cccgccagca gcagcaccag cgcgatggat gtgagttcgt
47941 cgcggctgag ccggtcggcg tcgtcgtcct ggacccggat c
                           (SEQ ID NO: 1)
```

FIG. 7-58

RECOMBINANT MEGALOMICIN BIOSYNTHETIC GENES AND USES THEREOF

CROSS-REFERENCE TO PRIORITY APPLICATION

This application claims priority to provisional U.S. patent application Serial No. 60/158,305, filed Oct. 8, 1999, and provisional U.S. patent application Serial No. 60/190,024, filed Mar. 17, 2000 under 35 U.S.C. §119(e). The content of the above referenced applications is incorporated herein by reference in its entirety.

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, megalomicin, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; and 5,712,146; Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes.

Modular PKSs are responsible for producing a large number of 12-, 14-, and 16-membered macrolide antibiotics including erythromycin, megalomicin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. The polyketide metabolites; E. Horwood: New York, 1991, incorporated herein by reference).

During the past half decade, the study of modular PKS function and specificity has been greatly facilitated by the plasmid-based Streptomyces coelicolor expression system developed with the 6-deoxyerythronolide B (6-dEB) synthase (DEBS) genes (see Kao et al., 1994, Science, 265: 509–512, McDaniel et al., 1993, Science 262: 1546–1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, Saccharopolyspora erythraea, allows more facile construction of recombinant PKSs, and reduces the complexity of PKS analysis by providing a "clean" host background. This system also expedited construction of the first combinatorial modular polyketide library in Streptomyces (see PCT publication No. WO 98/49315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, Curr. Opin. Microbiol. 1: 319–329; Carreras and Santi, 1998, Curr. Opin. Biotech. 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

Megalomicin is a macrolide antibiotic produced by Micromonospora megalomicea, a member of the Actinomycetales family of soil bacteria that produces many types of biologically active compounds. Megalomicin is a glycoside of erythromycin A, a widely used antibacterial drug with little or no antimalarial activity. Megalomicin has antibacterial properties similar to those of erythromycin, and in 1998, it was discovered also to have potent antiparasitic activity and low toxicity. The antiparasitic activity may be related to the effect megalomicin has on protein trafficking in eukaryotes, where it appears to inhibit vesicular transport between the medial and trans-Golgi, resulting in undersialylation of proteins. Hence, megalomicin offers an exciting opportunity to develop a new class of antiparasitic drugs with a different mechanism of action than the drugs currently in use and, therefore, possibly active against drug-resistant forms of Plasmodium falciparum.

The number and diversity of megalomicin derivatives have been limited due to the inability to manipulate the PKS genes, which have not previously been available in recombinant form. Genetic systems that allow rapid engineering of the megalomicin biosynthetic genes would be valuable for creating novel compounds for pharmaceutical, agricultural, and veterinary applications. The production of such compounds could be more readily accomplished if the heterologous expression of the megalomicin biosynthetic genes in Streptomyces coelicolor and S. lividans and other host cells were possible. The present invention meets these and other needs.

SUMMARY OF THE INVENTION

The present invention provides recombinant methods and materials for expressing PKS enzymes and polyketide modification enzymes derived in whole and in part from the megalomicin biosynthetic genes in recombinant host cells. The invention also provides the polyketides produced by such PKS enzymes. The invention provides in recombinant form all of the genes for the proteins that constitute the complete PKS that ultimately results, in *Micromonospora megalomicea,* in the production of megalomicin. Thus, in one embodiment, the invention is directed to recombinant materials comprising nucleic acids with nucleotide sequences encoding at least one domain, module, or protein encoded by a megalomicin PKS gene. In one preferred embodiment of the invention, the DNA compounds of the invention comprise a coding sequence for at least one and preferably two or more of the domains of the loading module and extender modules 1 through 6, inclusive, of the megalomicin PKS.

In one embodiment, the invention provides a recombinant expression vector that comprises a heterologous promoter positioned to drive expression of one or more of the megalomicin biosynthetic genes. In a preferred embodiment, the promoter is derived from another PKS gene. In a related embodiment, the invention provides recombinant host cells comprising one or more expression vectors that produce(s) megalomicin or a megalomicin derivative or precursor. In a preferred embodiment, the host cell is *Streptomyces lividans* or *S. coelicolor.*

In another embodiment, the invention provides a recombinant expression vector that comprises a promoter positioned to drive expression of a hybrid PKS comprising all or part of the megalomicin PKS and at least a part of a second PKS. In a related embodiment, the invention provides recombinant host cells comprising the vector that produces the hybrid PKS and its corresponding polyketide. In a preferred embodiment, he host cell is *Streptomyces lividans* or *S. coelicolor.*

In a related embodiment, the invention provides recombinant materials for the production of libraries of polyketides wherein the polyketide members of the library are synthesized by hybrid PKS enzymes of the invention. The resulting polyketides can be further modified to convert them to other useful compounds, such as antibiotics, motilides, and antiparasitics, typically through hydroxylation and/or glycosylation. Modified macrolides provided by the invention that are useful intermediates in the preparation of antiparasitics are of particular benefit.

In another related embodiment, the invention provides a method to prepare a nucleic acid that encodes a modified PKS, which method comprises using the megalomicin PKS encoding sequence as a scaffold and modifying the portions of the nucleotide sequence that encode enzymatic activities, either by mutagenesis, inactivation, deletion, insertion, or replacement. The thus modified megalomicin PKS encoding nucleotide sequence can then be expressed in a suitable host cell and the cell employed to produce a polyketide different from that produced by the megalomicin PKS. In addition, portions of the megalomicin PKS coding sequence can be inserted into other PKS coding sequences to modify the products thereof.

In another related embodiment, the invention is directed to a multiplicity of cell colonies, constituting a library of colonies, wherein each colony of the library contains an expression vector for the production of a modular PKS derived in whole or in part from the megalomicin PKS. Thus, at least a portion of the modular PKS is identical to that found in the PKS that produces megalomicin and is identifiable as such. The derived portion can be prepared synthetically or directly from DNA derived from organisms that produce megalomicin. In addition, the invention provides methods to screen the resulting polyketide and antibiotic libraries.

The invention also provides novel polyketides, motilides, antibiotics, antiparasitics and other useful compounds derived therefrom. The compounds of the invention can also be used in the manufacture of another compound. In a preferred embodiment, the compounds of the invention are formulated in a mixture or solution for administration to an animal or human.

In a specific embodiment, the invention provides an isolated nucleic acid fragment comprising a nucleotide sequence encoding a domain of megalomicin polyketide synthase (PKS) or a megalomicin modification enzyme. The isolated nucleic acid fragment can be a DNA or a RNA. Preferably, the isolated nucleic acid fragment is a recombinant DNA compound.

The isolated nucleic acid fragment can comprise a single, multiple or all the open reading frame(s) (ORF) of the megalomicin PKS or a megalomicin modification enzyme. Exemplary ORFs of megalomicin PKS include the ORFs of the megAI, megAII and megAIII genes. The isolated nucleic acid fragment can also encode a single, multiple, or all of the domains of the megalomicin PKS. Exemplary domains of the megalomicin PKS include a TE domain, a KS domain, an AT domain, an ACP domain, a KR domain, a DH domain and an ER domain. In a preferred embodiment, the nucleic acid fragment encodes a module of the megalomicin PKS. In another preferred embodiment, the nucleic acid fragment encodes the loading module, a thioesterase domain, and all six extender modules of the megalomicin PKS.

Megalomicin modification enzymes include those enzymes involved in the conversion of 6-dEB into a megalomicin such as the enzymes encoded by the megE, meg BV, megCIII, megK, megDI and megG (renamed megY) genes. Megalomicin modification enzymes also include those enzymes involved in the biosynthesis of mycarose, megosamine or desosamine, which are used as biosynthetic intermediates in the biosynthesis of various megalomicin species and other related polyketides. The enzymes that are involved in biosynthesis of mycarose, megosamine or desosamine are described in FIGS. 5 and 10.

In a preferred embodiment, the invention provides an isolated nucleic acid fragment which hybridizes to a nucleic acid having a nucleotide sequence set forth in the SEQ. ID NO:1, under low, medium or high stringency. More preferably, the nucleic acid fragment comprises, consists or consists essentially of a nucleic acid having a nucleotide sequence set forth in the SEQ. ID NO:1.

In another specific embodiment, the invention provides a substantially purified polypeptide, which is encoded by a nucleic acid fragment comprising a nucleotide sequence encoding a domain of megalomicin polyketide synthase (PKS) or a megalomicin modification enzyme. The polypeptide can comprise a single domain, multiple domains or a full-length megalomicin PKS or megalomicin modification enzyme. Functional fragments, analogs or derivatives of the megalomicin PKS or megalomicin modification enzyme polypeptides are also provided. Preferably, such fragments, analogs or derivatives can be recognized by an antibody raised against a megalomicin PKS or megalomicin modification enzyme. Also preferably, such fragments, analogs or derivatives comprise an amino acid sequence that has at least 60% identity, more preferably at least 90% identity, to their wild type counterparts.

In still another specific embodiment, the invention provides an antibody, or a fragment or derivative thereof, which immuno-specifically binds to a domain of megalomicin polyketide synthase (PKS) or a megalomicin modification enzyme. The antibody can be a monoclonal or polyclonal antibody or an antibody fragment. Preferably, the antibody is a monoclonal antibody.

In yet another specific embodiment, the invention provides a recombinant DNA expression vector comprising the recombinant DNA compound encoding at least a domain of the megalomicin PKS or a megalomicin modification enzyme, wherein said domain is operably linked to a promoter. Preferably, the recombinant DNA expression vector further comprises an origin of replication or a segment of DNA that enables chromosomal integration.

In yet another specific embodiment, the invention provides a recombinant host cell comprising the above-described recombinant DNA expression vector encoding at least a domain of megalomicin PKS or the megalomicin modification enzyme. The recombinant host cells can be any suitable host cells including animal, mammalian, plant, fungal, yeast, and bacterial cells. Preferably, the recombinant host cells are Streptomyces cells, such as *Streptomyces lividans* and *S. coelicolor* cells, or ccharopolyspora cells, such as *Saccharopolyspora erythraea* cells. Also preferably, the recombinant host cells do not produce megalomicin in their untransformed, non-recombinant state.

When the recombinant host cell contains nucleic acid encoding more than one megalomicin PKS or megalomicin modification enzyme, or domains thereof, such nucleic acid material can be located at a single genetic locus, e.g., on a single plasmid or at a single chromosomal locus, or at different genetic loci, e.g., on separate plasmids and/or chromosomal loci. In one example, the invention provides a recombinant host cell, which comprises at least two separate autonomously replicating recombinant DNA expression vectors, and each of said vectors comprises a recombinant DNA compound encoding a megalomicin PKS domain or a megalomicin modification enzyme operably linked to a promoter. In another example, the invention provides a recombinant host cell, which comprises at least one autonomously replicating recombinant DNA expression vector and at least one modified chromosome, each of said vector(s) and each of said modified chromosome comprises a recombinant DNA compound encoding a megalomicin PKS domain or a megalomicin modification enzyme operably linked to a promoter. Preferably, the autonomously replicating recombinant DNA expression vector and/or the modified chromosome further comprises distinct selectable markers.

In a preferred embodiment, the cell comprises three different vectors, one of which is integrated into the chromosome and two of which are autonomously replicating, and each of the vectors comprises a meg PKS gene. Optionally, one or more of the meg PKS genes contains one or more domain alterations, such as a deletion or substitution of a meg PKS domain with a domain from another PKS.

In yet another specific embodiment, the invention provides a hybrid PKS, which is produced from a recombinant gene that comprises at least a portion of a megalomicin PKS gene and at least a portion of a second PKS gene for a polyketide other than megalomicin. For example, and without limitation, the second PKS gene can be a narbonolide PKS gene, an oleandolide PKS gene, or a rapamycin PKS gene. In one embodiment, the hybrid PKS is composed of a loading module and six extender modules, wherein at least one domain of any one of extender modules 1 through 6, inclusive, is a domain of an extender module of megalomicin PKS. In another preferred embodiment, the hybrid PKS comprises a megalomicin PKS that has a non-functional KS domain in module1.

In yet another specific embodiment, the invention provides a method of producing a polyketide, which method comprises growing the recombinant host cell comprising a recombinant DNA expression vector encoding at least a domain of the megalomicin PKS or a megalomicin modification enzyme under conditions whereby the megalomicin PKS domain or the megalomicin modification enzyme comprised by the recombinant expression vector is produced and the polyketide is synthesized by the cell, and recovering the synthesized polyketide. Preferably, the recombinant host cell comprises a recombinant expression vector that encodes at least a portion of a megAI, megAII, or megAIII gene.

These and other embodiments of the invention are described in more detail in the following description, the examples, and claims set forth below.

BRIEF DESCRIPTION OF THE FIGURES

FIG. 3 shows the structures of the megalomicins, azithromycin and erythromycin A.

FIG. 7 depicts nucleotide and amino acid sequence of *Micromonospora megalomicea* megalomicin biosynthetic genes (GenBank Accession No. AF263245, incorporated herein by reference).

DETAILED DESCRIPTION OF THE INVENTION

Figure 1:
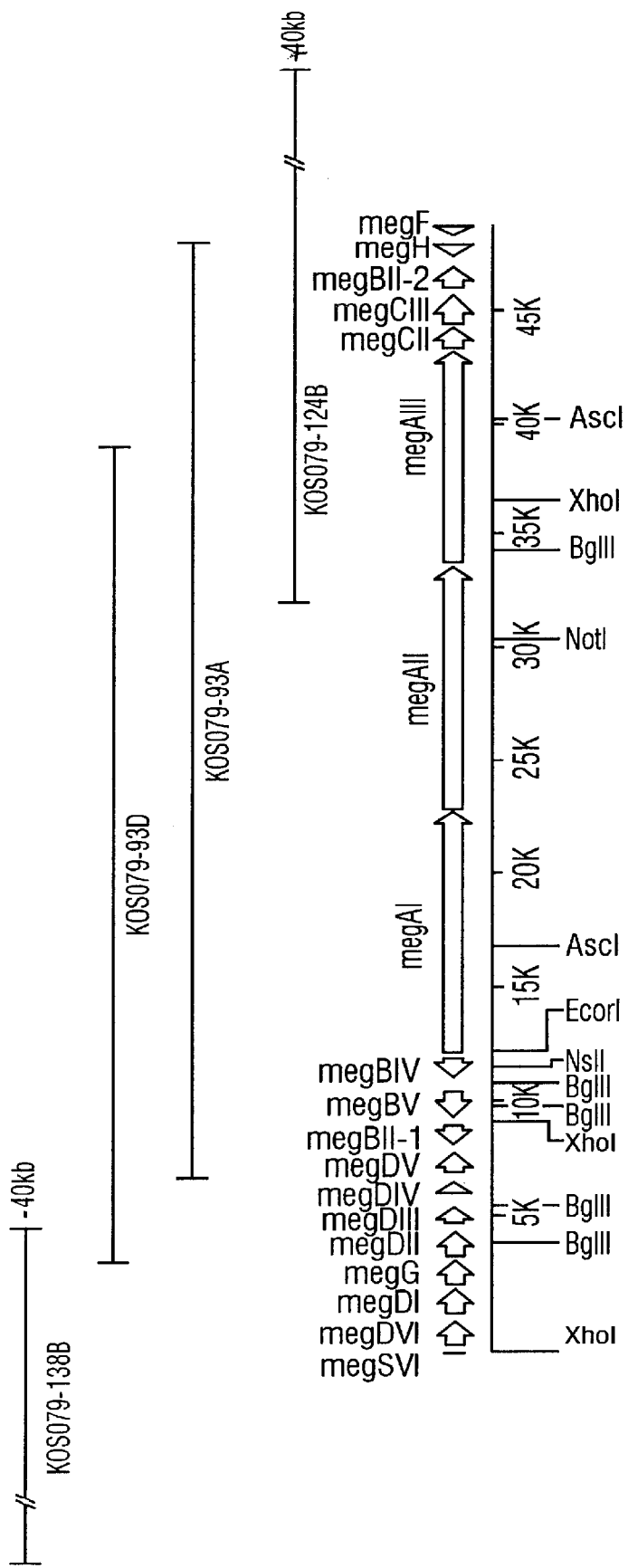
FIG. 1 shows restriction site and function maps of the insert DNA in cosmids pKOS079-138B, pKOS079-93D, pKOS079-93A, and pKOS079-124B of the invention. Various restriction sites (XhoI, BglII, NsiI) are also shown. The location of the megalomicin biosynthetic genes is shown below the solid lines indicating the cosmid inserts. The genes are shown as arrows pointing in the direction of transcription. The approximate size (in kilobase (kb) pairs) of the gene cluster is indicated in 5000 bp (i.e., 5K, 10K, and the like.) increments on a solid bar beneath the arrows indicating the genes.

The present invention provides useful compounds and methods for producing polyketides in recombinant host cells. As used herein, the term recombinant refers to a compound or composition produced by human intervention. The invention provides recombinant DNA compounds encoding all or a portion of the megalomicin biosynthetic genes. The invention provides recombinant expression vectors useful in producing the megalomicin PKS and hybrid PKSs composed of a portion of the megalomicin PKS in recombinant host cells. The invention also provides the polyketides produced by the recombinant PKS and polyketide modification enzymes.

To appreciate the many and diverse benefits and applications of the invention, the description of the invention below is organized as follows. In Section I, common definitions used throughout this application are provided. In Section II, structural and functional characteristics of megalomicin are described. In Section III, the recombinant megalomicin biosynthetic genes and other recombinant nucleic acids provided by the invention are described. In Section IV, polypeptides and proteins encoded by the megalomicin biosynthetic genes and antibodies that specifically bind to such polypeptides and proteins provided by the invention are described. In Section V, methods for heterologous expression of the megalomicin biosynthetic genes provided by the invention are described. In Section VI, the hybrid PKS genes provided by the invention are described. In Section VII, host cells containing multiple megalomicin biosynthetic genes and nucleic acid fragments on separate express vectors provided by the invention are described. In Section VIII, the polyketide compounds provided by the invention and pharmaceutical compositions of those compounds are described. The detailed description is followed by working examples illustrating the invention.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

Section I. Definitions

As used herein, domain refers to a portion of a molecule, e.g., proteins or nucleic acids, that is structurally and/or functionally distinct from another portion of the molecule.

As used herein, antibody includes antibody fragments, such as Fab fragments, which are composed of a light chain and the variable region of a heavy chain.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in in vitro systems designed to test or use such activities.

As used herein, a combination refers to any association between two or among more items.

As used herein, a composition refers to any mixture. It may be a solution, a suspension, liquid, powder, a paste, aqueous, non-aqueous or any combination thereof.

As used herein, derivative or analog of a molecule refers to a portion derived from or a modified version of the molecule.

As used herein, operably linked, operatively linked or operationally associated refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. To optimize expression and/or in vitro transcription, it may be helpful to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867–19870 (1991)) can be inserted immediately 5' of the start codon and may enhance expression. The desirability of (or need for) such modification may be empirically determined.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein: stringency of hybridization in determining percentage mismatch is as follows: (1) high stringency: 0.1×SSPE, 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures.

The term substantially identical or homologous or similar varies with the context as understood by those skilled in the relevant art and generally means at least 70%, preferably means at least 80%, more preferably at least 90%, and most preferably at least 95% identity.

As used herein, substantially identical to a product means sufficiently similar so that the property of interest is sufficiently unchanged so that the substantially identical product can be used in place of the product.

As used herein, isolated means that a substance is either present in a preparation at a concentration higher than that substance is found in nature or in its naturally occurring state or that the substance is present in a preparation that contains other materials with which the substance is not associated with in nature. As an example of the latter, an isolated meg PKS protein includes a meg PKS protein expressed in a *Streptomyces coelicolor* or *S. lividans* host cell.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, vector or plasmid refers to discrete elements that are used to introduce heterologous DNA into cells for either expression or replication thereof. Selection and use of such vehicles are well known within the skill of the artisan. An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

Section II. Megalomicins

The megalomicins were discovered in 1969 at Schering Corp. as antibacterial agents produced by *Micromonospora megalomicea* (see Weinstein et al., 1969, *J. Antibiotics* 22: 253–258, and U.S. Pat. No. 3,632,750, both of which are incorporated herein by reference). Although the initial structural assignment was in error, a thorough reassessment of NMR data coupled with an X-ray crystal structure of a megalomicin A derivative (see Nakagawa and Omura, "Structure and Stereochemistry of Macrolides" in *Macrolide Antibiotics* (S. Omura, ed.), Academic Press, NY, 1984, incorporated herein by reference) established the structures shown in FIG. 3. The megalomicins are 6-O-glycosides of erythromycin C with acetyl or propionyl groups esterified at the 3′″ or 4′″ hydroxyls of the mycarose sugar at the C-3-position. The C-6 sugar has been named "megosamine," although it had been identified 5 to 10 years earlier as L-rhodosamine or N-dimethyldaunosamine, deoxyamino sugars commonly present in the anthracycline antitumor drugs. The antibacterial potency, spectrum of activity, and toxicity ($LD_{50}$ acute, 7–7.5 g/kg s.c. or oral; subacute, >500 mg/kg) of the megalomicins is similar to that of erythromycin A.

The megalomicins have two modes of biological activity. As antibacterials, they act like the erythromycins, which inhibit protein synthesis at the translocation step by selective binding to the bacterial 50S ribosomal RNA. They also affect protein trafficking in eukaryotic cells (see Bonay et al., 1996, *J. Biol. Chem.* 271:3719–3726, incorporated herein by reference). Although the mechanism of action is not entirely clear, it appears to involve inhibition of vesicular transport between the medial and trans Golgi, resulting in undersialylation of proteins. The megalomicins also strongly inhibit the ATP-dependent acidification of lysosomes in vivo (see Bonay et al., 1997, *J. Cell. Sci.* 110:1839–1849, incorporated herein by reference) and cause an anomalous glycosylation of viral proteins, which may be responsible for their antiviral activity against herpes ($Tox_{50}$, 70–100 $\mu$M; see Alarcon et al., 1984, *Antivir. Res.* 4:231–243, and Alarcon et al., 1988, *FEBS Lett.* 231:207–211, both of which are incorporated herein by reference).

Strikingly, the megalomicins are potent antiparasitic agents, showing an $IC_{50}$ of 1 $\mu$g/ml in blocking intracellular replication of *Plasmodium falciparum* infected erythrocytes (see Bonay et al., 1998, *Antimicrob. Agents Chemother.* 42:2668–2673, incorporated herein by reference). The megalomicins are effective against *Trypanosoma cruzi* and *T. brucei* ($IC_{50}$, 0.2–2 $\mu$g/ml) plus *Leishmania donovani* and *L. major* promastigotes ($IC_{50}$, 3 and 8 $\mu$g/ml, respectively). Megalomicin is also active against the intracellular replicative, amastigote form of *T. cruzi*, completely preventing its replication in infected murine LLC/MK2 macrophages at a dose of 5 $\mu$g/ml. Importantly, the effective drug concentration is 500-fold less than the acute $LD_{50}$ in mammals, and there is no toxicity to BALB/c mice at doses (50 mg/kg) that are completely curative for *T. brucei* infections. Because the erythromycins do not have such activity, although azithromycin (FIG. 3) has been reported to be an effective acute and prophylactic treatment for malaria caused by *P. vivax* and *P. falciparum* (see Taylor et al., 1999, *Clin. Infect. Dis.* 28:74–81, incorporated herein by reference), the antiparasitic action of the megalomicins is unique and probably related to the presence of the deoxyamino sugar megosamine at C-6 (FIG. 3). Consequently, the megalomicins could be developed into potent antimalarial drugs with a high therapeutic index and be active against *P. falciparum* and other species that are resistant to currently used classes of antimalarials. They also could lead to potent antiparasitic agents against leishmaniasis, trypanosomiasis, and Chagas' disease. In view of the widespread use of the erythromycins and their good oral availability plus the low mammalian toxicity of macrolides in general, the megalomicins could be used prophylactically to combat malaria, and as fermentation products, the megalomicins should be relatively inexpensive to produce.

The megalomicins belong to the polyketide class of natural products whose members have diverse structural and pharmacological properties (see Monaghan and Tkacz, 1990, *Annu. Rev. Microbiol.* 44: 271, incorporated herein by reference). The megalomicins are assembled by polyketide synthases through successive condensations of activated coenzyme-A thioester monomers derived from small organic acids such as acetate, propionate, and butyrate. Active sites required for condensation include an acyltransferase (AT), acyl carrier protein (ACP), and beta-ketoacylsynthase (KS). Each condensation cycle results in a β-keto group that undergoes all, some, or none of a series of processing activities. Active sites that perform these reactions include a ketoreductase (KR), dehydratase (DH), and enoylreductase (ER). Thus, the absence of any beta-keto processing domain results in the presence of a ketone, a KR alone gives rise to a hydroxyl, a KR and DH result in an alkene, while a KR, DH, and ER combination leads to complete reduction to an alkane. After assembly of the polyketide chain, the molecule typically undergoes cyclization(s) and post-PKS modification (e.g. glycosylation, oxidation, acylation) to achieve the final active compound.

Figure 4:
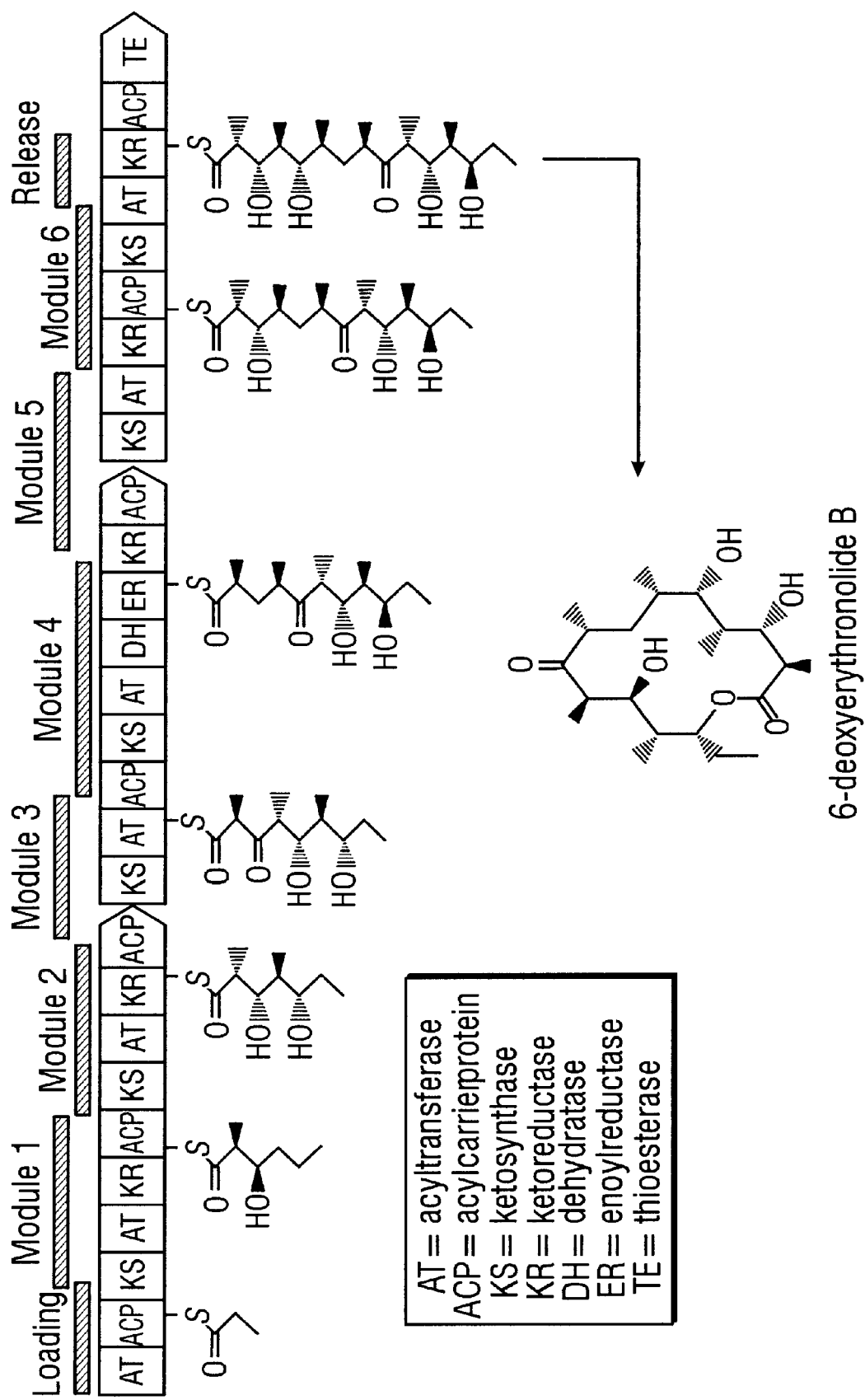
FIG. 4 shows the modules and domains of DEBS; the modules and domains of the megalomicin PKS are configured identically to those of DEBS.

Macrolides such as erythromycin and megalomicin are synthesized by modular PKSs (see Cane et al., 1998, *Science* 282: 63, incorporated herein by reference). For illustrative purposes, the PKS that produces the erythromycin polyketide (6-deoxyerythronolide B synthase or DEBS; see U.S. Pat. No. 5,824,513, incorporated herein by reference) is shown in FIG. 4. DEBS is the most characterized and extensively used modular PKS system. DEBS is particularly relevant to the present invention in that it synthesizes the same polyketide, 6-deoxyerythronolide B (6-dEB), synthesized by the megalomicin PKS. In modular PKS enzymes such as DEBS and the megalomicin PKS, the enzymatic steps for each round of condensation and reduction are encoded within a single "module" of the polypeptide (i.e., one distinct module for every condensation cycle). DEBS consists of a loading module and 6 extender modules and a chain terminating thioesterase (TE) domain within three extremely large polypeptides encoded by three open reading frames (ORFs, designated eryAI, eryAII, and eryAIII).

Each of the three polypeptide subunits of DEBS (DEBSI, DEBSII, and DEBSIII) contains 2 extender modules, DEBSI additionally contains the loading module. Collectively, these proteins catalyze the condensation and appropriate reduction of 1 propionyl CoA starter unit and 6 methylmalonyl CoA extender units. Modules 1, 2, 5, and 6 contain KR domains; module 4 contains a complete set, KR/DH/ER, of reductive and dehydratase domains; and module 3 contains no functional reductive domain. Following the condensation and appropriate dehydration and reduction reactions, the enzyme bound intermediate is lactonized by the TE at the end of extender module 6 to form 6-dEB.

More particularly, the loading module of DEBS consists of two domains, an acyl-transferase (AT) domain and an acyl carrier protein (ACP) domain. In other PKS enzymes, the loading module is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. The AT domain of the loading module recognizes a particular acyl-CoA (propionyl for DEBS, which can also accept acetyl) and transfers it as a thiol ester to the ACP of the loading module. Concurrently, the AT on each of the extender modules recognizes a particular extender-CoA (methylmalonyl for DEBS) and transfers it to the ACP of that module to form a thioester. Once the PKS is primed with acyl- and malonyl-ACPs, the acyl group of the loading module migrates to form a thiol ester (transesterification) at the KS of the first extender module; at this stage, extender module 1 possesses an acyl-KS and a methylmalonyl ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a polyketone, from which the name polyketide arises. Commonly, however, the beta keto group of each two-carbon unit is modified just after it has been added to the growing polyketide chain but before it is transferred to the next module by either a KR, a KR plus a DH, or a KR, a DH, and an ER. As noted above, modules may contain additional enzymatic activities as well.

Figure 5A:
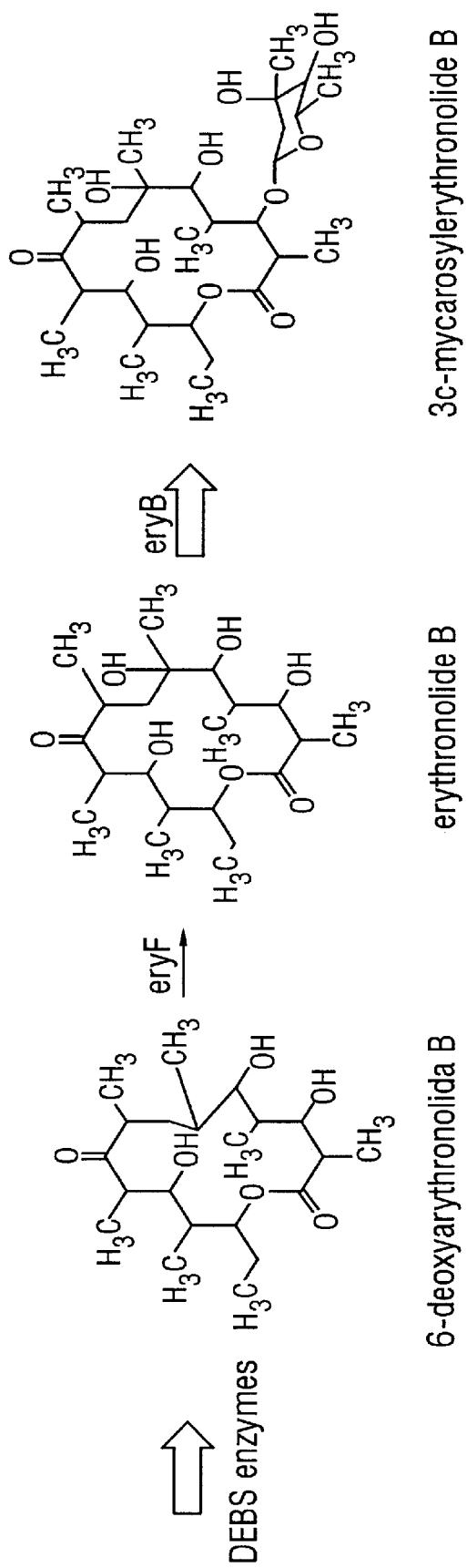
FIG. 5 shows the compounds and reactions in the erythromycin biosynthetic pathway and also for megalomicin biosynthesis. Genes that produce the various enzymes that catalyze each of the steps in the biosynthetic pathway are indicated.
Figure 5B:
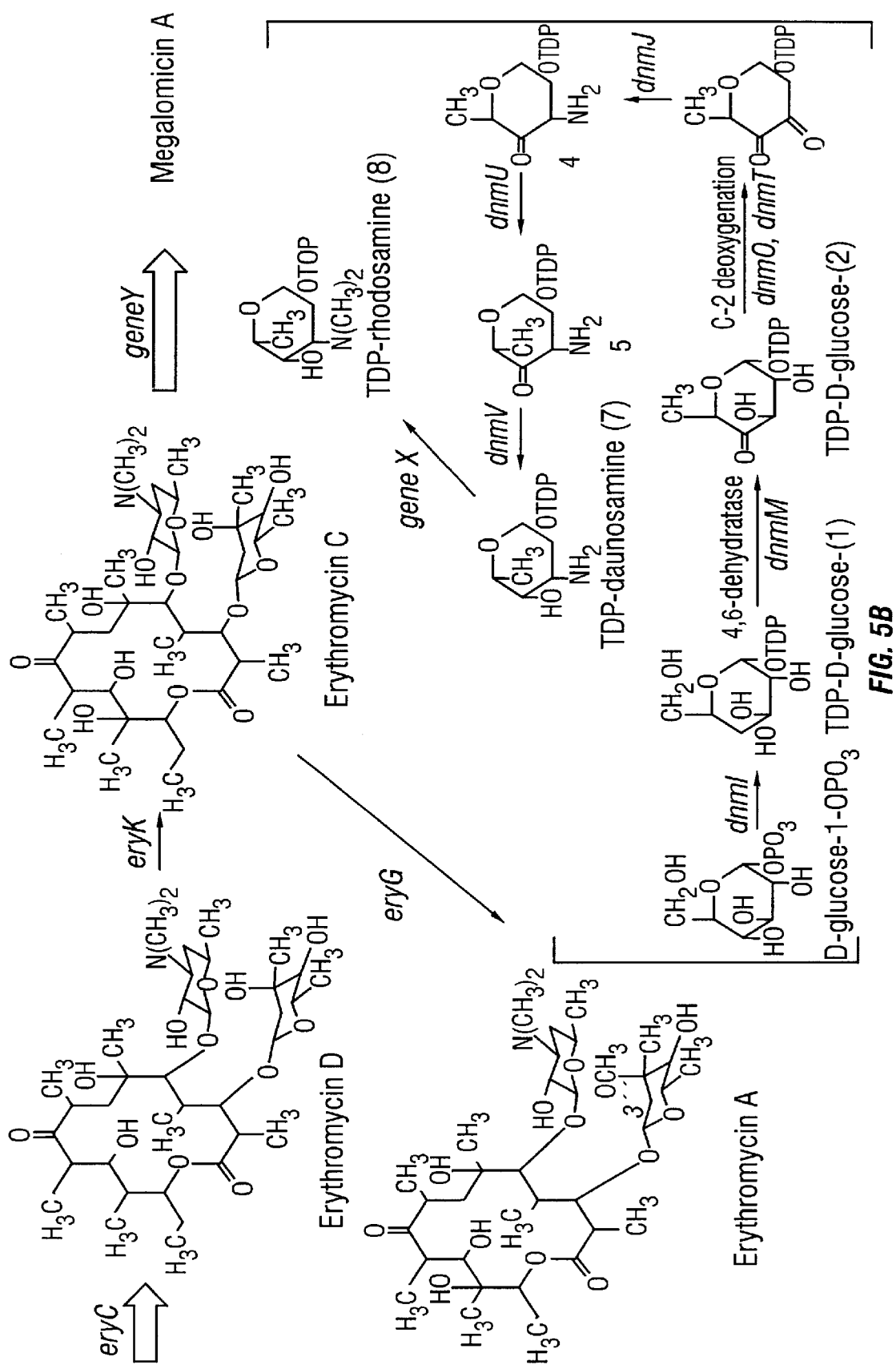

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring or modification enzymes; these enzymes add carbohydrate groups or methyl groups, or make other modifications, i.e., oxidation or reduction, on the polyketide core molecule. For example, the final steps in conversion of 6-dEB to erythromycin A include the actions of a number of modification enzymes, such as: C-6 hydroxylation, attachment of mycarose and desosamine sugars, C-12 hydroxylation (which produces erythromycin C), and conversion of mycarose to cladinose via O-methylation, as shown in FIG. 5.

With this overview of PKS and post-PKS modification enzymes, one can better appreciate the recombinant megalomicin biosynthetic genes provided by the invention and their function, as described in the following Section.

Section III: The Megalomicin Biosynthetic Genes and Nucleic Acid Fragments

The megalomicin PKS was isolated and cloned by the following procedure. Genomic DNA was isolated from a megalomicin producing strain of *Micromonospora megalomicea* subsp. *nigra* (ATCC 27598), partially digested with a restriction enzyme, and cloned into a commercially available cosmid vector to produce a genomic library. This library was then probed with probes generated from the erythromycin biosynthetic genes as well as from cosmids identified as containing sequence homologous to erythromycin biosynthetic genes. This probing identified a set of cosmids, which were analyzed by DNA sequence analysis and restriction enzyme digestion, which revealed that the desired DNA had been isolated and that the entire PKS gene cluster was contained in overlapping segments of four of the cosmids identified. FIG. 1 shows the cosmids and the portions of the megalomicin biosynthetic gene cluster in the insert DNA of the cosmids. FIG. 1 shows that the complete megalomicin biosynthetic gene cluster is contained within the insert DNA of cosmids pKOS079-138B, pKOS079-124B, pKOS079-93D, and pKOS079-93A. Cosmid pKOS079-93A was deposited with the American Type Culture Collection (10801 University Blvd., Manassas, Va.) on Oct. 3, 2002 in accordance with the terms of the Budapest Treaty and is available under accession number PTA-2555. Various additional reagents of the invention can be isolated from these cosmids. DNA sequence analysis was also performed on the various subclones of the invention, as described herein. Further analysis of these cosmids and subclones prepared from the cosmids facilitated the identification of the location of various megalomicin biosynthetic genes, including the ORFs encoding the PKS, modules encoded by those ORFs, and coding sequences for megalomicin modification enzymes. The location of these genes and modules is shown on FIG. 2.

Those of skill in the art will recognize that, due to the degenerate nature of the genetic code, a variety of DNA compounds differing in their nucleotide sequences can be used to encode a given amino acid sequence of the invention. The native DNA sequence encoding the megalomicin PKS and other biosynthetic enzymes and other biosynthetic enzymes of *Micromonospora megalomicea* is shown herein merely to illustrate a preferred embodiment of the invention, and the invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences encoded by the DNA sequences shown herein merely illustrate preferred embodiments of the invention.

The recombinant nucleic acids, proteins, and peptides of the invention are many and diverse. To facilitate an understanding of the invention and the diverse compounds and methods provided thereby, the following description of the various regions of the megalomicin PKS and the megalomicin modification enzymes and corresponding coding sequences is provided. To facilitate description of the invention, reference to a PKS, protein, module, or domain herein can also refer to DNA compounds comprising coding sequences therefor and vice versa. Also, unless otherwise indicated, reference to a heterologous PKS refers to a PKS or DNA compounds comprising coding sequences therefor from an organism other than *Micromonospora megalomicea*. In addition, reference to a PKS or its coding sequence includes reference to any portion thereof.

Thus, the invention provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form. The DNA molecules of the invention comprise one or more sequences that encode one or more domains (or fragments of such domains) of one or more modules in one or more of the ORFs of the megalomicin PKS and sequences that encode megalomicin modification enzymes from the megalomicin biosynthetic gene cluster. Examples of PKS domains include the KS, AT, DH, KR, ER, ACP, and TE domains of at least one of the 6 extender modules and loading module of the three proteins encoded by the three ORFs of the megalomicin PKS gene cluster. Examples of megalomicin modification enzymes include those that synthesize the mycarose, desosamine, and megosamine moieties, those that transfer those sugar moieties to the polyketide 6-dEB, those that hydroxylate the polyketide at C-6 and C-12, and those that acylate the sugar moieties.

In an especially preferred embodiment, the DNA molecule is a recombinant DNA expression vector or plasmid, as described in more detail in the following Section. Generally, such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions).

Figure 2:
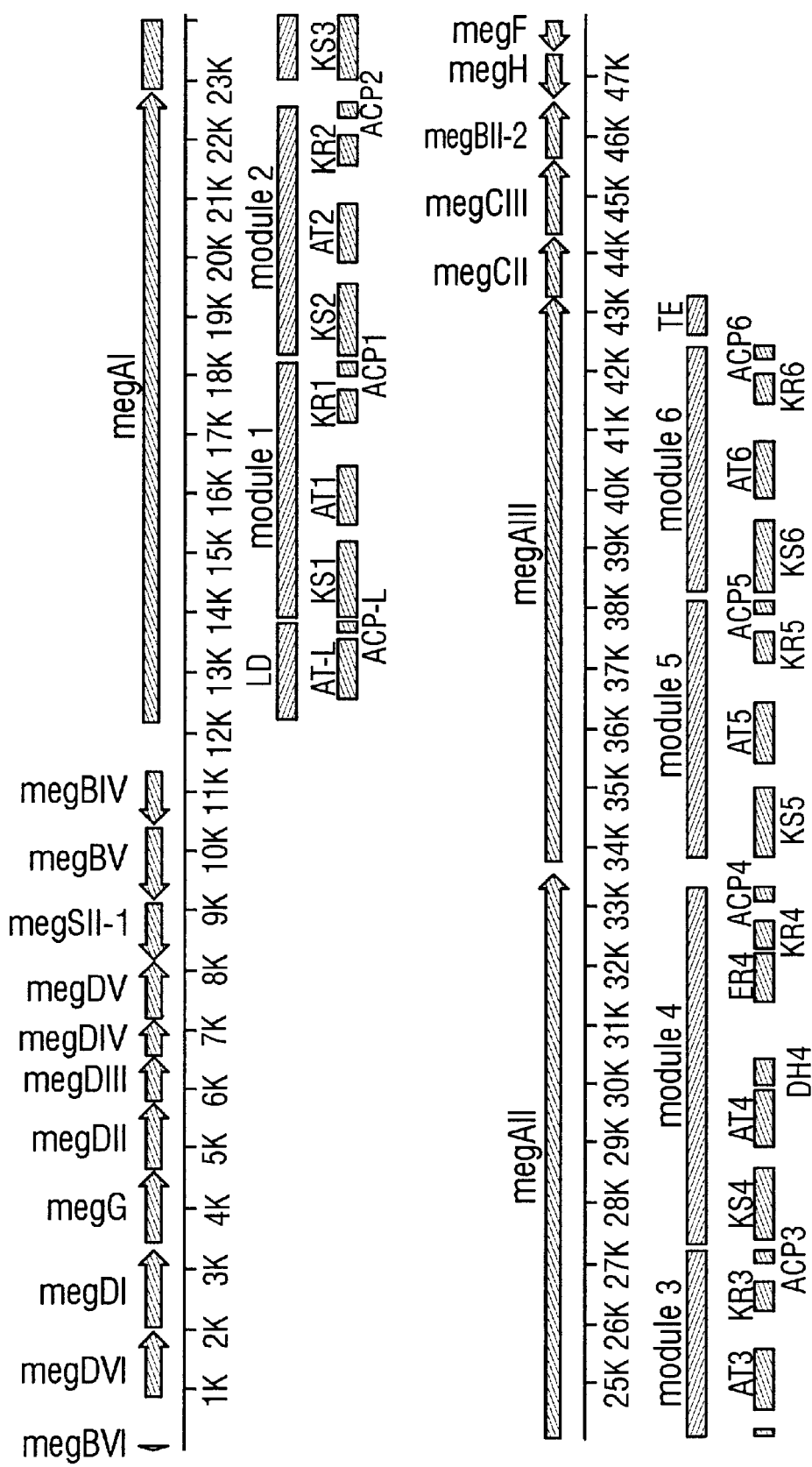
FIG. 2 shows a more detailed map of the megalomicin biosynthetic gene cluster. The various open reading frames are shown as arrows pointing in the direction of transcription. A line indicates the size in base pairs (in 1000 bp increments) of the gene cluster. The various domains of the megalomicin PKS are also shown. Other genes of the megalomicin biosynthetic gene cluster not shown in this Figure are located in the insert DNA of cosmids pKOS0138B and pKOS0124B.

The megalomicin PKS gene cluster comprises three ORFs (megAI, megAII, and megAIII). Each ORF encodes two extender modules of the PKS; the first ORF also encodes the loading module. Each extender module is composed of at least a KS, an AT, and an ACP domain. The locations of the various encoding regions of these ORFs are shown in FIG. 2 and described with reference to the sequence information below. The megalomicin PKS produces the polyketide known as 6-dEB, shown in FIG. 4. In megalomicin-producing organisms, 6-dEB is converted to erythromycin C by a set of modification enzymes. Thus, 6-dEB is converted to erythronolide B by the megF gene product (a homolog of the eryF gene product), then to 3-alpha-mycarosyl-erythronolide B by the megBV gene product (a homolog of the eryBV gene product), then to erythromycin D by the megCIII gene product (a homolog of the eryCIII gene product, then to erythromycin C by the megK gene product (a homolog of the eryK gene product).

In addition to these modification enzymes, such megalomicin-producing organisms also contain the modification enzymes necessary for the biosynthesis of the desosamine and mycarose moieties that are similarly utilized in erythromycin biosynthesis, as shown in FIG. 5. Megalomicin A contains the complete erythromycin C structure, and its biosynthesis additionally involves the formation of L-megosamine (L-rhodosamine) and its attachment to the C-6 hydroxyl (FIGS. 3 and 5, inset), followed by acylation of the C-3''' and(or) C-4''' hydroxyls as the terminal steps. L-megosamine is the same as N-dimethyl-L-daunosamine; the daunosamine genes have been characterized from *Streptomyces peucetius* (see Colombo and Hutchinson, *J. Indust. Microbiol. Biotechnol.*, in press; Otten et al., 1996, *J Bacteriol* 178:7316–7321, and references cited therein). Some of the rhodosamine genes also have been cloned and partially characterized from another anthracycline producing Streptomyces sp. (see Torkkell et al., 1997, *Mol. Gen. Genet.* 256(2):203–209). Because the timing of the glycosylation with TDP-megosamine in relation to the addition of mycarose and desosamine to erythronolide B, plus the C-12 hydroxylation, is unknown, the pathway could involve a different order of glycosylation and C-12 hydroxylation steps than the one shown in FIG. 5. Regardless, the megalomicin biosynthetic gene cluster contains the genes to make L-rhodosamine and attach it to the correct macrolide substrate.

Figure 6:
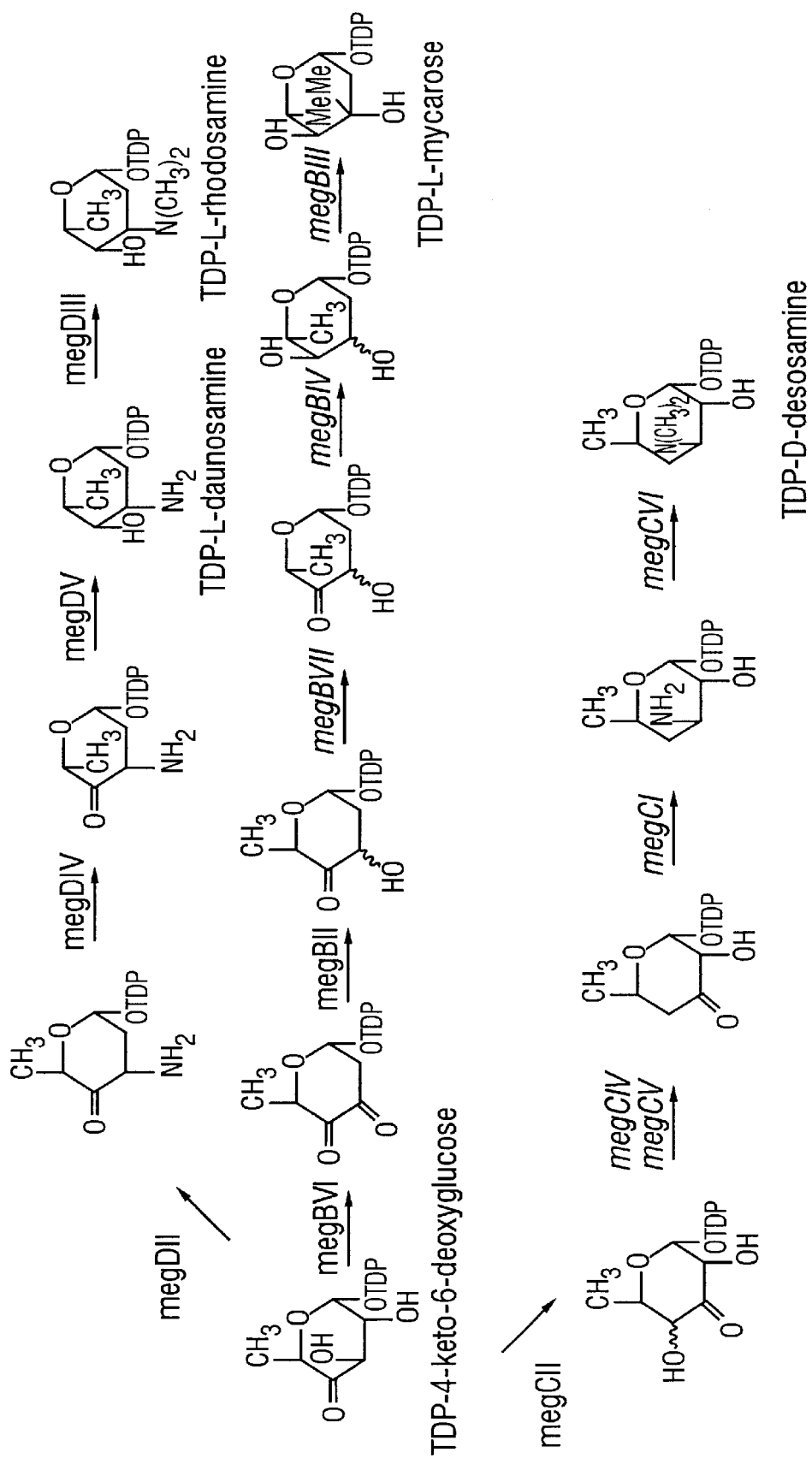
FIG. 6 shows the biosynthetic pathway for the formation of desosamine, rhodosamine, and mycarose, as well as the genes that produce the various enzymes that catalyze each of the steps in the biosynthetic pathway.

The biosynthetic pathways to make the glycosides desosamine, mycarose, and megosamine are shown in FIG. 6. The present invention provides the genes for each biosynthetic pathway shown in this Figure, and these recombinant genetic pathways can be used alone or in any combination to confer the pathway to a heterologous host.

The megalomicin PKS locus is similar to the eryA locus in size and organization. Most of the deoxysugar biosynthesis genes are homologs of the eryB mycarose and eryC desosamine biosynthesis and glycosyl attachment genes from *Saccharopolyspora erythraea* (see Summers et al., 1997, *Microbiol.* 143:3251–3262; Haydock et al., 1991, *Mol. Gen. Genet.* 230:120–128; Gaisser et al., 1997, *Mol Gen Genet*, 256:239–251; Gaisser et al., 1998, *Mol Gen Genet.* 257:78–88, incorporated herein by reference) or the picC homologs from the picromycin and narbomycin producer (see PCT patent publication No. 99/61599 and Xue et al., 1998, *Proc. Nat. Acad. Sci. USA* 95, 12111–12116, incorporated herein by reference). The TDP-megosamine biosynthesis genes are homologs of the dnm genes (see FIG. 5) and the pikromycin N-dimethyltransferase gene or its homologs reported in a cluster of L-rhodosamine biosynthesis genes. The putative TDP-megosamine glycosyltransferase gene product (geneX in FIG. 5) closely resembles the deduced products of the eryBV, eryCIII, dnmS, and pikromycin desVII genes, even though it recognizes different substrates than the products of each of these genes.

The following Table 1 shows the location of the genes in the *Micromonospora megalomicea* megalomicin biosynthetic pathway in the DNA sequence set forth in SEQ ID NO:1 (see also FIG. 7; note some gene designations maybe different in FIG. 7).

TABLE 1

Megalomicin Biosynthetic Gene Cluster
*Micromonospora megalomicea* subsp. *nigra* (ATCC27598)

| Location | Description |
|---|---|
| 1 . . . 2451 | sequence from cosmid pKOS079-138B |
| complement (1 . . . 144) | megBVI (or megT), TDP-4-keto-6-deoxyglucose-2,3-dehydratase |
| 928 . . . 2061 | megDVI, TDP-4-keto-6-deoxyglucose 3,4-isomerase |
| 2072 . . . 3382 | megDI, TDP-megosaminyl transferase (eryCIII homolog) |
| 2452 . . . 40397 | sequence of cosmid pKOS079-93D |
| 3462 . . . 4634 | megG(or megY), mycarosyl acyltransferase |
| 4651 . . . 5775 | megDII, deoxysugar transaminase (eryCI, DnrJ homolog) |
| 5822 . . . 6595 | megDIII, TDP-daunosaminyl-N,N-dimethyltransferase (eryCVI homolog) |
| 6592 . . . 7197 | megDIV, TDP-4-keto-6-deoxyglucose 3,5-epimerase (eryBVII, dnmU homolog) |
| 7220 . . . 8206 | megDV, TDP-hexose 4-ketoreductase (eryBIV, dnmV homolog) |
| complement (8228 . . . 9220) | megBII-1 or megDVII, TDP-4-keto-L-6-deoxy-hexose 2,3-reductase |
| complement (9226 . . . 10479) | megBV, TDP-mycarosyl transferase |
| complement (10483 . . . 11424) | megBIV, TDP-hexose 4-ketoreductase |
| 12181 . . . 22821 | megAI |
| 12181 . . . 13791 | Loading Module (L) |
| 12505 . . . 13470 | AT-L |
| 13576 . . . 13791 | ACP-L |
| 13849 . . . 18207 | Extender Module 1 (1) |
| 13849 . . . 15126 | KS1 |
| 15427 . . . 16476 | AT1 |
| 17155 . . . 17694 | KR1 |
| 17947 . . . 18207 | ACP1 |
| 18268 . . . 22575 | Extender Module 2 (2) |
| 18268 . . . 19548 | KS2 |
| 19876 . . . 20910 | AT2 |
| 21517 . . . 22053 | KR2 |
| 22318 . . . 22575 | ACP2 |
| 22867 . . . 33555 | megAII |
| 22957 . . . 27258 | Extender Module 3 (3) |
| 22957 . . . 24237 | KS3 |
| 24544 . . . 25581 | AT3 |
| 26230 . . . 26733 | KR3 (inactive) |
| 26998 . . . 27258 | ACP3 |
| 27313 . . . 33312 | Extender Module 4 (4) |
| 27393 . . . 28590 | KS4 |
| 28897 . . . 29931 | AT4 |
| 29953 . . . 30477 | DH4 |
| 31396 . . . 32244 | ER4 |
| 32257 . . . 32799 | KR4 |
| 33052 . . . 33312 | ACP4 |
| 33666 . . . 43271 | megAIII |
| 33780 . . . 38120 | Extender Module 5 (5) |
| 33780 . . . 35027 | KS5 |
| 35385 . . . 36419 | AT5 |
| 37068 . . . 37604 | KR5 |
| 37860 . . . 38120 | ACP5 |
| 38187 . . . 42425 | Extender Module 6 (6) |
| 38187 . . . 39470 | KS6 |
| 39795 . . . 40811 | AT6 |
| 40398 . . . 46641 | sequences from cosmid pKOS079-93A |
| 41406 . . . 41936 | KR6 |
| 42168 . . . 42425 | ACP6 |
| 42585 . . . 43271 | TE |
| 43268 . . . 44344 | megCII, TDP-4-keto-6-deoxyglucose 3,4-isomerase |
| 44355 . . . 45623 | megCIII, TDP-desosaminyl transferase |
| 45620 . . . 46591 | megBII, TDP-4-keto-6-deoxy-L-glucose 2,3 dehydratase |
| complement (46660 . . . 47403) | megH, TEII |
| complement (47411 . . . 47980) | megF, C-6 hydroxylase |

In a specific embodiment, the invention provides an isolated nucleic acid fragment comprising a nucleotide sequence encoding a domain of the megalomicin polyketide synthase or a megalomicin modification enzyme. The isolated nucleic acid fragment can be a DNA or a RNA. Preferably, the isolated nucleic acid fragment is a recombinant DNA compound. A nucleotide sequence that is complementary to the nucleotide sequence encoding a domain of megalomicin PKS or a megalomicin modification enzyme is also provided.

The isolated nucleic acid fragment can comprise a single, multiple or all the open reading frame(s) (ORF) of the megalomicin PKS or the megalomicin modification enzyme. Exemplary ORFs of megalomicin PKS include the ORFs of the megAI, megAII and megAIII genes. The isolated nucleic acids of the invention also include nucleic acids that encode one or more domains and one or more modules of the megalomicin PKS. Exemplary domains of the megalomicin PKS include a TE domain. a KS domain, an AT domain, an ACP domain, a KR domain, a DH domain and an ER domain. In a preferred embodiment, the nucleic acid comprises the coding sequence for a loading module, a thioesterase domain, and all six extender modules of the megalomicin PKS.

Megalomicin modification enzymes include those enzymes involved in the conversion of 6-DEB into a megalomicin such as the enzymes encoded by megF, meg BV, megCIII, megK, megDI and megG (or megY). Megalomicin modification enzymes also include those enzymes involved in the biosynthesis of mycarose, megosamine or desosamine, which are used as biosynthetic intermediates in the biosynthesis of various megalomicin species and other related polyketides. The enzymes that are involved in biosynthesis of mycarose, megosamine or desosamine are described in FIGS. 5 and 10. The megalomicin PKS and megalomicin modification enzymes are collectively referred to as megalomicin biosynthetic enzymes; the genes encoding such enzymes are collectively referred to as megalomicin biosynthetic genes; and nucleic acids that comprise a portion of or entire megalomicin biosynthetic genes are collectively referred to as megalomicin biosynthetic nucleic acid(s).

In specific embodiments, the megalomicin biosynthetic nucleic acids comprise the sequence of SEQ ID NO:1, or the coding regions thereof, or nucleotide sequences encoding, in whole or in part, a megalomicin biosynthetic enzyme protein. The isolated nucleic acids typically consists of at least 25 (continuous) nucleotides, 50 nucleotides, 100 nucleotides, 150 nucleotides, or 200 nucleotides of megalomicin biosynthetic nucleic acid sequence, or a full-length megalomicin biosynthetic coding sequence. In another embodiment, the nucleic acids are smaller than 35, 200, or 500 nucleotides in length. Nucleic acids can be single or double stranded. Nucleic acids that hybridize to or are complementary to the foregoing sequences, in particular the inverse complement to nucleic acids that hybridize to the foregoing sequences (i.e., the inverse complement of a nucleic acid strand has the complementary sequence running in reverse orientation to the strand so that the inverse complement would hybridize without mismatches to the nucleic acid strand) are also provided. In specific aspects, nucleic acids are provided which comprise a sequence complementary to (specifically are the inverse complement of) at least 10, 25, 50, 100, or 200 nucleotides or the entire coding region of a megalomicin biosynthetic gene.

The megalomicin biosynthetic nucleic acids provided herein include those with nucleotide sequences encoding substantially the same amino acid sequences as found in native megalomicin biosynthetic enzyme proteins, and those encoding amino acid sequences with functionally equivalent amino acids, as well as megalomicin biosynthetic enzyme derivatives or analogs as described in Section IV.

Some regions within the megalomicin PKS genes are highly homologous or identical to one another, as can be readily identified by an analysis of the sequence. The coding sequence for the KS and AT domains of module 2 shares significant identity with the coding sequence for the KS and AT domains of module 6. This sequence homology or identity at the nucleic acid. e.g., DNA, level can render the nucleic acid unstable in certain host cells. To improve the stability of the nucleic acids comprising a portion or the entire megalomicin PKS genes and megalomicin modification enzyme genes, the nucleic acid or DNA sequences can be changed to reduce or abolish the sequence homology or identity. Preferably, the DNA codons of homologous regions within the PKS or the megalomicin modification enzyme coding sequence are changed to reduce or abolish the sequence homology or identity without changing the amino acid sequences encoded by said changed DNA codons (see the examples below). The stability of the nucleic acid or DNA can also be improved by codon changes that reduce or abolish the sequence homology or identity while also changing the amino acid sequence, provided that the amino acid sequence change(s) does not substantially change the desired activity of the encoded megalomicin PKS. Thus, for example, one can simply substitute for the megAIII ORF an ORF from eryAIII, oleAIII, picAIII, or orpicAIV genes.

The recombinant DNA compounds of the invention that encode the megalomicin PKS and modification proteins or portions thereof are useful in a variety of applications. While many of these applications relate to the heterologous expression of the megalomicin biosynthetic genes or the construction of hybrid PKS enzymes, many useful applications involve the natural megalomicin producer *Micromonospora megalomicea*. For example, one can use the recombinant DNA compounds of the invention to disrupt the megalomicin biosynthetic genes by homologous recombination in *Micromonospora megalomicea*. The resulting host cell is a preferred host cell for making polyketides modified by oxidation, hydroxylation, glycosylation, and acylation in a manner similar to megalomicin, because the genes that encode the proteins that perform these reactions are of course present in the host cell, and because the host cell does not produce megalomicin that could interfere with production or purification of the polyketide of interest.

One illustrative recombinant host cell provided by the present invention expresses a recombinant megalomicin PKS in which the module 1 KS domain is inactivated by deletion or other mutation. In a preferred embodiment, the inactivation is mediated by a change in the KS domain that renders it incapable of binding substrate (called a KS1° mutation). In a particularly preferred embodiment, this inactivation is rendered by a mutation in the codon for the active site cysteine that changes the codon to another codon, such as an alanine codon. Such constructs are especially useful when placed in translational reading frame with extender modules 1 and 2 of a megalomicin or the corresponding modules of another PKS. The utility of these constructs is that host cells expressing, or cell free extracts containing, a PKS comprising the protein encoded thereby can be fed or supplied with N-acylcysteamine thioesters of precursor molecules to prepare a polyketide of interest. See U.S. patent application Ser. No. 09/492,773, filed Jan. 27, 2000, and PCT patent publication No. 00/44717, both of which are incorporated herein by reference. Such KS1° constructs of the invention are useful in the production of 13-substituted-megalomicin compounds in *Micromonospora megalomicea* host cells. Preferred compounds of the invention include those compounds in which the substituent at the 13-position is propyl, vinyl, propargyl, other lower alkyl, and substituted alkyl.

In a variant of this embodiment, one can employ a megalomicin PKS in which the ACP domain of module 1 has been rendered inactive. In another embodiment, one can delete the loading domain of the megalomicin PKS and provide monoketide substrates for processing by the remainder of the PKS.

The compounds of the invention can also be used to construct recombinant host cells of the invention in which coding sequences for one or more domains or modules of the megalomicin PKS or for another megalomicin biosynthetic gene have been deleted by homologous recombination with the *Micromonospora megalomicea* chromosomal DNA. Those of skill in the art will appreciate that the compounds used in the recombination process are characterized by their homology with the chromosomal DNA and not by encoding a functional protein due to their intended function of deleting or otherwise altering portions of chromosomal DNA. For this and a variety of other applications, the compounds of the present invention include not only those DNA compounds that encode functional proteins but also those DNA compounds that are complementary or identical to any portion of the megalomicin biosynthetic genes.

Thus, the invention provides a variety of modified *Micromonospora megalomicea* host cells in which one or more of the megalomicin biosynthetic genes have been mutated or disrupted. Transformation systems for *M. megalomicea* have been described by Hasegawa et al., 1991, *J. Bacteriol.* 173:7004–11; and Takada et al., 1994, *J. Antibiot.* 47:1167–1170, both of which are incorporated herein by reference. These cells are especially useful when it is desired to replace the disrupted function with a gene product expressed by a recombinant DNA expression vector. While such expression vectors of the invention are described in more detail in the following Section, those of skill in the art will appreciate that the vectors have application to *M. megalomicea* as well. Such *M. megalomicea* host cells can be preferred host cells for expressing megalomicin derivatives of the invention. Particularly preferred host cells of this type include those in which the coding sequence for the loading module has been mutated or disrupted, those in which one or more of any of the PKS gene ORFs has been mutated or disrupted, and/or those in which the genes for one or more modification (glycosylation, acylation, hydroxylation) have been mutated or disrupted.

While the present invention provides many useful compounds having application to, and recombinant host cells derived from, *Micromonospora megalomicea*, many important applications of the present invention relate to the heterologous expression of all or a portion of the megalomicin biosynthetic genes in cells other than *M. megalomicea*, as described in Section V.

Section IV: The Megalomicin Biosynthetic Enzymes and Antibodies Recognizing Such Enzymes In another specific embodiment, the invention provides a substantially purified polypeptide, which is encoded by a nucleic acid fragment comprising a nucleotide sequence encoding a domain of megalomicin polyketide synthase (PKS) or a megalomicin modification enzyme. The polypeptide can comprise a single domain, multiple domains or a full-length megalomicin PKS or megalomicin modification enzyme. Functional fragments, analogs or derivatives of the megalomicin PKS or megalomicin modification enzyme polypeptides are also provided. Preferably, such fragments, analogs or derivatives can be recognized an antibody raised against a megalomicin PKS or megalomicin modification enzyme. Also preferably, such fragments, analogs or derivatives comprise an amino acid sequence that has at least 60% identity, more preferably at least 90% identity to their wild type counterparts.

An exemplary nucleotide sequence encoding, and the corresponding amino acid sequence of, a megalomicin biosynthetic enzyme is disclosed in SEQ ID NO:1. Homologs (e.g., nucleic acids of the above-listed genes of species other than *Micromonospora megalomicea*) or other related sequences (e.g., paralogs) can be obtained by low, moderate or high stringency hybridization with all or a portion of the particular sequence provided as a probe using methods well known in the art for nucleic acid hybridization and cloning (e.g., as described in Section III) in accordance with the methods of the present invention.

The megalomicin biosynthetic enzyme proteins, or domains thereof, of the present invention can be obtained by methods well known in the art for protein purification and recombinant protein expression in accordance with the methods of the present invention. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. Transcriptional and translational signals can be supplied by the native promoter for a megalomicin biosynthetic gene and/or flanking regions.

A variety of host-vector systems may be utilized to express the protein coding sequence. These include but are not limited to mammalian cell systems infected with virus (e.g. vaccinia virus, adenovirus, and the like); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their properties. Depending on the host-vector system utilized, any one of a number of suitable transcription and translation elements may be used.

In a specific embodiment, a vector is used that comprises a promoter operably linked to nucleic acid sequences encoding a megalomicin biosynthetic enzyme, or a domain, fragment, derivative or homolog, thereof, one or more origins of replication, and optionally, one or more selectable markers (e.g., an antibiotic resistance gene).

Expression vectors containing the sequences of interest can be identified by three general approaches: (a) nucleic acid hybridization, (b) presence or absence of "marker" gene function, and (c) expression of the inserted sequences. In the first approach, megalomicin biosynthetic nucleic acid sequences can be detected by nucleic acid hybridization to probes comprising sequences homologous and complementary to the inserted sequences. In the second approach, the recombinant vector/host system can be identified and selected based upon the presence or absence of certain "marker" functions (e.g., binding to an anti-megalomicin biosynthetic enzyme antibody, resistance to antibiotics, occlusion body formation in baculovirus, and the like) caused by insertion of the sequences of interest in the vector. For example, if a megalomicin biosynthetic gene, or portion thereof, is inserted within the marker gene sequence of the vector, recombinants containing the megalomicin biosynthetic gene fragment will be identified by the absence of the marker gene function. In the third approach, recombinant expression vectors can be identified by assaying for the megalomicin biosynthetic gene products expressed by the recombinant vector. Such assays can be based, for example, on the physical or functional properties of the interacting species in in vitro assay systems, e.g., megalomicin synthesis activity, immunoreactivity to antibodies specific for the protein.

Once recombinant megalomicin biosynthetic genes or nucleic acids are identified, several methods known in the art can be used to propagate them in accordance with the methods of the present invention. Once a suitable host system and growth conditions have been established, recombinant expression vectors can be propagated and amplified in quantity. As previously described, the expression vectors or derivatives which can be used include, but are not limited to: human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered megalomicin biosynthetic enzymes may be controlled. Furthermore, different host cells have characteristic and specific mechanisms for the translational and post-translational processing and modification (e.g. glycosylation, phosphorylation, and the like) of proteins. Appropriate cell lines or host systems can be chosen to ensure the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extent.

In particular, megalomicin biosynthetic enzyme derivatives can be made by altering their sequences by substitutions, additions or deletions that provide for functionally equivalent molecules. Due to the degeneracy of nucleotide coding sequences, other DNA sequences which encode substantially the same amino acid sequence as an megalomicin biosynthetic gene can be used in the practice of the present invention. These include but are not limited to nucleotide sequences comprising all or portions of megalomicin biosynthetic genes that are altered by the substitution of different codons that encode the amino acid residue within the sequence, thus producing a silent change. Likewise, the megalomicin biosynthetic enzyme derivatives of the invention include, but are not limited to, those containing, as a primary amino acid sequence, all or part of the amino acid sequence of megalomicin biosynthetic enzymes, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, the nucleic acids encoding proteins and proteins consisting of or comprising a domain or a fragment of megalomicin biosynthetic enzyme consisting of at least 6 (continuous) amino acids are provided. In other embodiments, the domain or fragment consists of at least 10, 20, 30, 40, or 50 amino acids of a megalomicin biosynthetic enzyme. In specific embodiments, such domains or fragments are not larger than 35, 100 or 200 amino acids. Derivatives or analogs of megalomicin biosynthetic enzyme include but are not limited to molecules comprising regions that are substantially homologous to megalomicin biosynthetic enzyme in various embodiments, at least 30%, 40%, 50%, 60%, 70%, 80%, 90% or 95% identity over an amino acid sequence of identical size or when compared to an aligned sequence in which the alignment is done by a computer homology program known in the art in accordance with the methods of the present invention or whose encoding nucleic acid is capable of hybridizing to a sequence encoding a megalomicin biosynthetic enzyme under stringent, moderately stringent, or nonstringent conditions.

The megalomicin biosynthetic enzyme domains, derivatives and analogs of the invention can be produced by various methods known in the art in accordance with the methods of the present invention. The manipulations which result in their production can occur at the gene or protein level. For example, the cloned megalomicin biosynthetic gene sequence can be modified by any of numerous strategies known in the art (Sambrook et al., 1990, *Molecular Cloning, A Laboratory Manual*, 2d ed., Cold Spring Harbor laboratory, Cold Spring Harbor, N.Y.) in accordance with the methods of the present invention. The sequences can be cleaved at appropriate sites with restriction endonuclease(s), followed by further enzymatic modification if desired, isolated, and ligated in vitro.

Additionally, the megalomicin biosynthetic enzyme-encoding nucleotide sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used in accordance with the methods of the present invention, including but not limited to, chemical mutagenesis and in vitro site-directed mutagenesis (Hutchinson et al., *J. Biol. Chem.* 253:6551–6558 (1978)), use of TAB® linkers (Pharmacia), and the like.

Once a recombinant cell expressing a megalomicin biosynthetic enzyme protein, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product, and the like.

The megalomicin biosynthetic enzyme proteins may be isolated and purified by standard methods known in the art or recombinant host cells expressing the complexes or proteins in accordance with the methods of the invention, including but not restricted to column chromatography (e.g., ion exchange, affinity, gel exclusion, reversed-phase high pressure, fast protein liquid, and the like), differential centrifugation, differential solubility, or by any other standard technique used for the purification of proteins. Functional properties may be evaluated using any suitable assay known in the art in accordance with the methods of the present invention.

Alternatively, once a megalomicin biosynthetic enzyme or its domain or derivative is identified, the amino acid sequence of the protein can be deduced from the nucleotide sequence of the gene which encodes it. As a result, the protein or its domain or derivative can be synthesized by standard chemical methods known in the art in accordance with the methods of the present invention (see Hunkapiller et al, *Nature* 310:105–111 (1984)).

Manipulations of megalomicin biosynthetic enzymes may be made at the protein level. Included within the scope of the invention are megalomicin biosynthetic enzyme domains, derivatives or analogs or fragments, which are differentially modified during or after translation, e.g., by glycosylation, acetylation, phosphorylation, amidation, derivatization by known protecting/blocking groups, proteolytic cleavage, linkage to an antibody molecule or other cellular ligand, and the like. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, and the like.

In specific embodiments, the megalomicin biosynthetic enzymes are modified to include a fluorescent label. In other specific embodiments, the megalomicin biosynthetic enzyme is modified to have a heterofunctional reagent, such heterofunctional reagents can be used to crosslink the members of the complex.

In addition, domains, analogs and derivatives of a megalomicin biosynthetic enzyme can be chemically synthesized. For example, a peptide corresponding to a portion of a megalomicin biosynthetic enzyme, which comprises the desired domain or which mediates the desired activity in vitro can be synthesized by use of a peptide synthesizer. Furthermore, if desired. nonclassical amino acids or chemical amino acid analogs can be introduced as a substitution or addition into the megalomicin biosynthetic enzyme sequence. Non-classical amino acids include but are not limited to the D-isomers of the common amino acids, alpha-amino isobutyric acid, 4-aminobutyric acid, 2-aminobutyric acid, 6-amino hexanoic acid, Aib, 2-amino isobutyric acid, 3-amino propionoic acid, ornithine, norleucine, norvaline, hydroxyproline, sareosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

In cases where natural products are suspected of being mutant or are isolated from new species, the amino acid sequence of the megalomicin biosynthetic enzyme isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

The megalomicin biosynthetic enzyme proteins may also be analyzed by hydrophilicity analysis (Hopp and Woods, Proc. Natl. Acad. Sci. USA 78:3824–3828 (1981)). A hydrophilicity profile can be used to identify the hydrophobic and hydrophilic regions of the proteins, and help predict their orientation in designing substrates for experimental manipulation, such as in binding experiments, antibody synthesis, and the like. Secondary structural analysis can also be done to identify regions of the megalomicin biosynthetic enzyme that assume specific structures (Chou and Fasman, Biochemistry 13:222–23 (1974)). Manipulation, translation, secondary structure prediction, hydrophilicity and hydrophobicity profiles, open reading frame prediction and plotting, and determination of sequence homologies, can be accomplished using computer software programs available in the art.

Other methods of structural analysis including but not limited to X-ray crystallography (Engstrom, Biochem. Exp. Biol. 1 1:7–13 (1974)), mass spectroscopy and gas chromatography (Methods in Protein Science, J. Wiley and Sons, New York, 1997), and computer modeling (Fletterick and Zoller, eds., 1986, Computer Graphics and Molecular Modeling, In: Current Communications in Molecular Biology, Cold Spring Harbor Laboratory, Cold Spring Harbor Press, New York) can also be employed.

The invention also provides an antibody, or a fragment or derivative thereof, which immuno-specifically binds to a domain of megalomicin polyketide synthase (PKS) or a megalomicin modification enzyme. In a specific embodiment, an antibody which immuno-specifically binds to a domain of the megalomicin biosynthetic enzyme encoded by a nucleic acid that hybridizes to a nucleic acid having the nucleotide sequence set forth in the SEQ. ID NO:1, or a fragment or derivative of said antibody containing the binding domain thereof is provided. Preferably, the antibody is a monoclonal antibody.

The megalomicin biosynthetic enzyme protein and domains, fragments, homologs and derivatives thereof may be used as immunogens to generate antibodies which immunospecifically bind such immunogens. Such antibodies include but are not limited to polyclonal, monoclonal, chimeric, single chain, Fab fragments, and an Fab expression library.

Various procedures known in the art may be used for the production of polyclonal antibodies to a megalomicin biosynthetic enzyme protein of the invention, its domains, derivatives, fragments or analogs in accordance with the methods of the present invention.

For production of the antibody, various host animals can be immunized by injection with the native megalomicin biosynthetic enzyme protein or a synthetic version, or a derivative of the foregoing, such as a cross-linked megalomicin biosynthetic enzyme. Such host animals include but are not limited to rabbits, mice, rats, and the like. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and corynebacterium parvum.

For preparation of monoclonal antibodies directed towards a megalomicin biosynthetic enzyme or domains, derivatives, fragments or analogs thereof, any technique that provides for the production of antibody molecules by continuous cell lines in culture may be used. Such techniques include but are not restricted to the hybridoma technique originally developed by Kohler and Milstein (Nature 256:495–497 (1975)), the trioma technique, the human B-cell hybridoma technique (Kozbor et al., Immunology Today 4:72 (1983)), and the EBV hybridoma technique to produce human monoclonal antibodies (Cole et al., in Monoclonal Antibodies and Cancer Therapy, Alan R. Liss, Inc., pp. 77–96 (1985)). In an additional embodiment, monoclonal antibodies can be produced in germ-free animals (WO89/12690). Human antibodies may be used and can be obtained by using human hybridomas (Cote et al., Proc. Natl. Acad. Sci. USA 80:2026–2030 (1983)) or by transforming human B cells with EBV virus in vitro (Cole et al., in Monoclonal Antibodies and Cancer Therapy, Alan R. Liss, Inc., pp. 77–96 (1985)). Techniques developed for the production of "chimeric antibodies" (Morrison et al., Proc. Natl. Acad. Sci. USA 81:6851–6855 (1984); Neuberger et al., Nature 312:604–608 (1984); Takeda et al., Nature 314:452–454 (1985)) by splicing the genes from a mouse antibody molecule specific for the megalomicin biosynthetic enzyme protein together with genes from a human antibody molecule of appropriate biological activity can be used; such antibodies are within the scope of this invention.

Techniques described for the production of single chain antibodies (U.S. Pat. No. 4,946,778) can be adapted to produce megalomicin biosynthetic enzyme-specific single chain antibodies. An additional embodiment utilizes the techniques described for the construction of Fab expression libraries (Huse et al., Science 246:1275–1281 (1989)) to allow rapid and easy identification of monoclonal Fab fragments with the desired specificity for megalomicin biosynthetic enzyme, or domains, derivatives, or analogs thereof. Non-human antibodies can be "humanized" by known methods (see, e.g, U.S. Pat. No. 5,225,539).

Antibody fragments that contain the idiotypes of a megalomicin biosynthetic enzyme can be generated by techniques known in the art in accordance with the methods of the present invention. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab' fragments that can be generated by treating the antibody molecular with papain and a reducing agent, and Fv fragments.

In the production of antibodies, screening for the desired antibody can be accomplished by techniques known in the art in accordance with the methods of the present invention, e.g., ELISA (enzyme-linked immunosorbent assay). To select antibodies specific to a particular domain of the megalomicin biosynthetic enzyme, one may assay generated hybridomas for a product that binds to the fragment of a megalomicin biosynthetic enzyme that contains such a domain.

The foregoing antibodies can be used in methods known in the art relating to the localization and/or quantitation of megalomicin biosynthetic enzyme proteins, e.g., for imaging these proteins or measuring levels thereof in samples, in accordance with the methods of the present invention.

Section V: Heterologous Expression of the Megalomicin Biosynthetic Genes

In one important embodiment, the invention provides methods for the heterologous expression of one or more of the megalomicin biosynthetic genes and recombinant DNA expression vectors useful in the method. For purposes of the invention, any host cell other than *Micromonospora megalomicea* is a heterologous host cell. Thus, included within the scope of the invention in addition to isolated nucleic acids encoding domains, modules, or proteins of the megalomicin PKS and modification enzymes, are recombinant expression vectors that include such nucleic acids. The term expression vector refers to a nucleic acid that can be introduced into a host cell or cell-free transcription and translation system. An expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, are preferred and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli* yeast, Streptomyces, and other commonly used cells are widely known and commercially available. For example, suitable promoters for inclusion in the expression vectors of the invention include those that function in eucaryotic or procaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used.

Thus, recombinant expression vectors contain at least one expression system, which, in turn, is composed of at least a portion of the megalomicin PKS and/or other megalomicin biosynthetic gene coding sequences operably linked to a promoter and optionally termination sequences that operate to effect expression of the coding sequence in compatible host cells. The host cells are modified by transformation with the recombinant DNA expression vectors of the invention to contain the expression system sequences either as extrachromosomal elements or integrated into the chromosome. The resulting host cells of the invention are useful in methods to produce PKS and post-PKS modification enzymes as well as polyketides and antibiotics and other useful compounds derived therefrom.

Preferred host cells for purposes of selecting vector components for expression vectors of the present invention include fungal host cells such as yeast and procaryotic host cells such as *E. coli* and Streptomyces, but mammalian host cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference. Particularly preferred host cells for purposes of the present invention are Streptomyces and Saccharopolyspora host cells, as discussed in greater detail below.

In a preferred embodiment, the expression vectors of the invention are used to construct a heterologous recombinant Streptomyces host cell that expresses a recombinant PKS of the invention. Streptomyces is a convenient host for expressing polyketides, because polyketides are naturally produced in certain Streptomyces species, and Streptomyces cells generally produce the precursors needed to form the desired polyketide. Those of skill in the art will recognize that, if a Streptomyces host cell produces any portion of a PKS enzyme or produces a polyketide modification enzyme, the recombinant vector need drive expression of only those genes constituting the remainder of the desired PKS enzyme or other polyketide-modifying enzymes. Thus, such a vector may comprise only a single ORF, with the desired remainder of the polypeptides constituting the PKS provided by the genes on the host cell chromosomal DNA.

If a Streptomyces or other host cell ordinarily produces polyketides, it may be desirable to modify the host so as to prevent the production of endogenous polyketides prior to its use to express a recombinant PKS of the invention. Such modified hosts include *S. coelicolor* CH999 and similarly modified *S. lividans* described in U.S. Pat. No. 5,672,491, and PCT publication Nos. WO 95/08548 and WO 96/40968, incorporated herein by reference. In such hosts, it may not be necessary to provide enzymatic activities for all of the desired post-translational modifications of the enzymes that make up the recombinantly produced PKS, because the host naturally expresses such enzymes. In particular, these hosts generally contain holo-ACP synthases that provide the phosphopantotheinyl residue needed for functionality of the PKS.

The invention provides a wide variety of expression vectors for use in Streptomyces. The replicating expression vectors of the present invention include, for example and without limitation, those that comprise an origin of replication from a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and pSG5(ts) (Muth et al., 1989, *Mol. Gen. Genet.* 219: 341–348, and Bierman et al., 1992, *Gene* 116: 43–49, each of which is incorporated herein by reference), or a high copy number vector, such as plJ101 and pJV1 (see Katz et al., 1983, *J. Gen. Microbiol.* 129: 2703–2714; Vara et al., 1989, J. Bacteriol. 171: 5782–5781; and Servin-Gonzalez, 1993, Plasmid 30: 131–140, each of which is incorporated herein by reference), For non-replicating and integrating vectors and generally for any vector, it is useful to include at least an E. coli origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of S. lividans, can be employed for purposes of the present invention.

The Streptomyces recombinant expression vectors of the invention typically comprise one or more selectable markers, including antibiotic resistance conferring genes selected from the group consisting of the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Alternatively, several polyketides are naturally colored, and this characteristic can provide a built-in marker for identifying cells.

Megalomicins are currently produced only by the relatively genetically intractable host Micromonospora megalomicinea. This bacteria has not been commonly used in the fermentation industry for the large-scale production of antibiotics, and methods for high level production of megalomicin and its analogs are needed. In contrast, the streptomycete bacteria have been widely used for almost 50 years and are excellent hosts for production of megalomicin and its analogs. Streptomyces lividans and S. coelicolor have been developed for the expression of heterologous PKS systems. These organisms can stably maintain cloned heterologous PKS genes, express them at high levels under controlled conditions, and modify the corresponding PKS proteins (e.g., phosphopantotheinylation) so that they are capable of production of the polyketide they encode. Furthermore, these hosts contain the necessary pathways to produce the substrates required for polyketide synthesis; e.g. propionyl-CoA and methylmalonyl-CoA. A wide variety of cloning and expression vectors are available for these hosts, as are methods for the introduction and stable maintenance of large segments of foreign DNA. Relative to Micromonospora spp., S. lividans and S. coelicolor grow well on a number of media and have been adapted for high level production of polyketides in fermentors. If production levels are low, a number of rational approaches are available to improve yield (see Hosted and Baltz, 1996, Trends Biotechnol. 14(7):245–50, incorporated herein by reference). Empirical methods to increase the titers of these macrolides, long since proven effective for numerous bacterial polyketides, can also be employed.

Preferred Streptomyces host cell/vector combinations of the invention include S. coelicolor CH999 and S. lividans K4-114 host cells, which have been modified so as not to produce the polyketide actinorhodin, and expression vectors derived from the pRM1 and pRM5 vectors, as described in U.S. Pat. Nos. 5,830,750 and 6,022,731 and U.S. patent application Ser. No. 09/181,833, filed Oct. 28, 1998, each of which is incorporated herein by reference. These vectors are particularly preferred in that they contain promoters compatible with numerous and diverse Streptomyces spp. Particularly useful promoters for Streptomyces host cells include those from PKS gene clusters that result in the production of polyketides as secondary metabolites, including promoters from aromatic (Type II) PKS gene clusters. Examples of Type II PKS gene cluster promoters are act gene promoters and tcm gene promoters; an example of a Type I PKS gene cluster promoter are the promoters of the spiramycin PKS genes and DEBS genes. The present invention also provides the megalomicin biosynthetic gene promoters in recombinant form. These promoters can be used to drive expression of the megalomicin biosynthetic genes or any other coding sequence of interest in host cells in which the promoter functions, particularly Micromonospora megalomicea and generally any Streptomyces species.

As described above, particularly useful control sequences are those that alone or together with suitable regulatory systems activate expression during transition from growth to stationary phase in the vegetative mycelium. The promoter contained in the aforementioned plasmid pRM5, i.e., the actI/actIII promoter pair and the actII-ORF4 activator gene, is particularly preferred. Other useful Streptomyces promoters include without limitation those from the ermE gene and the melC1 gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene described above include dnrI, redD, and ptpA genes (see U.S. patent application Ser. No. 09/181,833, supra).

To provide a preferred host cell and vector for purposes of the invention, the megalomicin biosynthetic genes are placed on a recombinant expression vector and transferred to the non-macrolide producing hosts Streptomyces lividans K4-114 and S. coelicolor CH999. Transformation of S. lividans K4-114 or S. coelicolor CH999 with this expression vector results in a strain which produces detectable amounts of megalomicin as determined by analysis of extracts by LC/MS. As noted above, the present invention also provides recombinant DNA compounds in which the encoded megalomicin module 1 KS domain is inactivated (the KS1° mutation). The introduction into Streptomyces lividans or S. coelicolor of a recombinant expression vector of the invention that encodes a megalomicin PKS with a KS1° domain produces a host cell useful for making polyketides by a process known as diketide feeding. The resulting host cells can be fed or supplied with N-acylcysteamine thioesters of precursor molecules to prepare megalomicin derivatives. Such cells of the invention are especially useful in the production of 13-substituted-6-deoxyerythronolide B compounds in recombinant host cells. Preferred compounds of the invention include those compounds in which the substituent at the 13-position is propyl, vinyl, propargyl, other lower alkyl, and substituted alkyl. In a preferred embodiment, the meg PKS is produced from a recombinant construct in which the megAIII gene has been altered to abolish the regions of identical coding sequence it otherwise shares with the megAI gene, or a hybrid PKS is employed in which the megAIII gene product has been replaced by the oleAIII gene product. Recombinant oleAIII genes are described in, for example, PCT patent publication No. 00/026349 and U.S. patent application Ser. No. 09/428,517, filed Oct. 28, 1999, both of which are incorporated herein by reference.

The recombinant host cells of the invention can express all of the megalomicin biosynthetic genes or only a subset of the same. For example, if only the genes for the megalomicin PKS are expressed in a host cell that otherwise does not produce polyketide modifying enzymes that can act on the polyketide produced, then the host cell produces unmodified polyketides, called macrolide aglycones. Such macrolide aglycones can be hydroxylated and glycosylated by adding them to the fermentation of a strain such as, for example, *Streptomyces antibioticus* or *Saccharopolyspora erythraea*, that contains the requisite modification enzymes.

There are a wide variety of diverse organisms that can modify macrolide aglycones to provide compounds with, or that can be readily modified to have, useful activities. For example, as shown in FIG. 5, *Saccharopolyspora erythraea* can convert 6-dEB to a variety of useful compounds. The erythronolide 6-dEB is converted by the eryF gene product to erythronolide B, which is, in turn, glycosylated by the eryBV gene product to obtain 3-O-mycarosylerythronolide B, which contains L-mycarose at C-3. The eryCIII gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromcyin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product. The unmodified megalomicin compounds provided by the present invention, such as, for example, the 6-dEB or 6-dEB analogs, produced in *Streptomyces lividans*, can be provided to cultures of *S. erythraea* and converted to the corresponding derivatives of erythromycins A, B, C, and D in accordance with the procedure provided in the examples below. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, *Streptomyces venezuelae*, which produces picromycin, contains enzymes that can transfer a desosaminyl group to the C-5 hydroxyl and a hydroxyl group to the C-12 position. In addition, *S. venezuelae* contains a glucosylation activity that glucosylates the 2'-hydroxyl group of the desosamine sugar. This latter modification reduces antibiotic activity, but the glucosyl residue is removed by enzymatic action prior to release of the polyketide from the cell. Another organism, *S. narbonensis*, contains the same modification enzymes as *S. venezuelae*, except the C-12 hydroxylase. Thus, the present invention provides the compounds produced by hydroxylation and glycosylation of the macrolide aglycones of the invention by action of the enzymes endogenous to *S. narbonensis* and *S. venezuelae*.

Other organisms suitable for making compounds of the invention include *Micromonospora megalomicea* (discussed above), *Streptomyces antibioticus, S. fradiae*, and *S. thermotolerans*. *S. antibioticus* produces oleandomycin and contains enzymes that hydroxylate the C-6 and C-12 positions, glycosylate the C-3 hydroxyl with oleandrose and the C-5 hydroxyl with desosamine, and form an epoxide at C-8-C-8a. *S. fradiae* contains enzymes that glycosylate the C-5 hydroxyl with mycaminose and then the 4'-hydroxyl of mycaminose with mycarose, forming a disaccharide. *S. thermotolerans* contains the same activities as *S. fradiae*, as well as acylation activities. Thus, the present invention provides the compounds produced by hydroxylation and glycosylation of the macrolide aglycones of the invention by action of the enzymes endogenous to *S. antibioticus, S. fradiae*, and *S. thermotolerans*.

The present invention also provides methods and genetic constructs for producing the glycosylated and/or hydroxylated compounds of the invention directly in the host cell of interest. Thus, the recombinant genes of the invention, which include recombinant megAI, megAII, and megAIII genes with one or more deletions and/or insertions, including replacements of a megA gene fragment with a gene fragment from a heterologous PKS gene (as discussed in the next Section), can be included on expression vectors suitable for expression of the encoded gene products in *Saccharopolyspora erythraea, Streptomyces antibioticus, S. venezuelae, S. narbonensis, Micromonospora megalomicea, S. fradiae*, and *S. thermotolerans*.

A number of erythromycin high-producing strains of *Saccharopolyspora erythraea* and *Streptomyces fradiae* have been developed, and in a preferred embodiment, the megalomicin PKS and/or other megalomicin biosynthetic genes are introduced into such strains (or erythromycin non-producing mutants thereof) to provide the corresponding modified megalomicin compounds in high yields. Those of skill in the art will appreciate that *S. erythraea* contains the desosamine and mycarose biosynthetic and transfer genes as well as DEBS, which, as noted above, makes the same macrolide aglycone, 6-dEB, as the megalomicin PKS. *S. erythraea* does not make megosamine or its corresponding transferase gene, and does not contain the acylation gene of *Micromonospora megalomicea*. Finally, the *S. erythraea* eryG gene product converts mycarose to cladinose, which does not occur in *M. megalomicea*. Thus, the present invention provides a wide variety of *S. erythraea* recombinant host cells, including, for example, those that contain:

(i) wild-type erythromycin biosynthetic genes with recombinant megosamine biosynthetic and transfer genes, with and without megalomicin acylation genes;

(ii) wild-type erythromycin biosynthetic genes except eryG, with recombinant megosamine biosynthetic and transfer genes, with and without megalomicin acylation genes; and (iii) as in (i) and (ii), except that the eryA genes are inactive or deleted and recombinant megA genes have been introduced.

The invention provides other *S. erythraea* strains as well, including those in which any one or more of the erythromycin biosynthetic genes have been deleted or otherwise rendered inactive and in which at least one megalomicin biosynthetic gene has been introduced.

For example, the present invention enables one to express the megosamine genes in a *Saccharopolyspora erythraea* eryG mutant in which the erythromycin C made by this mutant is converted to megalomicin A. Alternatively, one could use an erythromycin C high -producing strain of *S. erythraea* in biotransformation methods in which the erythromycin C is fed to a *Streptomyces lividans* strain carrying only the megosamine biosynthesis and glycosyltransferase genes. As another alternative, one could use a strain of *S. lividans* that carries suitable erythromycin production genes along with the daunosamine biosynthesis genes plus geneX and geneY of FIG. 5, or all of the megosamine biosynthesis genes, to produce megalomicin A.

All or some of the megalomicin gene cluster can be easily cloned under control of a suitable promoter in pCK7 or pSET152 either in one or two plasmids and introduced into the *Saccharopolyspora erythraea* eryG mutant. The actII-ORF4/actIp system and the phiC31/int system in pSET function well in this organism (see Rowe et al., 1998, *Gene*, 216:215–23, incorporated herein by reference). Alternatively, the megosamine biosynthesis genes are introduced into *Streptomyces lividans* on the same plasmids and the production of megalomicin A or its precursor mediated by bioconversion, done by feeding erythronolide B, 3-alpha-mycarosylerythronolide B, erythromycin D or erythromycin C to the *S. lividans* strain.

Lack of adequate resistance to megalomicin A in *S. erythraea* or *S. lividans* is not expected, because both organisms have MLS resistance genes (ermE and mgt/lrm, respectively), which confer resistance to several 14-membered macrolides (see Cundliffe, 1989, *Annu. Rev. Microbiol.* 43:207–33; Jenkins and Cundliffe, 1991, *Gene* 108:55–62; and Cundliffe, 1992, *Gene*, 115:75–84, each of which is incorporated herein by reference). One can also readily determine the level of resistance of the *S. erythraea* eryG mutant and the *S. lividans* host cells to megalomicin A, both in plate tests and in liquid medium. One can repeat the bioconversion method using an eryG mutant of a high erythromycin A producing *S. erythraea* strain (or an eryB or eryC mutant, as necessary) to determine the level at which megalomicin A can be produced. Furthermore, if experience shows that high level megalomicin A production requires a higher level of resistance to this macrolide than present in *S. erythraea* or *S. lividans*, the necessary megalomicin self-resistance genes will be cloned from *M. megalomicea* and moved into either one of the heterologous hosts. This will be straightforward work since self-resistance genes are usually found in the cluster of macrolide biosynthesis genes and can be identified by their homology to known macrolide resistance genes and(or) by the resistance phenotype they impart to a strain that normally is sensitive.

Alternatively, geneX and geneY (FIG. 5) can be added to cassettes containing the relevant daunosamine (dnm) biosynthesis genes (FIG. 5) to provide the ability to make TDP-megosamine in vivo and attach it to an erythromycin algycone. The TDP-daunosamine biosynthesis genes can be re-cloned from *Streptomyces peucetius* on two compatible and mutually selectable plasmids. When an *S. lividans* strain containing these two plasmids and the dnmS gene for TDP-daunosamine glycosyltransferase is grown in the presence of added epsilon-rhodomycinone, its glycoside with L-daunosamine, called rhodomycin D, is produced in good yield. Thus, bioconversion of one of the erythromycins to megalomicin A should be observed when geneX and geneY are present. One can construct all five combination—the two N-dimethyltransferase genes and the three glycosyltransferase genes—to discriminate geneX and geneY from those connected with mycarose and desosamine biosynthesis and attachment in the megalomicin pathway.

Because the timing of megosamine addition is unknown, one can test erythronolide B, 3-alpha-mycarosylerythronolide B, erythromycin D and erythromycin C as substrates provided to a strain that expresses the megosamine biosynthetic and transferase genes. There is need to test the C3''' and(or) C4''' acylated metabolites like megalomicin C1, because these metabolites are made from megalomicin A and not the converse, based on the precedents in the biosynthesis of tylosin (see Arisawa et al., 1994, *Appl. Environ. Microbiol.* 60: 2657–2661), carbomycin (see Epp et al., 1989, *Gene* 85:293–301), and midecamycin (see Hara and Hutchinson, 1992, *J. Bacteriol.* 174, 5141–5144). If C-6 glycosylation of erythronolide B or 3-alpha-mycarosylerythronolide B (FIG. 5) happens before addition of desosamine to C-5, then the erythromycin genes might not be able to complete formation of megalomicin A from some mono or diglycoside if the erythromycin glycosyltransferases cannot tolerate a C-6 glycoside. Although unexpected, such an outcome could be circumvented in accordance with the methods of the invention by cloning further megalomicin biosynthesis genes into the appropriate *S. erythraea* background or into *S. lividans*—specifically, the necessary deoxysugar biosynthesis and attachment genes—to create a recombinant strain that produces megalomicin A.

The acyltransferase gene that adds acetate or propionate to the C3''' or C4''' positions of mycarose in megalomicin B, C1 and C2 (FIG. 3) is contained within the cosmids of the invention and can be identified by scanning the sequence data for the megalomicin gene cluster to locate homologs of carE and mdmB or their acyA homologs from the tylosin producer. The carE and acyA genes govern C4''' acylation in the carbomycin and tylosin pathway, respectively. The megalomicin homolog has the equivalent function in megalomicin biosynthesis (but is specific for C3''' and C4''' acylation). The gene can be cloned under control of a suitable promoter and introduced into *S. lividans* to produce the desired acyl derivative of megalomicin A. Alternatively, introduction of the carE gene can form megalomicin B. This gene can be cloned from the carbomycin, spiramycin or tylosin producers.

If the amount of megalomicin produced by an *S. erythraea* or *S. lividans* or other recombinant host cell is less than desired, yield can be improved by optimizing the growth medium and fermentation conditions, by increasing expression of the gene(s) that appear to be rate limiting, based on the level of pathway intermediates that are accumulated by the recombinant strain constructed, and by reconstructing the ery, dnm, and megalomicin biosynthesis genes on vectors like pSET152 that can be integrated into the genome to provide a stabler recombinant strain for strain improvement.

In another embodiment, the present invention provides recombinant vectors encoding one or more of the megosamine, desosamine, and mycarose biosynthetic and transfer genes and heterologous host cells comprising those vectors. In this embodiment of the invention, the heterologous host cell is typically a cell that is unable to produce the sugar and transfer it to a polyketide unless the vector of the invention is introduced. For example, neither *Streptomyces lividans* nor *S. coelicolor* is naturally capable of making megosamine, desosamine, or mycarose or transferring those moieties to a polyketide. However, the present invention provides recombinant *Streptomyces lividans* and *S. coelicolor* host cells that are capable of making megosamine, desosamine, and/or mycarose and transferring those moieties to a polyketide.

Moreover, additional recombinant gene products can be expressed in the host cell to improve production of a desired polyketide. As but one non-limiting example, certain of the recombinant PKS proteins of the invention may produce a polyketide other than or in addition to the predicted polyketide, because the polyketide is cleaved from the PKS by the thioesterase (TE) domain in module 6 prior to processing by other domains on the PKS, in particular, any KR, DH, and/or ER domains in module 6. The production of the predicted polyketide can be increased in such instances by deleting the TE domain coding sequences from the gene and, optionally, expressing the TE domain as a separate protein. See Gokhale et al., February 1999, "Mechanism and specificity of the terminal thioesterase domain from the erythromycin polyketide synthase," *Chem. & Biol* 6: 117–125, incorporated herein by reference.

Thus, in one important aspect, the present invention provides methods, expression vectors, and recombinant host cells that enable the production of megalomicin and hydroxylated and glycosylated derivatives of megalomicin in heterologous host cells. The present invention also provides methods for making a wide variety of polyketides derived in part from the megalomicin PKS or other biosynthetic genes, as described in the following Section.

Section VI: Hybrid PKS Genes

The present invention provides recombinant DNA compounds encoding each of the domains of each of the modules of the megalomicin PKS as well as the other megalomicin biosynthetic enzymes. The availability of these compounds permits their use in recombinant procedures for production of desired portions of the megalomicin PKS fused to or expressed in conjunction with all or a portion of a heterologous PKS and, optionally, one or more polyketide modification enzymes. These compounds also permit the modification of polyketides with the various megalomicin modification enzymes. The resulting hybrid PKS can then be expressed in a host cell to produce a desired polyketide or modified form thereof.

Thus, in accordance with the methods of the invention, a portion of the megalomicin biosynthetic gene coding sequence that encodes a particular activity can be isolated and manipulated, for example, to replace the corresponding region in a different modular PKS gene or modification enzyme gene. In addition, coding sequences for individual proteins, modules, domains, and portions thereof of the megalomicin PKS can be ligated into suitable expression systems and used to produce the portion of the protein encoded. The resulting protein can be isolated and purified or can may be employed in situ to effect polyketide synthesis. Depending on the host for the recombinant production of the domain, module, protein, or combination of proteins, suitable control sequences such as promoters, termination sequences, enhancers, and the like are ligated to the nucleotide sequence encoding the desired protein in the construction of the expression vector, as described above.

In one important embodiment, the invention thus provides hybrid PKS enzymes and the corresponding recombinant DNA compounds that encode those hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS. In one preferred embodiment, the first PKS is most but not all of the megalomicin PKS, and the second PKS is only a portion of a non-megalomicin PKS. An illustrative example of such a hybrid PKS includes a megalomicin PKS in which the megalomicin PKS loading module has been replaced with a loading module of another PKS. Another example of such a hybrid PKS is a megalomicin PKS in which the AT domain of extender module 3 is replaced with an AT domain that binds only malonyl CoA. In another preferred embodiment, the first PKS is most but not all of a non-megalomicin PKS, and the second PKS is only a portion of the megalomicin PKS. An illustrative example of such a hybrid PKS includes a rapamycin PKS in which an AT specific for malonyl CoA is replaced with the AT from the megalomicin PKS specific for methylmalonyl CoA. Other illustrative hybrid PKSs of the invention are described below.

Those of skill in the art will recognize that all or part of either the first or second PKS in a hybrid PKS of the invention need not be isolated from a naturally occurring source. For example, only a small portion of an AT domain determines its specificity. See PCT patent application No. WO US99/15047, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

With this general background regarding hybrid PKSs of the invention, one can better appreciate the benefit provided by the DNA compounds of the invention that encode the individual domains, modules, and proteins that comprise the megalomicin PKS. As described above, the megalomicin PKS is comprised of a loading module, six extender modules composed of a KS, AT, ACP, and zero, one, two, or three KR, DH, and ER domains, and a thioesterase domain. The DNA compounds of the invention that encode these domains individually or in combination are useful in the construction of the hybrid PKS encoding DNA compounds of the invention. For example, a DNA compound of the invention that encodes an extender module or portion of an extender module is useful in the construction of a coding sequence that encodes a protein subcomponent of a PKS. The DNA compound of the invention that comprises a coding sequence of a PKS subunit protein is useful in the construction of an expression vector that drives expression of the subunit in a host cell that expresses the other subunits and so produces a functional PKS.

The recombinant DNA compounds of the invention that encode the loading module of the megalomicin PKS and the corresponding polypeptides encoded thereby are useful for a variety of applications. In one embodiment, a DNA compound comprising a sequence that encodes the megalomicin PKS loading module is inserted into a DNA compound that comprises the coding sequence for one or more heterologous PKS extender modules. The resulting construct, in which the coding sequence for the loading module of the heterologous PKS is replaced by that for the coding sequence of the megalomicin PKS loading module provides a novel PKS. Examples include the DEBS, rapamycin, FK-506, FK-520, rifamycin, and avermectin PKS coding sequences. In another embodiment, a DNA compound comprising a sequence that encodes the megalomicin PKS loading module is inserted into a DNA compound that comprises the coding sequence for the megalomicin PKS or a recombinant megalomicin PKS that produces a megalomicin derivative.

In another embodiment, a portion of the loading module coding sequence is utilized in conduction with a heterologous coding sequence. In this embodiment, the invention provides, for example, replacing the methylmalonyl CoA (propionyl) specific AT with a malonyl CoA (acetyl), ethylmalonyl CoA (butyryl), or other CoA specific AT. In addition, the AT and/or ACP can be replaced by another AT and/or another ACP or an inactivated KS, such as a $KS^Q$, an AT, and/or another ACP. The resulting heterologous loading module coding sequence can be utilized in conjunction with a coding sequence for a PKS that synthesizes megalomicin, a megalomicin derivative, or another polyketide.

The recombinant DNA compounds of the invention that encode the first extender module of the megalomicin PKS and the corresponding polypeptides encoded thereby are useful for a variety of applications. In one embodiment, a DNA compound comprising a sequence that encodes the megalomicin PKS first extender module is inserted into a DNA compound that comprises the coding sequence for a heterologous PKS. The resulting construct, in which the coding sequence for a module of the heterologous PKS is either replaced by that for the first extender module of the megalomicin PKS or the latter is merely added to coding sequences for modules of the heterologous PKS, provides a novel PKS coding sequence. In another embodiment, a DNA compound comprising a sequence that encodes the first extender module of the megalomicin PKS is inserted into a DNA compound that comprises coding sequences for the megalomicin PKS or a recombinant megalomicin PKS that produces a megalomicin derivative.

In another embodiment, a portion or all of the first extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (which includes inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS, from a gene for a PKS that produces a polyketide other than megalomicin, or from chemical synthesis. The resulting heterologous first extender module coding sequence can be utilized in conjunction with a coding sequence for a PKS that synthesizes megalomicin, a megalomicin derivative, or another polyketide.

Those of skill in the art will recognize, however, that deletion of the KR domain of extender module 1 or insertion of a DH domain or DH and KR domains into extender module 1 will prevent the typical cyclization of the polyketide at the hydroxyl group created by the KR if such hybrid module is employed as a first extender module in a hybrid PKS or is otherwise involved in producing a portion of the polyketide at which cyclization is to occur. Such deletions or insertions can be useful, however, to create linear molecules or to induce cyclization at another site in the molecule.

As noted above, the invention also provides recombinant PKSs and recombinant DNA compounds and vectors that encode such PKSs in which the KS domain of the first extender module has been inactivated. Such constructs are typically expressed in translational reading frame with the first two extender modules on a single protein, with the remaining modules and domains of a megalomicin, megalomicin derivative, or hybrid PKS expressed as one or more, typically two, proteins to form the multi-protein functional PKS. The utility of these constructs is that host cells expressing, or cell free extracts containing, the PKS encoded thereby can be fed or supplied with N-acylcysteamine thioesters of precursor molecules to prepare megalomicin derivative compounds. See U.S. patent application Ser. No. 09/492,733, filed Jan. 27, 2000, and PCT publication Nos. WO 00/44717, 99/03986 and 97/02358, each of which is incorporated herein by reference.

The recombinant DNA compounds of the invention that encode the second extender module of the megalomicin PKS and the corresponding polypeptides encoded thereby are useful for a variety of applications. In one embodiment, a DNA compound comprising a sequence that encodes the megalomicin PKS second extender module is inserted into a DNA compound that comprises the coding sequence for a heterologous PKS. The resulting construct, in which the coding sequence for a module of the heterologous PKS is either replaced by that for the second extender module of the megalomicin PKS or the latter is merely added to coding sequences for the modules of the heterologous PKS, provides a novel PKS. In another embodiment, a DNA compound comprising a sequence that encodes the second extender module of the megalomicin PKS is inserted into a DNA compound that comprises the coding sequences for the megalomicin PKS or a recombinant megalomicin PKS that produces a megalomicin derivative.

In another embodiment, a portion or all of the second extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (or inactivating) the KR; replacing the KR with a KR, a KR and a DH, or a KR, DH, and ER; and/or inserting a DH or a DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS, from a coding sequence for a PKS that produces a polyketide other than megalomicin, or from chemical synthesis. The resulting heterologous second extender module coding sequence can be utilized in conjunction with a coding sequence from a PKS that synthesizes megalomicin, a megalomicin derivative, or another polyketide.

The recombinant DNA compounds of the invention that encode the third extender module of the megalomicin PKS and the corresponding polypeptides encoded thereby are useful for a variety of applications. In one embodiment, a DNA compound comprising a sequence that encodes the megalomicin PKS third extender module is inserted into a DNA compound that comprises the coding sequence for a heterologous PKS. The resulting construct, in which the coding sequence for a module of the heterologous PKS is either replaced by that for the third extender module of the megalomicin PKS or the latter is merely added to coding sequences for the modules of the heterologous PKS, provides a novel PKS. In another embodiment, a DNA compound comprising a sequence that encodes the third extender module of the megalomicin PKS is inserted into a DNA compound that comprises coding sequences for the megalomicin PKS or a recombinant megalomicin PKS that produces a megalomicin derivative.

In another embodiment, a portion or all of the third extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting the inactive KR; and/or replacing the KR with an active KR, or a KR and DH, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS, from a gene for a PKS that produces a polyketide other than megalomicin, or from chemical synthesis. The resulting heterologous third extender module coding sequence can be utilized in conjunction with a coding sequence for a PKS that synthesizes megalomicin, a megalomicin derivative, or another polyketide.

The recombinant DNA compounds of the invention that encode the fourth extender module of the megalomicin PKS and the corresponding polypeptides encoded thereby are useful for a variety of applications. In one embodiment, a DNA compound comprising a sequence that encodes the megalomicin PKS fourth extender module is inserted into a DNA compound that comprises the coding sequence for a heterologous PKS. The resulting construct, in which the coding sequence for a module of the heterologous PKS is either replaced by that for the fourth extender module of the megalomicin PKS or the latter is merely added to coding sequences for the modules of the heterologous PKS, provides a novel PKS. In another embodiment, a DNA compound comprising a sequence that encodes the fourth extender module of the megalomicin PKS is inserted into a DNA compound that comprises coding sequences for the megalomicin PKS or a recombinant megalomicin PKS that produces a megalomicin derivative.

In another embodiment, a portion of the fourth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting or inactivating any one, two, or all three of the ER, DH, and KR; and/or replacing any one, two, or all three of the ER, DH, and KR with either a KR, a DH and KR, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS (except for the DH and ER domains), from a coding sequence for a PKS that produces a polyketide other than megalomicin, or from chemical synthesis. The resulting heterologous fourth extender module coding sequence can be utilized in conjunction with a coding sequence for a PKS that synthesizes megalomicin, a megalomicin derivative, or another polyketide.

The recombinant DNA compounds of the invention that encode the fifth extender module of the megalomicin PKS and the corresponding polypeptides encoded thereby are useful for a variety of applications. In one embodiment, a DNA compound comprising a sequence that encodes the megalomicin PKS fifth extender module is inserted into a DNA compound that comprises the coding sequence for a heterologous PKS. The resulting construct, in which the coding sequence for a module of the heterologous PKS is either replaced by that for the fifth extender module of the megalomicin PKS or the latter is merely added to coding sequences for the modules of the heterologous PKS, provides a novel PKS. In another embodiment, a DNA compound comprising a sequence that encodes the fifth extender module of the megalomicin PKS is inserted into a DNA compound that comprises the coding sequence for the megalomicin PKS or a recombinant megalomicin PKS that produces a megalomicin derivative.

In another embodiment, a portion or all of the fifth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or 2-hydroxymalonyl CoA specific AT; deleting (or inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS, from a coding sequence for a PKS that produces a polyketide other than megalomicin, or from chemical synthesis. The resulting heterologous fifth extender module coding sequence can be utilized in conjunction with a coding sequence for a PKS that synthesizes megalomicin, a megalomicin derivative, or another polyketide.

The recombinant DNA compounds of the invention that encode the sixth extender module of the megalomicin PKS and the corresponding polypeptides encoded thereby are useful for a variety of applications. In one embodiment, a DNA compound comprising a sequence that encodes the megalomicin PKS sixth extender module is inserted into a DNA compound that comprises the coding sequence for a heterologous PKS. The resulting construct, in which the coding sequence for a module of the heterologous PKS is either replaced by that for the sixth extender module of the megalomicin PKS or the latter is merely added to coding sequences for the modules of the heterologous PKS, provides a novel PKS. In another embodiment, a DNA compound comprising a sequence that encodes the sixth extender module of the megalomicin PKS is inserted into a DNA compound that comprises the coding sequences for the megalomicin PKS or a recombinant megalomicin PKS that produces a megalomicin derivative.

In another embodiment, a portion or all of the sixth extender module coding sequence is utilized in conjunction with other PKS coding sequences to create a hybrid module. In this embodiment the invention provides, for example, replacing the methylmalonyl CoA specific AT with a malonyl CoA, ethylmalonyl CoA, or 2-hydroxymalonyl CoA specific AT; deleting or inactivating the KR or replacing the KR with another KR, a KR and DH, or a KR, DH, and an ER; and/or inserting a DH or a DH and ER. In addition, the KS and/or ACP can be replaced with another KS and/or ACP. In each of these replacements or insertions, the heterologous KS, AT, DH, KR, ER, or ACP coding sequence can originate from a coding sequence for another module of the megalomicin PKS, from a coding sequence for a PKS that produces a polyketide other than megalomicin, or from chemical synthesis. The resulting heterologous sixth extender module coding sequence can be utilized in conjunction with a coding sequence for a PKS that synthesizes megalomicin, a megalomicin derivative, or another polyketide.

The sixth extender module of the megalomicin PKS is followed by a thioesterase domain. This domain is important in the cyclization of the polyketide and its cleavage from the PKS. The present invention provides recombinant DNA compounds that encode hybrid PKS enzymes in which the megalomicin PKS is fused to a heterologous thioesterase or a heterologous PKS is fused to the megalomicin PKS thioesterase. Thus, for example, a thioesterase domain coding sequence from another PKS gene can be inserted at the end of the sixth (or other final) extender module coding sequence in recombinant DNA compounds of the invention or the megalomicin PKS thioesterase can be similarly fused to a heterologous PKS. Recombinant DNA compounds encoding this thioesterase domain are useful in constructing DNA compounds that encode the megalomicin PKS, a PKS that produces a megalomicin derivative, and a PKS that produces a polyketide other than megalomicin or a megalomicin derivative.

Thus, the hybrid modules of the invention are incorporated into a PKS to provide a hybrid PKS of the invention. A hybrid PKS of the invention can result not only:

(i) from fusions of heterologous domain (where heterologous means the domains in a module are derived from at least two different naturally occurring modules) coding sequences to produce a hybrid module coding sequence contained in a PKS gene whose product is incorporated into a PKS, but also:

(ii) from fusions of heterologous modules (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more megalomicin PKS genes with one or more non-megalomicin PKS genes, including both naturally occurring and recombinant non-megalomicin PKS genes, and (iv) from combinations of the foregoing.

Various hybrid PKSs of the invention illustrating these various alternatives are described herein.

An example of a hybrid PKS comprising fused modules results from fusion of the loading module of either the DEBS PKS or the narbonolide PKS (see PCT patent application No. US99/11814, incorporated herein by reference) with extender modules 1 and 2 of the megalomicin PKS to produce a hybrid megAI gene. Co-expression of either one of these two hybrid megAI genes with the megAII and megAIII genes in suitable host cells, such as Streptomcyes lividans, results in expression of a hybrid PKS of the invention that produces 6-deoxyerythronolide B (the polyketide product of the natural megA genes) in recombinant host cells. Co-expression of either one of these two hybrid megAI genes with the eryAII and eryAIII genes similarly results in the production of 6-dEB, while co-expression with the analogous narbonolide PKS genes, picAII, picAIII and picAIV, results in the production of 3-deoxy-3-oxo-6-dEB (3-keto-6-dEB), useful in the production of ketolides, compounds with potent anti-bacterial activity.

Another example of a hybrid PKS comprising a hybrid module is prepared by co-expressing the megAI and megAII genes with a megAIII hybrid gene encoding extender module 5 and the KS and AT of extender module 6 of the megalomicin PKS fused to the ACP of module 6 and the TE of the narbonolide PKS. The resulting hybrid PKS of the invention produces 3-keto-6-dEB. This compound can also be prepared by a recombinant megalomicin derivative PKS of the invention in which the KR domain of module 6 of the megalomicin PKS has been deleted. Moreover, the invention provides hybrid PKSs in which not only the above changes have been made but also the AT domain of module 6 has been replaced with a malonyl-specific AT. These hybrid PKSs produce 2-desmethyl-3-deoxy-3-oxo-6-dEB, a useful intermediate in the preparation of 2-desmethyl ketolides, compounds with potent antibiotic activity.

Another illustrative example of a hybrid PKS includes the hybrid PKS of the invention resulting only from the latter change in the hybrid PKS just described. Thus, co-expression of the megAI and megAII genes with a hybrid megAIII gene in which the AT domain of module 6 has been replaced by a malonyl-specific AT results in the expression of a hybrid PKS that produces 2-desmethyl-6-dEB in recombinant host cells. This compound is a useful intermediate for making 2-desmethyl erythromycins in recombinant host cells of the invention, as well as for making 2-desmethyl semi-synthetic ketolides.

While many of the hybrid PKSs described above are composed primarily of megalomicin PKS proteins, those of skill in the art recognize that the present invention provides many different hybrid PKSs, including those composed of only a small portion of the megalomicin PKS. For example, the present invention provides a hybrid PKS in which a hybrid eryAI gene that encodes the megalomicin PKS loading module fused to extender modules 1 and 2 of DEBS is coexpressed with the eryAII and eryAIII genes. The resulting hybrid PKS produces 6-dEB, the product of the native DEBS. When the construct is expressed in *Saccharopolyspora erythraea* host cells (either via chromosomal integration in the chromosome or via a vector that encodes the hybrid PKS), the resulting recombinant host cell of the invention produces erythromycins. Another illustrative example is the hybrid PKS of the invention composed of the megAI and eryAII and eryAIII gene products. This construct is also useful in expressing erythromycins in *Saccharopolyspora erythraea* host cells. In a preferred embodiment, the *S. erythraea* host cells are eryAI mutants that do not produce 6-deoxyerythronolide B.

Another example is the hybrid PKS of the invention composed of the products of the picAI and picAII genes (the two proteins that comprise the loading module and extender modules 1–4, inclusive, of the narbonolide PKS) and the megAIII gene. The resulting hybrid PKS produces the macrolide aglycone 3-hydroxy-narbonolide in *Streptomyces lividans* host cells and the corresponding erythromycins in *Saccharopolyspora erythraea* host cells.

Each of the foregoing hybrid PKS enzymes of the invention, and the hybrid PKS enzymes of the invention generally, can be expressed in a host cell that also expresses a functional oleP gene product. The oleP gene encodes an oleandomycin modification enzyme, and expression of the gene together with a hybrid PKS of the invention provides the compounds of the invention in which a C-8 hydroxyl, a C-8a or C-8-C-8a epoxide is present.

Recombinant methods for manipulating modular PKS genes to make hybrid PKS enzymes are described in U.S. Pat. Nos. 5,672,491; 5,843,718; 5,830,750; and 5,712,146; and in PCT publication Nos. 98/49315 and 97/02358, each of which is incorporated herein by reference. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319–329, and Baltz, 1998, *Trends Microbiol.* 6:76–83, incorporated herein by reference). Because of the similar activity of the megalomicin PKS and DEBS (both PKS enzymes produce the macrolide aglycone 6-dEB), these methods can be readily applied to the recombinant megalomicin PKS genes of the invention.

These techniques include: (i) deletion or insertion of modules to control chain length, (ii) inactivation of reduction/dehydration domains to bypass beta-carbon processing steps, (iii) substitution of AT domains to alter starter and extender units, (iv) addition of reduction/dehydration domains to introduce catalytic activities, and (v) substitution of ketoreductase KR domains to control hydroxyl stereochemistry. In addition, engineered blocked mutants of DEBS have been used for precursor directed biosynthesis of analogs that incorporate synthetically derived starter units. For example, more than 100 novel polyketides were produced by engineering single and combinatorial changes in multiple modules of DEBS. Hybrid PKS enzymes based on DEBS with up to three catalytic domain substitutions were constructed by cassette mutagenesis, in which various DEBS domains were replaced with domains from the rapamycin PKS (see Schweke et al., 1995, *Proc. Nat. Acad. Sci. USA* 92, 7839–7843, incorporated herein by reference) or one more of the DEBS KR domains was deleted. Functional single domain replacements or deletions were combined to generate DEBS enzymes with double and triple catalytic domain substitutions (see McDaniel et al., 1999, *Proc. Nat. Acad Sci. USA* 96, 1846–1851, incorporated herein by reference). By providing the analogous megalomicin/rapamycin hybrid PKS enzymes, the present invention provides alternative means to make these polyketides.

Methods for generating libraries of polyketides have been greatly improved by cloning PKS genes as a set of three or more mutually selectable plasmids, each carrying a different wild-type or mutant PKS gene, then introducing all possible combinations of the plasmids with wild-type, mutant, and hybrid PKS coding sequences into the same host (see U.S. patent application Serial No. 60/129,731, filed Apr. 16, 1999, and PCT Pub. No. 98/27203, each of which is incorporated herein by reference). This method can also incorporate the use of a KS1° mutant, which by mutational biosynthesis can produce polyketides made from diketide starter units (see Jacobsen et al., 1997, *Science* 277, 367–369, incorporated herein by reference), as well as the use of a truncated gene that leads to 12-membered macrolides or an elongated gene that leads to 16-membered ketolides. Moreover, by utilizing in addition one or more vectors that encode glycosyl biosynthesis and transfer genes, such as those of the present invention for megosamine, desosamine, oleandrose, cladinose, and/or mycarose (in any combination), a large collection of glycosylated polyketides can be prepared.

The following Table lists references describing illustrative PKS genes and corresponding enzymes that can be utilized in the construction of the recombinant hybrid PKSs and the corresponding DNA compounds that encode them of the invention. Also presented are various references describing tailoring enzymes and corresponding genes that can be employed in accordance with the methods of the invention.

Avermectin
U.S. Pat. No. 5,252,474 to Merck.
MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, *Gene* 115: 119–125, Complex Organization of the *Streptomyces avermitilis* genes encoding the avermectin polyketide synthase.

Candicidin (FR008)
Hu et al., 1994, *Mol. Microbiol.* 14: 163–172.
Epothilone
PCT Pub. No. 00/031247 to Kosan.
Erythromycin
PCT Pub. No. 93/13663 to Abbott.
U.S. Pat. No. 5,824,513 to Abbott.
Donadio et al., 1991, *Science* 252:675–9.
Cortes et al., Nov. 8, 1990, *Nature* 348:176–8, An unusually large multifunctional polypeptide in the erythromycin producing polyketide synthase of *Saccharopolyspora erythraea*.
Glycosylation Enzymes
PCT Pub. No. 97/23630 to Abbott.
FK-506
Motamedi et al., 1998, The biosynthetic gene cluster for the macrolactone ring of the immunosuppressant FK506, *Eur. J. biochem.* 256: 528–534.
Motamedi et al., 1997, Structural organization of a multifunctional polyketide synthase involved in the biosynthesis of the macrolide immunosuppressant FK506, *Eur. J. Biochem.* 244: 74–80.
Methyltransferase
U.S. Pat. No. 5,264,355, issued Nov. 23, 1993, Methylating enzyme from Streptomyces MA6858. 31-O-desmethyl-FK506 methyltransferase.
Motamedi et al., 1996, Characterization of methyltransferase and hydroxylase genes involved in the biosynthesis of the immunosuppressants FK506 and FK520, *J. Bacteriol.* 178: 5243–5248.
FK-520
PCT Pub. No. 00/20601 to Kosan.
See also Nielsen et al., 1991, *Biochem.* 30:5789–96 (enzymology of pipecolate incorporation).
Lovastatin
U.S. Pat. No. 5,744,350 to Merck.
Narbomycin (and Picromycin)
PCT Pub. No. WO US99/61599 to Kosan.
Nemadectin
MacNeil et al., 1993, supra.
Niddamycin
Kakavas et al., 1997, Identification and characterization of the niddamycin polyketide synthase genes from *Streptomyces caelestis, J. Bacteriol.* 179: 7515–7522.
Oleandomycin
Swan et al., 1994, Characterization of a *Streptomyces antibioticus* gene encoding a type I polyketide synthase which has an unusual coding sequence, *Mol. Gen. Genet.* 242: 358–362.
PCT Pub. No. 00/026349 to Kosan.
Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.
Platenolide
EP Pub. No. 791,656 to Lilly.
Rapamycin
Schwecke et al., August 1995, The biosynthetic gene cluster for the polyketide rapamycin, *Proc. Natl. Acad. Sci. USA* 92:7839–7843.
Aparicio et al., 1996, Organization of the biosynthetic gene cluster for rapamycin in *Streptomyces hygroscopicus:* analysis of the enzymatic domains in the modular polyketide synthase, *Gene* 169: 9–16.
Rifamycin
August et al., Feb. 13, 1998, Biosynthesis of the ansamycin antibiotic rifamycin: deductions from the molecular analysis of the rifbiosynthetic gene cluster of *Amycolatopsis mediterranei* S669, *Chemistry & Biology*, 5(2): 69–79.

Soraphen

U.S. Pat. No. 5,716,849 to Novartis.

Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

EP Pub. No. 791,655 to Lilly.

Kuhstoss et al., 1996, *Gene* 183:231–6., Production of a novel polyketide through the construction of a hybrid polyketide synthase.

U.S. Pat. No. 5,876,991 to Lilly.

Tailoring Enzymes

Merson-Davies and Cundliffe, 1994, *Mol. Microbiol.* 13: 349–355. Analysis of five tylosin biosynthetic genes from the tylBA region of the *Streptomyces fradiae* genome. As the above Table illustrates, there are a wide variety of PKS genes that serve as readily available sources of DNA and sequence information for use in constructing the hybrid PKS-encoding DNA compounds of the invention.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a cognate KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5) :1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, Dissecting and Exploiting Intermodular Communication in Polyketide Synthases", *Science* 284: 482–485, incorporated herein by reference.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Thus, as one illustrative example, the invention provides a hybrid PKS that contains the naturally occurring loading module and thioesterase domain as well as extender modules one, two, four, and six of the megalomicin PKS and further contains hybrid or heterologous extender modules three and five. Hybrid or heterologous extender modules three and five contain AT domains specific for malonyl CoA and derived from, for example, the rapamycin PKS genes.

The invention also provides libraries of PKS genes, PKS proteins, and ultimately, of polyketides, that are constructed by generating modifications in the megalomicin PKS so that the protein complexes produced have altered activities in one or more respects and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on the polyketide, protein, and the encoding nucleotide sequence levels.

As described above, a modular PKS "derived from" the megalomicin or other naturally occurring PKS includes a modular PKS (or its corresponding encoding gene(s)) that retains the scaffolding of the utilized portion of the naturally occurring gene. Not all modules need be included in the constructs; however, the constructs can also comprise more than six modules. On the constant scaffold, at least one enzymatic activity is mutated, deleted, replaced, or inserted so as to alter the activity of the resulting PKS relative to the original (native) PKS. Alteration results when these activities are deleted or are replaced by a different version of the activity, or simply mutated in such a way that a polyketide other than the natural product results from these collective activities. This occurs because there has been a resulting alteration of the starter unit and/or extender unit, stereochemistry, chain length or cyclization, and/or reductive or dehydration cycle outcome at a corresponding position in the product polyketide. Where a deleted activity is replaced, the origin of the replacement activity may come from a corresponding activity in a different naturally occurring PKS or from a different region of the megalomicin PKS. Any or all of the megalomicin PKS genes may be included in the derivative or portions of any of these may be included, but the scaffolding of a functional PKS protein is retained in whatever derivative is constructed. The derivative preferably contains a thioesterase activity from the megalomicin or another PKS.

Thus, a PKS derived from the megalomicin PKS includes a PKS that contains the scaffolding of all or a portion of the megalomicin PKS. The derived PKS also contains at least two extender modules that are functional, preferably three extender modules, and more preferably four or more extender modules, and most preferably six extender modules. The derived PKS also contains mutations, deletions, insertions, or replacements of one or more of the activities of the functional modules of the megalomicin PKS so that the nature of the resulting polyketide is altered at both the protein and DNA sequence levels. Particular preferred embodiments include those wherein a KS, AT, or ACP domain has been deleted or replaced by a version of the activity from a different PKS or from another location within the same PKS. Also preferred are derivatives where at least one non-condensation cycle enzymatic activity (KR, DH, or ER) has been deleted or added or wherein any of these activities has been mutated so as to change the structure of the polyketide synthesized by the PKS.

Conversely, also included within the definition of a PKS derived from the megalomicin PKS are functional non-megalomicin PKS modules or their encoding genes wherein at least one domain or coding sequence therefor of a megalomicin PKS module has been inserted. Exemplary is the use of the megalomicin AT for extender module 2, which accepts a methylmalonyl CoA extender unit rather than malonyl CoA, to replace a malonyl specific AT in another PKS. Other examples include insertion of portions of non-condensation cycle enzymatic activities or other regions of megalomicin synthase activity into a heterologous PKS at both the DNA and protein levels.

Thus, there are at least five degrees of freedom for constructing a hybrid PKS in terms of the polyketide that will be produced. First, the polyketide chain length is determined by the number of extender modules in the PKS, and the present invention includes hybrid PKSs that contain 6, as wells as fewer or more than 6, extender modules. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit, such as acetyl, butyryl, and the like. As noted above, another method for varying loading module specificity involves inactivating the KS activity in extender module 1 (KS1) and providing alternative substrates, called diketides, that are chemically synthesized analogs of extender module 1 diketide products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide.

Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the stereochemistry when there is a complete KR/DH/ER available.

Thus, the modular PKS systems generally and the megalomicin PKS system particularly permit a wide range of polyketides to be synthesized. As compared to the aromatic PKS systems, the modular PKS systems accept a wider range of starter units, including aliphatic monomers (acetyl, propionyl, butyryl, isovaleryl, and the like.), aromatics (aminohydroxybenzoyl), alicyclics (cyclohexanoyl), and heterocyclics (thiazolyl). Certain modular PKSs have relaxed specificity for their starter units (Kao et al., 1994, *Science,* supra). Modular PKSs also exhibit considerable variety with regard to the choice of extender units in each condensation cycle. The degree of beta-ketoreduction following a condensation reaction can be altered by genetic manipulation (Donadio et al., 1991, *Science,* supra; Donadio et al., 1993, *Proc. Natl. Acad. Sci. USA* 90: 7119–7123). Likewise, the size of the polyketide product can be varied by designing mutants with the appropriate number of modules (Kao et al., 1994, *J. Am. Chem. Soc.* 116:11612–11613). Lastly, modular PKS enzymes are particularly well known for generating an impressive range of asymmetric centers in their products in a highly controlled manner. The polyketides, antibiotics, and other compounds produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular, such as the megalomicin, PKS scaffold is virtually unlimited.

While hybrid PKSs are most often produced by "mixing and matching" portions of PKS coding sequences, mutations in DNA encoding a PKS can also be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, *Proc. Natl. Acad. Sci. USA* 82: 448; Geisselsoder et al., 1987, *BioTechniques* 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, *Methods Enzymol.* 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e g., Dalbie-McFarland et al., 1982, *Proc. Natl. Acad. Sci. USA* 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals, in accordance with the methods of the present invention. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemical mutagens, transformed into *E. coli* and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER can correspond to a KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies. The invention provides a variety of recombinant DNA compounds in which the various coding sequences for the domains and modules of the megalomicin PKS are flanked by non-naturally occurring restriction enzyme recognition sites.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length enables the production of quite large libraries.

Methods for introducing the recombinant vectors of the invention into suitable hosts are known to those of skill in the art and typically include the use of $CaCl_2$ or agents such as other divalent cations, lipofection, DMSO, protoplast transformation, conjugation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) the proteins produced from the coding sequences; (3) the polyketides produced from the proteins assembled into a functional PKS; and (4) antibiotics or compounds with other desired activities derived from the polyketides. Of course, combination libraries can also be constructed wherein members of a library derived, for example, from the megalomicin PKS can be considered as a part of the same library as those derived from, for example, the rapamycin PKS or DEBS.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art and can be applied in accordance with the methods of the present invention. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 137:167–173, incorporated herein by reference, and in the Examples below.

The invention provides methods for the preparation of a large number of polyketides. These polyketides are useful intermediates in formation of compounds with antibiotic or other activity through hydroxylation, epoxidation, and glycosylation reactions as described above. In general, the polyketide products of the PKS must be further modified, typically by hydroxylation and glycosylation, to exhibit potent antibiotic activity. Hydroxylation results in the novel polyketides of the invention that contain hydroxyl groups at C-6, which can be accomplished using the hydroxylase encoded by the eryF gene, and/or C-12, which can be accomplished using the hydroxylase encoded by the picK or eryK gene. Also, the oleP gene is available in recombinant form, which can be used to express the oleP gene product in any host cell. A host cell, such as a Streptomyces host cell or a *Saccharopolyspora erythraea* host cell, modified to express the oleP gene thus can be used to produce polyketides comprising the C-8-C-8a epoxide present in oleandomycin. Thus the invention provides such modified polyketides. The presence of hydroxyl groups at these positions can enhance the antibiotic activity of the resulting compound relative to its unhydroxylated counterpart.

Methods for glycosylating polyketides are generally known in the art and can be applied in accordance with the methods of the present invention; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine, mycarose, and/ or megosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosylases. In addition, synthetic chemical methods may be employed.

The antibiotic modular polyketides may contain any of a number of different sugars, although D-desosamine, or a close analog thereof, is most common. Erythromycin, picromycin, megalomicin, narbomycin, and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides. thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea* or *Streptomyces venezuelae* or other host cell to make the conversion, preferably using mutants unable to synthesize macrolides, as discussed in the preceding Section.

Thus, a wide variety of polyketides can be produced by the hybrid PKS enzymes of the invention. These polyketides are useful as antibiotics and as intermediates in the synthesis of other useful compounds, as described in the following section.

Section VII: Host Cells Containing Multiple Expression Vectors

A recombinant host cell of the invention may contain nucleic acid encoding a megalomicin PKS domain, module, or protein, or megalomicin modification enzyme at a single genetic locus, e.g., on a single plasmid or at a single chromosomal locus, or at different genetic loci, e.g., on separate plasmids and/or chromosomal loci. By "multiple" is meant two or more; by "vector" is meant a nucleic acid molecule which can be used to transform host systems and which contains an independent expression system containing a coding sequence under control of a promoter and optionally a selectable marker and any other suitable sequences regulating expression. Typical such vectors are plasmids, but other vectors such as phagemids, cosmids, viral vectors and the like can be used according to the nature of the host. Of course, one or more of the separate vectors may integrate into the chromosome of the host (selection may not be required for maintenance of integrated vectors).

In one embodiment, the invention provides a recombinant host cell, which comprises at least two separate autonomously replicating recombinant DNA expression vectors, each of said vectors comprises a recombinant DNA compound encoding a megalomicin PKS domain or a megalomicin modification enzyme operably linked to a promoter. In another embodiment, the invention provides a recombinant host cell, which comprises at least one autonomously replicating recombinant DNA expression vector and at least one modified chromosome, each of said vector(s) and each of said modified chromosome comprises a recombinant DNA compound encoding a megalomicin PKS domain or a megalomicin modification enzyme operably linked to a promoter. Preferably, the autonomously replicating recombinant DNA expression vector and/or the modified chromosome further comprises distinct selectable markers.

The above multiple-vector (chromosome) expression systems can also be used for expressing heterogeneous polyketide biosynthetic enzymes, e.g., for expressing *Micromonospora megalomicea* megalomicin PKS protein, module, or domain or a megalomicin modification enzyme with a PKS protein, module, or domain, or modification enzyme from other origins in the same host cells. By placing various activities on different expression vectors, a high degree of variation can be achieved in an efficient manner. A variety of hosts can be used; any suitable host cell that can maintain multiple vectors can readily be used. Preferred hosts include Streptomyces, yeast, *E. coli*, other actinomycetes, and plant cells, and mammalian or insect cells or other suitable recombinant hosts can also be used. Preferred among yeast strains are *Saccharomyces cerevisiae* and *Pichia pastoris*. Preferred actinomycetes include various strains of Streptomyces.

If one chooses to use a host cell that does not naturally produce a polyketide, then one may need to ensure that the recombinant host is modified to also contain a holo ACP synthase activity that effects pantetheinylation of the acyl carrier protein. See PCT Pub. No. WO 97/13845, incorporated herein by reference. One of the multiple vectors may be used for this purpose. This activation step is necessary for activation of the ACP. The expression system for the holo ACP synthase may be supplied on a vector separate from that carrying a PKS coding sequence or may be supplied on the same vector or may be integrated into the chromosome of the host, or may be supplied as an expression system for a fusion protein with all or a portion of a polyketide synthase (see U.S. Pat. No. 6,033,883, incorporated herein by reference).

It should be noted that in some recombinant hosts, it may also be necessary to activate the polyketides produced through postsynthesis modifications when polyketides having such modifications are desired. If this is the case for a particular host, the host will be modified, for example by transformation, to contain those enzymes necessary for effecting these modifications. Among such enzymes, for example, are glycosylation enzymes. The use of multiple vectors can facilitate the introduction of expression systems for such enzymes.

In a preferred embodiment, the multiple vector system is used to assemble rapidly and efficiently a combinatorial library of polyketides and the PKS/modification enzymes that produce them. In an illustrative embodiment, the multiple vector system comprises four different vectors, one comprising the megAI gene, one the megAII gene, one the megAIII gene, and one the modification enzyme(s) gene(s). Each of these vectors can be modified to make a set of vectors. For example, one set could contain all possible AT substitutions in the loading and first and second extender modules of the megAI gene product. Another set could contain expression systems for a variety of different modification enzymes. With these four vectors sets and by combining each member of each set with each member of the other three sets, a very large library of cells, vector sets, and polyketides can be rapidly and efficiently assembled.

The combinatorial potential of a modular PKS such as the megalomicin PKS (ignoring the additional potential of different modification enzyme systems) is minimally given by: $AT_L \times (AT_E \times 4)_M$ where $AT_L$ is the number of loading acyl transferases, $AT_E$ is the number of extender acyl transferases, and M is the number of modules in the gene cluster. The number 4 is present in the formula because this represents the number of ways a keto group can be modified by either 1) no reaction; 2) KR activity alone; 3) KR+DH activity; or 4) KR+DH+ER activity. It has been shown that expression of only the first two modules of the erythromycin PKS resulted in the production of a predicted truncated triketide product (See Kao et al., *J. Am. Chem. Soc.*, 116:11612–11613 ((1994)). A novel 12-membered macrolide similar to methymycin aglycone was produced by expression of modules 1–5 of this PKS in *S. coelicolor* (See Kao et al., *J. Am. Chem. Soc.*, 117:9105–9106(1995)). This work shows that PKS modules are functionally independent so that lactone ring size can be controlled by the number of modules present.

In addition to controlling the number of modules, the modules can be genetically modified, for example, by the deletion of a ketoreductase domain as described by Donadio et al., *Science*, 252:675–679 (1991); and Donadio et al., *Gene*, 115:97–103 (1992). In addition, the mutation of an enoyl reductase domain was reported by Donadio, et al., *Proc. Natl. Acad. Sci.*, 90:7119–7123 (1993). These modifications also resulted in modified PKS and thus modified polyketides.

As stated above, in the present invention, the coding sequences for catalytic activities derived from the megalomicin PKS systems found in nature can be used in their native forms or modified by standard mutagenesis techniques to delete or diminish activity or to introduce an activity into a module in which it was not originally present. For example, a KR activity can be introduced into a module normally lacking that function.

In one embodiment of the invention herein, a single host cell is modified to contain a multiplicity of vectors, each vector contributing a portion of the synthesis of a megalomicin PKS and modification enzyme (if any) system. Each of the multiple vectors for production of the megalomicin PKS system typically encodes at least two modules, and at least one of the vectors integrates into the chromosome of the host. Integration can be effected using suitable phage or integrating vectors or by homologous recombination. If homologous recombination is used, the integration event may also be designed to delete endogenous PKS genes residing in the chromosome, as described in the PCT application WO 95/08548. In these embodiments, too, a selectable marker such as hygromycin or thiostrepton resistance can be,included in the vector that effects integration.

As mentioned above, additional enzymes that effect post-translational modifications to the enzyme systems in the megalomicin PKS may be introduced into the host through suitable recombinant expression systems. In addition, enzymes that activate the polyketides themselves, for example, through glycosylation may be added. It may also be desirable to modify the cell to produce more of a particular substrate utilized in polyketide biosynthesis. For example, it is generally believed that malonyl CoA levels in yeast are higher than methylmalonyl CoA; if yeast is chosen as a host, it may be desirable to increase methylmalonyl CoA levels by the addition of one or more biosynthetic enzymes therefor.

The multiple-vector expression system can also be used to make polyketides produced by the addition of synthetic starter units to a PKS that contains an inactivated ketosynthase (KS) in the first module. As noted above, this modification permits the system to incorporate a suitable diketide thioester such as 3-hydroxy-2-methyl pantonoic acid-N-acetyl cysteamine thioester, or similar thioesters of diketide analogs, as described by Jacobsen et al., *Science*, 277:367–369 (1997). The construction of PKS modules containing inactivated ketosynthase regions can be conducted by methods known in the art, such as the method described in U.S. Pat. No. 6,080,555 and PCT publication Nos. WO 99/03986 and 97/02358, each of which is incorporated herein by reference, in accordance with the methods of the present invention.

The multiple-vector expression system can be used to produce polyketides in hosts that normally do not produce them, such as *E. coli* and yeast. It also provides more efficient means to provide a variety of polyketide products by supplying the elements of the introduced PKS, whether in an *E. coli* or yeast host or in other more traditionally used hosts, such as Streptomyces. The invention also includes libraries of polyketides prepared using the methods of the invention.

Section VIII: Compounds

The methods and recombinant DNA compounds of the invention are useful in the production of polyketides. In one important aspect, the invention provides methods for making antibiotic compounds related in structure to erythromycin, a potent antibiotic compound. The invention also provides novel ketolide compounds, polyketide compounds with potent antibiotic activity of significant interest due to activity against antibiotic resistant strains of bacteria. See Griesgraber et al., 1996, *J. Antibiot.* 49: 465–477, incorporated herein by reference. Most if not all of the ketolides prepared to date are synthesized using erythromycin A, a derivative of 6-dEB, as an intermediate. In one embodiment, the present invention provides the 3-keto derivatives of the megalomicins for use as antibiotics. In particular, the 3-keto derivative of megalomicin A is a preferred ketolide of the invention. These compounds can be made chemically, substantially in accordance with the procedures for making ketolides described in the prior art, or in recombinant host cells of the invention in which the megosamine and desosamine biosynthetic and transferase genes are present but which do not make or transfer the mycarose moiety and/or the PKS has been modified to delete the KR domain of extender module 6. The invention also provides methods for making intermediates useful in preparing traditional, 6-dEB- and erythromycin-derived ketolide compounds. See Griesgraber et al., supra; Agouridas et al., 1998, *J. Med. Chem.* 41: 4080–4100, U.S. Pat. Nos. 5,770,579; 5,760,233; 5,750,510; 5,747,467; 5,747, 466; 5,656,607; 5,635,485; 5,614,614; 5,556,118; 5,543, 400; 5,527,780; 5,444,051; 5,439,890; 5,439,889; and PCT publication Nos. WO 98/09978 and 98/28316, each of which is incorporated herein by reference.

As noted above, the hybrid PKS genes of the invention can be expressed in a host cell that contains the desosamine, megosamine, and/or mycarose biosynthetic genes and corresponding transferase genes as well as the required hydroxylase gene(s), which may, for example and without limitation, be either picK, megK, or eryK (for the C-12 position) and/or megF oreryF (for the C-6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone, as described above.

The compounds of the invention are thus optionally glycosylated forms of the polyketide set forth in formula (1) below which are hydroxylated at either the C-6 or the C-12 or both. The compounds of formula (1) can be prepared using the loading and the six extender modules of a modular PKS, modified or prepared in hybrid form as herein described. These polyketides have the formula:

(2)

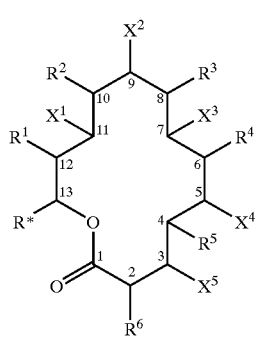

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ independently two H, H and OH, or =O; or each of $X^1$–$X^5$ is independently H and the compound of formula (2) contains a double-bond in the ring adjacent to the position of said X at 2–3, 4–5, 6–7, 8–9 and/or 10–11;

with the proviso that:

at least two of $R^1$–$R^6$ are alkyl (1–4C).

Preferred compounds comprising formula 2 are those wherein at least three of $R^1$–$R^5$ are alkyl (1–4C), preferably methyl or ethyl; more preferably wherein at least four of $R^1$–$R^5$ are alkyl (1–4C), preferably methyl or ethyl. Also preferred are those wherein $X^2$ is two H, =O, or H and OH, and/or $X^3$ is H, and/or $X^1$ is OH and/or $X^4$ is OH and/or $X^5$ is OH. Also preferred are compounds with variable R* when $R^1$–$R^5$ is methyl, $X^2$ is =O, and $X^1$, $X^4$ and $X^5$ are OH. The glycosylated forms (i.e., mycarose or cladinose at C-3, desosamin e at C-5, and/or megosamine at C-6) of the foregoing, are also preferred.

As described above, there are a wide variety of diverse organisms that can modify compounds s uch as those described herein to provide compounds with or that can be readily modified to have useful activities. For example, Saccharopolyspora erythraea can convert 6-dEB to a variety of useful compounds. The compounds provided by the present invention can be provided to cultures of Saccharopolyspora erythraea and converted to the corresponding derivatives of erythromycins A, B, C, and D in accordance with the procedure provided in the Examples, below. To ensure that only the desired compound is produced, one can use an S. erythraea eryA mutant that is unable to produce 6-dEB but can still carry out the desired conversions (Weber et al., 1985, J. Bacteriol. 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production. Each of the erythromycins A, B, C, and D has antibiotic activity, although erythromycin A has the highest antibiotic activity. Moreover, each of these compounds can form, under treatment with mild acid, a C-6 to C-9 hemiketal with motilide activity. For formation of hemiketals with motilide activity, erythromycins B, C, and D, are preferred, as the presence of a C-12 hydroxyl allows the formation of an inactive compound that has a hemiketal formed between C-9 and C-12.

Thus, the present invention provides the compounds produced by hydroxylation and glycosylation of the compounds of the invention by action of the enzymes endogenous to Saccharopolyspora erythraea and mutant strains of S. erythraea. Such compounds are useful as antibiotics or as motilides directly or after chemical modification. For use as antibiotics, the compounds of the invention can be used directly without further chemical modification. Erythromycins A, B, C, and D all have antibiotic activity, and the corresponding compounds of the invention that result from the compounds being modified by Saccharopolyspora erythraea also have antibiotic activity. These compounds can be chemically modified, however, to provide other compounds of the invention with potent antibiotic activity. For example, alkylation of erythromycin at the C-6 hydroxyl can be used to produce potent antibiotics (clarithromycin is C-6-O-methyl), and other useful modifications are described in, for example, Griesgraber et al., 1996, J. Antibiot. 49: 465–477, Agouridas et al., 1998, J. Med. Chem. 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; and 5,439,889; and PCT publication Nos. WO 98/09978 and 98/28316, each of which is incorporated herein by reference.

For use as motilides, the compounds of the invention can be used directly without further chemical modification. Erythromycin and certain erythromycin analogs are potent agonists of the motilin receptor that can be used clinically as prokinetic agents to induce phase III of migrating motor complexes, to increase esophageal peristalsis and LES pressure in patients with GERD, to accelerate gastric emptying in patients with gastric paresis, and to stimulate gall bladder contractions in patients after gallstone removal and in diabetics with autonomic neuropathy. See Peeters, 1999, Motilide Web Site, http://www.med.kuleuven. ac.be/med/gih/motilid.htm, and Omura et al., 1987, Macrolides with gastrointestinal motor stimulating activity, J. Med. Chem. 30: 1941–3). The corresponding compounds of the invention that result from the compounds of the invention being modified by Saccharopolyspora erythraea also have motilide activity, particularly after conversion, which can also occur in vivo, to the C-6 to C-9 hemiketal by treatment with mild acid. Compounds lacking the C-12 hydroxyl are especially preferred for use as motilin agonists. These compounds can also be further chemically modified, however, to provide other compounds of the invention with potent motilide activity.

Moreover, and also as noted above, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. In addition to *Saccharopolyspora erythraea, Streptomyces venezuelae, S. narbonensis, S. antibioticus, Micromonospora megalomicea, S. fradiae,* and *S. thermotolerans* can also be used. In addition to antibiotic activity, compounds of the invention produced by treatment with *M. megalomicea* enzymes can have antiparasitic activity as well. Thus, the present invention provides the compounds produced by hydroxylation and glycosylation by action of the enzymes endogenous to *S. erythraea, S. venezuelae, S. narbonensis, S. antibioticus, M. megalomicea, S. fradiae,* and *S. thermotolerans.*

The present invention also provides methods and genetic constructs for producing the glycosylated and/or hydroxylated compounds of the invention directly in the host cell of interest. Thus, the recombinant genes of the invention, which include recombinant megAI, megAII, and megAIII genes with one or more deletions and/or insertions, including replacements of a megA gene fragment with a gene fragment from a heterologous PKS gene, can be included on expression vectors suitable for expression of the encoded gene products in *Saccharopolyspora erythraea, Micromonospora megalomicea, S. venezuelae, S. narbonensis, S. antibioticus, S. fradiae,* and *S. thermotolerans.*

The compounds of the invention can be produced by growing and fermenting the host cells of the invention under conditions known in the art for the production of other polyketides. The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX,* Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the invention and shall not be construed as being a limitation on the scope of the invention or claims.

EXAMPLE 1

Cloning and Characterization of the Megalomicin Biosynthetic Gene Cluster from *Micromonospora meglomicea*

Experimental Procedures

Bacterial Strains, Media, and Growth Conditions

Routine DNA manipulations were performed in *Escherichia coli* XL1 Blue or *E. coli* XL1 Blue MR (Stratagene) using standard culture conditions (Sambrook et al., 1989). *M. megalomicea* subs. *nigra* NRRL3275 was obtained from the ATCC collection and cultured according to recommended protocols. For isolation of genomic DNA, *M. megalomicea* was grown in TSB (Hopwood et al., 1985) at 30° C. *S. lividans* K4-114. (Ziermann and Betlach, 1999), which carries a deletion of the actinorhodin biosynthetic gene cluster, was used as the host for expression of the megAI-AIII genes. *S. lividans* strains were maintained on R5 agar at 30° C. and grown in liquid YEME for preparation of protoplasts (Hopwood et al., 1985). *S. erythraea* NRRL2338 was used for expression of the megosamine genes. *S. erythraea* strains were maintained on R5 agar at 34° C. and grown in liquid TSB for preparation of protoplasts.

Manipulation of DNA and Organisms

Manipulation and transformation of DNA in *E. coli* was performed by standard procedures (Sambrook et al., 1989) or by suppliers protocols. Protoplasts of *S. lividans* and *S.*

*erythraea* were generated for transformation by plasmid DNA using the standard procedure. *S. lividans* transformants were selected on R5 using 2 ml of a 0.5 mg/ml thiostrepton overlay. *S. erythraea* transformants were selected on R5 using 1.5 ml of a 0.6 mg/ml apramycin overlay.

Isolation of the meg Gene Cluster

A cosmid library was prepared in SuperCos (Stratagene) from *M. megalomicea* total DNA partially digested with Sau3A I, and introduced into *E. coli* using a Gigapack III XL (Stratagene) in-vitro packaging kit. $^{32}$P-labelled DNA probes encompassing the KS2 domain from ery DEBS, or a mixture of segments encompassing modules 1 and 2 from ery DEBS were used separately to screen the cosmid library by colony hybridization. Several colonies which hybridized with the probes were further analyzed by sequencing the ends of their cosmid inserts using T3 and T7 primers. BLAST (Altschul et al., 1990) analysis of the sequences revealed several colonies with DNA sequences highly homologous to genes from the ery cluster. Together with restriction analysis, this led to the isolation of two overlapping cosmids, pKOS079-93A and pKOS079-93D which covered ~45 kb of the meg cluster. A 400 bp PCR fragment was generated from the left end of and pKOS079-93D and used to reprobe the cosmid library. Likewise, a 200 bp PCR fragment generated from the right end of pKOS079-93A was used to reprobe the cosmid library. Analysis of hybridizing colonies as described above resulted in identification of two additional cosmids, pKOS079-138B and pKOS79-124B which overlap the previous two cosmids. BLAST analysis of the far left and right end sequences of these cosmids indicated no homology to any known genes related to polyketide biosynthesis and therefore indicates that the set of four cosmids spans the entire megalomicin biosynthetic gene cluster.

DNA Sequencing and Analysis

PCR-based double stranded DNA sequencing was performed on a Beckman CEQ 2000 capillary sequencer using reagents and protocols provided by the manufacturer. A shotgun library of the entire cosmid pKOS079-93D insert was made as follows: DNA was first digested with Dra I to eliminate the vector fragment, then partially digested with Sau3A I. After agarose electrophoresis, bands between 1–3 kb were excised from the gel and ligated with BamH I digested pUC19. Another shotgun library was generated from a 12 kb Xho I/EcoR I fragment subcloned from cosmid pKOSO79-93A to extend the sequence to the megF gene. A 4 kb Bgl II/Xho I fragment from cosmid pKOS079-138B was sequenced by primer walking to extend the sequencing to the megT gene. Sequence was assembled using Sequencher (Gene Codes Corp.) software package and analyzed with Mac Vector (Oxford Molecular Group) and the NCBI BLAST server (www.ncbi.nlm.nih.gov/BLAST/).

Plasmids

Plasmid pKOS108-6 is a modified version of pKAO127'kan' (Ziermann and Betlach, 1999; Ziermann and Betlach, 2000) in which the eryAI-III genes between the Pac I and EcoR I sites have been replaced with the megAI-III genes. This was done by first substituting a synthetic nucleotide DNA duplex (5'-TAAGAATTCGGAGATCTGGCCTCAGCTCTAGAC (SEQ ID NO: 21), complementary oligo 5'-AATTGTCTAGAGCTGAGGCCAGATCTCCGAATT CTTAAT (SEQ ID NO: 22)) between the Pac I and EcoR I sites of the pKAO127'kan' vector fragment. The 22 kb EcoR I/Bgl II fragment from cosmid pKOS079-93D containing the megAI-II genes was inserted into EcoR I and Bgl II sites of the resulting plasmid to generate pKOS024-84. A 12 kb Bgl II/BbvC I fragment containing the megAIII and part of the megCII gene was subcloned from pKOS079-93A and excised as a Bgl II/Xba I fragment and ligated into the corresponding sites of pKOS024-84 to yield the final expression plasmid pKOS108-06.

The megosamine integrating vector, pKOS97-42, was constructed as follows: A subclone was generated containing the 4 kb Xho I/Sca I fragment from pKOS79-138B together with the 1.7 kb Sca I/Pst I fragment from pKOS79-93D in Litmus 28 (Stratagene). The entire 5.7 kb fragment was then excised as a Spe I/Pst I fragment and combined with the 6.3 kb Pst I/EcoR I fragment from KOS79-93D and EcoR I/Xba I digested pSET152 (Bierman et al., 1992) to construct plasmid pKOS97-42.

Production and Analysis of Secondary Metabolites

Fermentation for production of polyketide, LC/MS analysis, and quantification of 6-dEB for *S. lividans* K4-114/pKOS108-6 and *S. lividans* K4-114/pKAO127'kan' were essentially as previously described (Xue et al., 1999). *S. erythraea* NRRL2338 and *S. erythraea*/pKOS97-42 were grown for 6 days in F1 media (Brünker et al., 1998). Samples of broth were clarified in a microcentrifuge (5 min. 13,000 rpm). For LC/MS preparation, isopropanol was added to the supernatant (1:2 ratio) and centrifuged again. Erythromycins and megalomicins were detected by electrospray mass spectrometry and quantity was determined by evaporative light scattering detection (ELSD). The LC retention time and mass spectra of erythromycin and megalomicins were identical to known standards.

Nucleotide Sequence of the meg Gene Cluster

Figure 9:
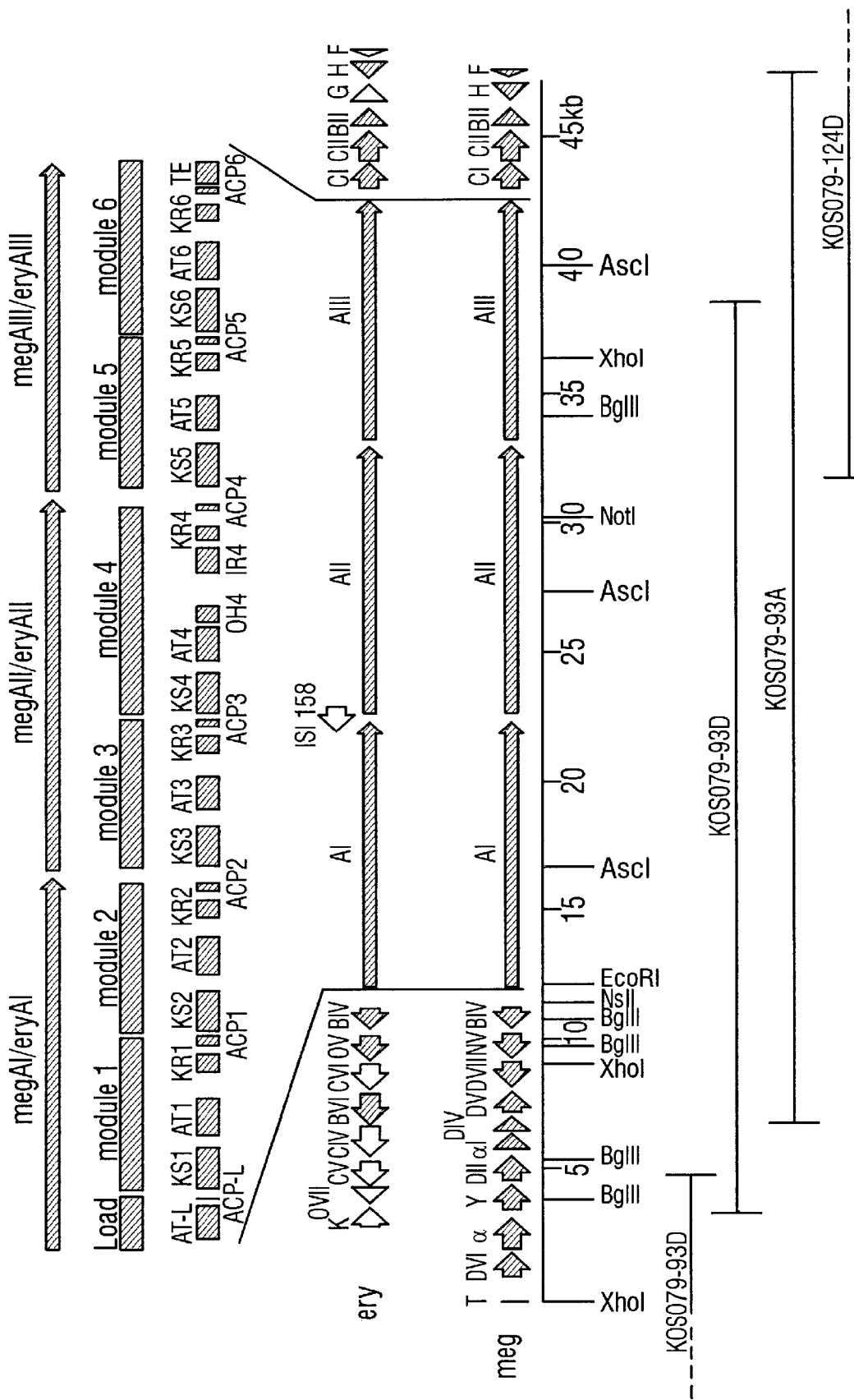
FIG. 9 depicts the cloned megalomicin biosynthetic gene cluster and certain cosmids of the invention that comprise portions of the cluster.

A series of 4 overlapping inserts containing the meg cluster (FIG. 9) were isolated from a cosmid library prepared from total genomic DNA of *M. megalomicea* and covers >100 kb of the genome. A contiguous 48 kb segment which encodes the megalomicin PKS and several deoxysugar biosynthetic genes was sequenced and analyzed. The segment contains 17 complete ORFs as well as an incomplete ORF at each end, organized as shown in FIG. 9.

PKS genes. The ORFs megAI, megAII and megAIII encode the polyketide synthase responsible for synthesis of 6-dEB. The enzyme complex, meg DEBS, is highly similar to ery DEBS, with each of the three predicted polypeptides sharing an average of 83% overall similarity with their ery PKS counterpart. Both PKSs are composed of 6 modules (2 modules per polypeptide) and each module is organized in the identical manner (FIG. 9). A dendrogram analysis (Schwecke et al., 1995) employing 70 acyltranferase (AT) domains revealed that the 6 meg extender AT domains cluster with AT domains that incorporate methylmalonyl CoA (not shown). The loading module of meg DEBS also lacks a $KS^Q$ domain which is utilized by most macrolide PKSs for decarboxylation of the starter unit to initiate polyketide synthesis (Bisang et al., 1999; Kuhstoss et al., 1996; Kakavas et al., 1997; Xue et al., 1998), implying that priming begins with a propionate unit. In addition, a conserved Gly to Pro substitution in the NADPH-binding region of the ketoreductase (KR) domain of module 3 is observed in meg DEBS, which has been proposed to account for its inactivity in ery DEBS (Donadio et al., 1991).

Deoxysugar Genes

BLAST (Altschul et al., 1990) analysis of the genes flanking the PKS indicated that 12 complete ORFs and 1 partial ORF appear to encode functions required for synthesis of one of the three megalomicin deoxysugars. Assignment of each ORF to a specific deoxysugar pathway was made based on comparison to the ery genes and other related genes involved in deoxysugar biosynthesis (Table 2).

TABLE 2

Deduced functions of genes identified in the megalomicin gene cluster.

| Gene | Closest Match (polypeptide)[a] | % Sim[a] | Proposed Pathway | Proposed Function | Reference |
|---|---|---|---|---|---|
| megT | EryBVI | | Mycarose/ Megosamine | 2,3-Dehydratase | (Summers et al., 1997; Gaisser et al., 1997) |
| megDVI | EryCII | 63 | Megosamine | 3,4-Isomerase | (Summers et al., 1997) |
| megDI | EryCIII | 79 | Megosamine | Glycosyltransferase | (Summers et al., 1997) |
| megY | AcyA (S. thermotolerans) | 52 | | Mycarose O-acyl-transferase | (Arisawa et al., 1994) |
| megDII | EryCI | 58 | Megosamine | Aminotransferase | (Dhillon et al., 1989; Summers et al., 1997) |
| megDIII | DesVI (S. venezuelae) | 61 | Megosamine | Dimethyltransferase | (Xue et al., 1998) |
| megDIV | DmnU (S. peucetius) | 65 | Megosamine | 3,5-Epimerase | (Olano et al., 1999) |
| megDV | Dehydrogenase (A. orientalis) | 61 | Megosamine | 4-Ketoreductase | (Summers et al., 1997; van Wageningen et al., 1998) |
| megDVII | EryBII | 73 | Megosamine | 2,3-Reductase | (Summers et al., 1997) |
| megBV | EryBV | 86 | Mycarose | Glycosyltransferase | (Summers et al., 1997; Gaisser et al., 1997) |
| megBIV | EryBIV | 80 | Mycarose | 4-Ketoreductase | (Summers et al., 1997; Gaisser et al., 1997) |
| megAI | EryAI | 81 | 6-dEB | Polyketide Synthase | (Donadio and Katz, 1992) |
| megAII | EryAII | 85 | 6-dEB | Polyketide Synthase | (Donadio and Katz, 1992) |
| megAIII | EryAIII | 83 | 6-dEB | Polyketide Synthase | (Donadio and Katz, 1992) |
| megCII | EryCII | 82 | Desosamine | 3,4-Isomerase | (Summers et al., 1997) |
| megCIII | EryCIII | 89 | Desosamine | Glycosylyltransferase | (Summers et al., 1997) |
| megBII | EryBII | 87 | Mycarose | 2,3-Reductase | (Summers et al., 1997) |
| megH | EryH | 84 | | Thioesterase | (Haydock et al., 1991) |
| megF | EryF | | | C-6 Hydroxylase | (Weber et al., 1991) |

[a]Determined by BLASTX analysis using default parameters.

Three ORFs, megBV, megCIII and megDI, encode glycosyltransferases, apparently one for attachment of each deoxysugar to the macrolide. MegBV was most similar to EryBV, the erythromycin mycarosyltransferase, and hence was assigned to the mycarose pathway in the meg cluster. The closest match for both of the remaining glycosyltransferases was EryCIII, the desosaminyltransferase in erythromycin biosynthesis. Given the higher degree of similarity between EryCIII and MegCIII (Table 2), MegCIII was designated the desosaminyltransferase, leaving MegDI as the proposed megosaminyltransferase. In similar fashion, assignments were made accordingly for; MegCII and MegDVI, two putative 3,4-isomerases similar to EryCII; MegBII and MegDVII, 2,3-reductases homologous to EryBII; MegBIV and MegDV, putative 4-ketoreductases similar to EryBIV (Table 2). The remaining ORFs involved in deoxysugar biosynthesis, megT, megDII, megDIII and megDIV, each encode a putative 2,3-dehydratase, aminotransferase, dimethyltransferase and 3,5-epimerase, respectively (Table 2). Since both the megosamine and desosamine pathways require an aminotransferase and a dimethyltransferase, and since mycarose and megosamine each require a 2,3-dehydratase and a 3,5-epimerase, assignments of these four genes to a specific pathway could not be made on the basis of sequence comparison alone. However, the latter three are implicated in megosamine biosynthesis by experiments described below.

Other Genes

Two additional complete ORFs, designated megY and megH and an incomplete ORF, designated megF, were also identified in the cluster. MegH and MegF share high degrees of similarity with EryH and EryF. EryH and homologs in other macrolide gene clusters are thioesterase-like proteins with unknown function in polyketide gene clusters (Haydock et al., 1991; Xue et al., 1998; Butler et al., 1999; Tang et al., 1999). EryF encodes the erythronolide B C-6 hydroxylase (FIG. 8) (Weber et al., 1991; Andersen and Hutchinson, 1992). MegY does not have an ery counterpart but appears to belong to a (small) family of O-acyltransferases that transfer short acyl chains to macrolides. Two classes exist: AcyA and MdmB transfer acetyl or propionyl groups to the C-3 hydroxyls on 16-membered macrolide rings (Arisawa et al., 1994; Hara and Hutchinson, 1992); CarE and Mpt transfer isovalerate or propionate to the mycarosyl moiety of carbomycin and midecamycin, respectively (Epp et al., 1989; Arisawa et al., 1993; Gu et al., 1996). The structures of various megalomicins suggest that MegY belongs to the latter class and is the acyltransferase which converts megalomicin A to megalomicins B, C1, or C2 (verified experimentally below).

Heterologous Expression of the meg PKS Genes

The wild type and genetically modified versions of the ery DEBS have been used extensively in heterologous Streptomyces hosts for enzyme studies and the production of novel polyketide compounds. Given the similarities between the ery and meg DEBSs, production characteristics were compared in a commonly used Streptomyces host strain. The three megA ORFs were cloned into the expression plasmid pKAO127'kan' (Ziermann and Betlach, 1999) in place of the eryA ORFs. Both plasmids, pKAO127'kan' encoding ery DEBS and pKOS108-06 encoding meg DEBS, were introduced in Streptomyces lividans K4-114 and the production of 6-dEB was determined in shake-flask fermentations. The production profiles were similar in both cases and the maximum titer of 6-dEB was between 30–40 mg/L. In addition, both PKSs produced small amounts (~5%) of 8,8a-deoxyoleandolide, which results from the priming of the PKS with acetate instead of propionate (Kao et al., 1994b). This observation indicates that the loading AT domains of the PKSs display similar relaxed specificities towards starter units.

Conversion of Erythromycin to Megalomicin in *S. erythraea*

An examination of the meg cluster revealed that the putative megosamine biosynthetic genes are clustered directly upstream of the PKS genes. If the hypothesis that these genes are sufficient for biosynthesis and attachment of megosamine to an erythromycin intermediate is correct, then functional expression of these genes in a strain which produces erythromycin, such as *S. erythraea*, should result in production of megalomicin. A 12 kb DNA fragment carrying all the genes between the leftmost XhoI site and the EcoRI site (FIG. 9) was integrated in the chromosome of *S. erythraea* using the site-specific integrating vector pSET152 (Bierman et al., 1992). It was surmised that the left and right ends of this fragment would contain necessary promoter regions for transcription of the convergent set of genes in *M. megalomicea* and that they would likely operate in *S. erythraea*.

Fermentation broth from *S. erythraea*/KOS97-42, which contains the integrated meg genes, was analyzed by LC/MS and compared to LC/MS profiles of the parent *S. erythraea* strain without the meg genes, as well as to megalomicin standards purified from *M. megalomicea*. The new strain was found to produce a mixture of erythromycin A and various megalomicins (~4:1 ratio), thereby showing that the predicted megosamine biosynthetic and glycosyltransferase genes are contained within the cloned meg fragment. The two most abundant congeners identified were megalomicins B and C1. Megalomicin A and C2 were also detected in smaller amounts. The presence of the megalomicins B, C1 and C2 also provides direct evidence for the function of the O-acyl transferase, MegY, which is present in the integrated meg fragment.

Discussion

The homologies observed among modular PKSs enabled the use of ery PKS genes to clone the meg biosynthetic gene cluster from *M. megalomicea*. The close similarities between the megalomicin and erythromycin biosynthetic pathways is also reflected in the overall organization of their genes and in the high degree of homology of the corresponding individual gene-encoded polypeptides. Production of 6-dEB from meg DEBS in *S. lividans* and conversion of erythromycin to megalomicin using the megD genes in *S. erythraea* provides direct evidence that the identified gene cluster is responsible for synthesis of megalomicin.

As seen in FIG. 9, the ~40 kb segments of the two clusters beginning with ery/megBV on the left through the ery/megF genes retain a nearly identical organizational arrangement. The notable differences in this region are eryG and IS1136 which are absent from the segment of the meg cluster analyzed. The eryG gene encodes an S-adenosylmethionine (SAM)-dependent mycarosyl methyltransferase that converts erythromycin C to erythromycin A (FIG. 8) (Weber et al., 1990; Haydock et al., 1991). The mycarose moiety is modified by esterification (MegY) in megalomicin biosynthesis (FIG. 8) and, therefore, the absence of an eryG homolog would be expected in the meg cluster. The IS1136 element located between eryAI and eryAII (Donadio and Staver, 1993) is not known to play a role in erythromycin biosynthesis and its origin in the ery cluster has not been determined.

Figure 8A:
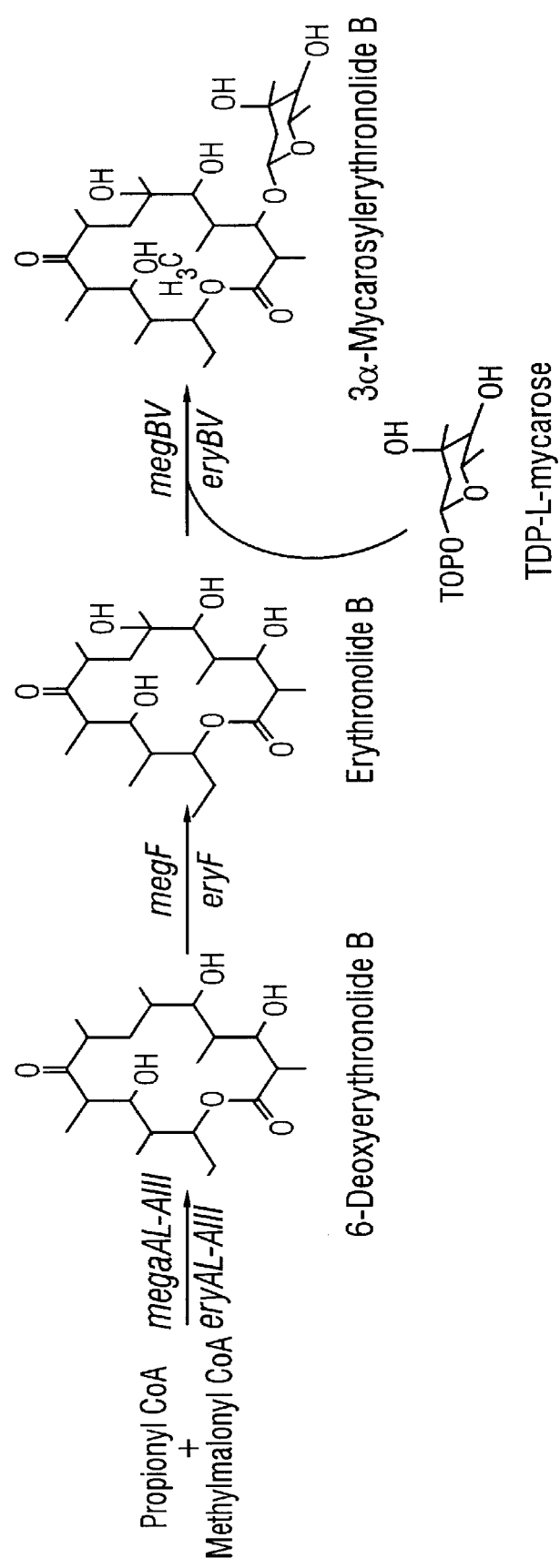
FIG. 8 depicts the biosynthesis of the erythromycins and megalomicins and the enzymes that mediate the biosynthesis of each.
Figure 8B:
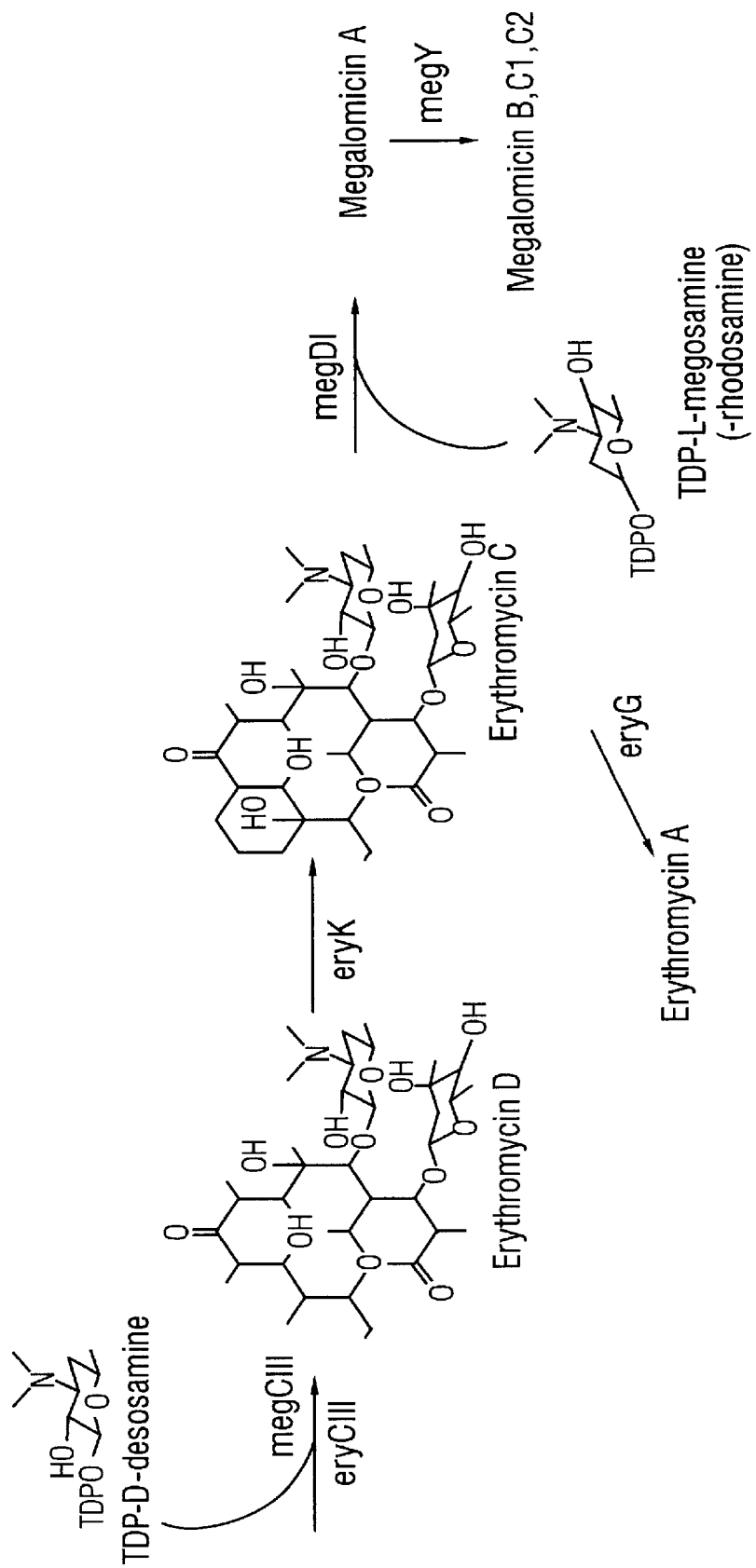

Upstream of the common meg/eryBIV and BV genes, the gene clusters diverge. The ~6 kb segment between eryBV and eryK, the left border of the ery gene cluster (Pereda et al., 1997), contains the remaining genes required for mycarose (eryBVI and BVII) and desosamine biosynthesis (eryCIV, CV, and CVI) and the C-12 hydroxylase (eryK) (Stassi et al., 1993). In contrast, the region upstream of megBV encodes a set of genes (megDI-DVII and megY) which can account for all the activities unique to megalomicin biosynthesis (FIG. 9). Since introduction of this meg DNA segment into *S. erythraea* results in production of megalomicins, it is clear that these genes encode the functions for TDP-megosamine biosynthesis and transfer to its putative substrate erythromycin C, and to acylate megalomicin A (FIG. 8). The remaining region upstream of megDVI should therefore encode genes only for mycarose and desosamine biosynthesis.

Olano et al. (Olano et al., 1999) have recently described a pathway for biosynthesis of TDP-L-daunosamine, a deoxysugar component of the antitumor compounds daunorubicin and doxorubicin produced by *Streptomyces peucetius*. Their pathway proposes four steps from the intermediate TDP-4-keto-6-deoxyglucose controlled by the gene cluster dnmJQTUVZ, although the functions for dnmQ and dnmZ could not be identified and the precise order of reactions in the pathway could not be determined. The genes dnmT, dnmU, dnmJ and dnmV each have proposed counterparts in the meg cluster, megT, megDIV, megDII, and megDV, respectively (see FIG. 10).

Figure 10A:
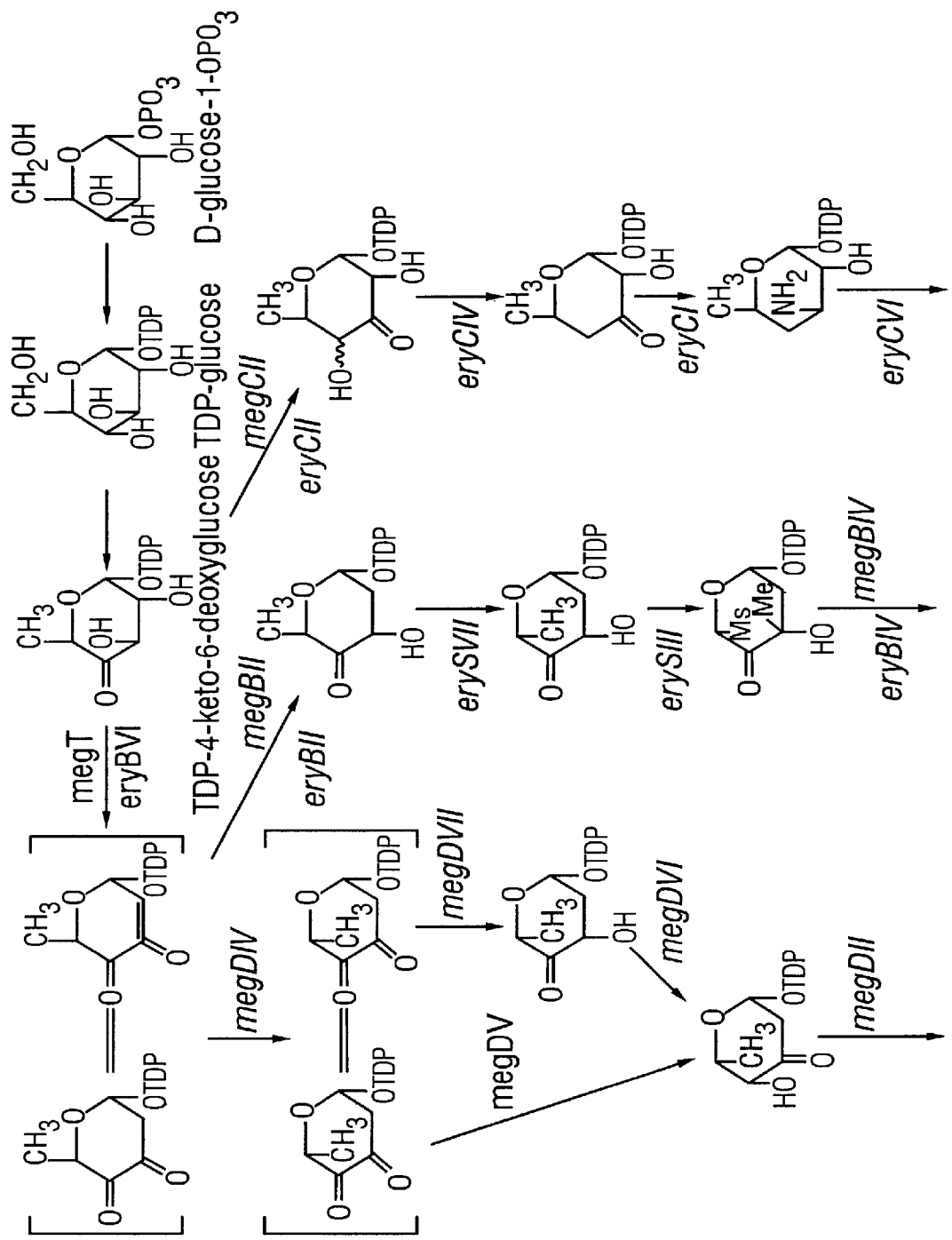
FIG. 10 depicts the biosynthesis of megosamine, mycarose, and desosamine.
Figure 10B:
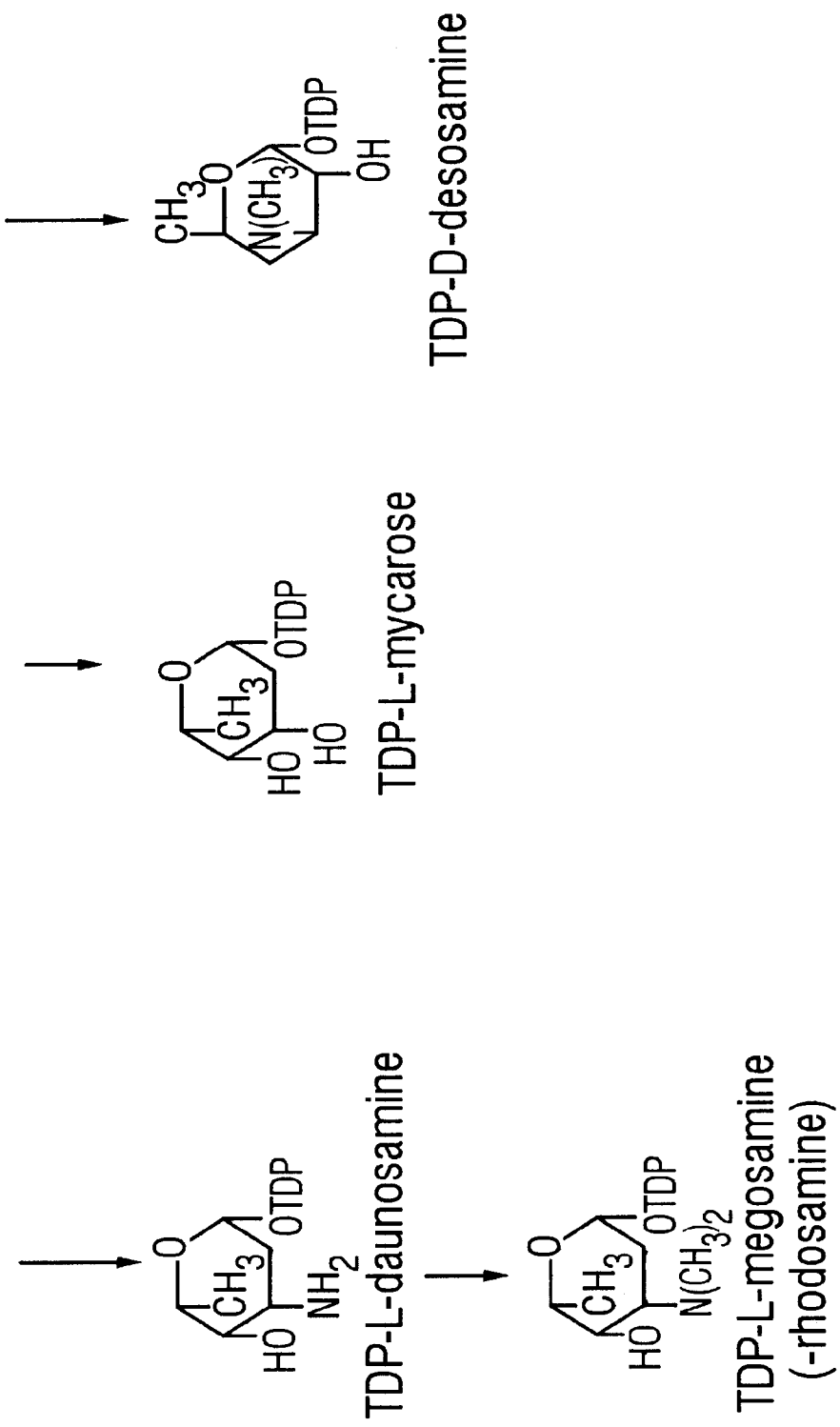

It is possible to describe a pathway to convert TDP-2,6-dideoxy-3,4-diketo-D-hexose (or its enol tautomer), the last intermediate common to the mycarose and megosamine pathways, to TDP-megosamine through the sequence of 5-epimerization, 4-ketoreduction, 3-amination, and 3-N-dimethylation employing the genes megDIV, megDV, megDII, and megDIII. This employs the same functions proposed for biosynthesis of TDP-daunosamine by Olano et al., but in a different sequential order. However, it does not account for the megDVI and megDVII genes since their activities are not required for this route. A parallel pathway which employs these genes is also shown in FIG. 10. In this alternate route, 2,3-reduction and 3,4-tautomerization are performed by the megDVII and megDVI gene products, respectively. A unified single pathway that employs both 4-ketoreduction (megDV) and 2,3-reduction (megDVII) could not be determined. Because the entire gene set from megDVI through megDVII was introduced in *S. erythraea* to produce TDP-megosamine, it is not possible to determine which, if either, of the two alternative pathways is operative, but this can be addressed through systematic gene disruption and complementation.

The 48 kb segment sequenced also contains genes required for synthesis of TDP-L-mycarose and TDP-D-desosamine (FIG. 10). For the latter, megCII, which encodes a putative 3,4-isomerase, the first step in the committed TDP-desosamine pathway, appears to be translationally coupled to megAIII, almost exactly as its erythromycin counterpart, eryCII, was found translationally coupled to eryAIII (Summers et al., 1997). The high degree of similarity between MegCII and EryCII suggests that the pathway to desosamine in the megalomicin- and erythromycin-producing organisms are most likely the same. Similarly, the finding that megBII and megBIV, encoding a 2,3-reductase and 4-ketoreductase, contain close homologs in the mycarose pathway for erythromycin also suggests that TDP-L-mycarose synthesis in the two host organisms is the same.

Of interest are the two genes that encode putative 2,3-reductases, megBII and megDVII. Because MegBII most closely resembles EryBII, a known mycarose biosynthetic enzyme (Weber et al., 1990), and because megBII resides in the same location of the meg cluster as its counterpart in the ery cluster, megBII is assigned to the mycarose pathway and megDVII to the megosamine pathway. Furthermore, the lower degree of similarity between MegDVII and either EryBII or MegBII (Table 2) provides a basis for assigning the opposite L and D isomeric substrates to each of the enzymes (FIG. 10). Finally, megT, which encodes a putative 2,3-dehydratase, is also related to a gene in the ery mycarose pathway, eryBVI. In *S. erythraea*, the proposed intermediate generated by EryBVI represents the first committed step in the biosynthesis of mycarose (FIG. 10). However, the proposed pathways in FIG. 10 suggest this may be an intermediate common to both mycarose and megosamine biosynthesis in *M. megalomicea*. Therefore, megT is named following the designation of the equivalent gene in the daunosamine pathway, dnmT (Olano et al., 1999)

The preferred host-vector system for expression of meg DEBS described here has been used previously for the heterologous expression of modular PKS genes from the erythromycin (Kao et al., 1994a; Ziermann and Betlach, 1999), picromycin (Tang et al., 1999) and oleandomycin pathways, as well as for the generation of novel polyketide backbones where domains have been removed, added or exchanged in various combinations (McDaniel et al., 1999). Recently, hybrid polyketides have been generated through the co-expression of subunits from different PKS systems (Tang et al., 2000).

Expression of the megDVI-megDVII segment in *S. erythraea* and the corresponding production of megalomicins in this host establishes the likely order of sugar attachment in megalomicin synthesis. Furthermore, it provides a means to produce megalomicin in a more genetically friendly host organism, leading to the creation of megalomicin analogs by manipulating the PKS. Over 60 6-dEB analogs have been produced by combinatorial biosynthesis using the ery PKS (McDaniel et al., 1999; Xue et al., 1999). The titers of megalomicin could also be significantly increased above the 5 mg/L obtained from *M. megalomiciea* by introducing the genes into an industrially optimized strain of *S. erythraea*, many of which can produce as much as 10 g/L of erythromycin.

References

Kao, C. M., Katz, L. and Khosla, C. (1994a) Engineered biosynthesis of a complete macrolactone in a heterologous host. *Science* 265: 509–512.

Kao, C. M., Luo, G., Katz, L., Cane, D. E. and Khosla, C. (1994b) Engineered biosynthesis of a triketide lactone from an incomplete modular polyketide synthase. *J. Am. Chem. Soc.* 116: 11612–11613.

McDaniel, R., Thamchaipenet, A., Gustafsson, C., Fu, H., Betlach, M., Betlach, M. et al. (1999) Multiple genetic modifications of the erythromycin gene cluster to produce a library of novel "unnatural" natural products. *Proc. Natl. Acad. Sci. USA* 96: 1846–1851.

Olano, C., Lomovskaya, N., Fonstein, L., Roll, J. T. and Hutchinson, C. R. (1999) A two-plasmid system for the glycosylation of polyketide antibiotics: bioconversion of e-rhodomycinone to rhodomycin D. *Chem. & Biol.* 6: 845–855.

Tang, L., Fu, H., Betlach, M. C. and McDaniel, R. (1999) Elucidating the mechanism of chain termination switching in the picromycin/methymycin polyketide synthase. *Chem. & Biol.* 6: 553–558.

Tang, L., Fu, H. and McDaniel, R. (2000) Formation of functional heterologous complexes using subunits from the picromycin, erythromycin, and oleandomycin polyketide synthases. *Chem. & Biol.* 7: 77–84.

Weber, J. M., Leung, J. O., Maine, G. T., Potenz, R. H., Paulus, T. J. and DeWitt, J. P. (1990) Organization of a cluster of erythromycin genes in *Saccharopolyspora erythraea*. *J. Bacteriol.* 172: 2372–2383.

Weber, J. M., Leung. J. O., Swanson, S. J., Idler, K. B. and McAlpine, J. B. (1991) An erythromycin derivative produced by targeted gene disruption in *Saccharopolyspora erythraea*. *Science* 252: 114–117.

Xue, Q., Ashley, G., Hutchinson. C. R. and Santi, D. V. (1999) A multi-plasmid approach to preparing large libraries of polyketides. *Proc. Natl. Acad. Sci. USA* 96: 11740–11745.

Xue, Y., Zhao, L., Liu, H.-w. and Sherman, D. H. (1998) A gene cluster for the macrolide antibiotic biosynthesis in *Streptomyces venezuelae*: Architecture of metabolic diversity. *Proc. Natl. Acad. Sci. USA* 95: 12111–12116.

Ziermann, R. and Betlach, M. (2000) A two-vector system for the production of recombinant polyketides in Streptomyces. *J. Ind. Microbiol. Biotech.* 24: 46–50.

Ziermann, R. and Betlach, M. C. (1999) Recombinant polyketide synthesis in Streptomyces: Engineering of improved host strains. *Biotechniques* 26: 106–110.

EXAMPLE 2

Stabilizing meg PKS Expression Plasmid by Codon Engineering

Materials and Methods

All bacterial strains were cultured and transformed as described in Example 1.

Fermentation of Streptomyces and Diketide Feeding

Primary Streptomyces transformants were picked and placed in 6 mL of TSB liquid medium with 50 $\mu$/L of thiostrepton and grown at 30° C. When the culture showed some growth (3–4 days), it was transferred into a 250 mL flask containing 50 mL of R6 medium (pH 7.0) with 25 ug/L of thiostrepton and 1 g/L of diketide ((2s,3R)2-methyl-3-hydroxyhexanoate N-propionyl cysteamine thioester) and placed in a 30° C. incubator for 7 days.

Changing Codons and Making Plasmids

There are several identical sequences in the coding sequences for module 2 and module 6 of the megalomicin PKS gene cluster. Expression plasmids containing the full length megalomicin PKS appeared to be somewhat unstable and subject to deletion in recA$^+$ strains like ET124567 and Streptomyces by intra-plasmid homologous recombination. To prevent significant homologous recombination and so stabilize expression plasmids, the codons of two regions of the module 6 coding sequence that are identical to regions in the module 2 coding sequence were changed without changing the sequence of protein encoded. The two regions changed in module 6 were from the base at position 26739 to the base at position 27, 267 and from the base at position 27,697 to the base at position 27, 987, which are identical to the regions from the base at position 6810 to the base at position 7338 and from the base at position 7778 to the base at position 8068, respectively. The start codon of the loading domain of the meg PKS was set to be the $1^{st}$ base. These sequences are shown below > 6810–7338 Sequence in Module 2

TTGCAGCGGTTGTCGGTGGCGGTGCGGGAGGGCGTCGGGTGTTGGGTGTGGTGGTGGGT  (SEQ ID NO: 23)
TCGGCGGTGAATCAGGATGGGGCGAGTAATGGGTTGGCGGCGCCGTCGGGGGTGGCGCAG
CAGCGGGTGATTCGGCGGGCGTGGGGTCGTGCGGGTGTGTCGGGTGGGGATGTGGGTGTG
GTGGAGGCGCATGGGACGGGGACGCGGTTGGGGGATCCGGTGGAGTTGGGGGCGTTGTTG
GGGACGTATGGGGTGGGTCGGGGTGGGGTGGGTCCGGTGGTGGTGGGTTCGGTGAAGGCG
AATGTGGGTCATGTGCAGGCGGCGGCGGGTGTGGTGGGTGTGATCAAGGTGGTGTTGGGG
TTGGGTCGGGGGTTGGTGGGTCCGATGGTGTGTCGGGGTGGGTTGTCGGGGTTGGTGGAT
TGGTCGTCGGGTGGGTTGGTGGTGGCGGATGGGGTGCGGGGGTGGCCGGTGGGTGTGGAT
GGGGTGCGTCGGGGTGGGGTGTCGGCGTTTGGGGTGTCGGGGACGAAT

> 26736–27267 Sequence in Module 6

CTGCAGCGGTTGTCGGTGGCGGTGCGGGAGGGCGTCGGGTGTTGGGTGTGGTGGTGGGT  (SEQ ID NO: 24)
TCGGCGGTGAATCAGGATGGGGCGAGTAATGGGTTGGCGGCGCCGTCGGGGGTGGCGCAG
CAGCGGGTGATTCGGCGGGCGTGGGGTCGTGCGGGTGTGTCGGGTGGGGATGTGGGTGTG
GTGGAGGCGCATGGGACGGGGACGCGGTTGGGGGATCCGGTGGAGTTGGGGGCGTTGTTG
GGGACGTATGGGGTGGGTCGGGGTGGGGTGGGTCCGGTGGTGGTGGGTTCGGTGAAGGCG
AATGTGGGTCATGTGCAGGCGGCGGCGGGTGTGGTGGGTGTGATCAAGGTGGTGTTGGGG
TTGGGTCGGGGGTTGGTGGGTCCGATGGTGTGTCGGGGTGGGTTGTCGGGGTTGGTGGAT
TGGTCGTCGGGTGGGTTGGTGGTGGCGGATGGGGTGCGGGGGTGGCCGGTGGGTGTGGAT
GGGGTGCGTCGGGGTGGGGTGTCGGCGTTTGGGGTGTCGGGGAGGAAT

> 26736–27267 Sequence with Codon Changes

CTGCAGCGCCTCTCCGTCGCCGTCCGCGAGGGCCGCCGAGTCCTCGGCGTCGTCGTCGGC  (SEQ ID NO: 25)
TCGGCCGTCAACCAAGACGGCGCGTCAAACGGCCTCGCCGCGCCCTCCGGCGTCGCCCAG
CAGCGCGTCATACGCCGCGCGTGGGGACGCGCCGGAGTATCGGGCGGCGACGTCGGAGTC
GTCGAGGCCCACGGCACCGGCACCCGCCTCGGGGATCCCGTCGAGCTGGGCGCCCTCCTG
GGCACGTACGGCGTCGGCCGCGGCGGCGTCGGCCCGGTCGTCGTCGGCAGCGTCAAGGCC
AACGTCGGCCACGTCCAGGCCGCGGCCGGCGTCGTCGGGGTCATCAAGGTCGTCCTCGGC
CTCGGCCGCGGGCTGGTCGGCCCCGATGGTCTGCCGCGGCGGCCTCAGCGGCCTCGTCGAC
TGGTCGTCCGGCGGCCTGGTCGTCGCGGACGGGGTCCGCGGCTGGCCGGTCGGCGTCGAC
GGCGTCCGCCGGGGCGGCGTCTCGGCGTTCGCGTCAGCGGGACGAAT

> 6978–7337 Sequence in Module 2

GGTGGAGTGTGATGCGGTGGTGTCGTCGGTGGTGGGGTTTTCGGTGTTGGGGGTGTTGGA  (SEQ ID NO: 26)
GGGTCGGTCGGGTGCGCCGTCGTTGGATCGGGTGGATGTGGTGCAGCCGGTGTTGTTCGT
GGTGATGGTGTCGTTGGCGCGGTTGTGGCGGTGGTGTGGGGTTGTGCCTGCGGCGGTGGT
GGGTCATTCGCAGGGGAGATCGCGGCGGCGGTGGTGGCGGGGGTGTTGTCGGTGGGTGA
TGGTGCGCGGGTGGTGGCGTTGCGGGCGCGGGCGTTGCGGGCGTTGGCCGG

> 27697–27987 Sequence in Module 6

GGTGGAGTGTGATGCGGTGGTGTCGTCGGTGGTGGGGTTTTCGGTGTTGGGGGTGTTGGA  (SEQ ID NO: 27)
GGGTCGGTCGGGTGCGCCGTCGTTGGATCGGGTGGATGTGGTGCAGCCGGTGTTGTTCGT
GGTGATGGTGTCGTTGGCGCGGTTGTGGCGGTGGTGTGGGGTTGTGCCTGCGGCGGTGGT

-continued

```
GGGTCATTCGCAGGGGGAGATCGCGGCGGCGGTGGTGGCGGGGGTGTTGTCGGTGGGTGA

TGGTGCGCGGGTGGTGGCGTTGCGGGCGCGGGCGTTGCGGGCGTTGGCCGG
```

> 27697–27987 Sequence with Codon Changes

```
CGTGGAGTGCGATGCGGTCGTGTCGAGCGTCGTCGGCTTCAGCGTGCTGGGCGTCCTGGA    (SEQ ID NO: 28)

GGGCCGCAGCGGCGCCCCGAGCCTGGACCGCGTCGACGTGGTCCAGCCGGTCCTGTTCGT

GGTCATGGTCAGCCTGGCCCGCCTGTGGCGCTGGTGCGGCGTGGTCCCGGCCGCCGTGGT

CGGCCACAGCCAGGGCGAGATCGCCGCCGCGGTCGTGGCCGGCGTCCTGAGCGTCGGCGA

CGGCGCCCGCGTCGTGGCCCTGCGCGCCCGCGCCCTGCGCGCCCTGGCCGG
```

Three pieces of DNA from the two regions above were synthesized, the sequences verified by sequencing, and then cloned into pCR-BluntII-TOPO (Retrogen), as shown in Table 3, below.

TABLE 3

Plasmids containing synthesized DNA

| Plasmids | Cloning sites and positions in meg PKS |
|---|---|
| pKOS97-1613 | PstI-BamHI, 26,739th–26,947th base |
| PKOS97-1622 | BamHI-BsmI, 26,947th–27,267th base |
| PKOS97-1628 | SfaNI-FseI, 27,697th–27,987th base |

Assembly of the Expression Plasmid

First, ligation of the PstI-BamHI fragment of pKOS97-1613, the BamHI-BsmI fragment of pKOS97-1622 and BsmI-PstI linearized pKOS97-90 produced pKOS97-151. Then, the insertion of the SfaNI-FseI fragment of pKOS97-1628 into pKOS97-151 gave rise to pKSO97-152. Then, the PstI-BlpI fragment of pKOS97-125 was used to replace the PstI-BlpI fragment of pKOS97-90a and produced pKOS97-160.

The final expression plasmid (in pRM5) pKOS97-162 was the result of BglII-NheI fragment of pKOS97-160 inserted into BglII-NheI sites of pKOS108-04.

Another expression plasmid pKOS97-152a was made by a four-fragment ligation. The four fragments were a BlpI-XbaI fragment (containing a cos site) of pKOS97-92a, a BglII-PstI fragment of pKOS97-81, a PstI-BlpI fragment of pKOS97-152, and a BglII-XbaI fragment of pKOS108-04 (as the vector).

Tests of the constructed plasmids showed that the plasmids containing the modified coding sequences were more stable than plasmids containing unmodified coding sequence.

EXAMPLE 3
Construction of Ole-Meg Hybrid PKS
Construction of pRM1-based pKOS098-48 for the Expression of OlePKS Modules 1–4

The 240-bp fragment containing the 3'-end portion of oleAII gene (at nt 11210–11452; the first base of the start codon of oleAII is nt 1) was PCR amplified with primers N98-38-1 (5'GAACAACTCCTGTCTGCGGCCGCG-3') (SEQ ID NO: 29) and N98-38-3 (5'-CG GAATTCTCTAGAGTCACGTCTCCAACCGCTTGTC GAGG-3') (SEQ ID NO: 30). The fragment contains a naturally occurring NotI site at its 5'-end and the engineered XbaI (bold) and EcoRI sites (underline) at its 3'-end following the oleAII stop codon. pKOS38-189 was digested with EcoRI and NotI to give five fragments of 8 kb, 5 kb, 4 kb, 2.5 kb and 2 kb. The 8-kb EcoRI-NotI fragment containing oleAII gene nt 2961 to nt 11210 and the 240-bp NotI, EcoRI treated PCR fragment were ligated into litmus 28 at the EcoRI site via a three-fragment ligation to give pKOS98-46. The 8.2-kb EoRI fragment from pKOS98-46 was cloned into pKOS38-174, a pRM1 derived plasmid containing oleAI and nt 1 to nt 2960 of oleAII to give pKOS98-48.

Construction of pSET152-based pKOS98-60 for the Expression of megPKS Modules 5–6

The 360-bp fragment containing nt 1 to nt 366 of megAIII was PCR amplified with primers N98-40-3 (5'-TCTAGAC TTAATTAAGGAGGACACATATGAGCGA-GAGCA GC-GGCATGACCG-3') (SEQ ID NO: 31) and N98-40-2 (5'-AACGCCTCCCAG-GAGATCTCCAGCA-3') (SEQ ID NO: 32). A PacI site and a NdeI site as well as the ribosome binding site were introduced at the 5'-end of the megAI start codon. The 360-bp PacI-BglII fragment was inserted into pKOS108-06 replacing the 22-kb PacI-BglII fragment to yield pKOS98-55. The 10-kb PacI-XbaI fragment containing megAIII gene and the annealed oligos N98-23-1 (5'-AATTCATAGCCTAGGT-3') (SEQ ID NO: 33) and N98-23-2 (5'-CTAGACCTAGGCTATG-3') (SEQ ID NO: 34) were ligated to PacI and EcoRI treated pSET152 derivative pKOS98-14 via a three-fragment ligation to give pKOS98-60.

EXAMPLE 4
Conversion of Erythronolides to Erythromycins

A sample of a polyketide (~50 to 100 mg) is dissolved in 0.6 mL of ethanol and diluted to 3 mL with sterile water. This solution is used to overlay a three day old culture of Saccharopolyspora erythraea WHM34 (an eryA mutant) grown on a 100 mm R2YE agar plate at 30° C. After drying, the plate is incubated at 30° C. for four days. The agar is chopped and then extracted three times with 100 mL portions of 1% triethylamine in ethyl acetate. The extracts are combined and evaporated. The crude product is purified by preparative HPLC (C-18 reversed phase, water-acetonitrile gradient containing 1% acetic acid). Fractions are analyzed by mass spectrometry, and those containing pure compound are pooled, neutralized with triethylamine, and evaporated to a syrup. The syrup is dissolved in water and extracted three times with equal volumes of ethyl acetate. The organic extracts are combined, washed once with saturated aqueous NaHCO$_3$, dried over Na$_2$SO$_4$, filtered, and evaporated to yield ~0.15 mg of product. The product is a glycosylated and hydroxylated compound corresponding to erythromycin A, B, C, and D but differing therefrom as the compound provided differed from 6-dEB.

EXAMPLE 5
Measurement of Antibacterial Activity

Antibacterial activity is determined using either disk diffusion assays with *Bacillus cereus* as the test organism or by measurement of minimum inhibitory concentrations (MIC) in liquid culture against sensitive and resistant strains of *Staphylococcus pneumoniae*.

EXAMPLE 6
Evaluation of Antiparasitic Activity

Compounds can initially screened in vitro using cultures of *P. falciparum* FCR-3 and K1 strains, then in vivo using mice infected with *P. berghei*. Mammalian cell toxicity can be determined in FM3A or KB cells. Compounds can also be screened for activity against *P. berhei*. Compounds are also tested in animal studies and clinical trials to test the antiparasitic activity broadly (antimalarial, trypanosomiasis and Leishmaniasis).

The invention having now been described by way of written description and example, those of skill in the art will recognize that the invention can be practiced in a variety of embodiments and that the foregoing description and examples are for purposes of illustration and not limitation of the following claims.

What is claimed is:

1. An isolated polynucleotide comprising a nucleotide sequence encoding a domain of a megalomicin polyketide synthase (PKS) protein having the amino acid sequence of SEQ ID NO:13 as encoded by the megAI gene from *Micromonospora megalomicea*.

2. The isolated polynucleotide of claim 1, which comprises the PKS open reading frame (ORF) contained in SEQ ID NO:1 from base 12181 to base 22821.

3. The isolated polynucleotide of claim 1, wherein said nucleotide sequence encodes a module of said protein.

4. A recombinant DNA expression vector comprising the isolated polynucleotide of claim 1 operably linked to a promoter.

5. The polynucleotide of claim 1 that is cosmid pKOS079-93A.

6. A recombinant host cell, comprising the recombinant DNA expression vector of claim 4.

7. The recombinant host cell of claim 6, which is a Streptomyces or Saccharopolyspora host cell.

* * * * *

SEQUENCE LISTING

```
<160> NUMBER OF SEQ ID NOS:  34

<210> SEQ ID NO 1
<211> LENGTH: 47981
<212> TYPE: DNA
<213> ORGANISM: Micromonospora megalomicea
<220> FEATURE:
<221> NAME/KEY: CDS
<222> LOCATION: (1)...(144)
<223> OTHER INFORMATION: megBVI(megT), TDP-4-keto-6-deoxyglucose-2,
      3-dehydratase; SEQ ID NO: 2= translated amino acid sequence
<221> NAME/KEY: CDS
<222> LOCATION: (928)...(2061)
<223> OTHER INFORMATION: megDVI, TDP-4-keto-6-deoxyglucose 3,
      4-isomerase, TDP-4-keto-6-deoxyhexose 3,4-isomerase;
      SEQ ID NO: 3= translated amino acid sequence
<221> NAME/KEY: CDS
<222> LOCATION: (2072)...(3382)
<223> OTHER INFORMATION: megDI, rhodosaminyl transferase
      (eryCIII homolog), TDP-megosamine glycosyltransferase;
      SEQ ID NO: 4= translated amino acid sequence
<221> NAME/KEY: CDS
<222> LOCATION: (3462)...(4634)
<223> OTHER INFORMATION: megG(megY), mycarosyl acyltransferase,
      mycarose O-acyltransferase;
      SEQ ID NO: 5= translated amino acid sequence
<221> NAME/KEY: CDS
<222> LOCATION: (4651)...(5775)
<223> OTHER INFORMATION: megDII, deoxysugar transaminase
      (eryCI, DnrJ homolog), TDP-3-keto-6-deoxyhexose
      3-aminotransaminase;
      SEQ ID NO: 6= translated amino acid sequence
<221> NAME/KEY: CDS
<222> LOCATION: (5822)...(6595)
<223> OTHER INFORMATION: megDIII, daunosaminyl-N,N-dimethyltransferase
      (eryCVI homolog); SEQ ID NO: 7= translated amino acid sequence
<221> NAME/KEY: CDS
<222> LOCATION: (6592)...(7197)
<223> OTHER INFORMATION: megDIV, TDP-4-keto-6-deoxyglucose 3,
      5-epimerase (eryBVII, dnmU homolog),
      TDP-4-keto-6-deoxyhexose 3,5-epimerase;
      SEQ ID NO: 8= translated amino acid sequence
<221> NAME/KEY: CDS
<222> LOCATION: (7220)...(8206)
<223> OTHER INFORMATION: megDV, TDP-hexose 4-ketoreductase
      (eryBIV, dnmV homolog), TDP-4-keto-6-deoxyhexose 4-ketoreductase;
      SEQ ID NO NO: 9= translated amino acid sequence
<221> NAME/KEY: CDS
<222> LOCATION: (8228)...(9220)
<223> OTHER INFORMATION: megBII-1(megDVII), TDP-4-keto-L-6-deoxy-hexose
      2,3-reductase; SEQ ID NO: 10= translated amino acid sequence
<221> NAME/KEY: CDS
<222> LOCATION: (9226)...(10479)
<223> OTHER INFORMATION: megBV, mycarosyl transferase, mycarose
      glycosyltransferase; SEQ ID NO: 11= translated amino acid sequence
<221> NAME/KEY: CDS
<222> LOCATION: (10483)...(11424)
<223> OTHER INFORMATION: megBIV, TDP-hexose 4-ketoreductase,
      TDP-4-keto-6-deoxyhexose 4-ketoreductase;
      SEQ ID NO: 12= translated amino acid sequence
```

```
<221> NAME/KEY: CDS
<222> LOCATION: (12181)...(22821)
<223> OTHER INFORMATION: megAI; SEQ ID NO: 13= translated amino acid
      sequence
<221> NAME/KEY: misc_feature
<222> LOCATION: (12505)...(13470)
<223> OTHER INFORMATION: megAI, AT-L
<221> NAME/KEY: misc_feature
<222> LOCATION: (13576)...(13791)
<223> OTHER INFORMATION: megAI, ACP-L
<221> NAME/KEY: misc_feature
<222> LOCATION: (13849)...(15126)
<223> OTHER INFORMATION: megAI, KS1
<221> NAME/KEY: misc_feature
<222> LOCATION: (15427)...(16476)
<223> OTHER INFORMATION: megAI, AT1
<221> NAME/KEY: misc_feature
<222> LOCATION: (17155)...(17694)
<223> OTHER INFORMATION: megAI, KR1
<221> NAME/KEY: misc_feature
<222> LOCATION: (17947)...(18207)
<223> OTHER INFORMATION: megAI, ACP1
<221> NAME/KEY: misc_feature
<222> LOCATION: (18268)...(19548)
<223> OTHER INFORMATION: megAI, KS2
<221> NAME/KEY: misc_feature
<222> LOCATION: (19876)...(20910)
<223> OTHER INFORMATION: megAI, AT2
<221> NAME/KEY: misc_feature
<222> LOCATION: (21517)...(22053)
<223> OTHER INFORMATION: megAI, KR2
<221> NAME/KEY: misc_feature
<222> LOCATION: (22318)...(22575)
<223> OTHER INFORMATION: megAI, ACP2
<221> NAME/KEY: CDS
<222> LOCATION: (22867)...(33555)
<223> OTHER INFORMATION: megAII; SEQ ID NO: 14= translated amino acid
      sequence
<221> NAME/KEY: misc_feature
<222> LOCATION: (22957)...(24237)
<223> OTHER INFORMATION: megAII, KS3
<221> NAME/KEY: misc_feature
<222> LOCATION: (24544)...(25581)
<223> OTHER INFORMATION: megAII, AT3
<221> NAME/KEY: misc_feature
<222> LOCATION: (26230)...(26733)
<223> OTHER INFORMATION: megAII, KR3 (inactive)
<221> NAME/KEY: misc_feature
<222> LOCATION: (26998)...(27258)
<223> OTHER INFORMATION: megAII, ACP3
<221> NAME/KEY: misc_feature
<222> LOCATION: (27393)...(28590)
<223> OTHER INFORMATION: megAII, KS4
<221> NAME/KEY: misc_feature
<222> LOCATION: (28897)...(29931)
<223> OTHER INFORMATION: megAII, AT4
<221> NAME/KEY: misc_feature
<222> LOCATION: (29953)...(30477)
<223> OTHER INFORMATION: megAII, DH4
<221> NAME/KEY: misc_feature
<222> LOCATION: (31396)...(32244)
<223> OTHER INFORMATION: megAII, ER4
<221> NAME/KEY: misc_feature
<222> LOCATION: (32257)...(32799)
<223> OTHER INFORMATION: megAII, KR4
<221> NAME/KEY: misc_feature
<222> LOCATION: (33052)...(33312)
<223> OTHER INFORMATION: megAII, ACP4
<221> NAME/KEY: CDS
<222> LOCATION: (33666)...(43271)
<223> OTHER INFORMATION: megAIII; SEQ ID NO: 15= translated amino acid
      sequence
<221> NAME/KEY: misc_feature
<222> LOCATION: (33780)...(35027)
<223> OTHER INFORMATION: megAIII, KS5
<221> NAME/KEY: misc_feature
<222> LOCATION: (35385)...(36419)
<223> OTHER INFORMATION: megAIII, AT5
<221> NAME/KEY: misc_feature
```

```
<222> LOCATION: (37068)...(37604)
<223> OTHER INFORMATION: megAIII, KR5
<221> NAME/KEY: misc_feature
<222> LOCATION: (37860)...(38120)
<223> OTHER INFORMATION: megAIII, ACP5
<221> NAME/KEY: misc_feature
<222> LOCATION: (38187)...(39470)
<223> OTHER INFORMATION: megAIII, KS6
<221> NAME/KEY: misc_feature
<222> LOCATION: (39795)...(40811)
<223> OTHER INFORMATION: megAIII, AT6
<221> NAME/KEY: misc_feature
<222> LOCATION: (41406)...(41936)
<223> OTHER INFORMATION: megAIII, KR6
<221> NAME/KEY: misc_feature
<222> LOCATION: (42168)...(42425)
<223> OTHER INFORMATION: megAIII, ACP6
<221> NAME/KEY: misc_feature
<222> LOCATION: (42585)...(43271)
<223> OTHER INFORMATION: megAIII, TE
<221> NAME/KEY: CDS
<222> LOCATION: (43268)...(44344)
<223> OTHER INFORMATION: megCII, TDP-4-keto-6-deoxyglucose 3,
      4-isomerase;
      SEQ ID NO: 16= translated amino acid sequence
<221> NAME/KEY: CDS
<222> LOCATION: (44355)...(45623)
<223> OTHER INFORMATION: megCIII, desosaminyl transferase,
      desosamine glycosyltransferase;
      SEQ ID NO: 17= translated amino acid sequence
<221> NAME/KEY: CDS
<222> LOCATION: (45620)...(46591)
<223> OTHER INFORMATION: megBII-2(megBII), TDP-4-keto-6-deoxy-L-glucose
      2,3 dehydratase,
      TDP-4-keto-6-deoxyglucose 2,3 dehydratase;
      SEQ ID NO: 18= translated amino acid sequence
<221> NAME/KEY: CDS
<222> LOCATION: (46660)...(47403)
<223> OTHER INFORMATION: megH, TEII; SEQ ID NO: 19= translated amino
      acid sequence
<221> NAME/KEY: CDS
<222> LOCATION: (47411)...(47980)
<223> OTHER INFORMATION: megF, C-6 hydroxylase; SEQ ID NO:
      20= translated amino acid sequence

<400> SEQUENCE: 1
ctcgagccga tgctcggcgg cgcggtgggc caaccagtcg tggacgtcgt cggtggcggt      60
gggaggtccg ccgtgccgag tcaggaaacg tattgccgat tgtgtggatt ccggagtcgc     120
atgaccgttg acccgatccc ccatacgcct ctcccgtgat gtcgtgggcg gtccgtgcgg     180
taccgcccgg actgacattc gtcgatcaag acccgcccca gtgtagggct ccgcccgcga     240
cgggagaagg tccgtcgaac aacttccggg tgaccggtcg ccggcgtcgg tgaaacgggc     300
gtcggagcac ccgatcattg ctgtcggtga acttcctaac tgtcggcgcg cacatctttc     360
tgaccggtgt gttccgtggt atgacgcgtt cccggcccgt ctggaactgt gcgtgggact     420
gaccggttgc ggcgtgtttt cgcccgtttc cgaactgcgg attcgtcgat cgcgcaggtg     480
ggagcgggtg gctgaccggg atgatctgca atcatggcgc tcaatgacga tctcttgtag     540
catggtccgc gccgagggtc cgacaggccc gaaacgcccg gcatccagcc tgttcgacga     600
cgtcgacatc accgtgcaag ccgcgatgac accgacacca cgccatgctg gtgccgcact     660
ggaagggtgg cgcgatcagg gaaatggccg tgtcactaga cagacgccaa acagctgtcc     720
gggcctgcga aaacagcatc gatctgcgtc agccgttcat tgccccggcg caccgcctt      780 ggaaatccgt gccaccggtc gtccgcagtg acgatcgcgg acccgggttt cgagacagca     840
ggtagtaggc gatgcaggcg tttcgtctcg cgccggacgc gtcgcactag gtggaatccg     900
tcacagtctt caatccggga gcgttctatg gcagttggcg atcgaaggcg gctgggccgg     960
```

-continued

```
gagttgcaga tggcccgggg tctctactgg gggttcggtg ccaacggcga tctgtactcg    1020
atgctcctgt ccggacggga cgacgacccc tggacctggt acgaacggtt gcgggccgcc    1080
ggacggggac cgtacgccag tcgggccgga acgtgggtgg tcggtgacca ccggaccgcc    1140
gccgaggtgc tcgccgatcc gggcttcacc cacggcccgc ccgacgctgc ccggtggatg    1200
caggtggccc actgcccggc ggcctcctgg ccggcccct tccgggagtt ctacgcccgc     1260
accgaggacg cggcgtcggt gacagtggac gccgactggc tccagcagcg gtgcgccagg    1320
ctggtgaccg agctggggtc gcgcttcgat ctcgtgaacg acttcgcccg ggaggtcccg    1380
gtgctggcgc tcggtaccgc gcccgcactc aagggcgtgg accccgaccg tctccggtcc    1440
tggacctcgg cgacccgggt atgcctggac gcccaggtca gcccgcaaca gctcgcggtg    1500
accgaacagg cgctgaccgc cctcgacgag atcgacgcgg tcaccggcgg tcgggacgcc    1560
gcggtgctgg tgggggtggt ggcggagctg gcggccaaca cggtgggcaa cgccgtcctg    1620
gccgtcaccg agcttcccga actggcggca cgacttgccg acgacccgga gaccgcgacc    1680
cgtgtggtga cggaggtgtc gcggacgagt cccggcgtcc acctgaacg ccgcaccgcc     1740
gcgtcggacc gccgggtggg cggggtcgac gtcccgaccg gtggcgaggt gacagtggtc    1800
gtcgccgcgg cgaaccgtga tcccgaggtc ttcaccgatc ccgaccggtt cgacgtggac    1860
cgtggcggcg acgccgagat cctgtcgtcc cggcccggct cgccccgcac cgacctcgac    1920
gccctggtgg ccaccctggc cacggcggcg ctgcgggccg ccgcgccggt gttgccccgg    1980
ctgtcccgtt ccggccggt gatcagacga cgtcggtcac ccgtcgcccg tggtctcagc     2040
cgttgcccgg tcgagctgta gaggaagaac gatgcgcgtc gtgttttcat cgatggctgt    2100
caacagccat ctgttcgggc tggtcccgct cgcaagcgcc ttccaggcgg ccggacacga    2160
ggtacgggtc gtcgcctcgc cggccctgac cgacgacgtc accggtgccg gtctgaccgc    2220
cgtgcccgtc ggtgacgacg tggaacttgt ggagtggcac gcccacgcgg ccaggacat    2280
cgtcgagtac atgcggaccc tcgactgggt cgaccagagc cacaccacca tgtcctggga    2340
cgacctcctg gcatgcaga ccaccttcac cccgaccttc ttcgccctga tgagccccga     2400
ctcgctcatc gacgggatgg tcgagttctg ccgctcctgg cgtcccgact ggatcgtctg    2460
ggagccgctg accttcgccg ccccgatcgc ggcccgggtc accggaaccc cgcacgcccg    2520
gatgctgtgg ggtccggacg tcgccacccg ggcccggcag agcttcctgc gactgctggc    2580
ccaccaggag gtggagcacc gggaggatcc gctggccgag tggttcgact ggacgctgcg    2640
gcgcttcggc gacgacccgc acctgagctt cgacgaggaa ctggtgctgg ggcagtggac    2700
cgtggacccc atccccgagc cgctgcggat cgacaccggc gtccggacgg tgggcatgcg    2760
gtacgtcccc tacaacggcc cctcggtggt gcccgcctgg ctgttgcggg aacccgaacg    2820
tcggcgggtc tgcctgaccc tcggcggttc agcccgggaa cacggcatcg gcaggtctc    2880
catcggcgag atgttggacg ccatcgccga catcgacgcc gagttcgtgg ccaccttcga    2940
cgaccagcag ttggtcggcg tgggcagcgt tccgtaccg ccgggttcgt                3000
gccgatgaac gtcctgctgc ccacctgcgc ggccaccgtg caccacggcg caccggcag     3060
ttggctgacc gccgccatcc acggcgtacc gcagatcatc ctctcggacg ccgacaccga    3120
ggtgcacgcc aagcagctcc aggacctcgg cgcggggctg tcgctcccgg tcgcggggat    3180
gaccgccgag cacctgcgtg gggcgatcga cgggttctc gacgagcggg cgtaccgcct     3240
cggtgcggag cggatgcggg acgggatgcg gaccgacccg tcgccggccc aggtggtcgg    3300
catctgtcag gacctggccg ccgaccgggc ggcacgcggc aggcagccgc gtcgaaccgc    3360
```

```
cgagccgcac ctgccgcgat gacttccacc accaccggga ccggctgatg ccggtcccgg    3420
aatccacacg ccgactttcc ttctgacacg aggggggcccc ggtggttacc tccaccaact    3480
tggacacgac agcacggccg gcactgaact cgttgaccgg gatgcggttc gtcgccgcct    3540
tcctggtctt cttcacgcac gtcctgtcga ggctcatccc gaacagctac gtgtacgccg    3600
acggcctgga cgccttctgg cagaccaccg gacggggtggg ggtgtcgttc ttctttattc    3660
tcagcggttt cgtgctgacc tggtcggcgc gggccagcga ctcggtgtgg tcgttctggc    3720
gcagacgggt ctgcaagctc ttccccaacc acctggtcac cgccttcgcc gccgtggtgt    3780
tgttcctggt caccgggcag gcggtgagcg gtgaggcgct gatcccgaac ctcctgctga    3840
tccacgcctg gttcccggcc ctggagatct ccttcggcat caacccggtg agctggtcgt    3900
tggcctgcga ggcgttcttc tacctgtgct cccgctgtt cctgttctgg atctccggta    3960
tccgcccgga gcggctgtgg gcctgggccg ccgtggtgtt cgccgcgatc tgggcggtac    4020
cggtggtcgc cgacctcctg ctgccgagtt ccccgccgct gatcccgggg cttgagtact    4080
ccgccatcca ggactggttc ctctacacct tccctgcgac gcggagcctg gagttcatcc    4140
tcgggatcat cctggcccgc atcctgatca ccggtcggtg gatcaacgtc gggctgctcc    4200
ccgcggtgct gttgttcccg gtcttcttcg tcgcctcgct cttcctgccg ggtgtctacg    4260
ccatctcctc gtcgatgatg atccttcccc tggttctgat catcgccagc ggcgcgacgg    4320
ccgacctcca gcagaagcgc accttcatgc gtaaccgggt gatggtgtgg ctcggcgacg    4380
tctccttcgc gctctacatg gtccacttcc tggtgatcgt ctacggggcg gacctgctgg    4440
ggttcagcca gaccgaggac gccccgctgg gtctcgcact cttcatgatc attccgttcc    4500
tcgcggtctc cctggtgctg tcgtggctgc tgtacaggtt cgtcgagcta cccgtcatgc    4560
gtaactgggc ccgcccggcc tccgcccggc gcaaacccgc cacggaaccc gaacagaccc    4620
cttcccgccg gtaagaagga cggtgcatcg gtgaccacct acgtctggtc ctatctgttg    4680
gagtacgaga gggaacgagc cgacatcctc gatgcggtgc agaaggtctt cgccagtggc    4740
agcctgatcc tcggtcagag tgtggagaac ttcgagaccg agtacgcccg ctaccacggg    4800
atcgcgcact gcgtgggcgt cgacaacggc accaacgctg tgaaactcgc gctggagtcg    4860
gtaggtgtcg gacgcgacga cgaggtcgtc acggtctcca acaccgccgc ccccacagtc    4920
ctggccatcg acgagatcgg cgcccggccg gtcttcgtgg acgtccgcga cgaggactac    4980
ctcatggaca ccgacctggt ggaggcggcg gtcaccccgc gtaccaaggc catcgtcccg    5040
gtgcacctgt acgggcagtg cgtggacatg acagccctgc gggaactggc cgaccggcgg    5100
ggcctcaagc tcgtggagga ctgcgcccag gcccacggtg cccggcggga cggtcggctg    5160
gccgggacga tgagcgacgc ggcggccttc tcgttctacc cgacgaaggt cctcggcgcc    5220
tacgcgacgc gcggcgcgt cgtcaccaac gacgacgaga cagcccgcgc cctgcgacgg    5280
ctgcggtact acgggatgga ggaggtctac tacgtcaccc ggaccccggg tcacaacagc    5340
cgcctcgacg aggtgcaggc cgagatcctg cggcgcaaac tgacccggct cgacgcgtac    5400
gtcgcgggtc ggcgggcggt cgcccagcgg tacgtcgacg gctcgccga cctccaagac    5460
tcgcacggcc tcgaactccc agtggtcacc gacggcaacg aacacgtctt ctacgtgtac    5520
gtcgtccgcc acccgcgccg cgacgagatc atcaagcgtc tccgggacgg gtacgacatc    5580
tccctgaaca tcagctaccc ctggccggtg cacaccatga ccggcttcgc ccacctcggt    5640
gtcgcgtcgg ggtcgctgcc ggtcaccgaa cggctggccg gcgagatctt ctcccttccc    5700
```

-continued

```
atgtacccct ccctccctca cgacctgcag gacagggtga tcgaggcggt gcggaggtc    5760 atcaccgggc tgtgacgagc ccgcgtgtcg tcagcgaaga cccactctgg aagggccggt    5820
catgccgaac agccactcga ccacgtcgag caccgacgtc gccccgtacg agcgggcgga    5880
catctaccac gacttctacc acggccgtgg caagggatac cgtgccgaag ccgacgcgct    5940
cgtggaggtc gcccgcaagc acaccccaca ggcggcgacc ctgctggacg tggcctgcgg    6000
gaccggatcc cacctggtcg agctggcgga cagcttccgg gaggtggtgg ggtcgacct    6060 gtcggccgcc atgctcgcca ccgccgcccg caacgacccc gggcgggaac tgcaccaggg    6120
cgacatgcgc gacttctccc tcgaccgcag gttcgacgtc gtcacctgca tgttcagctc    6180
caccggttac ctcgtcgacg aggccgaact ggaccgtgcc gtggcgaacc tggccggtca    6240
cctcgcgcct ggcggcaccc tcgtcgtgga gccctggtgg ttcccggaga cgttccggcc    6300
cggctgggtc ggggccgacc tggtcaccag cggtgaccgg aggatctccc ggatgtcgca    6360
caccgtcccg gcgggtctgc ccgaccgcac cgcctcccgg atgaccatcc actacacggt    6420
ggggtcaccg gaggccggga tcgagcactt caccgaggtg cacgtgatga ccctgttcgc    6480
ccgcgccgcc tacgagcagg ccttccagcg ggcgggcctg agctgctcgt acgtcggcca    6540
cgacctgttc tcgccgggcc ttttcgtcgg gtcgccgcg gagccggggc ggtgagggtc    6600
gaggagctgg gcatcgaggg ggtcttcacc ttcacccccgc agacgttcgc cgacgagcgg    6660
ggggtgttcg gcacggcgta ccaggaggac gtgttcgtgg cggcgctcgg ccgcccgctg    6720
ttcccggtgg cccaggtcag caccacccgg tcccggcggg tgtggtccg ggggtgcac    6780 ttcacgacga tgcccggctc catggcgaag tacgtctact gcgccagggg tagggcgatg    6840
gacttcgccg tcgacatccg gcccggttcc ccgaccttcg gccgggccga gccggtcgag    6900
ctctccgccg agtcgatggt cgggctgtac cttcccgtgg gcatgggcca cctgttcgtc    6960
tccctggagg acgacaccac cctcgtctac ctgatgtccg ccggttacgt ccccgacaag    7020
gaacgggcgg tgcacccct ggatccggag ctggcgttgc cgatcccggc cgacctcgac    7080
ctcgtcatgt ccgagcggga ccgggtcgca cccaccctcc gggaggcccg ggaccagggg    7140
atcctgcccg actacgccgc ctgccgggcc gccgcgcacc gggtggtgcg gacgtgaccc    7200
cggccgggcg tgcgggccgg tggtggtgct cggcgcgtcg ggtttcctgg gttcggcggt    7260
cacccacgcc ctggccgacc tcccggtgcg ggtgcggctc gtcgcccggc gggaggtcgt    7320
cgtgccctcc ggtgccgtcg ccgactacga cacgcaccgg gtggacctca ccgaacccgg    7380
agcgctcgcg gaggtggtcg cggacgcccg ggcggtcttc ccgttcgccg cccagatcag    7440
gggtacgtca gggtggcgga tcagcgagga cgacgtggtc gccgaacgga cgaacgtcgg    7500
cctggtccgg gacctgatcg ccgtcctgtc ccgctcgccg cacgccccgg tggtggtctt    7560
cccgggcagc aacacgcagg tcggcagggt caccgccggc cgggtcatcg acggcagcga    7620
gcaggaccac cccgagggcg tctacgacag gcagaaacac accgggaac agctgctcaa    7680 ggaggccact gcgccgggg cgatccgggc gaccagtctg cggctgcccc cggtgttcgg    7740
ggtgcccgcc gccggcaccg ccgacgaccg ggggtggtc tccaccatga tccgtcgggc    7800
cctgaccggc caaccgctga cgatgtggca cgacggcacc gtccggcgtg aactgctgta    7860
cgtgaccgac gccgcccggg ccttcgtcac cgccctggac cacgccgacg cgctcgccgg    7920
acgccacttc ctgttgggga cggggcgttc ctggccgctg ggcgaggtct tccaggcggt    7980
ctcgcgcagc gtcgcccggc acaccggcga ggacccggtg ccggtggtct cggtgccgcc    8040
tccggcgcac atggacccgt cggacctgcg cagcgtggag gtcgaccccg cccggttcac    8100
```

-continued

```
ggctgtcacc gggtggcggg ccacggtcac gatggcggag gcggtcgacc ggacggtggc   8160
ggcgttggcc ccccgccggg ccgccgcccc gtccgagccc tcctgaccgg ggtcacccgg   8220
gttcgtccta cggcaccggc ccgtcgacgg ccggtgccgg aagatcgct  tcgagttccc   8280
ggagttcctc ctcgcccagc gtcagctcgg cggcccgtaa cgccgagtcg agctgctcgg   8340
gtgtgcgggg gccgatgaca cgcccagga  tcccggggcg ggacaggacc caggccagac   8400
cgacctcggc cgggtccgcg ccgaggcgtc ggcagtagtc ctcgtacgcc tcgacgaggg   8460
ggcgtacggg ggggaggagc acctgggcgc gtccctgcgc cgacttgacg gcggttccgg   8520
ctgccaactt ctccagtacg ccgctgagca gcccgccgtg caggggggac caggcgaaca   8580
cgcccacccc gtacgcctgg gcggcgggca ggacgtccag ctcggggtgg cggacggcca   8640
ggttgtacag gcactggtgg gagatcatgc cgagcaggtt gcggcgtgcc gcgctctcct   8700
gggcggcggc gatgtgccag cccgccaggt tggaggagcc gacgtacccg accttcccac   8760
tgccgaccag atgttcggcg gcctgccaca cctcgtccca cggtgcggcg cggtcgatgt   8820
ggtgcgtctg gtagatgtcg atgtggtcga ccccgaggcg gcggagggag ttctcgcagg   8880
cggcgacgat gtgtcgggcg gagagcccgc cgtcgttgac ccgttcgctc atctcgctgc   8940
ccaccttggt cgccaggacg gtctcctcgc gtcgacctcc gccctgggcg aaccaccgtc   9000
cgacgagttc ctcggtgtgg cccttgtaga gccgccagcc gtagatgtcg gcggtgtcga   9060
tgcagttgac gccccgctcg agggcgtggt ccatcagccg cagcgcgtcg tcgtcggtca   9120
cccgtccact gaagttcacg gtgccgagcc agagtcggct ggtgtgcaac gccgatcgtc   9180
cgacgcgtac ccgggcggac ccggccccgg tggttcccac gtcggtcacc tgtcggcgcg   9240
gtgctggtgg gcgagcgcct ccagcacggg tacgacctcg gcggggtcg  gcgcggccag   9300
cgcctcctgc cgcagcttct cggcgttctc ggcgtgggaa cggtcctcga ccactgtggc   9360
gagagcctgc cagagggtgt cggcgtcgac ctcgtccgga cggaggaaga cacccgctcc   9420
cagctcggcg gtgcgctgac cacgcaggac acagtcccac tcgtgggcga cggagatctg   9480
cggtacgccg tggtgcagcg cggtggccca gcttccggca ccgccgtggt ggatgacggc   9540
ggcacagccc ggcagcagga tgttcatggg aacgaagtcc accaggcgga cgttgtccgg   9600
caccgacgcc ggatcgagcc cggagcgggt caccacgatc tcgccgtcga accgcgcgag   9660
ggtggccagt gtccggagga actcctgcgg gttcgaggtg atgccagcg  ccgagtatcc   9720
cccggtgaag cagacccggc ggactccgtc cgaggtcctg agccactgcg gcacgacgga   9780
ggacccgttg tagggcaaag tccgggtgtg caccgactcc agtccggtct ccaggcggaa   9840
gctctcgggc agctggtcga cgctccactg tccgacagcg aggtcctcgc tgtagtcgag   9900
gccgaaccgg ccggcgacct cggtgagcca gccgccgagc gggtccggcc ggtcgtcggc   9960
gggacgctgc ccgcgcaggt cctggagcg  gctgcgaag  tagccggtga ggtcgctgcc  10020
ccacagcagc cgggcgtggg cggccccgca ggccttggcc gcgaccgccc cggcgaaggt  10080
gaagggctcc cagagcacca ggtcgggacg ccagtccatg gcgaactcga cgagttcgtc  10140
gacgaaggag tcgttgttga ccaccgggaa gacgaaccgg gaggtggcct cctcgatgcc  10200
gtgcaggaac tccacgagc  gcagttccgg tccgcgtcgg gcgaagtcca ggtcggtggt  10260
gtagcggtgc acctgcgcgg cggcctcagg ggagatgtcg aagagtcggt ggtccgagcc  10320
gagtggcacc gaggtcagtc ccgcgccgac gacgacgtcg gtgagctcgg gctgactggc  10380
caccccggacg tcgtggccgg cggtgtgcag cgcccaggcc aggggggacga ggccctggaa  10440
```

```
gtgggtacgg tgcgcgaacg aggtgagcag gacccgcact ggtcactcct tggtcgagat   10500
gagggcggca acgtccggt cgatgccctc ggccagcggc acccgggggt gccagccggt   10560
cagcgtccgg aactcggtgg agtcgaagtc gtcgctgcgg aagtcgttgg cctcggcgtt   10620
ctccggtgga gggacgctga cgacgggcac cgcagggttg ccggtctgac gtgccacgct   10680
ggcggcgacg gtctcgaaga tctcgccgag ggtcgggcc tcgtccgcgc tcggcgtcca   10740
gacgtcgccg accagcgcct cgtggttgtg cagtgcggcg gtgaacgcgg tggccacgtc   10800
ctcgacgtgc aggaggttgc ggcgcacgct gccctcgtgc acatcgtga tcggctcacc   10860 ggcgagggct cgccggatca tggcggtgac gacaccccgg ccggtctgcc ccgacgggcc   10920
gctgtggccg tagatcgcgg gcaggcgcag gatcaccccg tcgacgaccc cgtcctcggt   10980
ggcctgacgc aggatccgct cggcctcgat cttgtgctgg gcgtaccggc tggggcggc   11040 ggggttcgcg gcctgggtgg tgctggcgaa caggagcacc ggcgcgggtc cggtcttgc   11100 ccgcagcgcg gcgacgaggt cgcgcatgat gcccgcgttg acgcgttcgg cctcgggcac   11160
cgtggcggcg ctgcgccagg tcgacccgcc ggcggcgtag gcgaccagat gcacgacgac   11220
gtcggtgtcg gcgacgacct gcgcgacccg gccgggttcg agcaggtcga ctcgaaggtg   11280
ctcgatcccg gcgctgcctg gtggctggtc gcgagacccg gtgcgcgcga cggcccgcag   11340
tcggagaggg tgtgtggtaa attcgcgaag aagggcgctt ccgacgaatc cagaaacgcc   11400
gagaagtgtg acatgtcttg tcatctacta atgcattccg atagccaccg gcgcatggaa   11460
tccatttgtt ccccccaggg tggtgtcggg tgacaaatcc ggcctcaggt cggcctcaag   11520
cctctttcga gcgggtgctg aggcttcccg cgtaccctcg gtggcctgcg ttcgggcggg   11580
tgtcggggaa agggcggatc gaggagttcg gtagggcgtc gcggcgcgta ctccgggact   11640
gatccgggtc gacgccccga cgcgtgacag ggcgtcgatc cgtgccgccc gtaccgccgg   11700
ttttcggcga tggtcgcaga ttcctcccga cgtggtggac tcattggttc tcccgggtgt   11760
ggccgcaccg tcggtggcct cgtcgggggt gtcggagacc gggtcgatcg ccgtccccgg   11820
ccgtgccgac caggtcggt ccgtcgccga ggtgggtcac cgtcgggtgg accggtccg   11880 ccggcggcca ccgcccgatc gtgcccacct tcgcctccgc gggtaaatgc ttcgtcgatc   11940
tgatcgacac ttccggcgac gctatccacg gagcattccc cggcaccacc ggtcgatgcc   12000
tcgcgctttc caaacaggga aaacagcagc tcacagcggt tccaggcgcc gggcaatcct   12060
agcgaagagt ctcgatgggg tcaaggtgaa ttctgtcaca gatgtttttg ttaaatgtac   12120
tttcttcagc caccctcgac gttcatacaa ttggccggca tctctaccaa gggggagtga   12180
gtggttgacg tgcccgatct actcggcacc cggactccgc acccagggcc gctcccattc   12240
ccgtggcccc tgtgcggtca caacgaaccg gagctgcggg cccgcgcccg tcaattgcac   12300
gcatatctcg aaggcatttc cgaggatgac gtggtggccg tcggcgccgc cctcgcgcgc   12360
gagacacgcg cgcaggacgg gccgcaccgc gccgtcgtcg tggcctcctc ggtcaccgag   12420
ctgaccgccg cgctcgccgc cctcgcccag ggccgcccac acccctcggt ggtacgcggt   12480
gtcgcccgac ccacggcacc ggtggtgttc gtcctgcccg gtcagggcgc ccagtggccc   12540
ggcatggcga cccgactgct cgccgagtcg ccgtcttcg ccgcggcgat gcgggcctgc   12600
gagcgggcct tcgacgaggt caccgactgg tcgttgaccg aggtcctgga ctcacccgag   12660
cacctgcgcc gcgtcgaggt ggtccagccc gcgctcttcg cggtgcagac ctcactggcc   12720
gccctgtggc ggtcgttcgg ggtgcgaccc gacgccgtac tcggacacag catcggtgag   12780
ctggccgccg ccgaggtctg cggcgccgtc gacgtcgagg ccgccgcgcg ggccgccgcc   12840
```

```
ctgtggagcc gcgagatggt cccactggtg ggccggggtg acatggcggc ggtggcgctc      12900
tccccggccg agctggcagc ccgggtcgag cggtgggacg acgacgtcgt gccggccggg      12960
gtcaacggtc cccggtcggt gctgctcacc ggcgctcccg agcccatcgc acggcgggtc      13020
gccgagctgg cggcacaggg cgtacgcgcc caggtcgtca acgtgtcgat ggcggcgcac      13080
tcggcgcagg tcgacgccgt cgccgagggc atgcgctcgg cgctgacctg gttcgccccc      13140
ggcgactccg acgtgcccta ctacgccggc ctcaccggcg gcggctgga cacccgggaa       13200 ctcggcgccg accactggcc gcgcagtttc cggctcccgg tgcgcttcga cgaggcgacc      13260
cgtgcggtcc tggaactgca gcccggcacg ttcatcgagt cgagcccgca cccggtgctg      13320
gcggcctccc tgcagcagac cctcgacgag gtcgggtccc cggccgcgat cgtgccgacc      13380
ctgcaacgcg accagggcgg tctgcggcgg ttcctgctcg ccgtggcgca ggcgtacacc      13440
ggtggcgtga cagtcgactg gaccgccgcc taccccgggg tgaccccgg ccacctgccg        13500 tcggccgtcg ccgtcgagac cgacgaggga ccctcgacgg agttcgactg ggccgcgccc      13560
gaccacgtac tgcgcgcgcg gctgctggag atcgtcggcg ccgagacggc cgcgctcgcc      13620
gggcgggagg tcgacgcccg ggccaccttc cgggaactgg gcctcgactc ggtcctcgcg      13680
gtgcagctgc ggacccgcct cgccacgcg accgggcgg atctgcacat cgccatgctc        13740
tacgaccacc cgaccccgca cgccctcacc gaggcgctgc tgcgcggccc gcaggaggag      13800
ccggggcggg tgaggagac ggcacacccg acggaggccg aacccgacga acccgtcgcc       13860
gtggtcgcca tggcgtgccg gctgcccggc ggcgtcacct caccggagga gttctgggag      13920
ctgctggccg aggggcggga cgccgtcggc gggctgccca ccgaccgggg atgggacctg      13980
gactcgctgt ccacccgga cccgacccgg tcgggcacgg cgcaccagcg cgctggtggc       14040
ttcctcaccg gcgccacctc cttcgacgct gccttcttcg ggctgtcgcc acgggaggca      14100
ctggccgtcg agccgcagca gcggatcacg ttggagctgt cgtgggaggt gctggaacgc      14160
gccgggatcc ccccgacgtc gttgcggacc tccggaccg gggtgttcgt cggtctgatc       14220
ccccaggagt acggcccccg gctggccgag gggggtgagg gcgtcgaggg ctacctgatg      14280
accgggacca ccaccagcgt cgcctccggt cgggtcgcct acaccctcgg cctggaggg        14340 ccggcgatca gcgtcgacac cgcctgctcg tcgtcgctcg tcgccgtgca cctggcgtgc      14400
cagtcgctgc ggcgcggcga gtcgacgatg gcgctcgccg gtggcgtgac ggtgatgccg      14460
acaccgggca tgctcgtgga cttcagtcgg atgaactccc tcgcccccga cggacggtcc      14520
aaggcgttct cggccgccgc cgacgggttc ggcatggccg aaggcgcagg gatgctcctg      14580
ctggaacggc tctcggacgc ccgccgccac ggccacccgg tgctcgccgt gatcaggggc      14640
accgctgtca actccgacgg cgcgagcaac ggactctccg ccccgaacgg ccgggcccag      14700
gtccgggtga tccgacaggc cctcgccgag tccgggctga cgcccacac cgtcgacgtc       14760 gtggagaccc acggcaccgg caccgcctc ggtgatccga tcgaggcacg ggcgctctcc        14820
gacgcgtacg cggtgaccg tgagcacccg ctgcggatcg ctcggtcaa gtccaacatc        14880 gggcacaccc aggccgccgc cggtgtcgcc ggtctgatca aactggtgtt ggcgatgcag      14940
gccggtgtcc tgccccgcac cctgcacgcc gacgagccgt caccggagat cgactggtcc      15000
tcgggcgcga tcagcctgct ccaggagccc gctgcctggc ccgccggcga cggcccccgc       15060
cgggccgggg tgtcctcgtt cggcatcagc ggcaccaacg cacacgcgat catcgaggag      15120
gcgccgccga ccggtgacga cacccgaccc gaccggatgg gccggtggt gccctgggtg       15180
```

```
ctctcggcga gcaccggcga ggcgttgcgc gcccgggcgg cgcggctggc cgggcaccta    15240
cgcgagcacc ccgaccagga cctggacgac gtcgcctact cgctggccac cggtcgggcc    15300
gcgctggcgt accgtagtgg gttcgtgccc gccgacgcgt ccacgcgct gcggatcctc     15360
gacgaactcg ccgccggtgg atccggggac gcggtgaccg gcaccgcccg cgccccgcag    15420
cgcgtcgtct tcgtcttccc cggccaggga tggcagtggg cggggatggc agtcgacctg    15480
ctcgacggcg acccggtctt cgcctcggtg ctgcgggagt gcgccgacgc gttggaaccg    15540
tacctggact tcgagatcgt cccgttcctg cgggccgagg cgcagcgccg gaccccgac     15600
cacacgctct ccaccgaccg cgtcgacgtg gtccagccgg tgctgttcgc ggtgatggtg    15660
tccctggcgg cccggtggcg ggcgtacggg gtggaaccgg cggccgtcat cggacactcc    15720
caggggagat tgccgcggc gtgtgtggcc ggggcgctct cgctggacga cgcggcccgg     15780
gcggtggccc tgcgcagccg ggtcatcgcc accatgcccg gcaacggcgc gatgcctcg     15840
atcgccgcct ccgtcgacga ggtggcggcc cggatcgacg ggcgggtcga gatcgccgcc    15900
gtcaacggtc cgcgcgcgt ggtggtctcc ggcgaccgtg acgacctgga ccgcctggtc     15960
gcctcctgca ccgtcgaggg ggtgcgggcc aagcggctgc cggtggacta cgcgtcgcac    16020
tcctcgcacg tcgaggccgt ccgtgacgcg ctccacgccg aactcggcga gttccggccg    16080
ctgccgggct tcgtgccgtt ctactcgaca gtcaccggcc gctgggtcga gcccgccgaa    16140
ctcgacgccg ggtactggtt tcgcaacctg cgccacaggg tccggttcgc cgacgcggtc    16200
cgctccctcg ccgaccaggg gtacacgacg ttcctggagg tcagcgccca cccggtgctc    16260
accacggcga tcgaggagat cggtgaggac cgtggcggtg acctcgtcgc tgtccactcg    16320
ctgcgacgtg gggccggcgg tcccgtcgac ttcggctccg cgctggcccg cgccttcgtg    16380
gccggcgtcg cagtggactg ggagtcggcg taccagggtg ccggggcgcg tcgggtgccg    16440
ctgcccacgt accgttcca gcgtgagcgc ttctggttgg aaccgaatcc ggcccgcagg     16500
gtcgccgact ccgacgacgt ctcgtccctg cggtaccgca tcgaatggca cccgaccgat    16560
ccgggtgagc cggacggct cgacggcacc tggctgctgg cgacgtaccc cggtcgggcc     16620
gacgaccggg tcgaggcggc gcggcaggcg ctggagtccg ccggggcgcg ggtcgaggac    16680
ctggtggtgg agccccggac gggccgggtc gacctggtgc ggcggctcga cgccgtgggt    16740
ccggtggcgg gcgtgctctg cctgttcgct gtcgcggagc cggcggccga acactccccg    16800
ctggcggtga cgtcgttgtc ggacacgctc gacctgaccc aggcggtggc cgggtcgggc    16860
cgggagtgtc cgatctgggt ggtcaccgag aacgccgtcg ccgtcgggcc cttcgaacgg    16920
ctccgcgacc cggcccacgg cgcgctctgg gccctcggtc gggtcgtcgc cctggagaac    16980
cccgccgtct ggggcggcct ggtcgacgtg ccgtcgggtt cggtcgccga gctgtcgcgt    17040
cacctcggga cgaccctgtc cggcgccggc gaggaccagg tcgccctccg acccgacggg    17100
acgtacgccc gccggtggtg cagggcgggc gcgggcggca cgggccggtg gcagcccggg    17160
ggcacggtgc tcgtcaccgg cggcaccggc ggggtcggtc ggcacgtcgc ccggtggctg    17220
gcccgccagg gcacccgtg cctggtgctg gccagccgcc ggggaccgga cgccgacggg    17280
gtcgaggagc tactcaccga actcgccgac ctgggcaccc gggccaccgt caccgcctgc    17340
gacgtcaccg accgggagca gctccgtgcc ctcctcgcga ccgtcgacga cgagcacccg    17400
ctgtcggcg tgttccacgt cgccgcgacg ctcgacgacg gcaccgtcga ccctcacc     17460
ggtgaccgca tcgaacgggc caaccgggcg aaggtgctcg gtgcccgcaa cctgcacgag    17520
ctgacccggg acgccgacct cgacgcgttc gtgctcttct cctcctccac cgccgcgttc    17580
```

```
ggcgcgccgg ggctcggcgg ctacgtcccg ggcaacgcct acctcgacgg tctcgcccag    17640
cagcgacgca gcgagggact cccggccacc tcggtggcgt ggggtacctg ggcgggcagc    17700
gggatggccg agggtccggt cgccgaccgg ttccgccggc acgggtcat ggagatgcac     17760 cccgaccagg ccgtcgaggg tctccggggtg gcactggtgc agggtgaggt agccccgatc   17820
gtcgtcgaca tcaggtggga ccggttcctc ctcgcgtaca ccgcgcagcg ccccacccgg    17880
ctcttcgaca ccctcgacga ggcccgtcgg gccgcgcccg gtcccgacgc cgggccgggg    17940
gtggcggcgc tggccgggct gcccgtcggg gaacgcgaga aggcggtcct cgacctggta    18000
cggacgcacg cggctgccgt cctcggccac gcctcggccg agcaggtgcc cgtcgacagg    18060
gccttcgccg aactcggcgt cgactcgctg tcggccctgg aactgcgcaa ccggctgacc    18120
actgcgaccg gggtccggct ggccacgacg acggtcttcg accacccgga cgtacggacc    18180
ctggccggac acctggccgc cgaactgggc ggcggatcgg ggcgggagcg gcccggggc    18240 gaggccccga cggtggcccc gaccgacgag ccgatcgcca tcgtcgggat ggcctgccgg    18300
ctgccggggg gagtggactc accggagcag ctgtgggagt tgatcgtctc cgggcgggac   18360
accgcctcgg cggcacccgg ggaccggagc tgggatccgg cggagttgat ggtctccgac    18420
acgacgggca cccgtaccgc cttcggcaac ttcatgcccg gggcgggcga gttcgacgcg    18480
gcgttcttcg ggatctcgcc gcgtgaggcg ttggcgatgg atccgcagca gcggcacgcc    18540
ctggagacca cctgggaggc gctggagaac gccggtatcc ggcccgagtc gttgcgcggt    18600
acggacaccg gtgtcttcgt gggcatgtcc catcaggggt acgccaccgg ccgcccgaag    18660
cccgaggacg aggtcgacgg ctacctgttg acaggcaaca ccgcgagcgt cgcctccggt    18720
cggatcgcgt acgtgttggg gttggagggg ccggcgatca ctgtggacac ggcgtgttcg    18780
tcgtcgcttg tggcgttgca cgtggcgcg ggttcgttgc gttctgggga ctgtggtctg     18840
gcggtggcgg gtggggtgtc ggtgatggcc ggtccggagg tgttcaggga gttctcccgg    18900
cagggcgcgt tggctccgga cggcaggtgc aagcccttct cggacgaggc cgacggcttc    18960
ggtctggggg aggggtcggc cttcgtcgtg ttgcagcggt tgtcggtggc ggtgcgggag    19020
gggcgtcggg tgttgggtgt ggtggtgggt tcggcggtga atcaggatgg ggcgagtaat    19080
gggttggcgg cgccgtcggg ggtggcgcag cagcgggtga ttcggcgggc gtggggtcgt   19140
gcgggtgtgt cgggtgggga tgtggtgtgt gtggaggcgc atgggacggg gacgcggttg    19200
ggggatccgg tggagttggg ggcgttgttg gggacgtatg gggtgggtcg gggtggggtg    19260
ggtccggtgg tggtgggttc ggtgaaggcg aatgtgggtc atgtgcaggc ggcggcgggt    19320
gtggtgggtg tgatcaaggt ggtgttgggg ttgggtcggg ggttggtggg tccgatggtg    19380
tgtcggggtg ggttgtcggg gttggtggat tggtcgtcgg gtgggttggt ggtggcggat    19440
ggggtgcggg ggtggccggt gggtgtggat ggggtgcgtc ggggtggggt gtcggcgttt    19500
ggggtgtcgg ggacgaatgc tcatgtggtg gtggcggagg cgccggggtc ggtggtgggg    19560
gcggaacggc cggtggaggg gtcgtcgcgg gggttggtgg gggtggttgg tggtgtggtg    19620
ccggtggtgc tgtcggcaaa gaccgaaacc gccctgcacg cccaggcacg tcgactcgcc    19680
gaccacctga gacgcaccc cgacgtcccg atgaccgacg tggtgtggac gctgacgcag     19740
gcccgccaac gcttcgacag gcgcgcggtc ctcctcgccg ccgaccggac ccaggccgtg    19800
gaacggctgc gcggcctcgc cggggcgaa ccggggaccg gtgtggtgtc ggggtgcg      19860 tcgggtggtg gtgtggtgtt tgttttttcct ggtcagggtg gtcagtgggt ggggatggcg   19920
```

```
cggggttgt tgtcggttcc ggtgtttgtg gagtcggtgg tggagtgtga tgcggtggtg    19980
tcgtcggtgg tggggttttc ggtgttgggg gtgttggagg gtcggtcggg tgcgccgtcg    20040
ttggatcggg tggatgtggt gcagccggtg ttgttcgtgg tgatggtgtc gttggcgcgg    20100
ttgtggcggt ggtgtggggt tgtgcctgcg gcggtggtgg gtcattcgca gggggagatc    20160
gcggcggcgg tggtggcggg ggtgttgtcg gtgggtgatg gtgcgcgggt ggtggcgttg    20220
cgggcgcggg cgttgcgggc gttggccggc cacggcggca tggcctcggt acgccgaggc    20280
cgcgacgacg tacagaagct cctcgacagc ggcccctgga cggggaagct ggagatcgcc    20340
gcggtcaacg gccccgacgc ggtggtggtc tccggcgacc cccgagccgt gaccgagctg    20400
gtcgagcact gtgacgggat cggggtccgg gcccggacga tccccgtcga ctacgcctcc    20460
cactccgcac aggtcgagtc gctccgggag gagctgctct ccgtcctggc cgggatcgag    20520
ggccgcccgg cgacggtgcc gttctactcc accctcaccg gtgggttcgt cgacggcacc    20580
gaactggacg ccgactactg gtaccgcaac ctgcgccacc cggtgcggtt ccacgccgcc    20640
gtcgaggcgc tggcagcgcg tgacctcacc acgttcgtcg aggtcagccc gcaccccgtg    20700
ctgtcgatgg cggtcgggga gacgcttgcc gacgtggagt ccgccgtcac tgtgggcacc    20760
ctggaacgcg acaccgacga cgtcgagcgc ttcctcacct ccctcgccga ggcgcacgtc    20820
cacggcgtac ccgtggactg ggcggcggtc ctcggctccg gaaccctggt cgacctgccc    20880
acctatccct tccagggacg gcggttctgg ctgcaccccg accgtggtcc gcgtgacgat    20940
gtcgccgact ggttccaccg ggtcgactgg acggcgacgg ccaccgacgg gtcggcccga    21000
ctcgacggtc gctggctggt ggtcgtaccc gaggggtaca cggacgacgg ctgggtcgtg    21060
gaggtgcggg ccgccctcgc cgccggtggt gccgagccgg tggtgacgac ggtcgaggag    21120
gtcaccgacc gggtcggtga cagcgacgcg gtggtgtcga tgctcgggct ggccgacgac    21180
ggtgcggccg agaccctggc gctgctgcga cgactcgacg cacaggcgtc caccacccca    21240
ctgtgggtgg tcaccgtggg ggccgtcgcc ccgccggtc cggtgcagcg ccccgaacag    21300
gcgacggtgt gggggttggc ccttgtcgcc tccctggaac gcggacaccg gtggaccggc    21360
ctgctggatc tgccgcagac accggacccg cagctacgac cccggctggt cgaggcgctc    21420
gccggtgccg aggaccaggt agcggtccgc gccgacgccg tacacgcccg tcggatcgtc    21480
cccaccccgg tcaccggagc cgggccgtac accgccccgg gcgggacgat cctcgtcacc    21540
gggggcaccg ccggtctggg tgccgtcacc gcccgatggc tcgccgagcg cggtgccgaa    21600
cacctcgccc tggtcagccg gcgcgggccg ggcaccgccg gcgtcgacga ggtggtccgg    21660
gacctgaccg ggctcggcgt acgggtgtcg gtgcactcct gcgacgtcgg cgaccgcgag    21720
tcggtcggcg ccctggtgca ggagttgaca gcagccggtg acgtggtccg gggggtggtc    21780
cacgctgccg gtctgcccca gcaggtgcca ctgaccgaca tggacccggc cgacctcgcc    21840
gacgtggtgg ccgtgaaggt cgacggcgcg gtgcacctgg ccgacctgtg cccggaggcc    21900
gaactgttcc tgctgttctc ctccggggcc ggggtgtggg gcagtgcccg tcagggtgcg    21960
tacgccgccg gaaacgcctt cctggacgcc ttcgcccgac accggcggga ccgggtctg    22020 cccgccacct cggtggcgtg ggggctctgg gcggccgggg ggatgacagg ggaccaggag    22080
gcggtgtcgt tcctgcgtga gcggggcgta cggccgatgt cggtgccgag ggcactggaa    22140
gcgctggaac gggtcctcac cgccggggag accgcggtgg tcgtcgccga cgtcgactgg    22200
gcggccttcg ccgagtcgta cacctccgcc cggccccggc cgctgctcca ccggctcgtc    22260
acacctgcgg cggcggtcgg cgagcgcgac gagccgcgtg agcagaccct ccgggaccgg    22320
```

-continued

```
ctggcggccc tgccccgggc cgagcggtcg gcggagctgg tacgcctggt ccggcgggac    22380
gccgcagccg tgctcggcag cgacgcgaag gccgtacccg ccaccacgcc gttcaaggac    22440
ctcgggttcg actcgctggc cgcggtccgg ttccgtaacc ggctggccgc ccacaccggt    22500
ctgcgtctgc cggccaccct ggtcttcgag cacccgaacg ccgcagccgt cgccgacctc    22560
ctccacgacc gactcggcga ggccggcgag ccgaccccg tccggtcggt gggcgccgga     22620
ctggccgcgc tggagcaggc cctgcccgac gcctccgaca cggagcgggt cgagctggtc    22680
gagcgcctgg aacggatgct cgccgggctc cgccccgagg ccggagccgg ggccgacgcc    22740
ccgaccgccg gtgacgacct gggggaggcc ggcgtcgacg aactcctcga cgcgctcgaa    22800
cgggaactcg acgccaggtg aacccgaact gaccgcagcc gcagccgaag cagagaccga    22860
ggacctgtga ctgacaacga caaggtggcg gagtacctcc gtcgtgcgac gctcgacctg    22920
cgggccgccc gcaagcgcct gcgcgagctg caatccgacc cgatcgcggt cgtcggcatg    22980
gcctgccgcc taccgggcgg ggtgcacctc ccgcagcacc tgtgggacct cctgcgccag    23040
gggcacgaga cggtgtccac cttccccacc gggcgcggct gggacctggc cgggctcttc    23100
cacccggacc ccgaccaccc cggcaccagc tacgtcgacc ggggtgggtt cctcgacgac    23160
gtggcgggct tcgacgccga gttcttcggg atctccccgc gcgaggccac ggccatggac    23220
ccgcaacagc ggctgctgtt ggagaccagt tgggagctgg tggagagcgc cggcatcgat    23280
ccgcactccc tgcgtggcac cccgaccggc gtcttcctcg gcgtggcgcg gctcggctac    23340
ggcgagaacg gcaccgaagc cggtgacgcc gagggctatt cggtgaccgg ggtggcaccc    23400
gctgtcgcct ccgggcggat ctcctacgcc ctcgggctgg agggtccgtc gatcagcgtg    23460
gacaccgcgt gctcgtcgtc gttggtggcg ctgcacctgg cggtcgagtc gctgcggctg    23520
ggcgagtcga gtctcgctgt cgtcggcggg gcggcggtca tggcgacacc aggggtgttc    23580
gtcgacttca gccgccagcg ggcgttggcc gctgacggca ggtcgaaggc cttcggggcc    23640
gccgccgacg ggttcggctt ctccgagggg gtctccctcg tcctgctcga acggctctcc    23700
gaggccgaaa gcaacggcca cgaggtgttg gctgtcatcc gtggctccgc cctcaaccag    23760
gacgggccca gcaacggtct cgccgcgccg aacgggaccg cccagcgcaa ggtgatccgg    23820
caggcgctac gaaactgcgg cctgaccccg gccgacgtga acgccgtgga ggcgcacggc    23880
accggcacca cgctcggcga cccgatcgag gccaacgccc tgctggacac ctacggccgt    23940
gaccgggatc cggaccaccc gctgtggctg gggtcggtga agtcgaacat cggccacacg    24000
caggcggcgg cgggcgtcac cgggctgctc aagatggtgc tggcactgcg ccacgaggaa    24060
ctgcccgcca ccctgcacgt cgacgagccc accccgcacg tggactggtc ctcgggagcg    24120
gtacgcctgg cgaccggggg ccggccgtgg cggcggggtg accggccgag gcgggccggg    24180
gtgtcggcgt tcggcatcag cgggaccaac gcccacgtga tcgtcgagga ggcacccgag    24240
cggaccaccg agcgcaccgt cggcggcgac gtcggcccgg tcccgctcgt ggtgtccgcc    24300
cggtcggcgg cggcgctacg ggcccaggcg gcccaggtcg ccgagctggt ggagggctcc    24360
gacgtcgggc tggcggaggt cgggcggagc ctggccgtga cccgggcgcg acacgagcac    24420 cggcggcgg tggtggcgtc gacccgggcc gaggcggtgc gggggctgcg cgaggtcgcg    24480
gcggtcgaac cgcgcggcga ggacaccgtc accggggtcg ccgagacgtc cgggcgcacc    24540
gtcgtcttcc tcttcccggg acaggggtcc cagtgggtcg ggatgggcgc ggagctgctg    24600
gactcggcac cggcgttcgc cgacacgatc cgcgcctgcg acgaggcgat ggcaccgttg    24660
```

```
caggactggt cggtctccga cgtgctccgg caggagccgg gggcaccggg actggaccgg    24720
gtcgacgtgg tgcagccggt gctgttcgcg gtgatggtgt cgttggcgcg gttgtggcag    24780
tcgtacgggg tcaccccgc tgcggtggtg gggcactcgc aggggagat cgccgccgcc      24840 cacgtggcgg gtgcgctctc cctcgccgac gcggcgaggc tggtggtggg ccgcagccgg    24900
ttgctgcggt cgctgtccgg gggcggcggc atgagcgccg tcgcgctcgg tgaggccgag    24960
gtacgccgcc gactgcggtc gtgggaggac cggatctccg tggccgccgt caacggaccc    25020
cggtcggtgg tggtggccgg ggaaccggag gcgctgcggg agtggggacg ggagcgggag    25080
gccgagggcg tacgggtccg cgagatcgac gtcgactacg cctcgcactc gccgcagatc    25140
gacagggtcc gtgacgaact cctgacggtc acggggagga tcgagccccg gtcggcggag    25200
atcaccttct actcgacggt cgacgtccgt gctgtcgacg gcaccgacct ggacgcgggg    25260
tactggtacc gcaacctgcg ggagacggtc cggttcgccg acgcgatgac ccggttggcc    25320
gactcgggat acgacgcgtt cgtcgaggtc agcccgcatc cggtggtggt gtcggcggtc    25380
gccgaggcgg tcgaggaggc aggtgtcgag gacgccgtcg tcgtcggcac cctgtcccgg    25440
ggcgacggcg gaccggggc gttcctgcgg tcggcggcca ccgcccactg cgccggtgtg    25500
gacgtcgact ggacgcccgc cctcccggga gctgcgacga tcccgttgcc gacgtacccg    25560
ttccaacgga agccgtactg gctgcggtcg tctgctcccg cccccgcctc ccacgatctc    25620
gcctaccggg tgtcctggac gccgatcacc ccgcccgggg acggcgtact cgacggcgac    25680
tggctggtgg tgcaccccgg gggcagcacc ggatgggtcg acgggttggc ggcggcgatc    25740
accgccggcg gtggccgggt cgtcgcccac ccggtggact ccgtgacctc ccggaccggc    25800
ctggccgagg cgctcgcccg gcgggacggc acgttccggg gggtgctgtc gtgggtggcg    25860
accgacgaac ggcacgtcga ggccggtgcg gtcgccctgc tgaccctggc gcaggcgttg    25920
ggtgacgccg gaatcgacgc accactgtgg tgcctgaccc aggaggcggt ccgtaccccc    25980
gtcgacggtg acctggcccg accggcgcag gccgccctgc acggtttcgc ccaggtcgcc    26040
cggctggagc tggcccgccg cttcggtggg gtgctcgacc tgcccgccac cgtcgacgcc    26100
gccgggacgc gtctggtcgc ggcggtcctc gccggcggcg gcgaggacgt cgtcgccgtc    26160
cgtggcgacc gtctctacgg ccgtcgcctg gtcaggcga ccctgccgcc gcccggcggg      26220
gggttcaccc cgcacggcac cgtcctggtc accggcgcgg ccggtccggt gggcggtcgg    26280
ctggcccggt ggctcgccga acggggtgcc acccgactcg tcctgcccgg cgcacacccg    26340
ggcgaggagt tgctgaccgc gatccggggcc gccggtgcca ccgccgtggt gtgcgaaccg    26400
gaggcggagg cactgcgtac ggcgatcggc ggggagttgc cgaccgcgct cgtacacgcc    26460
gagacgttga cgaacttcgc cggcgtcgcc gacgccgacc ccgaggactt cgccgccacc    26520
gtcgcggcga agaccgcgct gccgacggtc tggcggagg tgctcggcga ccaccgcctc      26580
gaacgggagg tctactgctc gtcggtggcc ggggtctggg gtgggtcgg catggccgcg    26640 tacgccgccg gcagcgccta cctcgacgcc ctggtcgagc accgtcgcgc ccggggcac     26700 gccagcgcct cggtggcctg gaccccgtgg gccctgcccg gcgcggtcga cgacggtcgg    26760
ctgcgcgagc gcggcctgcg cagcctcgac gtggccgacg ccctcgggac gtgggaacgt    26820
ctgctccgcg ccggtgcgt gtcggtggcc gtcgccgacg tcgactggtc ggtcttcaca    26880
gagggtttcg cggccatccg gccgaccccg ctcttcgacg aactcctcga ccggcgcggg    26940
gaccccgacg gcgcgcccgt cgaccggccg ggggagccgg cgggcgagtg gggtcgacga    27000
atcgcggcgc tgtccccgca ggaacagcgg gagacgttgc tgaccctcgt cggcgagacg    27060
```

-continued

```
gtcgcggagg tgctgggaca cgagaccggc accgagatca acacccgtcg ggccttcagc    27120
gaactcggcc tcgactcgct gggctcgatg gccctgcgtc agcgcctggc ggcccgtacc    27180
ggcctgcgga tgccggcctc gctggtcttc gaccacccga cggtcaccgc gctcgcgcgg    27240
tacctgcgtc gactggtcgt cggggactcc gacccgaccc cggtacgggt gttcggcccc    27300
accgacgagg ccgaacccgt cgccgtggtc ggcatcggct gccggttccc cggcggcatc    27360
gccacccccg aggacctctg gcgggtggtg tccgagggca cctccatcac caccggattc    27420
cccaccgacc ggggctggga cctccggcgg ctctaccacc ccgacccgga ccaccccggc    27480
accagctacg tcgacagggg gggattcctc gacgggcccc cggacttcga ccccgggttc    27540
ttcgggatca ccccccgcga ggcgctggcg atggacccgc agcagcggct cacccctggag   27600 atcgcgtggg aggcggtgga acgggcgggc atcgacccgg agaccctcct cggcagcgac    27660
accggcgtct tcgtcggcat gaacggccag tcctacctgc aactgctgac cggggagggt    27720
gaccggctca acggctacca ggggttgggc aactcggcga gcgtgctctc cggccgtgtc    27780
gcctacacct tcgggtggga ggggccggcg ctgacggtgg acaccgcctg ctcgtcctcg    27840
ctggtcgcca tccacctcgc catgcagtcg ctgcgtcggg gtgagtgctc gctggcgttg    27900
gccggcgggg tgacggtcat ggccgacccg tacaccttcg tggacttcag cgcacagcgg    27960
gggctcgccg ccgacgggcg gtgcaaggcg ttctccgcgc aggccgacgg gttcgccctc    28020 gccgagggc tcgcggcgct cgtcctcgaa ccgttgtcca aggcgcggcg aaacggccac    28080
caggtgctgg cggtgctgcg cggcagcgcc gtcaaccagg acggggccag caacggcctc    28140
gccgccccga acgggccgtc gcaggaacgg gtgatcaggc aggccctgac cgcctccggg    28200
ctgcgtcccg ccgacgtcga catggtggag gcgcacggga cgggcaccga actcggcgac    28260
ccgatcgagg ccgggggcgct catcgcggcg tacggccggg accggaccg gccgctctgg    28320 ctgggctcgg tgaagacgaa catcggccac acccaggccg ccgccggtgc cgccggggtg    28380
atcaaggcgg tcctggcgat gcggcacggc gtactcccga ggtcgctgca cgccgacgag    28440
ttgtccccgc acatcgactg ggcggacggg aaggtcgagg tgctccgcga ggcacgacag    28500 tggcccccccg gtgagcgccc ccgccgcgcc ggggtgtcct ccttcggcgt cagcgggacc    28560
aacgcccacg tcatcgtcga ggaggcaccc gccgaaccgg accccgaacc ggttcccgcc    28620
gccccgggcg ggcccctgcc cttcgtcctg cacggacgca gcgtccagac ggtccggtcc    28680
caggcgcgga ccctcgccga acacctgcgc accaccggcc accgggacct cgccgacacc    28740
gcccgtaccc tggccaccgg tcgcgcccgt ttcgacgtcc gggccgcagt gctcggcacc    28800
gaccgggagg tgtctgcgc cgcccctcgac gcgctggcgc aggatcgccc ctcgcccgac    28860
gtcgtcgccc cggcggtctt cgccgcccgt accccgtcc tggtcttccc cgggcagggg    28920
tcgcagtggg tcgcatggc ccgtgacctg ctcgactcct ccgaggtgtt cgccgagtcg    28980
atgggccggt cgccgaggc gctgtcgccg tacaccgact gggacctgct cgacgtggtc    29040
cgtggggtcg gcgaccccga cccgtacgac cgggtggacg tgctccagcc ggtgctgttc    29100
gcggtgatgg tgtcgctggc gcggttgtgg cagtcgtacg gggtgactcc gggtgcggtg    29160
gtgggtcact cgcaggggga gatcgccgcc gcgcacgtgg ctggtgcgtt gtcgttggcc    29220
gacgccgcca gggtggtggc gttgcgcagc cgggtgctgc gggagctcga cgaccagggc    29280
ggcatggtgt cggtcggcac ctcccgcgcc gagttggact cggtcctgcg ccggtgggac    29340
gggcgggtcg cggtggcggc ggtgaacgga cccggcacgc tcgtggtggc cggacccacc    29400
```

```
gccgaactgg acgagttcct cgcggtggcc gaggcccgcg agatgaggcc gcgtcggatc   29460
gcggtgcgct acgcgtcgca ctccccggag gtggcccggg tcgaacagcg gctcgccgcc   29520
gaactcggca ccgtcaccgc cgtcggcggc acggtcccgc tctactccac cgccaccggg   29580
gacctcctcg acaccacagc catggacgcc gggtactggt accgcaacct gcgccaaccg   29640
gtgctgttcg agcacgccgt ccgcagcctc ctggagcggg gattcgagac gttcatcgag   29700
gtcagcccgc accctgtgct gctgatggcg gtcgaggaga ccgccgagga cgccgagcgc   29760
ccggtcaccg gcgtgccgac gctgcgccgc gaccacgacg ggccgtcgga gttcctccgc   29820
aacctcctgg gggcgcacgt gcacggggtc gacgtcgacc tgcgtccggc ggtcgcccac   29880
ggccgcctgg tcgacctgcc cacctacccc ttcgacaggc agcggctctg gcccaagccg   29940
caccgcaggg ccgacacctc gtcgctgggg gtccgtgact cgacccaccc gctgctgcac   30000
gccgcagtcg acgtacccgg tcacggcgga gcggtgttca ccgggcggct ctcccccgac   30060
gagcagcagt ggctgaccca gcacgtggtg ggtgggcgga acctggtgcc cggcagtgtc   30120
ctggtcgacc tcgcgctcac cgccggggcc gacgtcggcg tgccggtgct ggaggaactc   30180
gtcctgcagc agccgctggt gttgaccgcc gccggtgcgt tgctgcgcct gtcggtcggc   30240
gccgccgacg aggacgggcg gcggccggtc gagatccacg ccgccgagga cgtctccgac   30300
ccggccgagg cccggtggtc ggcgtacgcg accgggaccc tcgccgtcgg cgtggccggc   30360
ggcggccggg acggcacaca gtggcccccg cccggcgcca ccgccctgac gttgaccgac   30420
cactacgaca ccctcgccga actgggctac gagtacgggc cggcgttcca ggcgctgcgc   30480
gccgcgtggc agcacggcga cgtggtctac gcggaggtgt ccctcgacgc cgtcgaggag   30540
gggtacgcgt tcgacccggt gctgctcgac gccgtcgccc agaccttcgg cctgaccagt   30600 cgcgccccg ggaagctccc cttcgcctgg cggggcgtca ccctgcacgc caccggggcc   30660
actgcggtac gggtggtggc gaccccgcc ggaccggacg cggtggccct gcgggtcacc   30720
gacccgaccg gtcagctcgt cgccacggtg gacgccctgg tcgtcaggga cgccggggcg   30780
gatcgggacc agccgcgcgg ccgcgacggc gacctgcacc gcctggagtg ggtacgcctg   30840
gccaccccgg acccgacccc ggcggcggtg gtgcacgtgg cggccgacgg gctcgacgac   30900
ctgctgcgcg ccgtggtcc ggcaccacag gccgtcgtcg tccgctaccg tcccgacggc   30960
gacgacccga cggccgaggc ccgtcacggg gtgctctggg cggccacgct cgtgcgccgt   31020
tggctcgacg acgaccggtg gcccgccacc accctggtgg tggccacgtc cgcagggggtc   31080 gaggtctccc ccggggacga cgtgccgcgc cccggggccg ccgccgtgtg gggggtgctg   31140
cgctgcgccc aggcggagtc cccggaccgc ttcgtgctcg tcgacggcga cccggagacg   31200
cccccggcgg tgccggacaa tccgcagctc gcggtccgtg acggtgcggt gttcgtgcca   31260
cggctgacgc cgctcgccgg tcccgtgccg gccgtcgccg accgggcgta ccggctggtg   31320
cccggcaacg gcggctccat cgaggcagtg gccttcgccc ccgtccccga cgccgaccgg   31380
cccctggcgc cggaggaggt acgcgtcgcc gtccgcgcca ccggcgtgaa cttccgtgac   31440
gtcctgctcg cgctcggcat gtacccggaa ccggccgaga tggcaccgga gcgtccggt   31500 gtggtcaccg aggtcgggtc gggtgtccgg cggttcaccc ccggccaggc ggtgacgggc   31560
ctgttccagg gggccttcgg gccggtggcg gtcgccgacc accggctcct caccccggtc   31620
cccgacgggt ggcgggcggt ggacgccgca gccgtaccca tcgcgttcac caccgcccac   31680
tacgcgctgc acgacctggc cggggttgcag gccgggcagt ccgtgctggt ccacgccgcc   31740
gccggcgggg tggggatggc tgccgtcgcg ttggcccgtc gggccggggc ggaggtgttc   31800
```

```
gccacggcca gcccggccaa acacccgacg ctgcggcgcg tcggcctcga cgacgaccac  31860
atcgcctcgt cccgggagag cgggttcggt gagcggttcg ccgcgcgtac cggggggcgg  31920
ggcgtcgacg tggtcctgaa ctcgctcacc ggcgacctgc tcgacgagtc cgcgcggctg  31980
ctcgccgacg gcgggtctt cgtcgagatg ggcaagaccg acctgcggcc ggcggagcag  32040
ttccggggcc ggtacgtccc gttcgacctg gccgaggccg tcccgatcg gctcggcgag  32100 atcctggagg aggtcgtcgg tctgctggcc gccggtgccc tcgaccggtt gccggtgtcg  32160
gtgtgggagt tgtcggcggc cccggccgcg ctcacccaca tgagccgggg ccgacacgtg  32220
ggcaagctcg tcctcaccca gcccgccccc gtgcacccg acggaacggt gctggtcacc  32280
ggcgggaccg gcaccctggg gcggctggtc gcccgccacc tggtgaccgg gcacggcgta  32340
ccccacctcc tggtggccag ccggcgcggt ccggcggccc cgggcgcggc cgagctgcgc  32400
gccgacgtcg aaggcctcgg cgcgaccatc gagatcgtcg cctgcgacac cgccgaccgg  32460
gaggcgctcg cggcgctgct cgactcgatc cccgcggacc gtccgctgac cggggtggtg  32520
cacaccgccg ggtcctggc cgacgggctg gtcacctcca tcgacgggac cgccaccgat  32580
caggtcctgc gggccaaggt cgacgcggcg tggcacctgc acgacctgac ccgggacgcg  32640
gacctgagct tcttcgtgct gttctcgtcg gcggcgtcgg tgctggccgg tcccgggcag  32700
ggcgtgtacg cggcggccaa cggggtcctc aacgccctgg ccgggcaacg gcgggccctc  32760
ggactgcccg cgaaggcgct cgggtggggc ctgtgggcgc aggccagcga gatgaccagc  32820
ggcctcggtg accggatcgc ccgtaccggg gtcgccgcgc tgccgaccga gcgggcgctg  32880
gccctgttcg acgcggctct gcgcagcggc ggggaggtgc tgttcccgct gtctgtcgac  32940
aggtcggcgc tgcgccgggc cgagtacgtc cccgaggtgc tgcgcggcgc ggtccggtcc  33000
acgccacggg ccgccaacag ggccgagacc ccgggccggg gcctgctcga ccgtctcgtc  33060
ggtgcacccg agaccgatca ggtggccgcg ctggccgagc tggtccgctc gcacgcggcg  33120
gcggtcgccg gctacgactc ggccgaccag ctgcccgaac gcaaggcgtt caaggacctc  33180
gggttcgact cgctggcggc ggtggagctg cgcaaccggc tcggcgtcac caccggcgta  33240
cggctgccca gcacgctggt gttcgaccac ccgacaccgc tggcggtggc cgaacacctg  33300
cggtcggagt tgttcgccga ctccgcgccg gacgtcgggg tcggtgcgcg cctcgacgac  33360
ctggaacggg cgctcgacgc cctgcccgac gcgcagggac acgccgacgt cggggcccgc  33420
ctggaggcgc tgctgcgccg gtggcagagc cgacgacccc cggagaccga gccagtgacg  33480
atcagtgacg acgccagtga cgacgagctg ttctcgatgc tcgacaggcg tctcggcggg  33540
ggaggggacg tctaggtgac aggtcgattc cgccccgcgg cagtggaccg taccgccctg  33600
acaggtccac cgggttcgcg tcgcctccca cacccgacgg ccgggtatc cacggaaggg  33660 atccgatgag cgagagcagc ggcatgaccg aggaccgcct ccggcgctat ctcaagcgca  33720
ccgtcgccga actcgactcg gtgacaggtc ggctcgacga ggtcgagtac cgggcccgcg  33780
aaccgatcgc cgtcgtcggc atggcctgcc ggttccccgg gggtgtggac tcgcggagg  33840 cgttctggga gttcatccgc gacggtggtg acgcgatcgc cgaggcgccc acggaccgtg  33900 gctgccgcc ggcaccgcga ccccgcctcg gtggtctcct cgcggagccg ggcgcgttcg  33960
acgccgcctt cttcggcatc tcaccccgcg aggcgctcgc gacggacccc cagcagcgcc  34020
tgatgctgga gatcctctgg gaggcgttgg agcgtgcggc tttcgacccg tcgagcctgc  34080
gcggcagcgc cggtggcgtc ttcaccggtg tcggtgcggt ggactacgga cccaggccgg  34140
```

-continued

```
acgaggcacc cgaggaggtg ctcggctacg tcggcatcgg caccgcctcc agcgtcgcct      34200
ccggacgggt ggcgtacacc ctggggttgg agggtccagc cgtcaccgtc gacaccgcct      34260
gctcctccgg gctcaccgcg gtgcacctgg cgatggagtc gctgcgccgc gacgagtgca      34320
ccctggtcct cgccggtggg gtcaccgtga tgagcagccc gggtgcgttc accgagttcc      34380
gcagccaggg cggggttggcc gaggacggcc gctgcaaacc gttctcccgc gccgccgacg     34440
gcttcgggct cgccgagggg gccggggtcc tggtgctcca acggctgtcc gtcgcccggg      34500
ccgagggccg gccggtgctg gccgtactgc gtggctcggc gatcaaccag gacggtgcca      34560
gcaacgggct caccgcgccg agcggccccg cccagcggcg ggtgatcagg caggcgttgg      34620
agcgggcgcg gctgcgtccc gtcgacgtgg actacgtgga ggcccacggc accggcaccc      34680
ggctgggcga tccgatcgag gcgcacgccc tgctcgacac gtacggtgcc gaccgggaac      34740
ccggccgccc gctctgggtc ggatcggtga agtccaacat cggtcacacc caggcggcgg      34800
cgggggtggc cgggtgatg aagaccgtgc tggcgctgcg gcatcgggag atcccggcga       34860
cgttgcactt cgacgagccc tcgccgcacg tcgactggga ccggggtgcg gtgtcggtgg      34920
tgtccgagac ccggccctgg ccggtggggg agcgcccgcg ccgggcgggg gtgtcctcgt      34980
tcggcatcag cggcaccaac gcgcacgtca tcgtcgagga ggcgccgagc ccgcaggcgg      35040
ccgacctcga cccgaccccc ggcccggcaa ccggagcgac ccccggaacg gatgccgccc     35100
ccaccgccga gccgggtgcg gaggcggtcg cactggtgtt ctccgcgcgc gacgagcggg      35160
ccctgcgcgc ccaggcggcc cggctcgccg accgtctcac cgacgacccg gcccctcgt      35220
tgcgcgacac cgccttcacc ctggtcaccc gccgtgccac ctgggagcat cgggcggtcg      35280
tcgtcggcgg gggcgaggag gtcctcgccg gcctccgggc cgtcgccggg ggacgtcccg      35340
tcgacggagc cgtcagcggg cgggcgcgcg ccggccgccg ggtggtgctg gtcttccccg      35400
ggcagggcgc acagtggcag ggcatggccc gggacctgct cgcgcagtcg ccgaccttcg      35460
cggagtccat cgacgcctgc gagcgggcgc tcgccccgca cgtggactgg tcgctgcgcg      35520
aggtgctcga cggcgagcag tcgttggacc ccgtcgacgt ggtgcagccg gtgctgttcg      35580
cggtgatggt gtcgttggcg cggttgtggc agtcgtacgg ggtgactccg ggtgcggtgg      35640
tgggtcactc gcaggggggag atcgccgccg cgcacgtggc tggtgcgttg tcgttggccg      35700
acgccgccag ggtggtggcg ttgcgcagcc gggtgctgcg ccgtctcggt ggtcacggcg      35760
ggatggcgtc gttcgggctc caccccgacc aggccgccga gcggatcgcg cgcttcgcgg      35820
gtgcgctgac tgtcgcctcg gtcaacggtc cccgttcggt ggtgctggcc ggggagaacg      35880
gcccgttgga cgagctgatc gccgagtgcg aggccgaggg cgtgaccgcc cgtcggatcc      35940
ccgtcgacta cgcctcacac tccccgcagg tggagtcgct gcgtgaggag ctgctcgccg      36000
cactggccgg ggtccgtccg gtgtcggccg ggatcccccct gtactcgacc ctgaccggtc     36060
aggtcatcga aacggcgacg atggacgccg actactggtt cgccaacctc cgggagccgg      36120
tgcgcttcca ggacgccacc aggcagctcg ccgaggcggg gttcgacgcc ttcgtcgagg      36180
tcagcccgca cccggtgttg acagtcggtg tcgaggccac cctcgaggca gtgctgcccc      36240
ccgacgcgga tccgtgtgtc acaggcaccc tgcgccgcga acgcggcggt ctcgcgcagt      36300
tccacaccgc gctcgccgag gcgtacaccc gggggtgga ggtcgactgg cgtaccgcag       36360
tgggtgaggg acgccggtc gacctgccgg tctacccgtt ccaacgacag aacttctggc       36420
tcccggtccc cctgggccgg gtccccgaca ccggcgacga gtggcgttac cagctcgcct      36480
ggcaccccgt cgacctcggg cggtcctccc tggccggacg ggtcctggtg gtgaccggag      36540
```

```
cggcagtacc cccggcctgg acggacgtgg tccgcgacgg cctggaacag cgcggggcga    36600
ccgtcgtgtt gtgcaccgcg cagtcgcgcg cccggatcgg cgccgcactc gacgccgtcg    36660
acggcaccgc cctgtccact gtggtctctc tgctcgcgct cgccgagggc ggtgctgtcg    36720
acgaccccag cctggacacc ctcgcgttgg tccaggcgct cggcgcagcc gggatcgacg    36780
tccccctgtg gctggtgacc agggacgccg ccgccgtgac cgtcggagac gacgtcgatc    36840
cggcccaggc catggtcggt gggctcggcc gggtggtggg cgtggagtcc cccgcccggt    36900
ggggtggcct ggtggacctg cgcgaggccg acgccgactc ggcccggtcg ctggccgcca    36960
tactggccga cccgcgcggc gaggagcagt tcgcgatccg gcccgacggc gtcaccgtcg    37020
cccgtctcgt cccggcaccg gcccgcgcgg cgggtacccg gtggacgccg cgcgggaccg    37080
tcctggtcac cggcggcacc ggcggcatcg gcgcgcacct ggcccgctgg ctcgccggtg    37140
cgggcgccga gcacctggtg ctgctcaaca ggcggggagc ggaggcggcc ggtgccgccg    37200
acctgcgtga cgaactggtc gcgctcggca cgggagtcac catcacggcc tgcgacgtcg    37260
ccgaccgcga ccggttggcg gccgtcctcg acgccgcacg ggcgcaggga cggtggtca    37320 cggcggtgtt ccacgccgcc gggatctccc ggtccacagc ggtacaggag ctgaccgaga    37380
gcgagttcac cgagatcacc gacgcgaagg tgcgggtac ggcgaacctg gccgaactct    37440
gtcccgagct ggacgccctc gtgctgttct cctcgaacgc ggcggtgtgg ggcagcccgg    37500
ggctggcctc ctacgcggcg ggcaacgcct tcctcgacgc cttcgcccgt cgtggtcggc    37560
gcagtgggct gccggtcacc tcgatcgcct ggggtctgtg ggccgggcag aacatggccg    37620
gtaccgaggg cggcgactac ctgcgcagcc agggcctgcg cgccatggac ccgcagcggg    37680
cgatcgagga gctgcggacc accctggacg ccggggaccc gtgggtgtcg gtggtggacc    37740
tggaccggga gcggttcgtc gaactgttca ccgccgcccg ccgccggccc ctcttcgacg    37800
aactcggtgg ggtccgcgcc ggggccgagg agaccggtca ggaatcggat ctcgcccggc    37860
ggctggcgtc gatgccggag gccgaacgtc acgagcatgt cgcccggctg gtccgagccg    37920
aggtggcagc ggtgctgggc cacggcacgc cgacggtgat cgagcgtgac gtcgccttcc    37980
gtgacctggg attcgactcc atgaccgccg tcgacctgcg gaaccggctc gcggcggtga    38040
ccggggtccg ggtggccacg accatcgtct tcgaccaccc gacagtggac cgcctcaccg    38100
cgcactacct ggaacgactc gtcggtgagc cggaggcgac gaccccggct gcggcggtcg    38160
tcccgcaggc acccggggag gccgacgagc cgatcgcgat cgtcgggatg gcctgccgcc    38220
tcgccggtgg agtgcgtacc cccgaccagt tgtgggactt catcgtcgcc gacggcgacg    38280
cggtcaccga gatgccgtcg gaccggtcct gggacctcga cgcgctgttc gacccggacc    38340
ccgagcggca cggcaccagc tactcccggc acggcgcgtt cctggacggg gcggccgact    38400
tcgacgcggc gttcttcggg atctcgccgc gtgaggcgtt ggcgatggat ccgcagcagc    38460
ggcaggtcct ggagacgacg tgggagctgt tcgagaacgc cggcatcgac ccgcactccc    38520
tgcgcggtac ggacaccggt gtcttcctcg gcgctgcgta ccaggggtac ggccagaacg    38580
cgcaggtgcc gaaggagagt gagggttacc tgctcaccgg tggttcctcg gcggtcgcct    38640
ccggtcggat cgcgtacgtg ttggggttgg aggggccggc gatcactgtg gacacggcgt    38700
gttcgtcgtc gcttgtggcg ttgcacgtgg cggccgggtc gctgcgatcg ggtgactgtg    38760
ggctcgcggt ggcgggtggg gtgtcggtga tggccggtcc ggaggtgttc accgagttct    38820
ccaggcaggg cgcgctggcc cccgacggtc ggtgcaagcc cttctccgac caggccgacg    38880
```

```
ggttcggatt cgccgagggc gtcgctgtgg tgctcctgca gcggttgtcg gtggcggtgc  38940
gggaggggcg tcggtgtttg ggtgtggtgg tgggttcggc ggtgaatcag gatggggcga  39000
gtaatgggtt ggcggcgccg tcggggggtgg cgcagcagcg ggtgattcgg cgggcgtggg  39060
gtcgtgcggg tgtgtcgggt ggggatgtgg gtgtggtgga ggcgcatggg acggggacgc  39120
ggttggggga tccggtggag ttgggggcgt tgttggggac gtatgggggtg ggtcggggtg  39180
gggtgggtcc ggtggtggtg ggttcggtga aggcgaatgt gggtcatgtg caggcggcgg  39240
cgggtgtggt gggtgtgatc aaggtggtgt tgggggttggg tcgggggttg gtgggtccga  39300
tggtgtgtcg gggtgggttg tcggggttgg tggattggtc gtcgggtggg ttggtggtgg  39360
cggatgggt gcgggggtgg ccggtgggtg tggatgggggt gcgtcggggt gggggtgtcgg  39420
cgtttgggggt gtcggggacg aatgctcatg tggtggtggc ggaggcgccg gggtcggtgg  39480
tgggggcgga acggccggtg gagggggtcgt cgcggggggtt ggtgggggtg gctggtggtg  39540
tggtgccggt ggtgctgtcg gcaaagaccg aaaccgccct gaccgagctc gcccgacgac  39600
tgcacgacgc cgtcgacgac accgtcgccc tcccggcggt ggccgccacc ctcgccaccg  39660
gacgcgccca cctgccctac cgggccgccc tgctggcccg cgaccacgac gaactgcgcg  39720
acaggctgcg ggcgttcacc actggttcgg cggctcccgg tgtggtgtcg ggggtggcgt  39780
cgggtggtgg tgtggtgttt gttttttcctg gtcaggggtgg tcagtggggtg gggatggcgc  39840
gggggggtgtt gtcggttccg gtgtttgtgg agtcggtggt ggagtgtgat gcggtggtgt  39900
cgtcggtggt gggggttttcg gtgttggggg tgttggaggg tcggtcgggt gcgccgtcgt  39960
tggatcgggt ggatgtggtg cagccggtgt tgttcgtggt gatggtgtcg ttggcgcggt  40020
tgtggcggtg gtgtgggggtt gtgcctgcgg cggtggtggg tcattcgcag ggggagatcg  40080
cggcggcgt ggtggcgggg gtgttgtcgg tgggtgatgg tgcgcgggtg gtggcgttgc  40140
gggcgcgggc gttgcgggcg ttggccggcc acggcggcat ggtctccctc gcggtctccg  40200
ccgaacgcgc ccgggagctg atcgcaccct ggtccgaccg gatctcggtg gcggcggtca  40260
actccccgac ctcggtggtg gtctcggggtg acccacaggc cctcgccgcc ctcgtcgccc  40320
actgcgccga gaccggtgag cgggccaaga cgctgcctgt ggactacgcc tcccactccg  40380
cccacgtcga acagatccgc gacacgatcc tcaccgacct ggccgacgtc acggcgcgcc  40440
gacccgacgt cgccctctac tccacgctgc acggcgcccg gggcgccggc acggacatgg  40500
acgcccggta ctggtacgac aacctgcgct caccggtgcg cttcgacgag gccgtcgagg  40560
ccgccgtcgc cgacggctac cgggtcttcg tcgagatgag cccacacccg gtcctcaccg  40620
ccgcggtgca ggagatcgac gacgagacgg tggccatcgg ctcgctgcac cgggacaccg  40680
gcgagcggca cctggtcgcc gaactcgccc gggcccacgt gcacggcgta ccagtggact  40740
ggcgggcgat cctccccgcc acccacccgg ttcccctgcc gaactacccg ttcgaggcga  40800
cccggtactg gctcgccccg acggcggccg accaggtcgc cgaccaccgc taccgcgtcg  40860
actggcggcc cctggccacc accccggcgg agctgtccgg cagctacctc gtcttcggcg  40920
acgcccggga gaccctcggc cacagcgtcg agaaggccgc cgggctcctc gtcccggtgg  40980
ccgctcccga ccgggagtcc ctcgcggtcg ccctggacga ggcggccgga cgactcgccg  41040
gtgtgctctc cttcgccgcc gacaccgcca cccacctggc ccggcaccga ctcctcggcg  41100
aggccgacgt cgaggcccca ctctggctga tcaccagcgg cggcgtcgca ctcgacgacc  41160
acgacccgat cgactcgac caggcaatgg tgtgggggat cggacgggtg atgggtctgg  41220
agacccccgca ccggtgggggc ggcctggtgg acgtgaccgt cgaacccacc gccgaggacg  41280
```

```
gggtggtctt cgccgccctc ctggccgccg acgaccacga ggaccaggtg gcgctgcgcg      41340
acggcatccg ccacggccga cggctcgtcc gcgccccgct gaccacccga aacgccaggt      41400
ggacaccggc gggcacggcg ctcgtcacgg gcggtacggg tgccctcggc ggccacgtcg      41460
cgcggtacct ggcccggtcc ggggtgaccg atctcgtcct gctcagcagg agcggccccg      41520 acgcaccegg tgccgccgaa ctggccgccg aactggccga cctcggggcc gagccgagag      41580
tcgaggcgtg cgacgtcacc gacgggccac gcctgcgcgc cctggtgcag gagctacggg      41640
aacaggaccg gccggtccgg atcgtcgtcc acaccgcagg ggtgcccgac tcccgtcccc      41700
tcgaccggat cgacgaactg gagtcggtca gcgccgcgaa ggtgaccggg gcgcggctgc      41760
tcgacgagct ctgcccggac gccgacacct tcgtcctgtt ctcctcgggg gcgggagtgt      41820
ggggtagcgc gaacctgggc gcgtacgcgg cagccaacgc ctacctggac gccctggccc      41880
accgccgccg ccaggcgggc cgggccgcga cctcggtcgc ctgggggggcg tgggccggcg      41940 acggcatggc caccggcgac ctcgacgggc tgacccggcg cggtctgcgg gcgatggcac      42000
cggaccgggc gctgcgcgcc tgcaccaggc gttggaccac ccacgacacc tgtgtgtcgg      42060
tagccgacgt cgactgggac cgcttcgccg tgggtttcac cgccgcccgg cccagacccc      42120
tgatcgacga actcgtcacc tccgcgccgg tggccgcccc caccgctgcg gcggccccgg      42180
tcccggcgat gaccgccgac cagctactcc agttcacgcg ctcgcacgtg gccgcgatcc      42240
tcggtcacca ggaccecggac gcggtcgggt tggaccagcc cttcaccgag ctgggcttcg      42300
actcgctcac cgccgtcggc ctgcgcaacc agctccagca ggccaccggg cggacgctgc      42360
ccgccgccct ggtgttccag caccccacgg tacgcagact cgccgaccac ctcgcgcagc      42420
agctcgacgt cggcaccgcc ccggtcgagg cgacgggcag cgtcctgcgg gacggctacc      42480
ggcgggccgg gcagaccggc gacgtccggt cgtacctgga cctgctggcg aacctgtcgg      42540
agttccggga gcggttcacc gacgcggcga gcctgggcgg acagctggaa ctcgtcgacc      42600
tggccgacga atccggcccg gtcactgtga tctgttgcgc gggcactgcg gcgctctccg      42660
ggccgcacga gttcgcccga ctcgcctcgg cgctgcgcgg caccgtgccg gtgcgcgccc      42720
tcgcgcaacc cgggtacgag gcgggtgaac cggtgccggc gtcgatggag gcagtgctcg      42780
gggtgcaggc ggacgcggtc ctcgcggcac agggcgacac gccgttcgtg ctggtcggac      42840
actcggcggg ggccctgatg gcgtacgccc tggcgaccga gctggccgac cggggccacc      42900
cgccacgtgg cgtcgtgctc ctcgacgtgt acccaccegg tcaccaggag gcggtgcacg      42960
cctggctcgg cgagctgacc gccgccctgt tcgaccacga gaccgtacgg atggacgaca      43020
cccggctcac ggccctgggg gcgtacgaca ggctgaccgg caggtggcgt ccgagggaca      43080
ccggtctgcc cacgctggtg gtggccgcca gcgagccgat gggggagtgg ccggacgacg      43140
gttggcagtc cacgtggccg ttcgggcacg acagggtcac ggtgcccggt gaccacttct      43200
cgatggtgca ggagcacgcc gacgcgatcg cgcggcacat cgacgcctgg ttgagcgggg      43260
agagggcatg aacacgaccg atcgcgccgt gctgggccga cgactccaga tgatccgggg      43320
actgtactgg ggttacggca gcaacggaga cccgtacccg atgctgttgt gcgggcacga      43380
cgacgacccg caccgctggt accggggggct gggcggatcc ggggtccggc gcagccgtac      43440
cgagacgtgg gtggtgaccg accacgccac cgccgtgcgg gtgctcgacg acccgacctt      43500 cacccggggcc accggccgga cgccggagtg gatgcgggcc gcgggcgccc cggcctcgac      43560
ctgggcgcag ccgttccgtg acgtgcacgc cgcgtcctgg gacgccgaac tgcccgaccc      43620
```

```
gcaggaggtg gaggaccggc tgacgggtct cctgcctgcc ccggggaccc gcctggacct    43680
ggtccgcgac ctcgcctggc cgatggcgtc gcgggggtc ggcgcggacg accccgacgt     43740
gctgcgcgcc gcgtgggacg cccgggtcgg cctcgacgcc cagctcaccc cgcagccccct   43800 ggcggtgacc gaggcggcga tcgccgcgt gcccggggac ccgcaccggc gggcgctgtt     43860
caccgccgtc gagatgacag ccaccgcgtt cgtcgacgcg gtgctggcgg tgaccgccac    43920
ggcgggggcg gcccagcgtc tcgccgacga ccccgacgtc gccgcccgtc tcgtcgcgga    43980
ggtgctgcgc ctgcatccga cggcgcacct ggaacggcgt accgcggca ccgagacggt     44040 ggtgggcgag cacacggtcg cggcgggcga cgaggtcgtc gtggtggtcg ccgccgccaa    44100
ccgtgacgcg ggggtcttcg ccgacccgga ccgcctcgac ccggaccggg ccgacgccga    44160
ccgggccctg tccgcccagc gcggtcaccc cggccggttg gaggagctgg tggtggtcct    44220
gaccaccgcc gcactgcgca gcgtcgccaa ggcgctgccc ggtctcaccg ccggtggccc    44280
ggtcgtcagg cgacgtcgtt caccggtcct gcgagccacc gcccactgcc cggtcgaact    44340
ctgaggtgcc tgcgatgcgc gtcgtcttct cctccatggc cagcaagagc cacctgttcg    44400
gtctcgttcc cctcgcctgg gccttccgcg cggcgggcca cgaggtacgg gtcgtcgcct    44460
caccggctct caccgacgac atcacggcgg ccggactgac ggccgtaccg gtcggcaccg    44520
acgtcgacct tgtcgacttc atgacccacg ccgggtacga catcatcgac tacgtccgca    44580
gcctggactt cagcgagcgg gacccggcca cctccacctg gaccaccctg ctcggcatgc    44640
agaccgtcct caccccgacc ttctacgccc tgatgagccc ggactcgctg gtcgagggca    44700
tgatctcctt ctgtcggtcg tggcgacccg actggtcgtc tggaccgcag accttcgccg    44760
cgtcgatcgc ggcgacggtg accggcgtgg cccacgcccg actcctgtgg ggacccgaca    44820
tcacggtacg ggcccggcag aagttcctcg ggctgctgcc cggacagccc gccgcccacc    44880
gggaggaccc cctcgccgag tggctcacct ggtctgtgga gaggttcggc ggccgggtgc    44940
cgcaggacgt cgaggagctg gtggtcgggc agtggacgat cgaccccgcc ccggtcggga    45000
tgcgcctcga caccgggctg aggacggtgg gcatgcgcta cgtcgactac aacgccccgt    45060
cggtggtgcc ggactggctg cacgacgagc cgacccgccg acgggtctgc ctcaccctgg    45120
gcatctccag ccgggagaac agcatcgggc aggtctccgt cgacgacctg ttgggtgcgc    45180
tcggtgacgt cgacgccgag atcatcgcga cagtggacga gcagcagctc gaaggcgtcg    45240
cccacgtccc ggccaacatc cgtacggtcg ggttcgtccc gatgcacgca ctgctgccga    45300
cctgcgcggc gacggtgcac cacggcggtc ccggcagctg gcacaccgcc gccatccacg    45360
gcgtgccgca ggtgatcctg cccgacggct gggacaccgg ggtccgcgcc cagcggaccg    45420
aggaccaggg ggcgggcatc gccctgccgg tgcccgagct gacctccgac cagctccgcg    45480
aggcggtgcg gcggtcctg gacgatcccg ccttcaccgc cggtgcggcg cggatgcggg    45540
ccgacatgct cgccgagccg tcccccgccg aggtcgtcga cgtctgtgcg gggctggtcg    45600
gggaacggac cgccgtcgga tgagcaccga cgccacccac gtccggctcg ccggtgcgc     45660 cctgctgacc agccggctct ggctgggtac ggcagccctc gccggccagg acgacgccga    45720
cgcagtacgc ctgctcgacc acgcccgttc ccggggcgtc aactgcctcg acaccgccga    45780
cgacgactct gcgtcgacca gtgcccaggt cgccgaggag tcggtcggcc ggtggttggc    45840
cggggacacc ggtcggcggg aggagaccgt cctgtcggtg acgtggggtg tcccaccggg    45900
cgggcaggtc ggcggggggcg gcctctccgc ccggcagatc atcgcctcct gtgagggctc    45960
cctgcggcgt ctcggtgtcg accacgtcga cgtccttcac ctgccccggg tggaccgggt    46020
```

-continued

```
ggagccgtgg gacgaggtct ggcaggcggt ggacgccctc gtggccgccg gaaaggtctg    46080
ttacgtcggg tcgtcgggct tccccggatg gcacatcgtc gccgcccagg agcacgccgt    46140
ccgccgtcac cgcctcggcc tggtgtccca ccagtgtcgg tacgacctga cgtcgcgcca    46200
tcccgaactg gaggtcctgc ccgccgcgca ggcgtacggg ctcggggtct tcgccaggcc    46260
gacccgcctc ggcggtctgc tcggcggcga cggtccgggc gccgcagccg cacgggcgtc    46320
gggacagccg acggcactgc gctcggcggt ggaggcgtac gaggtgttct gcagagacct    46380
cggcgagcac cccgccgagg tcgcactggc gtgggtgctg tcccggcccg gtgtggcggg    46440
ggcggtcgtc ggtgcgcgga cgcccggacg gctcgactcc gcgctccgcg cctgcggcgt    46500
cgccctcggc gcgacggaac tcaccgccct ggacgggatc ttccccgggg tcgccgcagc    46560
aggggcggcc ccggaggcgt ggctacggtg agagcccgcc cctgacctgc gggaacccgt    46620
gtcggtgcgg cgggacggcc gccgcggtcc ccgcccggt cagccggtgg gggtgagccg    46680
cagcaggtcc ggcgccaccg actcggccac ctccccgacg tggtcggcga ggtagaagtg    46740
cccgcccggg aaggtccggg tacgccgggg gactaccgag tacggcagcc agcgttgggc    46800
gtcctccacc gtcgtcaacg ggtcggtgtc accgcagagg gtggtgatgc cggcccgcag    46860
cggcggcccg gcctgccagg cgtaggagcg cagcacccgg tggtcggccc gcagcaccgg    46920
cagcgacatg tccaacagcc cctggtcggc caatgcggcc tcgctgaccc cgagcctgcg    46980
catctgctcg acgagtccgt cctcgtcggg caggtcggtg cgccgctcgt ggacccgggg    47040
ggcggtctgc ccggagacga acaaccgcag cggtcgcacc cccggacgag cctccaggcg    47100
acgggcggtc tcgtaggcga ccagggcgcc catgctgtga ccgaacaggg cgaacggaac    47160
ctcgccgacg aggtcgcgca gcacggccgc gacctcgtcg gcgatctccc cggcggtgcc    47220
gagagcccgc tcgtcacgtc ggtcctgccg gcccgggtac tgcaccgccc acacgtcgac    47280
ctccggggcc agtgcccggg cgaggtcgag gtacgagtcg gcggcggctc ccgcgtgcgg    47340
gaagcagtac agccgggccc ggtgtccgtc ggcggacccg aaccgccgca accaggtgtt    47400
catcggtgtc tcatccgttc ggtcgcaccg gcaggtggtc gatgccgcgc agcaggagcg    47460
accgccgcca gacaacctcg tcggagggga agcccagcga cagcttcggg aagcggtcga    47520
acagggcccc cagggcgacc tctccctcca gcttggccag cgggcggccc atgcagtagt    47580
ggatgccgtg cccgaaggtg aggtgtcccc ggctgtccct ggtgacgtcg aaccggtcgg    47640
ggtcggggaa ctgtcccggg tcgcggttgg ccgccccgtt ggcgatcagg acggtgctgt    47700
acgccgggat cgtcaccccg ccgatctcca cctcggcggt ggcgaaccgg gtggtggtct    47760
ccggtggggc ctggtagcgc aggatctcct ccaccgctcc gggcagcagt gccgggtcct    47820
tccggaccag cgcgagctgg tcggggtggg tcagcagcag gtaggtgccg atcccgatga    47880
ggctcaccga cgcctcgaat cccgccagca gcagcaccag cgcgatggag gtgagttcgt    47940
cgcggctgag ccggtcggcg tcgtcgtcct ggacccggat c                         47981
```

<210> SEQ ID NO 2
<211> LENGTH: 48
<212> TYPE: PRT
<213> ORGANISM: Micromonospora megalomicea

<400> SEQUENCE: 2

Met Gly Asp Arg Val Asn Gly His Ala Thr Pro Glu Ser Thr Gln Ser
 1               5                  10                  15

Ala Ile Arg Phe Leu Thr Arg His Gly Gly Pro Pro Thr Ala Thr Asp

```
                 20                  25                  30

Asp Val His Asp Trp Leu Ala His Arg Ala Ala Glu His Arg Leu Glu
             35                  40                  45

<210> SEQ ID NO 3
<211> LENGTH: 377
<212> TYPE: PRT
<213> ORGANISM: Micromonospora megalomicea

<400> SEQUENCE: 3

Met Ala Val Gly Asp Arg Arg Leu Gly Arg Glu Leu Gln Met Ala
 1               5                  10                  15

Arg Gly Leu Tyr Trp Gly Phe Gly Ala Asn Gly Asp Leu Tyr Ser Met
             20                  25                  30

Leu Leu Ser Gly Arg Asp Asp Pro Trp Thr Trp Tyr Glu Arg Leu
             35                  40                  45

Arg Ala Ala Gly Arg Gly Pro Tyr Ala Ser Arg Ala Gly Thr Trp Val
 50                  55                  60

Val Gly Asp His Arg Thr Ala Ala Glu Val Leu Ala Asp Pro Gly Phe
 65                  70                  75                  80

Thr His Gly Pro Pro Asp Ala Ala Arg Trp Met Gln Val Ala His Cys
                 85                  90                  95

Pro Ala Ala Ser Trp Ala Gly Pro Phe Arg Glu Phe Tyr Ala Arg Thr
                100                 105                 110

Glu Asp Ala Ala Ser Val Thr Val Asp Ala Asp Trp Leu Gln Gln Arg
                115                 120                 125

Cys Ala Arg Leu Val Thr Glu Leu Gly Ser Arg Phe Asp Leu Val Asn
130                 135                 140

Asp Phe Ala Arg Glu Val Pro Val Leu Ala Leu Gly Thr Ala Pro Ala
145                 150                 155                 160

Leu Lys Gly Val Asp Pro Asp Arg Leu Arg Ser Trp Thr Ser Ala Thr
                165                 170                 175

Arg Val Cys Leu Asp Ala Gln Val Ser Pro Gln Gln Leu Ala Val Thr
                180                 185                 190

Glu Gln Ala Leu Thr Ala Leu Asp Glu Ile Asp Ala Val Thr Gly Gly
                195                 200                 205

Arg Asp Ala Ala Val Leu Val Gly Val Val Ala Glu Leu Ala Ala Asn
210                 215                 220

Thr Val Gly Asn Ala Val Leu Ala Val Thr Glu Leu Pro Glu Leu Ala
225                 230                 235                 240

Ala Arg Leu Ala Asp Asp Pro Glu Thr Ala Thr Arg Val Val Thr Glu
                245                 250                 255

Val Ser Arg Thr Ser Pro Gly Val His Leu Glu Arg Thr Ala Ala
                260                 265                 270

Ser Asp Arg Arg Val Gly Gly Val Asp Val Pro Thr Gly Gly Glu Val
                275                 280                 285

Thr Val Val Ala Ala Ala Asn Arg Asp Pro Glu Val Phe Thr Asp
                290                 295                 300

Pro Asp Arg Phe Asp Val Asp Arg Gly Gly Asp Ala Glu Ile Leu Ser
305                 310                 315                 320

Ser Arg Pro Gly Ser Pro Arg Thr Asp Leu Asp Ala Leu Val Ala Thr
                325                 330                 335

Leu Ala Thr Ala Ala Leu Arg Ala Ala Ala Pro Val Leu Pro Arg Leu
                340                 345                 350
```

```
Ser Arg Ser Gly Pro Val Ile Arg Arg Arg Ser Pro Val Ala Arg
        355                 360                 365

Gly Leu Ser Arg Cys Pro Val Glu Leu
        370                 375

<210> SEQ ID NO 4
<211> LENGTH: 436
<212> TYPE: PRT
<213> ORGANISM: Micromonospora megalomicea

<400> SEQUENCE: 4

Met Arg Val Val Phe Ser Ser Met Ala Val Asn Ser His Leu Phe Gly
 1               5                  10                  15

Leu Val Pro Leu Ala Ser Ala Phe Gln Ala Ala Gly His Glu Val Arg
            20                  25                  30

Val Val Ala Ser Pro Ala Leu Thr Asp Asp Val Thr Gly Ala Gly Leu
        35                  40                  45

Thr Ala Val Pro Val Gly Asp Asp Val Glu Leu Val Glu Trp His Ala
    50                  55                  60

His Ala Gly Gln Asp Ile Val Glu Tyr Met Arg Thr Leu Asp Trp Val
65                  70                  75                  80

Asp Gln Ser His Thr Thr Met Ser Trp Asp Asp Leu Leu Gly Met Gln
                85                  90                  95

Thr Thr Phe Thr Pro Thr Phe Ala Leu Met Ser Pro Asp Ser Leu
            100                 105                 110

Ile Asp Gly Met Val Glu Phe Cys Arg Ser Trp Arg Pro Asp Trp Ile
            115                 120                 125

Val Trp Glu Pro Leu Thr Phe Ala Ala Pro Ile Ala Ala Arg Val Thr
    130                 135                 140

Gly Thr Pro His Ala Arg Met Leu Trp Gly Pro Asp Val Ala Thr Arg
145                 150                 155                 160

Ala Arg Gln Ser Phe Leu Arg Leu Leu Ala His Gln Glu Val Glu His
                165                 170                 175

Arg Glu Asp Pro Leu Ala Glu Trp Phe Asp Trp Thr Leu Arg Arg Phe
            180                 185                 190

Gly Asp Asp Pro His Leu Ser Phe Asp Glu Glu Leu Val Leu Gly Gln
        195                 200                 205

Trp Thr Val Asp Pro Ile Pro Glu Pro Leu Arg Ile Asp Thr Gly Val
    210                 215                 220

Arg Thr Val Gly Met Arg Tyr Val Pro Tyr Asn Gly Pro Ser Val Val
225                 230                 235                 240

Pro Ala Trp Leu Leu Arg Glu Pro Glu Arg Arg Val Cys Leu Thr
                245                 250                 255

Leu Gly Gly Ser Ser Arg Glu His Gly Ile Gly Gln Val Ser Ile Gly
            260                 265                 270

Glu Met Leu Asp Ala Ile Ala Asp Ile Asp Ala Glu Phe Val Ala Thr
        275                 280                 285

Phe Asp Asp Gln Gln Leu Val Gly Val Gly Ser Val Pro Ala Asn Val
    290                 295                 300

Arg Thr Ala Gly Phe Val Pro Met Asn Val Leu Leu Pro Thr Cys Ala
305                 310                 315                 320

Ala Thr Val His His Gly Gly Thr Gly Ser Trp Leu Thr Ala Ala Ile
                325                 330                 335

His Gly Val Pro Gln Ile Ile Leu Ser Asp Ala Asp Thr Glu Val His
            340                 345                 350
```

```
Ala Lys Gln Leu Gln Asp Leu Gly Ala Gly Leu Ser Leu Pro Val Ala
        355                 360                 365

Gly Met Thr Ala Glu His Leu Arg Gly Ala Ile Glu Arg Val Leu Asp
        370                 375                 380

Glu Pro Ala Tyr Arg Leu Gly Ala Glu Arg Met Arg Asp Gly Met Arg
385                 390                 395                 400

Thr Asp Pro Ser Pro Ala Gln Val Val Gly Ile Cys Gln Asp Leu Ala
                405                 410                 415

Ala Asp Arg Ala Ala Arg Gly Arg Gln Pro Arg Thr Ala Glu Pro
        420                 425                 430

His Leu Pro Arg
        435

<210> SEQ ID NO 5
<211> LENGTH: 390
<212> TYPE: PRT
<213> ORGANISM: Micromonospora megalomicea

<400> SEQUENCE: 5

Met Val Thr Ser Thr Asn Leu Asp Thr Thr Ala Arg Pro Ala Leu Asn
 1               5                  10                  15

Ser Leu Thr Gly Met Arg Phe Val Ala Ala Phe Leu Val Phe Phe Thr
                20                  25                  30

His Val Leu Ser Arg Leu Ile Pro Asn Ser Tyr Val Tyr Ala Asp Gly
            35                  40                  45

Leu Asp Ala Phe Trp Gln Thr Thr Gly Arg Val Gly Val Ser Phe Phe
    50                  55                  60

Phe Ile Leu Ser Gly Phe Val Leu Thr Trp Ser Ala Arg Ala Ser Asp
65                  70                  75                  80

Ser Val Trp Ser Phe Trp Arg Arg Val Cys Lys Leu Phe Pro Asn
                85                  90                  95

His Leu Val Thr Ala Phe Ala Ala Val Val Leu Phe Leu Val Thr Gly
            100                 105                 110

Gln Ala Val Ser Gly Glu Ala Leu Ile Pro Asn Leu Leu Ile His
        115                 120                 125

Ala Trp Phe Pro Ala Leu Glu Ile Ser Phe Gly Ile Asn Pro Val Ser
        130                 135                 140

Trp Ser Leu Ala Cys Glu Ala Phe Phe Tyr Leu Cys Phe Pro Leu Phe
145                 150                 155                 160

Leu Phe Trp Ile Ser Gly Ile Arg Pro Glu Arg Leu Trp Ala Trp Ala
                165                 170                 175

Ala Val Val Phe Ala Ala Ile Trp Ala Val Pro Val Ala Asp Leu
        180                 185                 190

Leu Leu Pro Ser Ser Pro Leu Ile Pro Gly Leu Glu Tyr Ser Ala
        195                 200                 205

Ile Gln Asp Trp Phe Leu Tyr Thr Phe Pro Ala Thr Arg Ser Leu Glu
    210                 215                 220

Phe Ile Leu Gly Ile Ile Leu Ala Arg Ile Leu Ile Thr Gly Arg Trp
225                 230                 235                 240

Ile Asn Val Gly Leu Leu Pro Ala Val Leu Leu Phe Pro Val Phe Phe
                245                 250                 255

Val Ala Ser Leu Phe Leu Pro Gly Val Tyr Ala Ile Ser Ser Ser Met
        260                 265                 270

Met Ile Leu Pro Leu Val Leu Ile Ile Ala Ser Gly Ala Thr Ala Asp
```

```
                    275                 280                 285
Leu Gln Gln Lys Arg Thr Phe Met Arg Asn Arg Val Met Trp Leu
        290                 295                 300

Gly Asp Val Ser Phe Ala Leu Tyr Met Val His Phe Leu Val Ile Val
305                 310                 315                 320

Tyr Gly Ala Asp Leu Leu Gly Phe Ser Gln Thr Glu Asp Ala Pro Leu
                325                 330                 335

Gly Leu Ala Leu Phe Met Ile Ile Pro Phe Leu Ala Val Ser Leu Val
                340                 345                 350

Leu Ser Trp Leu Leu Tyr Arg Phe Val Glu Leu Pro Val Met Arg Asn
                355                 360                 365

Trp Ala Arg Pro Ala Ser Ala Arg Arg Lys Pro Ala Thr Glu Pro Glu
        370                 375                 380

Gln Thr Pro Ser Arg Arg
385                 390

<210> SEQ ID NO 6
<211> LENGTH: 374
<212> TYPE: PRT
<213> ORGANISM: Micromonospora megalomicea

<400> SEQUENCE: 6

Met Thr Thr Tyr Val Trp Ser Tyr Leu Leu Glu Tyr Glu Arg Glu Arg
1               5                   10                  15

Ala Asp Ile Leu Asp Ala Val Gln Lys Val Phe Ala Ser Gly Ser Leu
                20                  25                  30

Ile Leu Gly Gln Ser Val Glu Asn Phe Glu Thr Glu Tyr Ala Arg Tyr
            35                  40                  45

His Gly Ile Ala His Cys Val Gly Val Asp Asn Gly Thr Asn Ala Val
        50                  55                  60

Lys Leu Ala Leu Glu Ser Val Gly Val Gly Arg Asp Asp Glu Val Val
65                  70                  75                  80

Thr Val Ser Asn Thr Ala Ala Pro Thr Val Leu Ala Ile Asp Glu Ile
                85                  90                  95

Gly Ala Arg Pro Val Phe Val Asp Val Arg Asp Glu Asp Tyr Leu Met
            100                 105                 110

Asp Thr Asp Leu Val Glu Ala Ala Val Thr Pro Arg Thr Lys Ala Ile
        115                 120                 125

Val Pro Val His Leu Tyr Gly Gln Cys Val Asp Met Thr Ala Leu Arg
    130                 135                 140

Glu Leu Ala Asp Arg Arg Gly Leu Lys Leu Val Glu Asp Cys Ala Gln
145                 150                 155                 160

Ala His Gly Ala Arg Arg Asp Gly Arg Leu Ala Gly Thr Met Ser Asp
                165                 170                 175

Ala Ala Ala Phe Ser Phe Tyr Pro Thr Lys Val Leu Gly Ala Tyr Gly
                180                 185                 190

Asp Gly Gly Ala Val Val Thr Asn Asp Asp Glu Thr Ala Arg Ala Leu
            195                 200                 205

Arg Arg Leu Arg Tyr Tyr Gly Met Glu Glu Val Tyr Tyr Val Thr Arg
        210                 215                 220

Thr Pro Gly His Asn Ser Arg Leu Asp Glu Val Gln Ala Glu Ile Leu
225                 230                 235                 240

Arg Arg Lys Leu Thr Arg Leu Asp Ala Tyr Val Ala Gly Arg Arg Ala
                245                 250                 255
```

-continued

```
Val Ala Gln Arg Tyr Val Asp Gly Leu Ala Asp Leu Gln Asp Ser His
            260                 265                 270

Gly Leu Glu Leu Pro Val Val Thr Asp Gly Asn Glu His Val Phe Tyr
            275                 280                 285

Val Tyr Val Val Arg His Pro Arg Arg Asp Glu Ile Ile Lys Arg Leu
        290                 295                 300

Arg Asp Gly Tyr Asp Ile Ser Leu Asn Ile Ser Tyr Pro Trp Pro Val
305                 310                 315                 320

His Thr Met Thr Gly Phe Ala His Leu Gly Val Ala Ser Gly Ser Leu
                    325                 330                 335

Pro Val Thr Glu Arg Leu Ala Gly Glu Ile Phe Ser Leu Pro Met Tyr
            340                 345                 350

Pro Ser Leu Pro His Asp Leu Gln Asp Arg Val Ile Glu Ala Val Arg
            355                 360                 365

Glu Val Ile Thr Gly Leu
            370

<210> SEQ ID NO 7
<211> LENGTH: 257
<212> TYPE: PRT
<213> ORGANISM: Micromonospora megalomicea

<400> SEQUENCE: 7

Met Pro Asn Ser His Ser Thr Thr Ser Ser Thr Asp Val Ala Pro Tyr
1               5                   10                  15

Glu Arg Ala Asp Ile Tyr His Asp Phe Tyr His Gly Arg Gly Lys Gly
                20                  25                  30

Tyr Arg Ala Glu Ala Asp Ala Leu Val Glu Val Ala Arg Lys His Thr
            35                  40                  45

Pro Gln Ala Ala Thr Leu Leu Asp Val Ala Cys Gly Thr Gly Ser His
        50                  55                  60

Leu Val Glu Leu Ala Asp Ser Phe Arg Glu Val Val Gly Val Asp Leu
65                  70                  75                  80

Ser Ala Ala Met Leu Ala Thr Ala Ala Arg Asn Asp Pro Gly Arg Glu
                85                  90                  95

Leu His Gln Gly Asp Met Arg Asp Phe Ser Leu Asp Arg Arg Phe Asp
                100                 105                 110

Val Val Thr Cys Met Phe Ser Ser Thr Gly Tyr Leu Val Asp Glu Ala
            115                 120                 125

Glu Leu Asp Arg Ala Val Ala Asn Leu Ala Gly His Leu Ala Pro Gly
130                 135                 140

Gly Thr Leu Val Val Glu Pro Trp Trp Phe Pro Glu Thr Phe Arg Pro
145                 150                 155                 160

Gly Trp Val Gly Ala Asp Leu Val Thr Ser Gly Asp Arg Arg Ile Ser
                165                 170                 175

Arg Met Ser His Thr Val Pro Ala Gly Leu Pro Asp Arg Thr Ala Ser
                180                 185                 190

Arg Met Thr Ile His Tyr Thr Val Gly Ser Pro Glu Ala Gly Ile Glu
            195                 200                 205

His Phe Thr Glu Val His Val Met Thr Leu Phe Ala Arg Ala Ala Tyr
        210                 215                 220

Glu Gln Ala Phe Gln Arg Ala Gly Leu Ser Cys Ser Tyr Val Gly His
225                 230                 235                 240

Asp Leu Phe Ser Pro Gly Leu Phe Val Gly Val Ala Ala Glu Pro Gly
                245                 250                 255
```

Arg

<210> SEQ ID NO 8
<211> LENGTH: 201
<212> TYPE: PRT
<213> ORGANISM: Micromonospora megalomicea

<400> SEQUENCE: 8

```
Met Arg Val Glu Glu Leu Gly Ile Glu Gly Val Phe Thr Phe Thr Pro
 1               5                  10                  15
Gln Thr Phe Ala Asp Glu Arg Gly Val Phe Gly Thr Ala Tyr Gln Glu
                20                  25                  30
Asp Val Phe Val Ala Ala Leu Gly Arg Pro Leu Phe Pro Val Ala Gln
            35                  40                  45
Val Ser Thr Thr Arg Ser Arg Arg Gly Val Val Arg Gly Val His Phe
        50                  55                  60
Thr Thr Met Pro Gly Ser Met Ala Lys Tyr Val Tyr Cys Ala Arg Gly
 65                  70                  75                  80
Arg Ala Met Asp Phe Ala Val Asp Ile Arg Pro Gly Ser Pro Thr Phe
                85                  90                  95
Gly Arg Ala Glu Pro Val Glu Leu Ser Ala Glu Ser Met Val Gly Leu
            100                 105                 110
Tyr Leu Pro Val Gly Met Gly His Leu Phe Val Ser Leu Glu Asp Asp
        115                 120                 125
Thr Thr Leu Val Tyr Leu Met Ser Ala Gly Tyr Val Pro Asp Lys Glu
130                 135                 140
Arg Ala Val His Pro Leu Asp Pro Glu Leu Ala Leu Pro Ile Pro Ala
145                 150                 155                 160
Asp Leu Asp Leu Val Met Ser Glu Arg Asp Arg Val Ala Pro Thr Leu
                165                 170                 175
Arg Glu Ala Arg Asp Gln Gly Ile Leu Pro Asp Tyr Ala Ala Cys Arg
            180                 185                 190
Ala Ala Ala His Arg Val Val Arg Thr
        195                 200
```

<210> SEQ ID NO 9
<211> LENGTH: 328
<212> TYPE: PRT
<213> ORGANISM: Micromonospora megalomicea

<400> SEQUENCE: 9

```
Met Val Val Leu Gly Ala Ser Gly Phe Leu Gly Ser Ala Val Thr His
 1               5                  10                  15
Ala Leu Ala Asp Leu Pro Val Arg Val Arg Leu Val Ala Arg Arg Glu
                20                  25                  30
Val Val Val Pro Ser Gly Ala Val Ala Asp Tyr Glu Thr His Arg Val
            35                  40                  45
Asp Leu Thr Glu Pro Gly Ala Leu Ala Glu Val Ala Asp Ala Arg
        50                  55                  60
Ala Val Phe Pro Phe Ala Ala Gln Ile Arg Gly Thr Ser Gly Trp Arg
 65                  70                  75                  80
Ile Ser Glu Asp Asp Val Val Ala Glu Arg Thr Asn Val Gly Leu Val
                85                  90                  95
Arg Asp Leu Ile Ala Val Leu Ser Arg Ser Pro His Ala Pro Val Val
            100                 105                 110
```

```
Val Phe Pro Gly Ser Asn Thr Gln Val Gly Arg Val Thr Ala Gly Arg
            115                 120                 125

Val Ile Asp Gly Ser Glu Gln Asp His Pro Glu Gly Val Tyr Asp Arg
        130                 135                 140

Gln Lys His Thr Gly Glu Gln Leu Leu Lys Glu Ala Thr Ala Ala Gly
145                 150                 155                 160

Ala Ile Arg Ala Thr Ser Leu Arg Leu Pro Pro Val Phe Gly Val Pro
                165                 170                 175

Ala Ala Gly Thr Ala Asp Asp Arg Gly Val Val Ser Thr Met Ile Arg
            180                 185                 190

Arg Ala Leu Thr Gly Gln Pro Leu Thr Met Trp His Asp Gly Thr Val
        195                 200                 205

Arg Arg Glu Leu Leu Tyr Val Thr Asp Ala Ala Arg Ala Phe Val Thr
    210                 215                 220

Ala Leu Asp His Ala Asp Ala Leu Ala Gly Arg His Phe Leu Leu Gly
225                 230                 235                 240

Thr Gly Arg Ser Trp Pro Leu Gly Glu Val Phe Gln Ala Val Ser Arg
                245                 250                 255

Ser Val Ala Arg His Thr Gly Glu Asp Pro Val Pro Val Val Ser Val
            260                 265                 270

Pro Pro Pro Ala His Met Asp Pro Ser Asp Leu Arg Ser Val Glu Val
        275                 280                 285

Asp Pro Ala Arg Phe Thr Ala Val Thr Gly Trp Arg Ala Thr Val Thr
    290                 295                 300

Met Ala Glu Ala Val Asp Arg Thr Val Ala Ala Leu Ala Pro Arg Arg
305                 310                 315                 320

Ala Ala Ala Pro Ser Glu Pro Ser
                325

<210> SEQ ID NO 10
<211> LENGTH: 330
<212> TYPE: PRT
<213> ORGANISM: Micromonospora megalomicea

<400> SEQUENCE: 10

Met Gly Thr Thr Gly Ala Gly Ser Ala Arg Val Arg Val Gly Arg Ser
1               5                   10                  15

Ala Leu His Thr Ser Arg Leu Trp Leu Gly Thr Val Asn Phe Ser Gly
            20                  25                  30

Arg Val Thr Asp Asp Asp Ala Leu Arg Leu Met Asp His Ala Leu Glu
        35                  40                  45

Arg Gly Val Asn Cys Ile Asp Thr Ala Asp Ile Tyr Gly Trp Arg Leu
    50                  55                  60

Tyr Lys Gly His Thr Glu Glu Leu Val Gly Arg Trp Phe Ala Gln Gly
65                  70                  75                  80

Gly Gly Arg Arg Glu Glu Thr Val Leu Ala Thr Lys Val Gly Ser Glu
                85                  90                  95

Met Ser Glu Arg Val Asn Asp Gly Leu Ser Ala Arg His Ile Val
            100                 105                 110

Ala Ala Cys Glu Asn Ser Leu Arg Arg Leu Gly Val Asp His Ile Asp
        115                 120                 125

Ile Tyr Gln Thr His His Ile Asp Arg Ala Ala Pro Trp Asp Glu Val
    130                 135                 140

Trp Gln Ala Ala Glu His Leu Val Gly Ser Gly Lys Val Gly Tyr Val
145                 150                 155                 160
```

-continued

```
Gly Ser Ser Asn Leu Ala Gly Trp His Ile Ala Ala Gln Glu Ser
                165                 170                 175

Ala Ala Arg Arg Asn Leu Leu Gly Met Ile Ser His Gln Cys Leu Tyr
            180                 185                 190

Asn Leu Ala Val Arg His Pro Glu Leu Asp Val Leu Pro Ala Ala Gln
            195                 200                 205

Ala Tyr Gly Val Gly Val Phe Ala Trp Ser Pro Leu His Gly Gly Leu
    210                 215                 220

Leu Ser Gly Val Leu Glu Lys Leu Ala Ala Gly Thr Ala Val Lys Ser
225                 230                 235                 240

Ala Gln Gly Arg Ala Gln Val Leu Leu Pro Ala Val Arg Pro Leu Val
                245                 250                 255

Glu Ala Tyr Glu Asp Tyr Cys Arg Arg Leu Gly Ala Asp Pro Ala Glu
                260                 265                 270

Val Gly Leu Ala Trp Val Leu Ser Arg Pro Gly Ile Leu Gly Ala Val
            275                 280                 285

Ile Gly Pro Arg Thr Pro Glu Gln Leu Asp Ser Ala Leu Arg Ala Ala
    290                 295                 300

Glu Leu Thr Leu Gly Glu Glu Leu Arg Glu Leu Glu Ala Ile Phe
305                 310                 315                 320

Pro Ala Pro Ala Val Asp Gly Pro Val Pro
                325                 330

<210> SEQ ID NO 11
<211> LENGTH: 417
<212> TYPE: PRT
<213> ORGANISM: Micromonospora megalomicea

<400> SEQUENCE: 11

Met Arg Val Leu Leu Thr Ser Phe Ala His Arg Thr His Phe Gln Gly
 1               5                  10                  15

Leu Val Pro Leu Ala Trp Ala Leu His Thr Ala Gly His Asp Val Arg
            20                  25                  30

Val Ala Ser Gln Pro Glu Leu Thr Asp Val Val Gly Ala Gly Leu
        35                  40                  45

Thr Ser Val Pro Leu Gly Ser Asp His Arg Leu Phe Asp Ile Ser Pro
 50                  55                  60

Glu Ala Ala Ala Gln Val His Arg Tyr Thr Thr Asp Leu Asp Phe Ala
65                  70                  75                  80

Arg Arg Gly Pro Glu Leu Arg Ser Trp Glu Phe Leu His Gly Ile Glu
                85                  90                  95

Glu Ala Thr Ser Arg Phe Val Phe Pro Val Val Asn Asn Asp Ser Phe
            100                 105                 110

Val Asp Glu Leu Val Glu Phe Ala Met Asp Trp Arg Pro Asp Leu Val
        115                 120                 125

Leu Trp Glu Pro Phe Thr Phe Ala Gly Ala Val Ala Ala Lys Ala Cys
130                 135                 140

Gly Ala Ala His Ala Arg Leu Leu Trp Gly Ser Asp Leu Thr Gly Tyr
145                 150                 155                 160

Phe Arg Ser Arg Ser Gln Asp Leu Arg Gly Gln Arg Pro Ala Asp Asp
                165                 170                 175

Arg Pro Asp Pro Leu Gly Gly Trp Leu Thr Glu Val Ala Gly Arg Phe
            180                 185                 190

Gly Leu Asp Tyr Ser Glu Asp Leu Ala Val Gly Gln Trp Ser Val Asp
```

-continued

```
            195                 200                 205
Gln Leu Pro Glu Ser Phe Arg Leu Glu Thr Gly Leu Glu Ser Val His
        210                 215                 220
Thr Arg Thr Leu Pro Tyr Asn Gly Ser Ser Val Val Pro Gln Trp Leu
225                 230                 235                 240
Arg Thr Ser Asp Gly Val Arg Val Cys Phe Thr Gly Gly Tyr Ser
                245                 250                 255
Ala Leu Gly Ile Thr Ser Asn Pro Gln Glu Phe Leu Arg Thr Leu Ala
            260                 265                 270
Thr Leu Ala Arg Phe Asp Gly Glu Ile Val Val Thr Arg Ser Gly Leu
        275                 280                 285
Asp Pro Ala Ser Val Pro Asp Asn Val Arg Leu Val Asp Phe Val Pro
        290                 295                 300
Met Asn Ile Leu Leu Pro Gly Cys Ala Ala Val Ile His His Gly Gly
305                 310                 315                 320
Ala Gly Ser Trp Ala Thr Ala Leu His His Gly Val Pro Gln Ile Ser
                325                 330                 335
Val Ala His Glu Trp Asp Cys Val Leu Arg Gly Gln Arg Thr Ala Glu
            340                 345                 350
Leu Gly Ala Gly Val Phe Leu Arg Pro Asp Glu Val Asp Ala Asp Thr
        355                 360                 365
Leu Trp Gln Ala Leu Ala Thr Val Val Glu Asp Arg Ser His Ala Glu
        370                 375                 380
Asn Ala Glu Lys Leu Arg Gln Glu Ala Leu Ala Ala Pro Thr Pro Ala
385                 390                 395                 400
Glu Val Val Pro Val Leu Glu Ala Leu Ala His Gln His Arg Ala Asp
                405                 410                 415
Arg

<210> SEQ ID NO 12
<211> LENGTH: 313
<212> TYPE: PRT
<213> ORGANISM: Micromonospora megalomicea

<400> SEQUENCE: 12

Met Thr Arg His Val Thr Leu Leu Gly Val Ser Gly Phe Val Gly Ser
1               5                   10                  15
Ala Leu Leu Arg Glu Phe Thr Thr His Pro Leu Arg Leu Arg Ala Val
            20                  25                  30
Ala Arg Thr Gly Ser Arg Asp Gln Pro Pro Gly Ser Ala Gly Ile Glu
        35                  40                  45
His Leu Arg Val Asp Leu Leu Glu Pro Gly Arg Val Ala Gln Val Val
    50                  55                  60
Ala Asp Thr Asp Val Val Val His Leu Val Ala Tyr Ala Ala Gly Gly
65                  70                  75                  80
Ser Thr Trp Arg Ser Ala Ala Thr Val Pro Glu Ala Glu Arg Val Asn
                85                  90                  95
Ala Gly Ile Met Arg Asp Leu Val Ala Leu Arg Ala Arg Pro Gly
            100                 105                 110
Pro Ala Pro Val Leu Leu Phe Ala Ser Thr Thr Gln Ala Ala Asn Pro
        115                 120                 125
Ala Ala Pro Ser Arg Tyr Ala Gln His Lys Ile Glu Ala Glu Arg Ile
    130                 135                 140
Leu Arg Gln Ala Thr Glu Asp Gly Val Val Asp Gly Val Ile Leu Arg
```

```
            145                 150                 155                 160
Leu Pro Ala Ile Tyr Gly His Ser Gly Pro Ser Gly Gln Thr Gly Arg
                165                 170                 175

Gly Val Val Thr Ala Met Ile Arg Arg Ala Leu Ala Gly Glu Pro Ile
            180                 185                 190

Thr Met Trp His Glu Gly Ser Val Arg Arg Asn Leu Leu His Val Glu
        195                 200                 205

Asp Val Ala Thr Ala Phe Thr Ala Ala Leu His Asn His Glu Ala Leu
    210                 215                 220

Val Gly Asp Val Trp Thr Pro Ser Ala Asp Glu Ala Arg Pro Leu Gly
225                 230                 235                 240

Glu Ile Phe Glu Thr Val Ala Ala Ser Val Ala Arg Gln Thr Gly Asn
                245                 250                 255

Pro Ala Val Pro Val Val Ser Val Pro Pro Glu Asn Ala Glu Ala
                260                 265                 270

Asn Asp Phe Arg Ser Asp Asp Phe Asp Ser Thr Glu Phe Arg Thr Leu
            275                 280                 285

Thr Gly Trp His Pro Arg Val Pro Leu Ala Glu Gly Ile Asp Arg Thr
        290                 295                 300

Val Ala Ala Leu Ile Ser Thr Lys Glu
305                 310

<210> SEQ ID NO 13
<211> LENGTH: 3546
<212> TYPE: PRT
<213> ORGANISM: Micromonospora megalomicea

<400> SEQUENCE: 13

Met Val Asp Val Pro Asp Leu Leu Gly Thr Arg Thr Pro His Pro Gly
 1               5                  10                  15

Pro Leu Pro Phe Pro Trp Pro Leu Cys Gly His Asn Glu Pro Glu Leu
            20                  25                  30

Arg Ala Arg Ala Arg Gln Leu His Ala Tyr Leu Glu Gly Ile Ser Glu
        35                  40                  45

Asp Asp Val Val Ala Val Gly Ala Ala Leu Ala Arg Glu Thr Arg Ala
    50                  55                  60

Gln Asp Gly Pro His Arg Ala Val Val Ala Ser Ser Val Thr Glu
65                  70                  75                  80

Leu Thr Ala Ala Leu Ala Ala Leu Ala Gln Gly Arg Pro His Pro Ser
                85                  90                  95

Val Val Arg Gly Val Ala Arg Pro Thr Ala Pro Val Val Phe Val Leu
            100                 105                 110

Pro Gly Gln Gly Ala Gln Trp Pro Gly Met Ala Thr Arg Leu Leu Ala
        115                 120                 125

Glu Ser Pro Val Phe Ala Ala Ala Met Arg Ala Cys Glu Arg Ala Phe
    130                 135                 140

Asp Glu Val Thr Asp Trp Ser Leu Thr Glu Val Leu Asp Ser Pro Glu
145                 150                 155                 160

His Leu Arg Arg Val Glu Val Val Gln Pro Ala Leu Phe Ala Val Gln
                165                 170                 175

Thr Ser Leu Ala Ala Leu Trp Arg Ser Phe Gly Val Arg Pro Asp Ala
            180                 185                 190

Val Leu Gly His Ser Ile Gly Glu Leu Ala Ala Ala Glu Val Cys Gly
        195                 200                 205
```

-continued

```
Ala Val Asp Val Glu Ala Ala Arg Ala Ala Leu Trp Ser Arg
    210                 215                 220

Glu Met Val Pro Leu Val Gly Arg Gly Asp Met Ala Ala Val Ala Leu
225                 230                 235                 240

Ser Pro Ala Glu Leu Ala Ala Arg Val Glu Arg Trp Asp Asp Val
                245                 250                 255

Val Pro Ala Gly Val Asn Gly Pro Arg Ser Val Leu Leu Thr Gly Ala
            260                 265                 270

Pro Glu Pro Ile Ala Arg Arg Val Ala Glu Leu Ala Ala Gln Gly Val
            275                 280                 285

Arg Ala Gln Val Val Asn Val Ser Met Ala Ala His Ser Ala Gln Val
    290                 295                 300

Asp Ala Val Ala Glu Gly Met Arg Ser Ala Leu Thr Trp Phe Ala Pro
305                 310                 315                 320

Gly Asp Ser Asp Val Pro Tyr Tyr Ala Gly Leu Thr Gly Gly Arg Leu
                325                 330                 335

Asp Thr Arg Glu Leu Gly Ala Asp His Trp Pro Arg Ser Phe Arg Leu
            340                 345                 350

Pro Val Arg Phe Asp Glu Ala Thr Arg Ala Val Leu Glu Leu Gln Pro
    355                 360                 365

Gly Thr Phe Ile Glu Ser Ser Pro His Pro Val Leu Ala Ala Ser Leu
    370                 375                 380

Gln Gln Thr Leu Asp Glu Val Gly Ser Pro Ala Ala Ile Val Pro Thr
385                 390                 395                 400

Leu Gln Arg Asp Gln Gly Gly Leu Arg Arg Phe Leu Leu Ala Val Ala
                405                 410                 415

Gln Ala Tyr Thr Gly Gly Val Thr Val Asp Trp Thr Ala Ala Tyr Pro
            420                 425                 430

Gly Val Thr Pro Gly His Leu Pro Ser Ala Val Ala Val Glu Thr Asp
            435                 440                 445

Glu Gly Pro Ser Thr Glu Phe Asp Trp Ala Ala Pro Asp His Val Leu
450                 455                 460

Arg Ala Arg Leu Leu Glu Ile Val Gly Ala Glu Thr Ala Ala Leu Ala
465                 470                 475                 480

Gly Arg Glu Val Asp Ala Arg Ala Thr Phe Arg Glu Leu Gly Leu Asp
                485                 490                 495

Ser Val Leu Ala Val Gln Leu Arg Thr Arg Leu Ala Thr Ala Thr Gly
                500                 505                 510

Arg Asp Leu His Ile Ala Met Leu Tyr Asp His Pro Thr Pro His Ala
            515                 520                 525

Leu Thr Glu Ala Leu Leu Arg Gly Pro Gln Glu Glu Pro Gly Arg Gly
    530                 535                 540

Glu Glu Thr Ala His Pro Thr Glu Ala Glu Pro Asp Glu Pro Val Ala
545                 550                 555                 560

Val Val Ala Met Ala Cys Arg Leu Pro Gly Gly Val Thr Ser Pro Glu
                565                 570                 575

Glu Phe Trp Glu Leu Leu Ala Glu Gly Arg Asp Ala Val Gly Gly Leu
            580                 585                 590

Pro Thr Asp Arg Gly Trp Asp Leu Asp Ser Leu Phe His Pro Asp Pro
            595                 600                 605

Thr Arg Ser Gly Thr Ala His Gln Arg Ala Gly Gly Phe Leu Thr Gly
    610                 615                 620

Ala Thr Ser Phe Asp Ala Ala Phe Phe Gly Leu Ser Pro Arg Glu Ala
```

-continued

```
625             630             635             640
Leu Ala Val Glu Pro Gln Gln Arg Ile Thr Leu Glu Leu Ser Trp Glu
            645                 650             655
Val Leu Glu Arg Ala Gly Ile Pro Pro Thr Ser Leu Arg Thr Ser Arg
            660                 665             670
Thr Gly Val Phe Val Gly Leu Ile Pro Gln Glu Tyr Gly Pro Arg Leu
            675                 680             685
Ala Glu Gly Gly Glu Gly Val Glu Gly Tyr Leu Met Thr Gly Thr Thr
            690                 695             700
Thr Ser Val Ala Ser Gly Arg Val Ala Tyr Thr Leu Gly Leu Glu Gly
705             710             715                 720
Pro Ala Ile Ser Val Asp Thr Ala Cys Ser Ser Leu Val Ala Val
                725                 730             735
His Leu Ala Cys Gln Ser Leu Arg Arg Gly Glu Ser Thr Met Ala Leu
            740                 745             750
Ala Gly Gly Val Thr Val Met Pro Thr Pro Gly Met Leu Val Asp Phe
            755                 760             765
Ser Arg Met Asn Ser Leu Ala Pro Asp Gly Arg Ser Lys Ala Phe Ser
770             775                 780
Ala Ala Ala Asp Gly Phe Gly Met Ala Glu Gly Ala Gly Met Leu Leu
785             790             795             800
Leu Glu Arg Leu Ser Asp Ala Arg Arg His Gly His Pro Val Leu Ala
            805             810             815
Val Ile Arg Gly Thr Ala Val Asn Ser Asp Gly Ala Ser Asn Gly Leu
            820             825             830
Ser Ala Pro Asn Gly Arg Ala Gln Val Arg Val Ile Arg Gln Ala Leu
            835             840             845
Ala Glu Ser Gly Leu Thr Pro His Thr Val Asp Val Val Glu Thr His
850             855             860
Gly Thr Gly Thr Arg Leu Gly Asp Pro Ile Glu Ala Arg Ala Leu Ser
865             870             875             880
Asp Ala Tyr Gly Gly Asp Arg Glu His Pro Leu Arg Ile Gly Ser Val
            885             890             895
Lys Ser Asn Ile Gly His Thr Gln Ala Ala Ala Gly Val Ala Gly Leu
            900             905             910
Ile Lys Leu Val Leu Ala Met Gln Ala Gly Val Leu Pro Arg Thr Leu
            915             920             925
His Ala Asp Glu Pro Ser Pro Glu Ile Asp Trp Ser Ser Gly Ala Ile
            930             935             940
Ser Leu Leu Gln Glu Pro Ala Ala Trp Pro Ala Gly Glu Arg Pro Arg
945             950             955             960
Arg Ala Gly Val Ser Ser Phe Gly Ile Ser Gly Thr Asn Ala His Ala
                965             970             975
Ile Ile Glu Glu Ala Pro Pro Thr Gly Asp Asp Thr Arg Pro Asp Arg
            980             985             990
Met Gly Pro Val Val Pro Trp Val Leu Ser Ala Ser Thr Gly Glu Ala
            995                 1000            1005
Leu Arg Ala Arg Ala Ala Arg Leu Ala Gly His Leu Arg Glu His Pro
            1010            1015            1020
Asp Gln Asp Leu Asp Asp Val Ala Tyr Ser Leu Ala Thr Gly Arg Ala
1025            1030            1035            1040
Ala Leu Ala Tyr Arg Ser Gly Phe Val Pro Ala Asp Ala Ser Thr Ala
                1045            1050            1055
```

-continued

Leu Arg Ile Leu Asp Glu Leu Ala Ala Gly Ser Gly Asp Ala Val
         1060            1065            1070

Thr Gly Thr Ala Arg Ala Pro Gln Arg Val Val Phe Val Phe Pro Gly
     1075            1080            1085

Gln Gly Trp Gln Trp Ala Gly Met Ala Val Asp Leu Leu Asp Gly Asp
    1090           1095            1100

Pro Val Phe Ala Ser Val Leu Arg Glu Cys Ala Asp Ala Leu Glu Pro
1105            1110            1115            1120

Tyr Leu Asp Phe Glu Ile Val Pro Phe Leu Arg Ala Glu Ala Gln Arg
             1125            1130            1135

Arg Thr Pro Asp His Thr Leu Ser Thr Asp Arg Val Asp Val Val Gln
         1140            1145            1150

Pro Val Leu Phe Ala Val Met Val Ser Leu Ala Ala Arg Trp Arg Ala
         1155            1160            1165

Tyr Gly Val Glu Pro Ala Ala Val Ile Gly His Ser Gln Gly Glu Ile
         1170            1175            1180

Ala Ala Ala Cys Val Ala Gly Ala Leu Ser Leu Asp Asp Ala Ala Arg
1185            1190            1195            1200

Ala Val Ala Leu Arg Ser Arg Val Ile Ala Thr Met Pro Gly Asn Gly
             1205            1210            1215

Ala Met Ala Ser Ile Ala Ala Ser Val Asp Glu Val Ala Ala Arg Ile
             1220            1225            1230

Asp Gly Arg Val Glu Ile Ala Ala Val Asn Gly Pro Arg Ala Val Val
             1235            1240            1245

Val Ser Gly Asp Arg Asp Asp Leu Asp Arg Leu Val Ala Ser Cys Thr
1250            1255            1260

Val Glu Gly Val Arg Ala Lys Arg Leu Pro Val Asp Tyr Ala Ser His
1265            1270            1275            1280

Ser Ser His Val Glu Ala Val Arg Asp Ala Leu His Ala Glu Leu Gly
             1285            1290            1295

Glu Phe Arg Pro Leu Pro Gly Phe Val Pro Phe Tyr Ser Thr Val Thr
             1300            1305            1310

Gly Arg Trp Val Glu Pro Ala Glu Leu Asp Ala Gly Tyr Trp Phe Arg
             1315            1320            1325

Asn Leu Arg His Arg Val Arg Phe Ala Asp Ala Val Arg Ser Leu Ala
    1330            1335            1340

Asp Gln Gly Tyr Thr Thr Phe Leu Glu Val Ser Ala His Pro Val Leu
1345            1350            1355            1360

Thr Thr Ala Ile Glu Glu Ile Gly Glu Asp Arg Gly Gly Asp Leu Val
             1365            1370            1375

Ala Val His Ser Leu Arg Arg Gly Ala Gly Pro Val Asp Phe Gly
             1380            1385            1390

Ser Ala Leu Ala Arg Ala Phe Val Ala Gly Val Ala Val Asp Trp Glu
         1395            1400            1405

Ser Ala Tyr Gln Gly Ala Gly Ala Arg Arg Val Pro Leu Pro Thr Tyr
         1410            1415            1420

Pro Phe Gln Arg Glu Arg Phe Trp Leu Glu Pro Asn Pro Ala Arg Arg
1425            1430            1435            1440

Val Ala Asp Ser Asp Asp Val Ser Ser Leu Arg Tyr Arg Ile Glu Trp
             1445            1450            1455

His Pro Thr Asp Pro Gly Glu Pro Gly Arg Leu Asp Gly Thr Trp Leu
         1460            1465            1470

-continued

```
Leu Ala Thr Tyr Pro Gly Arg Ala Asp Asp Arg Val Glu Ala Ala Arg
            1475                1480                1485

Gln Ala Leu Glu Ser Ala Gly Ala Arg Val Glu Asp Leu Val Val Glu
        1490                1495                1500

Pro Arg Thr Gly Arg Val Asp Leu Val Arg Arg Leu Asp Ala Val Gly
1505                1510                1515                1520

Pro Val Ala Gly Val Leu Cys Leu Phe Ala Val Ala Glu Pro Ala Ala
                1525                1530                1535

Glu His Ser Pro Leu Ala Val Thr Ser Leu Ser Asp Thr Leu Asp Leu
            1540                1545                1550

Thr Gln Ala Val Ala Gly Ser Gly Arg Glu Cys Pro Ile Trp Val Val
        1555                1560                1565

Thr Glu Asn Ala Val Ala Val Gly Pro Phe Glu Arg Leu Arg Asp Pro
    1570                1575                1580

Ala His Gly Ala Leu Trp Ala Leu Gly Arg Val Val Ala Leu Glu Asn
1585                1590                1595                1600

Pro Ala Val Trp Gly Gly Leu Val Asp Val Pro Ser Gly Ser Val Ala
                1605                1610                1615

Glu Leu Ser Arg His Leu Gly Thr Thr Leu Ser Gly Ala Gly Glu Asp
            1620                1625                1630

Gln Val Ala Leu Arg Pro Asp Gly Thr Tyr Ala Arg Arg Trp Cys Arg
        1635                1640                1645

Ala Gly Ala Gly Gly Thr Gly Arg Trp Gln Pro Arg Gly Thr Val Leu
    1650                1655                1660

Val Thr Gly Gly Thr Gly Gly Val Gly Arg His Val Ala Arg Trp Leu
1665                1670                1675                1680

Ala Arg Gln Gly Thr Pro Cys Leu Val Leu Ala Ser Arg Arg Gly Pro
                1685                1690                1695

Asp Ala Asp Gly Val Glu Glu Leu Leu Thr Glu Leu Ala Asp Leu Gly
            1700                1705                1710

Thr Arg Ala Thr Val Thr Ala Cys Asp Val Thr Asp Arg Glu Gln Leu
        1715                1720                1725

Arg Ala Leu Leu Ala Thr Val Asp Asp Glu His Pro Leu Ser Ala Val
    1730                1735                1740

Phe His Val Ala Ala Thr Leu Asp Asp Gly Thr Val Glu Thr Leu Thr
1745                1750                1755                1760

Gly Asp Arg Ile Glu Arg Ala Asn Arg Ala Lys Val Leu Gly Ala Arg
                1765                1770                1775

Asn Leu His Glu Leu Thr Arg Asp Ala Asp Leu Asp Ala Phe Val Leu
            1780                1785                1790

Phe Ser Ser Ser Thr Ala Ala Phe Gly Ala Pro Gly Leu Gly Gly Tyr
        1795                1800                1805

Val Pro Gly Asn Ala Tyr Leu Asp Gly Leu Ala Gln Gln Arg Arg Ser
    1810                1815                1820

Glu Gly Leu Pro Ala Thr Ser Val Ala Trp Gly Thr Trp Ala Gly Ser
1825                1830                1835                1840

Gly Met Ala Glu Gly Pro Val Ala Asp Arg Phe Arg Arg His Gly Val
                1845                1850                1855

Met Glu Met His Pro Asp Gln Ala Val Glu Gly Leu Arg Val Ala Leu
            1860                1865                1870

Val Gln Gly Glu Val Ala Pro Ile Val Val Asp Ile Arg Trp Asp Arg
        1875                1880                1885

Phe Leu Leu Ala Tyr Thr Ala Gln Arg Pro Thr Arg Leu Phe Asp Thr
```

-continued

```
                1890                1895                1900
Leu Asp Glu Ala Arg Arg Ala Ala Pro Gly Pro Asp Ala Gly Pro Gly
1905                1910                1915                1920
Val Ala Ala Leu Ala Gly Leu Pro Val Gly Glu Arg Glu Lys Ala Val
                1925                1930                1935
Leu Asp Leu Val Arg Thr His Ala Ala Ala Val Leu Gly His Ala Ser
            1940                1945                1950
Ala Glu Gln Val Pro Val Asp Arg Ala Phe Ala Glu Leu Gly Val Asp
            1955                1960                1965
Ser Leu Ser Ala Leu Glu Leu Arg Asn Arg Leu Thr Thr Ala Thr Gly
            1970                1975                1980
Val Arg Leu Ala Thr Thr Thr Val Phe Asp His Pro Asp Val Arg Thr
1985                1990                1995                2000
Leu Ala Gly His Leu Ala Ala Glu Leu Gly Gly Ser Gly Arg Glu
                2005                2010                2015
Arg Pro Gly Gly Glu Ala Pro Thr Val Ala Pro Thr Asp Glu Pro Ile
            2020                2025                2030
Ala Ile Val Gly Met Ala Cys Arg Leu Pro Gly Gly Val Asp Ser Pro
            2035                2040                2045
Glu Gln Leu Trp Glu Leu Ile Val Ser Gly Arg Asp Thr Ala Ser Ala
            2050                2055                2060
Ala Pro Gly Asp Arg Ser Trp Asp Pro Ala Glu Leu Met Val Ser Asp
2065                2070                2075                2080
Thr Thr Gly Thr Arg Thr Ala Phe Gly Asn Phe Met Pro Gly Ala Gly
                2085                2090                2095
Glu Phe Asp Ala Ala Phe Phe Gly Ile Ser Pro Arg Glu Ala Leu Ala
            2100                2105                2110
Met Asp Pro Gln Gln Arg His Ala Leu Glu Thr Thr Trp Glu Ala Leu
            2115                2120                2125
Glu Asn Ala Gly Ile Arg Pro Glu Ser Leu Arg Gly Thr Asp Thr Gly
            2130                2135                2140
Val Phe Val Gly Met Ser His Gln Gly Tyr Ala Thr Gly Arg Pro Lys
2145                2150                2155                2160
Pro Glu Asp Glu Val Asp Gly Tyr Leu Leu Thr Gly Asn Thr Ala Ser
            2165                2170                2175
Val Ala Ser Gly Arg Ile Ala Tyr Val Leu Gly Leu Glu Gly Pro Ala
            2180                2185                2190
Ile Thr Val Asp Thr Ala Cys Ser Ser Ser Leu Val Ala Leu His Val
            2195                2200                2205
Ala Ala Gly Ser Leu Arg Ser Gly Asp Cys Gly Leu Ala Val Ala Gly
            2210                2215                2220
Gly Val Ser Val Met Ala Gly Pro Glu Val Phe Arg Glu Phe Ser Arg
2225                2230                2235                2240
Gln Gly Ala Leu Ala Pro Asp Gly Arg Cys Lys Pro Phe Ser Asp Glu
            2245                2250                2255
Ala Asp Gly Phe Gly Leu Gly Glu Gly Ser Ala Phe Val Val Leu Gln
            2260                2265                2270
Arg Leu Ser Val Ala Val Arg Glu Gly Arg Val Leu Gly Val Val
            2275                2280                2285
Val Gly Ser Ala Val Asn Gln Asp Gly Ala Ser Asn Gly Leu Ala Ala
            2290                2295                2300
Pro Ser Gly Val Ala Gln Gln Arg Val Ile Arg Arg Ala Trp Gly Arg
2305                2310                2315                2320
```

-continued

```
Ala Gly Val Ser Gly Gly Asp Val Gly Val Val Glu Ala His Gly Thr
            2325                2330                2335
Gly Thr Arg Leu Gly Asp Pro Val Glu Leu Gly Ala Leu Leu Gly Thr
            2340                2345                2350
Tyr Gly Val Gly Arg Gly Gly Val Gly Pro Val Val Gly Ser Val
            2355                2360            2365
Lys Ala Asn Val Gly His Val Gln Ala Ala Gly Val Val Gly Val
            2370            2375                2380
Ile Lys Val Val Leu Gly Leu Gly Arg Gly Leu Val Gly Pro Met Val
2385                2390                2395                2400
Cys Arg Gly Gly Leu Ser Gly Leu Val Asp Trp Ser Ser Gly Gly Leu
            2405                2410                2415
Val Val Ala Asp Gly Val Arg Gly Trp Pro Val Gly Val Asp Gly Val
            2420                2425                2430
Arg Arg Gly Gly Val Ser Ala Phe Gly Val Ser Gly Thr Asn Ala His
            2435                2440                2445
Val Val Val Ala Glu Ala Pro Gly Ser Val Val Gly Ala Glu Arg Pro
            2450                2455                2460
Val Glu Gly Ser Ser Arg Gly Leu Val Gly Val Val Gly Val Val
2465                2470                2475                2480
Pro Val Val Leu Ser Ala Lys Thr Glu Thr Ala Leu His Ala Gln Ala
            2485                2490                2495
Arg Arg Leu Ala Asp His Leu Glu Thr His Pro Asp Val Pro Met Thr
            2500                2505                2510
Asp Val Val Trp Thr Leu Thr Gln Ala Arg Gln Arg Phe Asp Arg Arg
            2515                2520                2525
Ala Val Leu Leu Ala Ala Asp Arg Thr Gln Ala Val Glu Arg Leu Arg
            2530                2535                2540
Gly Leu Ala Gly Gly Glu Pro Gly Thr Gly Val Ser Gly Val Ala
2545                2550                2555                2560
Ser Gly Gly Gly Val Val Phe Val Phe Pro Gly Gln Gly Gly Gln Trp
            2565                2570                2575
Val Gly Met Ala Arg Gly Leu Leu Ser Val Pro Val Phe Val Glu Ser
            2580                2585                2590
Val Val Glu Cys Asp Ala Val Val Ser Ser Val Val Gly Phe Ser Val
            2595                2600                2605
Leu Gly Val Leu Glu Gly Arg Ser Gly Ala Pro Ser Leu Asp Arg Val
            2610                2615                2620
Asp Val Val Gln Pro Val Leu Phe Val Val Met Val Ser Leu Ala Arg
2625                2630                2635                2640
Leu Trp Arg Trp Cys Gly Val Val Pro Ala Ala Val Val Gly His Ser
            2645                2650                2655
Gln Gly Glu Ile Ala Ala Ala Val Ala Gly Val Leu Ser Val Gly
            2660                2665                2670
Asp Gly Ala Arg Val Val Ala Leu Arg Ala Arg Ala Leu Arg Ala Leu
            2675                2680                2685
Ala Gly His Gly Gly Met Ala Ser Val Arg Arg Gly Arg Asp Asp Val
            2690                2695                2700
Gln Lys Leu Leu Asp Ser Gly Pro Trp Thr Gly Lys Leu Glu Ile Ala
2705                2710                2715                2720
Ala Val Asn Gly Pro Asp Ala Val Val Ser Gly Asp Pro Arg Ala
            2725                2730                2735
```

-continued

```
Val Thr Glu Leu Val Glu His Cys Asp Gly Ile Gly Val Arg Ala Arg
        2740                2745                2750

Thr Ile Pro Val Asp Tyr Ala Ser His Ser Ala Gln Val Glu Ser Leu
        2755                2760                2765

Arg Glu Glu Leu Leu Ser Val Leu Ala Gly Ile Glu Gly Arg Pro Ala
        2770                2775                2780

Thr Val Pro Phe Tyr Ser Thr Leu Thr Gly Gly Phe Val Asp Gly Thr
2785                2790                2795                2800

Glu Leu Asp Ala Asp Tyr Trp Tyr Arg Asn Leu Arg His Pro Val Arg
        2805                2810                2815

Phe His Ala Ala Val Glu Ala Leu Ala Ala Arg Asp Leu Thr Thr Phe
        2820                2825                2830

Val Glu Val Ser Pro His Pro Val Leu Ser Met Ala Val Gly Glu Thr
        2835                2840                2845

Leu Ala Asp Val Glu Ser Ala Val Thr Val Gly Thr Leu Glu Arg Asp
        2850                2855                2860

Thr Asp Asp Val Glu Arg Phe Leu Thr Ser Leu Ala Glu Ala His Val
2865                2870                2875                2880

His Gly Val Pro Val Asp Trp Ala Ala Val Leu Gly Ser Gly Thr Leu
        2885                2890                2895

Val Asp Leu Pro Thr Tyr Pro Phe Gln Gly Arg Arg Phe Trp Leu His
        2900                2905                2910

Pro Asp Arg Gly Pro Arg Asp Asp Val Ala Asp Trp Phe His Arg Val
        2915                2920                2925

Asp Trp Thr Ala Thr Ala Thr Asp Gly Ser Ala Arg Leu Asp Gly Arg
        2930                2935                2940

Trp Leu Val Val Val Pro Glu Gly Tyr Thr Asp Asp Gly Trp Val Val
2945                2950                2955                2960

Glu Val Arg Ala Ala Leu Ala Ala Gly Gly Ala Glu Pro Val Val Thr
        2965                2970                2975

Thr Val Glu Glu Val Thr Asp Arg Val Gly Asp Ser Asp Ala Val Val
        2980                2985                2990

Ser Met Leu Gly Leu Ala Asp Asp Gly Ala Ala Glu Thr Leu Ala Leu
        2995                3000                3005

Leu Arg Arg Leu Asp Ala Gln Ala Ser Thr Thr Pro Leu Trp Val Val
        3010                3015                3020

Thr Val Gly Ala Val Ala Pro Ala Gly Pro Val Gln Arg Pro Glu Gln
3025                3030                3035                3040

Ala Thr Val Trp Gly Leu Ala Leu Val Ala Ser Leu Glu Arg Gly His
        3045                3050                3055

Arg Trp Thr Gly Leu Leu Asp Leu Pro Gln Thr Pro Asp Pro Gln Leu
        3060                3065                3070

Arg Pro Arg Leu Val Glu Ala Leu Ala Gly Ala Glu Asp Gln Val Ala
        3075                3080                3085

Val Arg Ala Asp Ala Val His Ala Arg Arg Ile Val Pro Thr Pro Val
        3090                3095                3100

Thr Gly Ala Gly Pro Tyr Thr Ala Pro Gly Gly Thr Ile Leu Val Thr
3105                3110                3115                3120

Gly Gly Thr Ala Gly Leu Gly Ala Val Thr Ala Arg Trp Leu Ala Glu
        3125                3130                3135

Arg Gly Ala Glu His Leu Ala Leu Val Ser Arg Arg Gly Pro Gly Thr
        3140                3145                3150

Ala Gly Val Asp Glu Val Val Arg Asp Leu Thr Gly Leu Gly Val Arg
```

```
                3155                3160                3165
        Val Ser Val His Ser Cys Asp Val Gly Asp Arg Glu Ser Val Gly Ala
            3170                3175                3180

Leu Val Gln Glu Leu Thr Ala Ala Gly Asp Val Val Arg Gly Val Val
        3185                3190                3195                3200

His Ala Ala Gly Leu Pro Gln Gln Val Pro Leu Thr Asp Met Asp Pro
                    3205                3210                3215

Ala Asp Leu Ala Asp Val Val Ala Val Lys Val Asp Gly Ala Val His
                3220                3225                3230

Leu Ala Asp Leu Cys Pro Glu Ala Glu Leu Phe Leu Leu Phe Ser Ser
                3235                3240                3245

Gly Ala Gly Val Trp Gly Ser Ala Arg Gln Gly Ala Tyr Ala Ala Gly
            3250                3255                3260

Asn Ala Phe Leu Asp Ala Phe Ala Arg His Arg Arg Asp Arg Gly Leu
        3265                3270                3275                3280

Pro Ala Thr Ser Val Ala Trp Gly Leu Trp Ala Ala Gly Gly Met Thr
                    3285                3290                3295

Gly Asp Gln Glu Ala Val Ser Phe Leu Arg Glu Arg Gly Val Arg Pro
                3300                3305                3310

Met Ser Val Pro Arg Ala Leu Glu Ala Leu Glu Arg Val Leu Thr Ala
            3315                3320                3325

Gly Glu Thr Ala Val Val Ala Asp Val Asp Trp Ala Ala Phe Ala
        3330                3335                3340

Glu Ser Tyr Thr Ser Ala Arg Pro Arg Pro Leu Leu His Arg Leu Val
        3345                3350                3355                3360

Thr Pro Ala Ala Ala Val Gly Glu Arg Asp Glu Pro Arg Glu Gln Thr
                    3365                3370                3375

Leu Arg Asp Arg Leu Ala Ala Leu Pro Arg Ala Glu Arg Ser Ala Glu
                3380                3385                3390

Leu Val Arg Leu Val Arg Arg Asp Ala Ala Ala Val Leu Gly Ser Asp
            3395                3400                3405

Ala Lys Ala Val Pro Ala Thr Thr Pro Phe Lys Asp Leu Gly Phe Asp
            3410                3415                3420

Ser Leu Ala Ala Val Arg Phe Arg Asn Arg Leu Ala Ala His Thr Gly
        3425                3430                3435                3440

Leu Arg Leu Pro Ala Thr Leu Val Phe Glu His Pro Asn Ala Ala Ala
                    3445                3450                3455

Val Ala Asp Leu Leu His Asp Arg Leu Gly Glu Ala Gly Glu Pro Thr
                3460                3465                3470

Pro Val Arg Ser Val Gly Ala Gly Leu Ala Ala Leu Glu Gln Ala Leu
            3475                3480                3485

Pro Asp Ala Ser Asp Thr Glu Arg Val Glu Leu Val Glu Arg Leu Glu
        3490                3495                3500

Arg Met Leu Ala Gly Leu Arg Pro Glu Ala Gly Ala Gly Ala Asp Ala
        3505                3510                3515                3520

Pro Thr Ala Gly Asp Asp Leu Gly Glu Ala Gly Val Asp Glu Leu Leu
                    3525                3530                3535

Asp Ala Leu Glu Arg Glu Leu Asp Ala Arg
                3540                3545

<210> SEQ ID NO 14
<211> LENGTH: 3562
<212> TYPE: PRT
<213> ORGANISM: Micromonospora megalomicea
```

<400> SEQUENCE: 14

```
Met Thr Asp Asn Asp Lys Val Ala Glu Tyr Leu Arg Arg Ala Thr Leu
 1               5                  10                  15
Asp Leu Arg Ala Ala Arg Lys Arg Leu Arg Glu Leu Gln Ser Asp Pro
            20                  25                  30
Ile Ala Val Val Gly Met Ala Cys Arg Leu Pro Gly Gly Val His Leu
        35                  40                  45
Pro Gln His Leu Trp Asp Leu Leu Arg Gln Gly His Glu Thr Val Ser
50                  55                  60
Thr Phe Pro Thr Gly Arg Gly Trp Asp Leu Ala Gly Leu Phe His Pro
65                  70                  75                  80
Asp Pro Asp His Pro Gly Thr Ser Tyr Val Asp Arg Gly Gly Phe Leu
                85                  90                  95
Asp Asp Val Ala Gly Phe Asp Ala Glu Phe Phe Gly Ile Ser Pro Arg
            100                 105                 110
Glu Ala Thr Ala Met Asp Pro Gln Gln Arg Leu Leu Leu Glu Thr Ser
        115                 120                 125
Trp Glu Leu Val Glu Ser Ala Gly Ile Asp Pro His Ser Leu Arg Gly
130                 135                 140
Thr Pro Thr Gly Val Phe Leu Gly Val Ala Arg Leu Gly Tyr Gly Glu
145                 150                 155                 160
Asn Gly Thr Glu Ala Gly Asp Ala Glu Gly Tyr Ser Val Thr Gly Val
                165                 170                 175
Ala Pro Ala Val Ala Ser Gly Arg Ile Ser Tyr Ala Leu Gly Leu Glu
            180                 185                 190
Gly Pro Ser Ile Ser Val Asp Thr Ala Cys Ser Ser Ser Leu Val Ala
        195                 200                 205
Leu His Leu Ala Val Glu Ser Leu Arg Leu Gly Glu Ser Ser Leu Ala
210                 215                 220
Val Val Gly Gly Ala Ala Val Met Ala Thr Pro Gly Val Phe Val Asp
225                 230                 235                 240
Phe Ser Arg Gln Arg Ala Leu Ala Ala Asp Gly Arg Ser Lys Ala Phe
                245                 250                 255
Gly Ala Ala Ala Asp Gly Phe Gly Phe Ser Glu Gly Val Ser Leu Val
            260                 265                 270
Leu Leu Glu Arg Leu Ser Glu Ala Glu Ser Asn Gly His Glu Val Leu
        275                 280                 285
Ala Val Ile Arg Gly Ser Ala Leu Asn Gln Asp Gly Ala Ser Asn Gly
290                 295                 300
Leu Ala Ala Pro Asn Gly Thr Ala Gln Arg Lys Val Ile Arg Gln Ala
305                 310                 315                 320
Leu Arg Asn Cys Gly Leu Thr Pro Ala Asp Val Asp Ala Val Glu Ala
                325                 330                 335
His Gly Thr Gly Thr Thr Leu Gly Asp Pro Ile Glu Ala Asn Ala Leu
            340                 345                 350
Leu Asp Thr Tyr Gly Arg Asp Arg Asp Pro Asp His Pro Leu Trp Leu
        355                 360                 365
Gly Ser Val Lys Ser Asn Ile Gly His Thr Gln Ala Ala Ala Gly Val
370                 375                 380
Thr Gly Leu Leu Lys Met Val Leu Ala Leu Arg His Glu Glu Leu Pro
385                 390                 395                 400
Ala Thr Leu His Val Asp Glu Pro Thr Pro His Val Asp Trp Ser Ser
```

```
                       405                 410                 415
        Gly Ala Val Arg Leu Ala Thr Arg Gly Arg Pro Trp Arg Arg Gly Asp
                            420                 425                 430
        Arg Pro Arg Arg Ala Gly Val Ser Ala Phe Gly Ile Ser Gly Thr Asn
                    435                 440                 445
        Ala His Val Ile Val Glu Glu Ala Pro Glu Arg Thr Thr Glu Arg Thr
                450                 455                 460
        Val Gly Gly Asp Val Gly Pro Val Pro Leu Val Val Ser Ala Arg Ser
        465                 470                 475                 480
        Ala Ala Ala Leu Arg Ala Gln Ala Ala Gln Val Ala Glu Leu Val Glu
                        485                 490                 495
        Gly Ser Asp Val Gly Leu Ala Glu Val Gly Arg Ser Leu Ala Val Thr
                    500                 505                 510
        Arg Ala Arg His Glu His Arg Ala Ala Val Ala Ser Thr Arg Ala
                515                 520                 525
        Glu Ala Val Arg Gly Leu Arg Glu Val Ala Ala Val Glu Pro Arg Gly
        530                 535                 540
        Glu Asp Thr Val Thr Gly Val Ala Glu Thr Ser Gly Arg Thr Val Val
        545                 550                 555                 560
        Phe Leu Phe Pro Gly Gln Gly Ser Gln Trp Val Gly Met Gly Ala Glu
                        565                 570                 575
        Leu Leu Asp Ser Ala Pro Ala Phe Ala Asp Thr Ile Arg Ala Cys Asp
                    580                 585                 590
        Glu Ala Met Ala Pro Leu Gln Asp Trp Ser Val Ser Asp Val Leu Arg
                595                 600                 605
        Gln Glu Pro Gly Ala Pro Gly Leu Asp Arg Val Asp Val Val Gln Pro
        610                 615                 620
        Val Leu Phe Ala Val Met Val Ser Leu Ala Arg Leu Trp Gln Ser Tyr
        625                 630                 635                 640
        Gly Val Thr Pro Ala Ala Val Val Gly His Ser Gln Gly Glu Ile Ala
                        645                 650                 655
        Ala Ala His Val Ala Gly Ala Leu Ser Leu Ala Asp Ala Ala Arg Leu
                    660                 665                 670
        Val Val Gly Arg Ser Arg Leu Leu Arg Ser Leu Ser Gly Gly Gly Gly
                675                 680                 685
        Met Ser Ala Val Ala Leu Gly Glu Ala Glu Val Arg Arg Arg Leu Arg
        690                 695                 700
        Ser Trp Glu Asp Arg Ile Ser Val Ala Ala Val Asn Gly Pro Arg Ser
        705                 710                 715                 720
        Val Val Val Ala Gly Glu Pro Glu Ala Leu Arg Glu Trp Gly Arg Glu
                        725                 730                 735
        Arg Glu Ala Glu Gly Val Arg Val Arg Glu Ile Asp Val Asp Tyr Ala
                    740                 745                 750
        Ser His Ser Pro Gln Ile Asp Arg Val Arg Asp Glu Leu Leu Thr Val
                755                 760                 765
        Thr Gly Glu Ile Glu Pro Arg Ser Ala Glu Ile Thr Phe Tyr Ser Thr
        770                 775                 780
        Val Asp Val Arg Ala Val Asp Gly Thr Asp Leu Asp Ala Gly Tyr Trp
        785                 790                 795                 800
        Tyr Arg Asn Leu Arg Glu Thr Val Arg Phe Ala Asp Ala Met Thr Arg
                        805                 810                 815
        Leu Ala Asp Ser Gly Tyr Asp Ala Phe Val Glu Val Ser Pro His Pro
                    820                 825                 830
```

-continued

Val Val Val Ser Ala Val Ala Glu Ala Val Glu Glu Ala Gly Val Glu
            835                 840                 845

Asp Ala Val Val Val Gly Thr Leu Ser Arg Gly Asp Gly Gly Pro Gly
850                 855                 860

Ala Phe Leu Arg Ser Ala Ala Thr Ala His Cys Ala Gly Val Asp Val
865                 870                 875                 880

Asp Trp Thr Pro Ala Leu Pro Gly Ala Ala Thr Ile Pro Leu Pro Thr
                885                 890                 895

Tyr Pro Phe Gln Arg Lys Pro Tyr Trp Leu Arg Ser Ser Ala Pro Ala
            900                 905                 910

Pro Ala Ser His Asp Leu Ala Tyr Arg Val Ser Trp Thr Pro Ile Thr
            915                 920                 925

Pro Pro Gly Asp Gly Val Leu Asp Gly Asp Trp Leu Val Val His Pro
930                 935                 940

Gly Gly Ser Thr Gly Trp Val Asp Gly Leu Ala Ala Ile Thr Ala
945                 950                 955                 960

Gly Gly Gly Arg Val Ala His Pro Val Asp Ser Val Thr Ser Arg
            965                 970                 975

Thr Gly Leu Ala Glu Ala Leu Ala Arg Arg Asp Gly Thr Phe Arg Gly
            980                 985                 990

Val Leu Ser Trp Val Ala Thr Asp Glu Arg His Val Glu Ala Gly Ala
            995             1000                1005

Val Ala Leu Leu Thr Leu Ala Gln Ala Leu Gly Asp Ala Gly Ile Asp
        1010                1015                1020

Ala Pro Leu Trp Cys Leu Thr Gln Glu Ala Val Arg Thr Pro Val Asp
1025                1030                1035                1040

Gly Asp Leu Ala Arg Pro Ala Gln Ala Ala Leu His Gly Phe Ala Gln
                1045                1050                1055

Val Ala Arg Leu Glu Leu Ala Arg Arg Phe Gly Val Leu Asp Leu
            1060                1065                1070

Pro Ala Thr Val Asp Ala Ala Gly Thr Arg Leu Val Ala Ala Val Leu
        1075                1080                1085

Ala Gly Gly Gly Glu Asp Val Val Ala Val Arg Gly Asp Arg Leu Tyr
        1090                1095                1100

Gly Arg Arg Leu Val Arg Ala Thr Leu Pro Pro Gly Gly Gly Phe
1105                1110                1115                1120

Thr Pro His Gly Thr Val Leu Val Thr Gly Ala Ala Gly Pro Val Gly
                1125                1130                1135

Gly Arg Leu Ala Arg Trp Leu Ala Glu Arg Gly Ala Thr Arg Leu Val
        1140                1145                1150

Leu Pro Gly Ala His Pro Gly Glu Glu Leu Leu Thr Ala Ile Arg Ala
            1155                1160                1165

Ala Gly Ala Thr Ala Val Val Cys Glu Pro Glu Ala Glu Leu Arg
        1170                1175                1180

Thr Ala Ile Gly Gly Glu Leu Pro Thr Ala Leu Val His Ala Glu Thr
1185                1190                1195                1200

Leu Thr Asn Phe Ala Gly Val Ala Asp Ala Asp Pro Glu Asp Phe Ala
                1205                1210                1215

Ala Thr Val Ala Ala Lys Thr Ala Leu Pro Thr Val Leu Ala Glu Val
                1220                1225                1230

Leu Gly Asp His Arg Leu Glu Arg Glu Val Tyr Cys Ser Ser Val Ala
            1235                1240                1245

-continued

```
Gly Val Trp Gly Gly Val Gly Met Ala Ala Tyr Ala Ala Gly Ser Ala
            1250                1255                1260
Tyr Leu Asp Ala Leu Val Glu His Arg Arg Ala Arg Gly His Ala Ser
1265                1270                1275                1280
Ala Ser Val Ala Trp Thr Pro Trp Ala Leu Pro Gly Ala Val Asp Asp
            1285                1290                1295
Gly Arg Leu Arg Glu Arg Gly Leu Arg Ser Leu Asp Val Ala Asp Ala
            1300                1305                1310
Leu Gly Thr Trp Glu Arg Leu Leu Arg Ala Gly Ala Val Ser Val Ala
            1315                1320                1325
Val Ala Asp Val Asp Trp Ser Val Phe Thr Glu Gly Phe Ala Ala Ile
            1330                1335                1340
Arg Pro Thr Pro Leu Phe Asp Glu Leu Leu Asp Arg Arg Gly Asp Pro
1345                1350                1355                1360
Asp Gly Ala Pro Val Asp Arg Pro Gly Glu Pro Ala Gly Glu Trp Gly
            1365                1370                1375
Arg Arg Ile Ala Ala Leu Ser Pro Gln Glu Gln Arg Glu Thr Leu Leu
            1380                1385                1390
Thr Leu Val Gly Glu Thr Val Ala Glu Val Leu Gly His Glu Thr Gly
            1395                1400                1405
Thr Glu Ile Asn Thr Arg Arg Ala Phe Ser Glu Leu Gly Leu Asp Ser
            1410                1415                1420
Leu Gly Ser Met Ala Leu Arg Gln Arg Leu Ala Ala Arg Thr Gly Leu
1425                1430                1435                1440
Arg Met Pro Ala Ser Leu Val Phe Asp His Pro Thr Val Thr Ala Leu
            1445                1450                1455
Ala Arg Tyr Leu Arg Arg Leu Val Val Gly Asp Ser Asp Pro Thr Pro
            1460                1465                1470
Val Arg Val Phe Gly Pro Thr Asp Glu Ala Glu Pro Val Ala Val Val
            1475                1480                1485
Gly Ile Gly Cys Arg Phe Pro Gly Gly Ile Ala Thr Pro Glu Asp Leu
            1490                1495                1500
Trp Arg Val Val Ser Glu Gly Thr Ser Ile Thr Thr Gly Phe Pro Thr
1505                1510                1515                1520
Asp Arg Gly Trp Asp Leu Arg Arg Leu Tyr His Pro Asp Pro Asp His
            1525                1530                1535
Pro Gly Thr Ser Tyr Val Asp Arg Gly Gly Phe Leu Asp Gly Ala Pro
            1540                1545                1550
Asp Phe Asp Pro Gly Phe Phe Gly Ile Thr Pro Arg Glu Ala Leu Ala
            1555                1560                1565
Met Asp Pro Gln Gln Arg Leu Thr Leu Glu Ile Ala Trp Glu Ala Val
            1570                1575                1580
Glu Arg Ala Gly Ile Asp Pro Glu Thr Leu Leu Gly Ser Asp Thr Gly
1585                1590                1595                1600
Val Phe Val Gly Met Asn Gly Gln Ser Tyr Leu Gln Leu Leu Thr Gly
            1605                1610                1615
Glu Gly Asp Arg Leu Asn Gly Tyr Gln Gly Leu Gly Asn Ser Ala Ser
            1620                1625                1630
Val Leu Ser Gly Arg Val Ala Tyr Thr Phe Gly Trp Glu Gly Pro Ala
            1635                1640                1645
Leu Thr Val Asp Thr Ala Cys Ser Ser Ser Leu Val Ala Ile His Leu
            1650                1655                1660
Ala Met Gln Ser Leu Arg Arg Gly Glu Cys Ser Leu Ala Leu Ala Gly
```

```
                1665              1670              1675              1680
Gly Val Thr Val Met Ala Asp Pro Tyr Thr Phe Val Asp Phe Ser Ala
                     1685              1690              1695
Gln Arg Gly Leu Ala Ala Asp Gly Arg Cys Lys Ala Phe Ser Ala Gln
                     1700              1705              1710
Ala Asp Gly Phe Ala Leu Ala Glu Gly Val Ala Ala Leu Val Leu Glu
                     1715              1720              1725
Pro Leu Ser Lys Ala Arg Arg Asn Gly His Gln Val Leu Ala Val Leu
                     1730              1735              1740
Arg Gly Ser Ala Val Asn Gln Asp Gly Ala Ser Asn Gly Leu Ala Ala
1745                 1750              1755              1760
Pro Asn Gly Pro Ser Gln Glu Arg Val Ile Arg Gln Ala Leu Thr Ala
                     1765              1770              1775
Ser Gly Leu Arg Pro Ala Asp Val Asp Met Val Glu Ala His Gly Thr
                     1780              1785              1790
Gly Thr Glu Leu Gly Asp Pro Ile Glu Ala Gly Ala Leu Ile Ala Ala
                     1795              1800              1805
Tyr Gly Arg Asp Arg Asp Arg Pro Leu Trp Leu Gly Ser Val Lys Thr
                     1810              1815              1820
Asn Ile Gly His Thr Gln Ala Ala Ala Gly Ala Ala Gly Val Ile Lys
1825                 1830              1835              1840
Ala Val Leu Ala Met Arg His Gly Val Leu Pro Arg Ser Leu His Ala
                     1845              1850              1855
Asp Glu Leu Ser Pro His Ile Asp Trp Ala Asp Gly Lys Val Glu Val
                     1860              1865              1870
Leu Arg Glu Ala Arg Gln Trp Pro Pro Gly Glu Arg Pro Arg Arg Ala
                     1875              1880              1885
Gly Val Ser Ser Phe Gly Val Ser Gly Thr Asn Ala His Val Ile Val
                     1890              1895              1900
Glu Glu Ala Pro Ala Glu Pro Asp Pro Glu Pro Val Pro Ala Ala Pro
1905                 1910              1915              1920
Gly Gly Pro Leu Pro Phe Val Leu His Gly Arg Ser Val Gln Thr Val
                     1925              1930              1935
Arg Ser Gln Ala Arg Thr Leu Ala Glu His Leu Arg Thr Thr Gly His
                     1940              1945              1950
Arg Asp Leu Ala Asp Thr Ala Arg Thr Leu Ala Thr Gly Arg Ala Arg
                     1955              1960              1965
Phe Asp Val Arg Ala Ala Val Leu Gly Thr Asp Arg Glu Gly Val Cys
                     1970              1975              1980
Ala Ala Leu Asp Ala Leu Ala Gln Asp Arg Pro Ser Pro Asp Val Val
1985                 1990              1995              2000
Ala Pro Ala Val Phe Ala Ala Arg Thr Pro Val Leu Val Phe Pro Gly
                     2005              2010              2015
Gln Gly Ser Gln Trp Val Gly Met Ala Arg Asp Leu Leu Asp Ser Ser
                     2020              2025              2030
Glu Val Phe Ala Glu Ser Met Gly Arg Cys Ala Glu Ala Leu Ser Pro
                     2035              2040              2045
Tyr Thr Asp Trp Asp Leu Leu Asp Val Val Arg Gly Val Gly Asp Pro
                     2050              2055              2060
Asp Pro Tyr Asp Arg Val Asp Val Leu Gln Pro Val Leu Phe Ala Val
2065                 2070              2075              2080
Met Val Ser Leu Ala Arg Leu Trp Gln Ser Tyr Gly Val Thr Pro Gly
                     2085              2090              2095
```

-continued

```
Ala Val Val Gly His Ser Gln Gly Glu Ile Ala Ala His Val Ala
            2100                2105                2110
Gly Ala Leu Ser Leu Ala Asp Ala Ala Arg Val Val Ala Leu Arg Ser
        2115                2120                2125
Arg Val Leu Arg Glu Leu Asp Asp Gln Gly Gly Met Val Ser Val Gly
    2130                2135                2140
Thr Ser Arg Ala Glu Leu Asp Ser Val Leu Arg Arg Trp Asp Gly Arg
2145                2150                2155                2160
Val Ala Val Ala Ala Val Asn Gly Pro Gly Thr Leu Val Ala Gly
            2165                2170                2175
Pro Thr Ala Glu Leu Asp Glu Phe Leu Ala Val Ala Glu Ala Arg Glu
        2180                2185                2190
Met Arg Pro Arg Arg Ile Ala Val Arg Tyr Ala Ser His Ser Pro Glu
    2195                2200                2205
Val Ala Arg Val Glu Gln Arg Leu Ala Ala Glu Leu Gly Thr Val Thr
    2210                2215                2220
Ala Val Gly Gly Thr Val Pro Leu Tyr Ser Thr Ala Thr Gly Asp Leu
2225                2230                2235                2240
Leu Asp Thr Thr Ala Met Asp Ala Gly Tyr Trp Tyr Arg Asn Leu Arg
            2245                2250                2255
Gln Pro Val Leu Phe Glu His Ala Val Arg Ser Leu Leu Glu Arg Gly
        2260                2265                2270
Phe Glu Thr Phe Ile Glu Val Ser Pro His Pro Val Leu Leu Met Ala
        2275                2280                2285
Val Glu Glu Thr Ala Glu Asp Ala Glu Arg Pro Val Thr Gly Val Pro
    2290                2295                2300
Thr Leu Arg Arg Asp His Asp Gly Pro Ser Glu Phe Leu Arg Asn Leu
2305                2310                2315                2320
Leu Gly Ala His Val His Gly Val Asp Val Asp Leu Arg Pro Ala Val
            2325                2330                2335
Ala His Gly Arg Leu Val Asp Leu Pro Thr Tyr Pro Phe Asp Arg Gln
        2340                2345                2350
Arg Leu Trp Pro Lys Pro His Arg Arg Ala Asp Thr Ser Ser Leu Gly
        2355                2360                2365
Val Arg Asp Ser Thr His Pro Leu Leu His Ala Ala Val Asp Val Pro
    2370                2375                2380
Gly His Gly Gly Ala Val Phe Thr Gly Arg Leu Ser Pro Asp Glu Gln
2385                2390                2395                2400
Gln Trp Leu Thr Gln His Val Val Gly Gly Arg Asn Leu Val Pro Gly
            2405                2410                2415
Ser Val Leu Val Asp Leu Ala Leu Thr Ala Gly Ala Asp Val Gly Val
        2420                2425                2430
Pro Val Leu Glu Glu Leu Val Leu Gln Gln Pro Leu Val Leu Thr Ala
        2435                2440                2445
Ala Gly Ala Leu Leu Arg Leu Ser Val Gly Ala Ala Asp Glu Asp Gly
    2450                2455                2460
Arg Arg Pro Val Glu Ile His Ala Ala Glu Asp Val Ser Asp Pro Ala
2465                2470                2475                2480
Glu Ala Arg Trp Ser Ala Tyr Ala Thr Gly Thr Leu Ala Val Gly Val
            2485                2490                2495
Ala Gly Gly Gly Arg Asp Gly Thr Gln Trp Pro Pro Gly Ala Thr
        2500                2505                2510
```

-continued

```
Ala Leu Thr Leu Thr Asp His Tyr Asp Thr Leu Ala Glu Leu Gly Tyr
        2515                2520                2525

Glu Tyr Gly Pro Ala Phe Gln Ala Leu Arg Ala Ala Trp Gln His Gly
    2530                2535                2540

Asp Val Val Tyr Ala Glu Val Ser Leu Asp Ala Val Glu Glu Gly Tyr
2545                2550                2555                2560

Ala Phe Asp Pro Val Leu Leu Asp Ala Val Ala Gln Thr Phe Gly Leu
            2565                2570                2575

Thr Ser Arg Ala Pro Gly Lys Leu Pro Phe Ala Trp Arg Gly Val Thr
        2580                2585                2590

Leu His Ala Thr Gly Ala Thr Ala Val Arg Val Val Ala Thr Pro Ala
    2595                2600                2605

Gly Pro Asp Ala Val Ala Leu Arg Val Thr Asp Pro Thr Gly Gln Leu
    2610                2615                2620

Val Ala Thr Val Asp Ala Leu Val Val Arg Asp Ala Gly Ala Asp Arg
2625                2630                2635                2640

Asp Gln Pro Arg Gly Arg Asp Gly Asp Leu His Arg Leu Glu Trp Val
            2645                2650                2655

Arg Leu Ala Thr Pro Asp Pro Thr Pro Ala Ala Val Val His Val Ala
        2660                2665                2670

Ala Asp Gly Leu Asp Asp Leu Leu Arg Ala Gly Gly Pro Ala Pro Gln
    2675                2680                2685

Ala Val Val Val Arg Tyr Arg Pro Asp Gly Asp Asp Pro Thr Ala Glu
    2690                2695                2700

Ala Arg His Gly Val Leu Trp Ala Ala Thr Leu Val Arg Arg Trp Leu
2705                2710                2715                2720

Asp Asp Asp Arg Trp Pro Ala Thr Thr Leu Val Val Ala Thr Ser Ala
            2725                2730                2735

Gly Val Glu Val Ser Pro Gly Asp Asp Val Pro Arg Pro Gly Ala Ala
        2740                2745                2750

Ala Val Trp Gly Val Leu Arg Cys Ala Gln Ala Glu Ser Pro Asp Arg
    2755                2760                2765

Phe Val Leu Val Asp Gly Asp Pro Glu Thr Pro Pro Ala Val Pro Asp
    2770                2775                2780

Asn Pro Gln Leu Ala Val Arg Asp Gly Ala Val Phe Val Pro Arg Leu
2785                2790                2795                2800

Thr Pro Leu Ala Gly Pro Val Pro Ala Val Ala Asp Arg Ala Tyr Arg
            2805                2810                2815

Leu Val Pro Gly Asn Gly Gly Ser Ile Glu Ala Val Ala Phe Ala Pro
        2820                2825                2830

Val Pro Asp Ala Asp Arg Pro Leu Ala Pro Glu Glu Val Arg Val Ala
    2835                2840                2845

Val Arg Ala Thr Gly Val Asn Phe Arg Asp Val Leu Leu Ala Leu Gly
    2850                2855                2860

Met Tyr Pro Glu Pro Ala Glu Met Gly Thr Glu Ala Ser Gly Val Val
2865                2870                2875                2880

Thr Glu Val Gly Ser Gly Val Arg Arg Phe Thr Pro Gly Gln Ala Val
            2885                2890                2895

Thr Gly Leu Phe Gln Gly Ala Phe Gly Pro Val Ala Val Ala Asp His
        2900                2905                2910

Arg Leu Leu Thr Pro Val Pro Asp Gly Trp Arg Ala Val Asp Ala Ala
    2915                2920                2925

Ala Val Pro Ile Ala Phe Thr Thr Ala His Tyr Ala Leu His Asp Leu
```

-continued

```
                  2930                2935                2940
Ala Gly Leu Gln Ala Gly Gln Ser Val Leu Val His Ala Ala Gly
2945                2950                2955                2960

Gly Val Gly Met Ala Ala Val Ala Leu Ala Arg Arg Ala Gly Ala Glu
                2965                2970                2975

Val Phe Ala Thr Ala Ser Pro Ala Lys His Pro Thr Leu Arg Ala Leu
                2980                2985                2990

Gly Leu Asp Asp Asp His Ile Ala Ser Ser Arg Glu Ser Gly Phe Gly
                2995                3000                3005

Glu Arg Phe Ala Ala Arg Thr Gly Gly Arg Gly Val Asp Val Val Leu
            3010                3015                3020

Asn Ser Leu Thr Gly Asp Leu Leu Asp Glu Ser Ala Arg Leu Leu Ala
3025                3030                3035                3040

Asp Gly Gly Val Phe Val Glu Met Gly Lys Thr Asp Leu Arg Pro Ala
                3045                3050                3055

Glu Gln Phe Arg Gly Arg Tyr Val Pro Phe Asp Leu Ala Glu Ala Gly
            3060                3065                3070

Pro Asp Arg Leu Gly Glu Ile Leu Glu Glu Val Val Gly Leu Leu Ala
            3075                3080                3085

Ala Gly Ala Leu Asp Arg Leu Pro Val Ser Val Trp Glu Leu Ser Ala
3090                3095                3100

Ala Pro Ala Ala Leu Thr His Met Ser Arg Gly Arg His Val Gly Lys
3105                3110                3115                3120

Leu Val Leu Thr Gln Pro Ala Pro Val His Pro Asp Gly Thr Val Leu
                3125                3130                3135

Val Thr Gly Gly Thr Gly Thr Leu Gly Arg Leu Val Ala Arg His Leu
            3140                3145                3150

Val Thr Gly His Gly Val Pro His Leu Leu Val Ala Ser Arg Arg Gly
            3155                3160                3165

Pro Ala Ala Pro Gly Ala Ala Glu Leu Arg Ala Asp Val Glu Gly Leu
3170                3175                3180

Gly Ala Thr Ile Glu Ile Val Ala Cys Asp Thr Ala Asp Arg Glu Ala
3185                3190                3195                3200

Leu Ala Ala Leu Leu Asp Ser Ile Pro Ala Asp Arg Pro Leu Thr Gly
                3205                3210                3215

Val Val His Thr Ala Gly Val Leu Ala Asp Gly Leu Val Thr Ser Ile
                3220                3225                3230

Asp Gly Thr Ala Thr Asp Gln Val Leu Arg Ala Lys Val Asp Ala Ala
            3235                3240                3245

Trp His Leu His Asp Leu Thr Arg Asp Ala Asp Leu Ser Phe Phe Val
            3250                3255                3260

Leu Phe Ser Ser Ala Ala Ser Val Leu Ala Gly Pro Gly Gln Gly Val
3265                3270                3275                3280

Tyr Ala Ala Ala Asn Gly Val Leu Asn Ala Leu Ala Gly Gln Arg Arg
                3285                3290                3295

Ala Leu Gly Leu Pro Ala Lys Ala Leu Gly Trp Gly Leu Trp Ala Gln
                3300                3305                3310

Ala Ser Glu Met Thr Ser Gly Leu Gly Asp Arg Ile Ala Arg Thr Gly
                3315                3320                3325

Val Ala Ala Leu Pro Thr Glu Arg Ala Leu Ala Leu Phe Asp Ala Ala
                3330                3335                3340

Leu Arg Ser Gly Gly Glu Val Leu Phe Pro Leu Ser Val Asp Arg Ser
3345                3350                3355                3360
```

-continued

```
Ala Leu Arg Arg Ala Glu Tyr Val Pro Glu Val Leu Arg Gly Ala Val
            3365                3370                3375

Arg Ser Thr Pro Arg Ala Ala Asn Arg Ala Glu Thr Pro Gly Arg Gly
            3380                3385                3390

Leu Leu Asp Arg Leu Val Gly Ala Pro Glu Thr Asp Gln Val Ala Ala
            3395                3400                3405

Leu Ala Glu Leu Val Arg Ser His Ala Ala Val Ala Gly Tyr Asp
        3410                3415                3420

Ser Ala Asp Gln Leu Pro Glu Arg Lys Ala Phe Lys Asp Leu Gly Phe
3425                3430                3435                3440

Asp Ser Leu Ala Ala Val Glu Leu Arg Asn Arg Leu Gly Val Thr Thr
                3445                3450                3455

Gly Val Arg Leu Pro Ser Thr Leu Val Phe Asp His Pro Thr Pro Leu
                3460                3465                3470

Ala Val Ala Glu His Leu Arg Ser Glu Leu Phe Ala Asp Ser Ala Pro
                3475                3480                3485

Asp Val Gly Val Gly Ala Arg Leu Asp Asp Leu Glu Arg Ala Leu Asp
                3490                3495                3500

Ala Leu Pro Asp Ala Gln Gly His Ala Asp Val Gly Ala Arg Leu Glu
3505                3510                3515                3520

Ala Leu Leu Arg Arg Trp Gln Ser Arg Pro Pro Glu Thr Glu Pro
            3525                3530                3535

Val Thr Ile Ser Asp Asp Ala Ser Asp Asp Glu Leu Phe Ser Met Leu
            3540                3545                3550

Asp Arg Arg Leu Gly Gly Gly Gly Asp Val
        3555                3560

<210> SEQ ID NO 15
<211> LENGTH: 3201
<212> TYPE: PRT
<213> ORGANISM: Micromonospora megalomicea

<400> SEQUENCE: 15

Met Ser Glu Ser Ser Gly Met Thr Glu Asp Arg Leu Arg Arg Tyr Leu
 1               5                  10                  15

Lys Arg Thr Val Ala Glu Leu Asp Ser Val Thr Gly Arg Leu Asp Glu
            20                  25                  30

Val Glu Tyr Arg Ala Arg Glu Pro Ile Ala Val Gly Met Ala Cys
        35                  40                  45

Arg Phe Pro Gly Gly Val Asp Ser Pro Glu Ala Phe Trp Glu Phe Ile
    50                  55                  60

Arg Asp Gly Gly Asp Ala Ile Ala Glu Ala Pro Thr Asp Arg Gly Trp
65                  70                  75                  80

Pro Pro Ala Pro Arg Pro Arg Leu Gly Gly Leu Leu Ala Glu Pro Gly
                85                  90                  95

Ala Phe Asp Ala Ala Phe Phe Gly Ile Ser Pro Arg Glu Ala Leu Ala
                100                 105                 110

Thr Asp Pro Gln Gln Arg Leu Met Leu Glu Ile Ser Trp Glu Ala Leu
            115                 120                 125

Glu Arg Ala Gly Phe Asp Pro Ser Ser Leu Arg Gly Ser Ala Gly Gly
        130                 135                 140

Val Phe Thr Gly Val Gly Ala Val Asp Tyr Gly Pro Arg Pro Asp Glu
145                 150                 155                 160

Ala Pro Glu Glu Val Leu Gly Tyr Val Gly Ile Gly Thr Ala Ser Ser
```

-continued

```
                    165                 170                 175
        Val Ala Ser Gly Arg Val Ala Tyr Thr Leu Gly Leu Glu Gly Pro Ala
                    180                 185                 190
        Val Thr Val Asp Thr Ala Cys Ser Ser Gly Leu Thr Ala Val His Leu
                    195                 200                 205
        Ala Met Glu Ser Leu Arg Arg Asp Glu Cys Thr Leu Val Leu Ala Gly
                    210                 215                 220
        Gly Val Thr Val Met Ser Ser Pro Gly Ala Phe Thr Glu Phe Arg Ser
        225                 230                 235                 240
        Gln Gly Gly Leu Ala Glu Asp Gly Arg Cys Lys Pro Phe Ser Arg Ala
                    245                 250                 255
        Ala Asp Gly Phe Gly Leu Ala Glu Gly Ala Gly Val Leu Val Leu Gln
                    260                 265                 270
        Arg Leu Ser Val Ala Arg Ala Glu Gly Arg Pro Val Leu Ala Val Leu
                    275                 280                 285
        Arg Gly Ser Ala Ile Asn Gln Asp Gly Ala Ser Asn Gly Leu Thr Ala
                    290                 295                 300
        Pro Ser Gly Pro Ala Gln Arg Arg Val Ile Arg Gln Ala Leu Glu Arg
        305                 310                 315                 320
        Ala Arg Leu Arg Pro Val Asp Val Asp Tyr Val Glu Ala His Gly Thr
                    325                 330                 335
        Gly Thr Arg Leu Gly Asp Pro Ile Glu Ala His Ala Leu Leu Asp Thr
                    340                 345                 350
        Tyr Gly Ala Asp Arg Glu Pro Gly Arg Pro Leu Trp Val Gly Ser Val
                    355                 360                 365
        Lys Ser Asn Ile Gly His Thr Gln Ala Ala Gly Val Ala Gly Val
                    370                 375                 380
        Met Lys Thr Val Leu Ala Leu Arg His Arg Glu Ile Pro Ala Thr Leu
        385                 390                 395                 400
        His Phe Asp Glu Pro Ser Pro His Val Asp Trp Asp Arg Gly Ala Val
                    405                 410                 415
        Ser Val Val Ser Glu Thr Arg Pro Trp Pro Val Gly Glu Arg Pro Arg
                    420                 425                 430
        Arg Ala Gly Val Ser Ser Phe Gly Ile Ser Gly Thr Asn Ala His Val
                    435                 440                 445
        Ile Val Glu Glu Ala Pro Ser Pro Gln Ala Ala Asp Leu Asp Pro Thr
        450                 455                 460
        Pro Gly Pro Ala Thr Gly Ala Thr Pro Gly Thr Asp Ala Ala Pro Thr
        465                 470                 475                 480
        Ala Glu Pro Gly Ala Glu Ala Val Ala Leu Val Phe Ser Ala Arg Asp
                    485                 490                 495
        Glu Arg Ala Leu Arg Ala Gln Ala Ala Arg Leu Ala Asp Arg Leu Thr
                    500                 505                 510
        Asp Asp Pro Ala Pro Ser Leu Arg Asp Thr Ala Phe Thr Leu Val Thr
                    515                 520                 525
        Arg Arg Ala Thr Trp Glu His Arg Ala Val Val Gly Gly Gly Glu
        530                 535                 540
        Glu Val Leu Ala Gly Leu Arg Ala Val Ala Gly Gly Arg Pro Val Asp
        545                 550                 555                 560
        Gly Ala Val Ser Gly Arg Ala Arg Ala Gly Arg Val Val Leu Val
                    565                 570                 575
        Phe Pro Gly Gln Gly Ala Gln Trp Gln Gly Met Ala Arg Asp Leu Leu
                    580                 585                 590
```

-continued

```
Arg Gln Ser Pro Thr Phe Ala Glu Ser Ile Asp Ala Cys Glu Arg Ala
        595                 600                 605

Leu Ala Pro His Val Asp Trp Ser Leu Arg Glu Val Leu Asp Gly Glu
    610                 615                 620

Gln Ser Leu Asp Pro Val Asp Val Gln Pro Val Leu Phe Ala Val
625                 630                 635                 640

Met Val Ser Leu Ala Arg Leu Trp Gln Ser Tyr Gly Val Thr Pro Gly
                645                 650                 655

Ala Val Val Gly His Ser Gln Gly Glu Ile Ala Ala His Val Ala
            660                 665                 670

Gly Ala Leu Ser Leu Ala Asp Ala Arg Val Val Ala Leu Arg Ser
        675                 680                 685

Arg Val Leu Arg Arg Leu Gly His Gly Gly Met Ala Ser Phe Gly
    690                 695                 700

Leu His Pro Asp Gln Ala Glu Arg Ile Ala Arg Phe Ala Gly Ala
705                 710                 715                 720

Leu Thr Val Ala Ser Val Asn Gly Pro Arg Ser Val Val Leu Ala Gly
                725                 730                 735

Glu Asn Gly Pro Leu Asp Glu Leu Ile Ala Glu Cys Glu Ala Glu Gly
            740                 745                 750

Val Thr Ala Arg Arg Ile Pro Val Asp Tyr Ala Ser His Ser Pro Gln
        755                 760                 765

Val Glu Ser Leu Arg Glu Glu Leu Leu Ala Ala Leu Ala Gly Val Arg
    770                 775                 780

Pro Val Ser Ala Gly Ile Pro Leu Tyr Ser Thr Leu Thr Gly Gln Val
785                 790                 795                 800

Ile Glu Thr Ala Thr Met Asp Ala Asp Tyr Trp Phe Ala Asn Leu Arg
                805                 810                 815

Glu Pro Val Arg Phe Gln Asp Ala Thr Arg Gln Leu Ala Glu Ala Gly
            820                 825                 830

Phe Asp Ala Phe Val Glu Val Ser Pro His Pro Val Leu Thr Val Gly
        835                 840                 845

Val Glu Ala Thr Leu Glu Ala Val Leu Pro Pro Asp Ala Asp Pro Cys
    850                 855                 860

Val Thr Gly Thr Leu Arg Arg Glu Arg Gly Gly Leu Ala Gln Phe His
865                 870                 875                 880

Thr Ala Leu Ala Glu Ala Tyr Thr Arg Gly Val Glu Val Asp Trp Arg
                885                 890                 895

Thr Ala Val Gly Glu Gly Arg Pro Val Asp Leu Pro Tyr Pro Phe
            900                 905                 910

Gln Arg Gln Asn Phe Trp Leu Pro Val Pro Leu Gly Arg Val Pro Asp
        915                 920                 925

Thr Gly Asp Glu Trp Arg Tyr Gln Leu Ala Trp His Pro Val Asp Leu
    930                 935                 940

Gly Arg Ser Ser Leu Ala Gly Arg Val Leu Val Thr Gly Ala Ala
945                 950                 955                 960

Val Pro Pro Ala Trp Thr Asp Val Val Arg Asp Gly Leu Glu Gln Arg
                965                 970                 975

Gly Ala Thr Val Val Leu Cys Thr Ala Gln Ser Arg Ala Arg Ile Gly
            980                 985                 990

Ala Ala Leu Asp Ala Val Asp Gly Thr Ala Leu Ser Thr Val Val Ser
        995                 1000                1005
```

-continued

```
Leu Leu Ala Leu Ala Glu Gly Gly Ala Val Asp Asp Pro Ser Leu Asp
    1010                1015                1020
Thr Leu Ala Leu Val Gln Ala Leu Gly Ala Ala Gly Ile Asp Val Pro
1025                1030                1035                1040
Leu Trp Leu Val Thr Arg Asp Ala Ala Ala Val Thr Val Gly Asp Asp
                1045                1050                1055
Val Asp Pro Ala Gln Ala Met Val Gly Gly Leu Gly Arg Val Val Gly
            1060                1065                1070
Val Glu Ser Pro Ala Arg Trp Gly Gly Leu Val Asp Leu Arg Glu Ala
        1075                1080                1085
Asp Ala Asp Ser Ala Arg Ser Leu Ala Ala Ile Leu Ala Asp Pro Arg
    1090                1095                1100
Gly Glu Glu Gln Phe Ala Ile Arg Pro Asp Gly Val Thr Val Ala Arg
1105                1110                1115                1120
Leu Val Pro Ala Pro Ala Arg Ala Ala Gly Thr Arg Trp Thr Pro Arg
                1125                1130                1135
Gly Thr Val Leu Val Thr Gly Gly Thr Gly Gly Ile Gly Ala His Leu
            1140                1145                1150
Ala Arg Trp Leu Ala Gly Ala Gly Ala Glu His Leu Val Leu Leu Asn
        1155                1160                1165
Arg Arg Gly Ala Glu Ala Ala Gly Ala Ala Asp Leu Arg Asp Glu Leu
    1170                1175                1180
Val Ala Leu Gly Thr Gly Val Thr Ile Thr Ala Cys Asp Val Ala Asp
1185                1190                1195                1200
Arg Asp Arg Leu Ala Ala Val Leu Asp Ala Ala Arg Ala Gln Gly Arg
                1205                1210                1215
Val Val Thr Ala Val Phe His Ala Ala Gly Ile Ser Arg Ser Thr Ala
            1220                1225                1230
Val Gln Glu Leu Thr Glu Ser Glu Phe Thr Glu Ile Thr Asp Ala Lys
        1235                1240                1245
Val Arg Gly Thr Ala Asn Leu Ala Glu Leu Cys Pro Glu Leu Asp Ala
    1250                1255                1260
Leu Val Leu Phe Ser Ser Asn Ala Ala Val Trp Gly Ser Pro Gly Leu
1265                1270                1275                1280
Ala Ser Tyr Ala Ala Gly Asn Ala Phe Leu Asp Ala Phe Ala Arg Arg
            1285                1290                1295
Gly Arg Arg Ser Gly Leu Pro Val Thr Ser Ile Ala Trp Gly Leu Trp
        1300                1305                1310
Ala Gly Gln Asn Met Ala Gly Thr Glu Gly Gly Asp Tyr Leu Arg Ser
    1315                1320                1325
Gln Gly Leu Arg Ala Met Asp Pro Gln Arg Ala Ile Glu Glu Leu Arg
    1330                1335                1340
Thr Thr Leu Asp Ala Gly Asp Pro Trp Val Ser Val Asp Leu Asp
1345                1350                1355                1360
Arg Glu Arg Phe Val Glu Leu Phe Thr Ala Arg Arg Pro Leu
                1365                1370                1375
Phe Asp Glu Leu Gly Gly Val Arg Ala Gly Ala Glu Thr Gly Gln
            1380                1385                1390
Glu Ser Asp Leu Ala Arg Arg Leu Ala Ser Met Pro Glu Ala Glu Arg
        1395                1400                1405
His Glu His Val Ala Arg Leu Val Arg Ala Glu Val Ala Ala Val Leu
    1410                1415                1420
Gly His Gly Thr Pro Thr Val Ile Glu Arg Asp Val Ala Phe Arg Asp
```

-continued

Leu Gly Phe Asp Ser Met Thr Ala Val Asp Leu Arg Asn Arg Leu Ala
1425                 1430                 1435                 1440

Ala Val Thr Gly Val Arg Val Ala Thr Thr Ile Val Phe Asp His Pro
            1445                 1450                 1455

Thr Val Asp Arg Leu Thr Ala His Tyr Leu Glu Arg Leu Val Gly Glu
        1460                 1465                 1470

Pro Glu Ala Thr Thr Pro Ala Ala Val Val Pro Gln Ala Pro Gly
    1475                 1480                 1485

Glu Ala Asp Glu Pro Ile Ala Ile Val Gly Met Ala Cys Arg Leu Ala
1490                 1495                 1500

Gly Gly Val Arg Thr Pro Asp Gln Leu Trp Asp Phe Ile Val Ala Asp
1505                 1510                 1515                 1520

Gly Asp Ala Val Thr Glu Met Pro Ser Asp Arg Ser Trp Asp Leu Asp
            1525                 1530                 1535

Ala Leu Phe Asp Pro Asp Pro Glu Arg His Gly Thr Ser Tyr Ser Arg
        1540                 1545                 1550

His Gly Ala Phe Leu Asp Gly Ala Ala Asp Phe Asp Ala Ala Phe Phe
    1555                 1560                 1565

Gly Ile Ser Pro Arg Glu Ala Leu Ala Met Asp Pro Gln Gln Arg Gln
1570                 1575                 1580

Val Leu Glu Thr Thr Trp Glu Leu Phe Glu Asn Ala Gly Ile Asp Pro
1585                 1590                 1595                 1600

His Ser Leu Arg Gly Thr Asp Thr Gly Val Phe Leu Gly Ala Ala Tyr
            1605                 1610                 1615

Gln Gly Tyr Gly Gln Asn Ala Gln Val Pro Lys Glu Ser Glu Gly Tyr
        1620                 1625                 1630

Leu Leu Thr Gly Gly Ser Ser Ala Val Ala Ser Gly Arg Ile Ala Tyr
    1635                 1640                 1645

Val Leu Gly Leu Glu Gly Pro Ala Ile Thr Val Asp Thr Ala Cys Ser
1650                 1655                 1660

Ser Ser Leu Val Ala Leu His Val Ala Ala Gly Ser Leu Arg Ser Gly
1665                 1670                 1675                 1680

Asp Cys Gly Leu Ala Val Ala Gly Gly Val Ser Val Met Ala Gly Pro
            1685                 1690                 1695

Glu Val Phe Thr Glu Phe Ser Arg Gln Gly Ala Leu Ala Pro Asp Gly
        1700                 1705                 1710

Arg Cys Lys Pro Phe Ser Asp Gln Ala Asp Gly Phe Gly Phe Ala Glu
    1715                 1720                 1725

Gly Val Ala Val Val Leu Leu Gln Arg Leu Ser Val Ala Val Arg Glu
1730                 1735                 1740

Gly Arg Arg Val Leu Gly Val Val Gly Ser Ala Val Asn Gln Asp
1745                 1750                 1755                 1760

Gly Ala Ser Asn Gly Leu Ala Ala Pro Ser Gly Val Ala Gln Gln Arg
            1765                 1770                 1775

Val Ile Arg Arg Ala Trp Gly Arg Ala Gly Val Ser Gly Gly Asp Val
        1780                 1785                 1790

Gly Val Val Glu Ala His Gly Thr Gly Thr Arg Leu Gly Asp Pro Val
    1795                 1800                 1805

Glu Leu Gly Ala Leu Leu Gly Thr Tyr Gly Val Gly Arg Gly Gly Val
1810                 1815                 1820

Gly Pro Val Val Val Gly Ser Val Lys Ala Asn Val Gly His Val Gln
1825                 1830                 1835                 1840

1845                 1850                 1855

-continued

```
Ala Ala Ala Gly Val Gly Val Ile Lys Val Leu Gly Leu Gly
            1860            1865            1870
Arg Gly Leu Val Gly Pro Met Val Cys Arg Gly Leu Ser Gly Leu
        1875            1880            1885
Val Asp Trp Ser Ser Gly Gly Leu Val Val Ala Asp Gly Val Arg Gly
    1890            1895            1900
Trp Pro Val Gly Val Asp Gly Val Arg Arg Gly Gly Val Ser Ala Phe
1905            1910            1915            1920
Gly Val Ser Gly Thr Asn Ala His Val Val Ala Glu Ala Pro Gly
            1925            1930            1935
Ser Val Val Gly Ala Glu Arg Pro Val Glu Gly Ser Ser Arg Gly Leu
        1940            1945            1950
Val Gly Val Ala Gly Gly Val Val Pro Val Val Leu Ser Ala Lys Thr
    1955            1960            1965
Glu Thr Ala Leu Thr Glu Leu Ala Arg Arg Leu His Asp Ala Val Asp
        1970            1975            1980
Asp Thr Val Ala Leu Pro Ala Val Ala Ala Thr Leu Ala Thr Gly Arg
1985            1990            1995            2000
Ala His Leu Pro Tyr Arg Ala Ala Leu Leu Ala Arg Asp His Asp Glu
            2005            2010            2015
Leu Arg Asp Arg Leu Arg Ala Phe Thr Thr Gly Ser Ala Ala Pro Gly
        2020            2025            2030
Val Val Ser Gly Val Ala Ser Gly Gly Gly Val Phe Val Phe Pro
    2035            2040            2045
Gly Gln Gly Gly Gln Trp Val Gly Met Ala Arg Gly Leu Leu Ser Val
    2050            2055            2060
Pro Val Phe Val Glu Ser Val Glu Cys Asp Ala Val Val Ser Ser
2065            2070            2075            2080
Val Val Gly Phe Ser Val Leu Gly Val Leu Glu Gly Arg Ser Gly Ala
            2085            2090            2095
Pro Ser Leu Asp Arg Val Asp Val Gln Pro Val Leu Phe Val Val
        2100            2105            2110
Met Val Ser Leu Ala Arg Leu Trp Arg Trp Cys Gly Val Val Pro Ala
    2115            2120            2125
Ala Val Val Gly His Ser Gln Gly Glu Ile Ala Ala Ala Val Val Ala
    2130            2135            2140
Gly Val Leu Ser Val Gly Asp Gly Ala Arg Val Val Ala Leu Arg Ala
2145            2150            2155            2160
Arg Ala Leu Arg Ala Leu Ala Gly His Gly Gly Met Val Ser Leu Ala
            2165            2170            2175
Val Ser Ala Glu Arg Ala Arg Glu Leu Ile Ala Pro Trp Ser Asp Arg
        2180            2185            2190
Ile Ser Val Ala Ala Val Asn Ser Pro Thr Ser Val Val Ser Gly
    2195            2200            2205
Asp Pro Gln Ala Leu Ala Ala Leu Val Ala His Cys Ala Glu Thr Gly
    2210            2215            2220
Glu Arg Ala Lys Thr Leu Pro Val Asp Tyr Ala Ser His Ser Ala His
2225            2230            2235            2240
Val Glu Gln Ile Arg Asp Thr Ile Leu Thr Asp Leu Ala Asp Val Thr
            2245            2250            2255
Ala Arg Arg Pro Asp Val Ala Leu Tyr Ser Thr Leu His Gly Ala Arg
        2260            2265            2270
```

-continued

Gly Ala Gly Thr Asp Met Asp Ala Arg Tyr Trp Tyr Asp Asn Leu Arg
        2275                2280                2285

Ser Pro Val Arg Phe Asp Glu Ala Val Glu Ala Val Ala Asp Gly
        2290                2295                2300

Tyr Arg Val Phe Val Glu Met Ser Pro His Pro Val Leu Thr Ala Ala
2305                2310                2315                2320

Val Gln Glu Ile Asp Asp Glu Thr Val Ala Ile Gly Ser Leu His Arg
        2325                2330                2335

Asp Thr Gly Glu Arg His Leu Val Ala Glu Leu Ala Arg Ala His Val
        2340                2345                2350

His Gly Val Pro Val Asp Trp Arg Ala Ile Leu Pro Ala Thr His Pro
        2355                2360                2365

Val Pro Leu Pro Asn Tyr Pro Phe Glu Ala Thr Arg Tyr Trp Leu Ala
        2370                2375                2380

Pro Thr Ala Ala Asp Gln Val Ala Asp His Arg Tyr Arg Val Asp Trp
2385                2390                2395                2400

Arg Pro Leu Ala Thr Thr Pro Ala Glu Leu Ser Gly Ser Tyr Leu Val
        2405                2410                2415

Phe Gly Asp Ala Pro Glu Thr Leu Gly His Ser Val Glu Lys Ala Gly
        2420                2425                2430

Gly Leu Leu Val Pro Val Ala Ala Pro Asp Arg Glu Ser Leu Ala Val
        2435                2440                2445

Ala Leu Asp Glu Ala Ala Gly Arg Leu Ala Gly Val Leu Ser Phe Ala
        2450                2455                2460

Ala Asp Thr Ala Thr His Leu Ala Arg His Arg Leu Leu Gly Glu Ala
2465                2470                2475                2480

Asp Val Glu Ala Pro Leu Trp Leu Val Thr Ser Gly Val Ala Leu
        2485                2490                2495

Asp Asp His Asp Pro Ile Asp Cys Asp Gln Ala Met Val Trp Gly Ile
        2500                2505                2510

Gly Arg Val Met Gly Leu Glu Thr Pro His Arg Trp Gly Gly Leu Val
        2515                2520                2525

Asp Val Thr Val Glu Pro Thr Ala Glu Asp Gly Val Val Phe Ala Ala
        2530                2535                2540

Leu Leu Ala Ala Asp Asp His Glu Asp Gln Val Ala Leu Arg Asp Gly
2545                2550                2555                2560

Ile Arg His Gly Arg Arg Leu Val Arg Ala Pro Leu Thr Thr Arg Asn
        2565                2570                2575

Ala Arg Trp Thr Pro Ala Gly Thr Ala Leu Val Thr Gly Gly Thr Gly
        2580                2585                2590

Ala Leu Gly Gly His Val Ala Arg Tyr Leu Ala Arg Ser Gly Val Thr
        2595                2600                2605

Asp Leu Val Leu Leu Ser Arg Ser Gly Pro Asp Ala Pro Gly Ala Ala
        2610                2615                2620

Glu Leu Ala Ala Glu Leu Ala Asp Leu Gly Ala Glu Pro Arg Val Glu
2625                2630                2635                2640

Ala Cys Asp Val Thr Asp Gly Pro Arg Leu Arg Ala Leu Val Gln Glu
                2645                2650                2655

Leu Arg Glu Gln Asp Arg Pro Val Arg Ile Val His Thr Ala Gly
        2660                2665                2670

Val Pro Asp Ser Arg Pro Leu Asp Arg Ile Asp Glu Leu Ser Val
        2675                2680                2685

Ser Ala Ala Lys Val Thr Gly Ala Arg Leu Leu Asp Glu Leu Cys Pro

-continued

```
            2690                2695                2700
Asp Ala Asp Thr Phe Val Leu Phe Ser Ser Gly Ala Gly Val Trp Gly
2705                2710                2715                2720
Ser Ala Asn Leu Gly Ala Tyr Ala Ala Asn Ala Tyr Leu Asp Ala
                2725                2730                2735
Leu Ala His Arg Arg Arg Gln Ala Gly Arg Ala Ala Thr Ser Val Ala
                2740                2745                2750
Trp Gly Ala Trp Ala Gly Asp Gly Met Ala Thr Gly Asp Leu Asp Gly
            2755                2760                2765
Leu Thr Arg Arg Gly Leu Arg Ala Met Ala Pro Asp Arg Ala Leu Arg
            2770                2775                2780
Ala Cys Thr Arg Arg Trp Thr Thr His Asp Thr Cys Val Ser Val Ala
2785                2790                2795                2800
Asp Val Asp Trp Asp Arg Phe Ala Val Gly Phe Thr Ala Ala Arg Pro
                2805                2810                2815
Arg Pro Leu Ile Asp Glu Leu Val Thr Ser Ala Pro Val Ala Ala Pro
                2820                2825                2830
Thr Ala Ala Ala Ala Pro Val Pro Ala Met Thr Ala Asp Gln Leu Leu
                2835                2840                2845
Gln Phe Thr Arg Ser His Val Ala Ala Ile Leu Gly His Gln Asp Pro
                2850                2855                2860
Asp Ala Val Gly Leu Asp Gln Pro Phe Thr Glu Leu Gly Phe Asp Ser
2865                2870                2875                2880
Leu Thr Ala Val Gly Leu Arg Asn Gln Leu Gln Gln Ala Thr Gly Arg
                2885                2890                2895
Thr Leu Pro Ala Ala Leu Val Phe Gln His Pro Thr Val Arg Arg Leu
            2900                2905                2910
Ala Asp His Leu Ala Gln Gln Leu Asp Val Gly Thr Ala Pro Val Glu
            2915                2920                2925
Ala Thr Gly Ser Val Leu Arg Asp Gly Tyr Arg Arg Ala Gly Gln Thr
            2930                2935                2940
Gly Asp Val Arg Ser Tyr Leu Asp Leu Leu Ala Asn Leu Ser Glu Phe
2945                2950                2955                2960
Arg Glu Arg Phe Thr Asp Ala Ala Ser Leu Gly Gly Gln Leu Glu Leu
                2965                2970                2975
Val Asp Leu Ala Asp Gly Ser Gly Pro Val Thr Val Ile Cys Cys Ala
                2980                2985                2990
Gly Thr Ala Ala Leu Ser Gly Pro His Glu Phe Ala Arg Leu Ala Ser
            2995                3000                3005
Ala Leu Arg Gly Thr Val Pro Val Arg Ala Leu Ala Gln Pro Gly Tyr
            3010                3015                3020
Glu Ala Gly Glu Pro Val Pro Ala Ser Met Glu Ala Val Leu Gly Val
3025                3030                3035                3040
Gln Ala Asp Ala Val Leu Ala Ala Gln Gly Asp Thr Pro Phe Val Leu
                3045                3050                3055
Val Gly His Ser Ala Gly Ala Leu Met Ala Tyr Ala Leu Ala Thr Glu
                3060                3065                3070
Leu Ala Asp Arg Gly His Pro Pro Arg Gly Val Val Leu Leu Asp Val
                3075                3080                3085
Tyr Pro Pro Gly His Gln Glu Ala Val His Ala Trp Leu Gly Glu Leu
            3090                3095                3100
Thr Ala Ala Leu Phe Asp His Glu Thr Val Arg Met Asp Asp Thr Arg
3105                3110                3115                3120
```

```
Leu Thr Ala Leu Gly Ala Tyr Asp Arg Leu Thr Gly Arg Trp Arg Pro
              3125                3130                3135

Arg Asp Thr Gly Leu Pro Thr Leu Val Val Ala Ala Ser Glu Pro Met
          3140                3145                3150

Gly Glu Trp Pro Asp Asp Gly Trp Gln Ser Thr Trp Pro Phe Gly His
          3155                3160                3165

Asp Arg Val Thr Val Pro Gly Asp His Phe Ser Met Val Gln Glu His
          3170                3175                3180

Ala Asp Ala Ile Ala Arg His Ile Asp Ala Trp Leu Ser Gly Glu Arg
3185                3190                3195                3200

Ala

<210> SEQ ID NO 16
<211> LENGTH: 358
<212> TYPE: PRT
<213> ORGANISM: Micromonospora megalomicea

<400> SEQUENCE: 16

Met Asn Thr Thr Asp Arg Ala Val Leu Gly Arg Leu Gln Met Ile
1               5                   10                  15

Arg Gly Leu Tyr Trp Gly Tyr Gly Ser Asn Gly Asp Pro Tyr Pro Met
            20                  25                  30

Leu Leu Cys Gly His Asp Asp Pro His Arg Trp Tyr Arg Gly Leu
            35                  40                  45

Gly Gly Ser Gly Val Arg Arg Ser Arg Thr Glu Thr Trp Val Val Thr
        50                  55                  60

Asp His Ala Thr Ala Val Arg Val Leu Asp Asp Pro Thr Phe Thr Arg
65                  70                  75                  80

Ala Thr Gly Arg Thr Pro Glu Trp Met Arg Ala Ala Gly Ala Pro Ala
                85                  90                  95

Ser Thr Trp Ala Gln Pro Phe Arg Asp Val His Ala Ala Ser Trp Asp
            100                 105                 110

Ala Glu Leu Pro Asp Pro Gln Val Glu Asp Arg Leu Thr Gly Leu
            115                 120                 125

Leu Pro Ala Pro Gly Thr Arg Leu Asp Leu Val Arg Asp Leu Ala Trp
130                 135                 140

Pro Met Ala Ser Arg Gly Val Gly Ala Asp Asp Pro Asp Val Leu Arg
145                 150                 155                 160

Ala Ala Trp Asp Ala Arg Val Gly Leu Asp Ala Gln Leu Thr Pro Gln
                165                 170                 175

Pro Leu Ala Val Thr Glu Ala Ala Ile Ala Ala Val Pro Gly Asp Pro
            180                 185                 190

His Arg Arg Ala Leu Phe Thr Ala Val Glu Met Thr Ala Thr Ala Phe
            195                 200                 205

Val Asp Ala Val Leu Ala Val Thr Ala Thr Ala Gly Ala Ala Gln Arg
            210                 215                 220

Leu Ala Asp Asp Pro Asp Val Ala Ala Arg Leu Val Ala Glu Val Leu
225                 230                 235                 240

Arg Leu His Pro Thr Ala His Leu Glu Arg Arg Thr Ala Gly Thr Glu
                245                 250                 255

Thr Val Val Gly Glu His Thr Val Ala Ala Gly Asp Glu Val Val Val
            260                 265                 270

Val Val Ala Ala Ala Asn Arg Asp Ala Gly Val Phe Ala Asp Pro Asp
            275                 280                 285
```

```
Arg Leu Asp Pro Asp Arg Ala Asp Ala Asp Arg Ala Leu Ser Ala Gln
    290                 295                 300

Arg Gly His Pro Gly Arg Leu Glu Glu Leu Val Val Val Leu Thr Thr
305                 310                 315                 320

Ala Ala Leu Arg Ser Val Ala Lys Ala Leu Pro Gly Leu Thr Ala Gly
            325                 330                 335

Gly Pro Val Val Arg Arg Arg Ser Pro Val Leu Arg Ala Thr Ala
                340                 345                 350

His Cys Pro Val Glu Leu
        355

<210> SEQ ID NO 17
<211> LENGTH: 422
<212> TYPE: PRT
<213> ORGANISM: Micromonospora megalomicea

<400> SEQUENCE: 17

Met Arg Val Val Phe Ser Ser Met Ala Ser Lys Ser His Leu Phe Gly
1               5                   10                  15

Leu Val Pro Leu Ala Trp Ala Phe Arg Ala Ala Gly His Glu Val Arg
            20                  25                  30

Val Val Ala Ser Pro Ala Leu Thr Asp Ile Thr Ala Ala Gly Leu
        35                  40                  45

Thr Ala Val Pro Val Gly Thr Asp Val Asp Leu Val Asp Phe Met Thr
50                  55                  60

His Ala Gly Tyr Asp Ile Ile Asp Tyr Val Arg Ser Leu Asp Phe Ser
65                  70                  75                  80

Glu Arg Asp Pro Ala Thr Ser Thr Trp Asp His Leu Leu Gly Met Gln
                85                  90                  95

Thr Val Leu Thr Pro Thr Phe Tyr Ala Leu Met Ser Pro Asp Ser Leu
            100                 105                 110

Val Glu Gly Met Ile Ser Phe Cys Arg Ser Trp Arg Pro Asp Trp Ser
        115                 120                 125

Ser Gly Pro Gln Thr Phe Ala Ala Ser Ile Ala Ala Thr Val Thr Gly
    130                 135                 140

Val Ala His Ala Arg Leu Leu Trp Gly Pro Asp Ile Thr Val Arg Ala
145                 150                 155                 160

Arg Gln Lys Phe Leu Gly Leu Leu Pro Gly Gln Pro Ala Ala His Arg
                165                 170                 175

Glu Asp Pro Leu Ala Glu Trp Leu Thr Trp Ser Val Glu Arg Phe Gly
            180                 185                 190

Gly Arg Val Pro Gln Asp Val Glu Glu Leu Val Val Gly Gln Trp Thr
        195                 200                 205

Ile Asp Pro Ala Pro Val Gly Met Arg Leu Asp Thr Gly Leu Arg Thr
    210                 215                 220

Val Gly Met Arg Tyr Val Asp Tyr Asn Gly Pro Ser Val Val Pro Asp
225                 230                 235                 240

Trp Leu His Asp Glu Pro Thr Arg Arg Val Cys Leu Thr Leu Gly
                245                 250                 255

Ile Ser Ser Arg Glu Asn Ser Ile Gly Gln Val Ser Val Asp Asp Leu
            260                 265                 270

Leu Gly Ala Leu Gly Asp Val Asp Ala Glu Ile Ile Ala Thr Val Asp
        275                 280                 285

Glu Gln Gln Leu Glu Gly Val Ala His Val Pro Ala Asn Ile Arg Thr
```

-continued

```
            290                 295                 300
Val Gly Phe Val Pro Met His Ala Leu Leu Pro Thr Cys Ala Ala Thr
305                 310                 315                 320

Val His His Gly Gly Pro Gly Ser Trp His Thr Ala Ala Ile His Gly
                325                 330                 335

Val Pro Gln Val Ile Leu Pro Asp Gly Trp Asp Thr Gly Val Arg Ala
            340                 345                 350

Gln Arg Thr Glu Asp Gln Gly Ala Gly Ile Ala Leu Pro Val Pro Glu
        355                 360                 365

Leu Thr Ser Asp Gln Leu Arg Glu Ala Val Arg Arg Val Leu Asp Asp
    370                 375                 380

Pro Ala Phe Thr Ala Gly Ala Ala Arg Met Arg Ala Asp Met Leu Ala
385                 390                 395                 400

Glu Pro Ser Pro Ala Glu Val Val Asp Val Cys Ala Gly Leu Val Gly
                405                 410                 415

Glu Arg Thr Ala Val Gly
                420

<210> SEQ ID NO 18
<211> LENGTH: 323
<212> TYPE: PRT
<213> ORGANISM: Micromonospora megalomicea

<400> SEQUENCE: 18

Met Ser Thr Asp Ala Thr His Val Arg Leu Gly Arg Cys Ala Leu Leu
1               5                   10                  15

Thr Ser Arg Leu Trp Leu Gly Thr Ala Ala Leu Ala Gly Gln Asp Asp
            20                  25                  30

Ala Asp Ala Val Arg Leu Leu Asp His Ala Arg Ser Arg Gly Val Asn
        35                  40                  45

Cys Leu Asp Thr Ala Asp Asp Ser Ala Ser Thr Ser Ala Gln Val
    50                  55                  60

Ala Glu Glu Ser Val Gly Arg Trp Leu Ala Gly Asp Thr Gly Arg Arg
65                  70                  75                  80

Glu Glu Thr Val Leu Ser Val Thr Val Gly Val Pro Pro Gly Gly Gln
                85                  90                  95

Val Gly Gly Gly Leu Ser Ala Arg Gln Ile Ile Ala Ser Cys Glu
            100                 105                 110

Gly Ser Leu Arg Arg Leu Gly Val Asp His Val Asp Val Leu His Leu
        115                 120                 125

Pro Arg Val Asp Arg Val Glu Pro Trp Asp Glu Val Trp Gln Ala Val
    130                 135                 140

Asp Ala Leu Val Ala Ala Gly Lys Val Cys Tyr Val Gly Ser Ser Gly
145                 150                 155                 160

Phe Pro Gly Trp His Ile Val Ala Ala Gln Glu His Ala Val Arg Arg
                165                 170                 175

His Arg Leu Gly Leu Val Ser His Gln Cys Arg Tyr Asp Leu Thr Ser
            180                 185                 190

Arg His Pro Glu Leu Glu Val Leu Pro Ala Ala Gln Ala Tyr Gly Leu
        195                 200                 205

Gly Val Phe Ala Arg Pro Thr Arg Leu Gly Gly Leu Leu Gly Gly Asp
    210                 215                 220

Gly Pro Gly Ala Ala Ala Ala Arg Ala Ser Gly Gln Pro Thr Ala Leu
225                 230                 235                 240
```

```
Arg Ser Ala Val Glu Ala Tyr Glu Val Phe Cys Arg Asp Leu Gly Glu
                245                 250                 255

His Pro Ala Glu Val Ala Leu Ala Trp Val Leu Ser Arg Pro Gly Val
            260                 265                 270

Ala Gly Ala Val Val Gly Ala Arg Thr Pro Gly Arg Leu Asp Ser Ala
        275                 280                 285

Leu Arg Ala Cys Gly Val Ala Leu Gly Ala Thr Glu Leu Thr Ala Leu
    290                 295                 300

Asp Gly Ile Phe Pro Gly Val Ala Ala Gly Ala Ala Pro Glu Ala
305                 310                 315                 320

Trp Leu Arg

<210> SEQ ID NO 19
<211> LENGTH: 247
<212> TYPE: PRT
<213> ORGANISM: Micromonospora megalomicea

<400> SEQUENCE: 19

Met Asn Thr Trp Leu Arg Arg Phe Gly Ser Ala Asp Gly His Arg Ala
  1               5                  10                  15

Arg Leu Tyr Cys Phe Pro His Ala Gly Ala Ala Asp Ser Tyr Leu
             20                  25                  30

Asp Leu Ala Arg Ala Leu Ala Pro Glu Val Asp Val Trp Ala Val Gln
         35                  40                  45

Tyr Pro Gly Arg Gln Asp Arg Arg Asp Glu Arg Ala Leu Gly Thr Ala
     50                  55                  60

Gly Glu Ile Ala Asp Glu Val Ala Ala Val Leu Arg Asp Leu Val Gly
 65                  70                  75                  80

Glu Val Pro Phe Ala Leu Phe Gly His Ser Met Gly Ala Leu Val Ala
                 85                  90                  95

Tyr Glu Thr Ala Arg Arg Leu Glu Ala Arg Pro Gly Val Arg Pro Leu
            100                 105                 110

Arg Leu Phe Val Ser Gly Gln Thr Ala Pro Arg Val His Glu Arg Arg
        115                 120                 125

Thr Asp Leu Pro Asp Glu Asp Gly Leu Val Glu Gln Met Arg Arg Leu
    130                 135                 140

Gly Val Ser Glu Ala Ala Leu Ala Asp Gln Gly Leu Leu Asp Met Ser
145                 150                 155                 160

Leu Pro Val Leu Arg Ala Asp His Arg Val Leu Arg Ser Tyr Ala Trp
                165                 170                 175

Gln Ala Gly Pro Pro Leu Arg Ala Gly Ile Thr Thr Leu Cys Gly Asp
            180                 185                 190

Thr Asp Pro Leu Thr Thr Val Glu Asp Ala Gln Arg Trp Leu Pro Tyr
        195                 200                 205

Ser Val Val Pro Gly Arg Thr Arg Thr Phe Pro Gly Gly His Phe Tyr
    210                 215                 220

Leu Ala Asp His Val Gly Glu Val Ala Glu Ser Val Ala Pro Asp Leu
225                 230                 235                 240

Leu Arg Leu Thr Pro Thr Gly
                245

<210> SEQ ID NO 20
<211> LENGTH: 189
<212> TYPE: PRT
<213> ORGANISM: Micromonospora megalomicea
```

<400> SEQUENCE: 20

| | | | | | | | | | | | | | | |
|---|---|---|---|---|---|---|---|---|---|---|---|---|---|---|
| Ile | Arg | Val | Gln | Asp | Asp | Ala | Asp | Arg | Leu | Ser | Arg | Asp | Glu | Leu |
| 1 | | | | 5 | | | | | 10 | | | | | 15 |
| Thr | Ser | Ile | Ala | Leu | Val | Leu | Leu | Ala | Gly | Phe | Glu | Ala | Ser | Val |
| | | | 20 | | | | | 25 | | | | | 30 | |
| Ser | Leu | Ile | Gly | Ile | Gly | Thr | Tyr | Leu | Leu | Thr | His | Pro | Asp | Gln |
| | | 35 | | | | | 40 | | | | | 45 | | |
| Leu | Ala | Leu | Val | Arg | Lys | Asp | Pro | Ala | Leu | Leu | Pro | Gly | Ala | Val | Glu |
| | 50 | | | | | 55 | | | | | 60 | | | | |
| Glu | Ile | Leu | Arg | Tyr | Gln | Ala | Pro | Pro | Glu | Thr | Thr | Thr | Arg | Phe | Ala |
| 65 | | | | | 70 | | | | | 75 | | | | | 80 |
| Thr | Ala | Glu | Val | Glu | Ile | Gly | Gly | Val | Thr | Ile | Pro | Ala | Tyr | Ser | Thr |
| | | | | 85 | | | | | 90 | | | | | 95 | |
| Val | Leu | Ile | Ala | Asn | Gly | Ala | Ala | Asn | Arg | Asp | Pro | Gly | Gln | Phe | Pro |
| | | | 100 | | | | | 105 | | | | | 110 | | |
| Asp | Pro | Asp | Arg | Phe | Asp | Val | Thr | Arg | Asp | Ser | Arg | Gly | His | Leu | Thr |
| | | 115 | | | | | 120 | | | | | 125 | | | |
| Phe | Gly | His | Gly | Ile | His | Tyr | Cys | Met | Gly | Arg | Pro | Leu | Ala | Lys | Leu |
| | | 130 | | | | | 135 | | | | | 140 | | | |
| Glu | Gly | Glu | Val | Ala | Leu | Gly | Ala | Leu | Phe | Asp | Arg | Phe | Pro | Lys | Leu |
| 145 | | | | | 150 | | | | | 155 | | | | | 160 |
| Ser | Leu | Gly | Phe | Pro | Ser | Asp | Glu | Val | Val | Trp | Arg | Arg | Ser | Leu | Leu |
| | | | | 165 | | | | | 170 | | | | | 175 | |
| Leu | Arg | Gly | Ile | Asp | His | Leu | Pro | Val | Arg | Pro | Asn | Gly |
| | | | | 180 | | | | | 185 | | | |

<210> SEQ ID NO 21
<211> LENGTH: 33
<212> TYPE: DNA
<213> ORGANISM: Artificial Sequence
<220> FEATURE:
<223> OTHER INFORMATION: Synthetic nucleotide DNA duplex

<400> SEQUENCE: 21
taagaattcg gagatctggc ctcagctcta gac            33

<210> SEQ ID NO 22
<211> LENGTH: 39
<212> TYPE: DNA
<213> ORGANISM: Artificial Sequence
<220> FEATURE:
<223> OTHER INFORMATION: Complementary oligo

<400> SEQUENCE: 22
aattgtctag agctgaggcc agatctccga attcttaat      39

<210> SEQ ID NO 23
<211> LENGTH: 528
<212> TYPE: DNA
<213> ORGANISM: Micromonospora megalomicea

<400> SEQUENCE: 23
ttgcagcggt tgtcggtggc ggtgcgggag gggcgtcggg tgttgggtgt ggtggtgggt      60
tcggcggtga atcaggatgg ggcgagtaat gggttggcgg cgccgtcggg ggtggcgcag     120
cagcgggtga ttcggcgggc gtgggtcgt gcggtgtgt cggtgggga tgtgggtgtg       180 gtggaggcgc atgggacggg gacgcggttg ggggatccgg tggagttggg ggcgttgttg     240
gggacgtatg gggtgggtcg gggtgggtg ggtccggtgg tggtgggttc ggtgaaggcg     300

```
aatgtgggtc atgtgcaggc ggcggcgggt gtggtgggtg tgatcaaggt ggtgttgggg      360
ttgggtcggg ggttggtggg tccgatggtg tgtcggggtg ggttgtcggg gttggtggat      420
tggtcgtcgg gtgggttggt ggtggcggat ggggtgcggg ggtggccggt gggtgtggat      480
ggggtgcgtc ggggtggggt gtcggcgttt ggggtgtcgg ggacgaat                   528
```

<210> SEQ ID NO 24
<211> LENGTH: 528
<212> TYPE: DNA
<213> ORGANISM: Micromonospora megalomicea

<400> SEQUENCE: 24

```
ctgcagcggt tgtcggtggc ggtgcgggag gggcgtcggg tgttgggtgt ggtggtgggt       60
tcggcggtga atcaggatgg ggcgagtaat gggttggcgg cgccgtcggg ggtggcgcag      120
cagcgggtga ttcggcgggc gtggggtcgt gcgggtgtgt cgggtgggga tgtgggtgtg     180
gtggaggcgc atgggacggg gacgcggttg ggggatccgg tggagttggg ggcgttgttg      240
gggacgtatg gggtgggtcg gggtgggggtg ggtccggtgg tggtgggttc ggtgaaggcg     300
aatgtgggtc atgtgcaggc ggcggcgggt gtggtgggtg tgatcaaggt ggtgttgggg      360
ttgggtcggg ggttggtggg tccgatggtg tgtcggggtg ggttgtcggg gttggtggat      420
tggtcgtcgg gtgggttggt ggtggcggat ggggtgcggg ggtggccggt gggtgtggat      480
ggggtgcgtc ggggtggggt gtcggcgttt ggggtgtcgg ggacgaat                   528
```

<210> SEQ ID NO 25
<211> LENGTH: 528
<212> TYPE: DNA
<213> ORGANISM: Micromonospora megalomicea
<220> FEATURE:
<221> NAME/KEY: misc_feature
<222> LOCATION: (1)...(528)
<223> OTHER INFORMATION: Sequence with codon changes as described in the
      specification at page 99, line 22 thru page 101, line 23

<400> SEQUENCE: 25

```
ctgcagcgcc tctccgtcgc cgtccgcgag ggccgccgag tcctcggcgt cgtcgtcggc       60
tcggccgtca accaagacgg cgcgtcaaac ggcctcgccg cgccctccgg cgtcgcccag      120
cagcgcgtca tacgccgcgc gtggggacgc gccggagtat cgggcggcga cgtcggagtc      180
gtcgaggccc acggcaccgg cacccgcctc ggggatcccg tcgagctggg cgccctcctg      240
ggcacgtacg gcgtcggccg cggcggcgtc ggcccggtcg tcgtcggcag cgtcaaggcc      300
aacgtcggcc acgtccaggc cgcggccggc gtcgtcgggg tcatcaaggt cgtcctcggc      360
ctcggccgcg ggctggtcgg cccgatggtc tgccgcggcg gcctcagcgg cctcgtcgac     420
tggtcgtccg gcgccctggt cgtcgcggac ggggtccgcg gctggccggt cggcgtcgac     480
ggcgtccgcc ggggcggcgt ctcggcgttc ggcgtcagcg ggacgaat                   528
```

<210> SEQ ID NO 26
<211> LENGTH: 291
<212> TYPE: DNA
<213> ORGANISM: Micromonospora megalomicea

<400> SEQUENCE: 26

```
ggtggagtgt gatgcggtgg tgtcgtcggt ggtggggttt cggtgttgg gggtgttgga       60 gggtcggtcg ggtgcgccgt cgttggatcg ggtggatgtg gtgcagccgg tgttgttcgt     120
ggtgatggtg tcgttggcgc ggttgtggcg gtggtgtggg gttgtgcctg cggcggtggt     180
```

```
gggtcattcg caggggggaga tcgcggcggc ggtggtggcg ggggtgttgt cggtgggtga     240
tggtgcgcgg gtggtggcgt tgcgggcgcg ggcgttgcgg gcgttggccg g               291
```

<210> SEQ ID NO 27
<211> LENGTH: 291
<212> TYPE: DNA
<213> ORGANISM: Micromonospora megalomicea

<400> SEQUENCE: 27

```
ggtggagtgt gatgcggtgg tgtcgtcggt ggtggggttt tcggtgttgg gggtgttgga      60
gggtcggtcg ggtgcgccgt cgttggatcg ggtggatgtg gtgcagccgg tgttgttcgt    120
ggtgatggtg tcgttggcgc ggttgtggcg gtggtgtggg gttgtgcctg cggcggtggt    180
gggtcattcg caggggggaga tcgcggcggc ggtggtggcg ggggtgttgt cggtgggtga   240
tggtgcgcgg gtggtggcgt tgcgggcgcg ggcgttgcgg gcgttggccg g             291
```

<210> SEQ ID NO 28
<211> LENGTH: 291
<212> TYPE: DNA
<213> ORGANISM: Micromonospora megalomicea
<220> FEATURE:
<221> NAME/KEY: misc_feature
<222> LOCATION: (1)...(291)
<223> OTHER INFORMATION: Sequence with codon changes as described in the
      specification at page 99, line 22 thru page 101, line 23

<400> SEQUENCE: 28

```
cgtggagtgc gatgcggtcg tgtcgagcgt cgtcggcttc agcgtgctgg gcgtcctgga     60
gggccgcagc ggcgccccga gcctggaccg cgtcgacgtg gtccagccgg tcctgttcgt   120
ggtcatggtc agcctggccc gcctgtggcg ctggtgcggc gtggtcccgg ccgccgtggt   180
cggccacagc cagggcgaga tcgccgccgc ggtcgtggcc ggcgtcctga gcgtcggcga   240
cggcgcccgc gtcgtggccc tgcgcgcccg cgccctgcgc gccctggccg g             291
```

<210> SEQ ID NO 29
<211> LENGTH: 24
<212> TYPE: DNA
<213> ORGANISM: Artificial Sequence
<220> FEATURE:
<223> OTHER INFORMATION: PCR primer

<400> SEQUENCE: 29

```
gaacaactcc tgtctgcggc cgcg                                            24
```

<210> SEQ ID NO 30
<211> LENGTH: 40
<212> TYPE: DNA
<213> ORGANISM: Artificial Sequence
<220> FEATURE:
<223> OTHER INFORMATION: PCR primer

<400> SEQUENCE: 30

```
cggaattctc tagagtcacg tctccaaccg cttgtcgagg                           40
```

<210> SEQ ID NO 31
<211> LENGTH: 51
<212> TYPE: DNA
<213> ORGANISM: Artificial Sequence
<220> FEATURE:
<223> OTHER INFORMATION: PCR primer

<400> SEQUENCE: 31

```
tctagactta attaaggagg acacatatga gcgagagcag cggcatgacc g                51

<210> SEQ ID NO 32
<211> LENGTH: 25
<212> TYPE: DNA
<213> ORGANISM: Artificial Sequence
<220> FEATURE:
<223> OTHER INFORMATION: PCR primer

<400> SEQUENCE: 32
aacgcctccc aggagatctc cagca                                             25

<210> SEQ ID NO 33
<211> LENGTH: 16
<212> TYPE: DNA
<213> ORGANISM: Artificial Sequence
<220> FEATURE:
<223> OTHER INFORMATION: Oligo

<400> SEQUENCE: 33
aattcatagc ctaggt                                                       16

<210> SEQ ID NO 34
<211> LENGTH: 16
<212> TYPE: DNA
<213> ORGANISM: Artificial Sequence
<220> FEATURE:
<223> OTHER INFORMATION: Oligo

<400> SEQUENCE: 34
ctagacctag gctatg                                                       16
```